US012673068B2

(12) United States Patent
Krivega et al.

(10) Patent No.: US 12,673,068 B2
(45) Date of Patent: Jul. 7, 2026

(54) BIOLOGIC AGENTS AND METHODS OF USE

(71) Applicant: SonoThera, Inc., South San Francisco, CA (US)

(72) Inventors: Ivan Krivega, Burlingame, CA (US); Margarita Krivega, South San Francisco, CA (US); Kenneth Greenberg, Berkeley, CA (US); Steven B. Feinstein, Highland Park, IL (US)

(73) Assignee: Sono Thera, Inc., South San Fransisco, CA (US)

( * ) Notice: Subject to any disclaimer, the term of this patent is extended or adjusted under 35 U.S.C. 154(b) by 0 days.

(21) Appl. No.: 19/353,536

(22) Filed: Oct. 8, 2025

(65) Prior Publication Data

US 2026/0124227 A1    May 7, 2026

Related U.S. Application Data

(63) Continuation of application No. PCT/US2025/024558, filed on Apr. 14, 2025.

(60) Provisional application No. 63/709,966, filed on Oct. 21, 2024, provisional application No. 63/634,905, filed on Apr. 16, 2024.

(51) Int. Cl.
| | |
|---|---|
| A61K 31/7088 | (2006.01) |
| A61K 41/00 | (2020.01) |
| A61K 47/26 | (2006.01) |
| A61K 48/00 | (2006.01) |
| C12N 15/11 | (2006.01) |
| C12N 15/63 | (2006.01) |

(52) U.S. Cl.
CPC ...... *A61K 31/7088* (2013.01); *A61K 41/0028* (2013.01); *A61K 47/26* (2013.01); *A61K 48/0058* (2013.01); *A61K 48/0083* (2013.01); *C12N 15/11* (2013.01); *C12N 15/63* (2013.01); *C12N 2830/34* (2013.01)

(58) Field of Classification Search
CPC .... C12N 15/63; C12N 16/11; A61K 41/0028; A61K 48/0058
See application file for complete search history.

(56) References Cited

FOREIGN PATENT DOCUMENTS

| WO | WO-2021209574 A1 | 10/2021 |
|---|---|---|
| WO | WO-2025221675 A1 | 10/2025 |

OTHER PUBLICATIONS

Abstract and Case Policies and Procedures. American College of Cardiology 74th Annual Scientific Session & Expo. pp. 1-8. (2024).
ASH Abstract Acceptance: Poster Presentation (Abstract #2232); Email from Surabhi Rao dated Oct. 2, 2024. pp. 1-6. (2024).
Benthall, Katie, et al. Cellular Phenotyping of Non-Human Primate and Mouse Kidney and Liver Following a Novel Targeted Transcutaneous Ultrasound-Mediated Gene Delivery Demonstrates Gene Expression in Clinically Relevant Cell Types. Molecular Therapy. vol. 32. No. 4. Cell Press. (2024).
Benthall, Katie; et al. Development of a Non-viral Gene Therapy for X-linked Alport Syndrome by Targeted Transcutaneous Ultrasound-Mediated Gene Delivery: TH-OR90. Journal of the American Society of Nephrology 35(10S):10.1681/ASN.2024qxx815yr. (2024).
Campbell, Barry, et al. Non-viral Gene Delivery Utilizing Transcutaneous Ultrasound Enables Rapid and Robust Gene Expression. American Society of Gene & Cell Therapy. pp. 1. (2023).
Castle, Jason W., et al. Therapeutic ultrasound: increased HDL-cholesterol following infusions of acoustic microspheres and apolipoprotein AI plasmids. Atherosclerosis 241.1: 92-99. (2015).
Chan, Jonathan, et al. Non-viral, Ultrasound Mediated Gene Delivery to the Heart of Mice and Macaques. Toxicology Research Laboratory & SonoThera, Sessions 2024. pp. 1-3. (2024).
Chan, Jonathan, et al. Non-viral, Ultrasound Mediated Gene Delivery to the Heart of Mice and Non-Human Primates. American Heart Association. pp. 1. (2024).
Chen, Shuyuan, et al. Optimization of ultrasound parameters for cardiac gene delivery of adenoviral or plasmid deoxyribonucleic acid by ultrasound-targeted microbubble destruction. Journal of the American College of Cardiology 42.2: 301-308. (2003).
Chen, Shuyuan, et al. Successful ß cells islet regeneration in streptozotocin-induced diabetic baboons using ultrasound-targeted microbubble gene therapy with cyclinD2/CDK4/GLP1. Cell Cycle 13.7: 1145-1151. (2014).

(Continued)

*Primary Examiner* — Jane J Zara
(74) *Attorney, Agent, or Firm* — WILSON SONSINI GOODRICH & ROSATI

(57) ABSTRACT

Disclosed herein are nucleic acid compositions and methods of use. The nucleic acid compositions may have a therapeutic nucleic acid sequence operably linked to a nuclear targeting sequence that increases expression of the therapeutic nucleic acid in a cell by at least 1.25 fold; at least 80% sequence identity to SEQ ID NO: 6; or a first regulatory element comprising a promoter sequence operably linked to a hemoglobin subunit gamma intron (hBGi) sequence, and a second regulatory element comprising a woodchuck hepatitis posttranscriptional regulatory element (WPRE) sequence. The nucleic acid compositions with these features may enhance therapeutic nucleic acid transfection and expression. Also disclosed herein are transgenes optimized for gene therapy applications, including novel FVIII transgene sequences, in which the B domain may be non-naturally occurring the A1 and/or A3 domain may include at least one amino acid substitution.

18 Claims, 19 Drawing Sheets

Specification includes a Sequence Listing.

(56)            References Cited

OTHER PUBLICATIONS

Dittmar, Kristin M., et al. Pulsed high-intensity focused ultrasound enhances systemic administration of naked DNA in squamous cell carcinoma model: initial experience. Radiology 235.2: 541-546. (2005).

Frederich, Bert, et al. Kidney-targeted non-viral gene delivery using a novel, noninvasive, transcutaneous, ultrasound delivery platform enables redosable, titratable, and durable gene expression in healthy mice and NHPs, and polycystic kidneys mouse model. American Society of Gene & Cell Therapy. pp. 1. (2024).

Frederich, Bert J., et al. Kidney-Targeted Delivery of Non-viral Nucleic Acids Using Noninvasive Transcutaneous Ultrasound Enables Safe, Re-dosable, Titratable, and Durable Gene Expression in Mice and Nonhuman Primates. American Society of Nephrology. pp. 1. (2024).

Frederich, Bert J., et al. Kidney-Targeted Non-Viral Gene Delivery Using a Novel Noninvasive Transcutaneous Ultrasound Delivery Platform Enables Redosable, Titratable, and Durable Gene Expression in Healthy Mice and NHPs, and Polycystic Kidneys Mouse Model. Molecular Therapy. vol. 32. No. 4. Cell Press. (2024).

Helfield, Brandon, et al. Biophysical insight into mechanisms of sonoporation. Proceedings of the National Academy of Sciences 113.36: 9983-9988. (2016).

Huber, P. E. et al. Focused ultrasound (HIFU) induces localized enhancement of reporter gene expression in rabbit carotid artery. Gene Therapy 10(18):1600-1607 (2003).

Krivega, Ivan, et al. Development of a non-viral genetic medicine for Hemophilia A by targeted transcutaneous ultrasound-mediated gene delivery. ESGCT, SonoThera. pp. 1-15. (2024).

Krivega, Ivan, et al. Development of a non-viral genetic medicine for X-linked Alport syndrome by targeted transcutaneous ultrasound-mediated gene delivery. European Society of Gene & Cell Therapy. pp. 1. (2024).

Krivega, Ivan, et al. Engineering FVIII Protein for Enhancing Expression and Secretion Profile to Achieve Normal Level of FVIII in Plasma Utilizing Noninvasive Transcutaneous Ultrasound Mediated Gene Delivery. Blood 144. Supplement 1: 7458-7458. (2024).

Krivega, Ivan, et al. Engineering FVIII protein for enhancing expression and secretion profile to achieve normal level of FVIII in plasma utilizing noninvasive transcutaneous ultrasound mediated gene delivery. International Society on Thrombosis and Haemostasis, Inc. pp. 1-15. (2024).

Krivega, Ivan, et al. Non-Viral Gene Therapy for DMD Allowing Full-Length Dystrophin Delivery to Skeletal, Cardiac, and Diaphragm Muscles. MDA conference 2025. pp. 1-14. (2025).

Krivega, Ivan, et al. Non-Viral Genetic Medicine for Targeted Delivery of Full-Length Dystrophin to Skeletal, Cardiac, and Diaphragm Muscles in DMD Mouse Models and Non-Human Primates. American Society of Gene & Cell Therapy 2025 Annual Meeting. pp. 1. (2025).

Krivega, Margarita, et al. Development of a Next-Generation Non-Viral Human FVIII Therapeutic Administered through Targeted Transcutaneous Ultrasound Enables Normal Physiological Levels of FVIII Transgene Expression in a Redosable and Titratable Manner. Molecular Therapy. vol. 32. No. 4.: Cell Press. (2024).

Krivega, Margarita, et al. Development of a non-viral genetic medicine for ADPKD administered through targeted transcutaneous ultrasound mediated delivery. American Society of Nephrology. pp. 1. (2024).

Krivega, Margarita, et al. Development of a Non-viral Genetic Medicine for ADPKD Administered through Targeted Transcutaneous Ultrasound-Mediated Delivery: TH-PO431. Journal of the American Society of Nephrology 35.10S: 10-1681. (2024).

Krivega, Margot, et al. Development of a next-generation non-viral human FVIII therapeutic administered through targeted transcutaneous ultrasound enables normal physiological levels of FVIII transgene expression in a redosable and titratable manner. American Society of Gene & Cell Therapy. pp. 1. (2024).

Manson, M. et al. Transcutaneous ultrasound-mediated gene delivery into canine livers achieves therapeutic levels of factor VIII expression. blood advances: vol. 6, No. 12, 3557-3568 (2022).

Mehier-Humbert, Sophie, et al. Ultrasound-mediated gene delivery: kinetics of plasmid internalization and gene expression. Journal of Controlled Release 104.1: 203-211. (2005).

Miao, Carol H., et al. Enhanced Gene Expression of Factor VIII by Ultrasound-Mediated Gene Delivery in Dogs. Molecular Therapy 23: S107. (2015).

Miao, Carol H., et al. High-level factor Vill gene expression in vivo achieved by nonviral liver-specific gene therapy vectors. Human gene therapy 14.14: 1297-1305. (2003).

Miao, Carol H., et al. Ultrasound enhances gene delivery of human factor IX plasmid. Human gene therapy 16.7: 893-905. (2005).

Noble, Misty L., et al. Improved luciferase gene expression using ultrasound targeted microbubble destruction therapy in swine. AIP Conference Proceedings. vol. 1503. No. 1. American Institute of Physics. (2012).

Noble-Vranish, Misty L., et al. Ultrasound-mediated gene therapy in swine livers using single-element, multi-lensed, high-intensity ultrasound transducers. Molecular Therapy Methods & Clinical Development 10: 179-188. (2018).

Rao, Surabhi, et al. Targeted non-viral gene delivery through transcutaneous ultrasound enables rapid, robust, redosable, titratable, and durable gene expression in the liver in murine and NHP models. American Society of Gene & Cell Therapy 2024. pp. 1. (2024).

Rao, Surabhi et al. Targeted non-viral gene delivery through transcutaneous ultrasound enables rapid, robust, redosable, titratable, and durable gene expression in the liver in murine and NHP models. SonoThera Inc. pp. 1-2. (2024).

Rao, Surabhi, et al. Targeted Non-Viral Gene Delivery through Transcutaneous Ultrasound Enables Robust, Redosable, Titratable, and Durable FVIII and FIX Gene Expression in the Liver in Murine Models. Emerging Tools, Techniques, and Artificial Intelligence in Hematology. 2232, p. 1. (2024).

Schultz, Christopher W. et al. Selecting the optimal parameters for sonoporation of pancreatic cancer in a pre-clinical model. Cancer Biology & Therapy 22(3):204-215 (2021).

Shimamura, Munehisa, et al. Gene transfer into adult rat spinal cord using naked plasmid DNA and ultrasound microbubbles. The Journal of Gene Medicine: A cross-disciplinary journal for research on the science of gene transfer and its clinical applications 7.11: 1468-1474. (2005).

Song, Shuxian, et al. Ultrasound-mediated gene delivery of factor VIII plasmids for hemophilia A gene therapy in mice. Molecular Therapy-Nucleic Acids 27: 916-926. (2022).

Song, Zhaojun, et al. Noninvasive, targeted gene therapy for acute spinal cord injury using LIFU-mediated BDNF-loaded cationic nanobubble destruction. Biochemical and biophysical research communications 496.3: 911-920. (2018).

Zhang, G., et al. Hydroporation as the mechanism of hydrodynamic delivery. Gene therapy 11.8: 675-682. (2004).

Orlova, N.A. et al. Blood Clotting Factor VIII: From Evolution to Therapy. Acta naturae 5(2):19-39 (2013).

PCT/US2025/024558 International Search Report and Written Opinion dated Jul. 14, 2025.

Prasad, Tekkatte Krishnamurthy, and Nalam Madhusudhana Rao. The role of plasmid constructs containing the SV40 DNA nuclear-targeting sequence in cationic lipid-mediated DNA delivery. Cell Molecular Biology Letters 10(2):203-215 (2005).

Van Gaal, Ethlinn V. B. et al. DNA nuclear targeting sequences for non-viral gene delivery. Pharmaceutical research 28(7):1707-1722 (2011).

BIOLOGIC AGENTS AND METHODS OF USE

CROSS-REFERENCE TO RELATED APPLICATIONS

This application is a continuation of International Application No. PCT/US2025/024558, filed Apr. 14, 2025, which claims the benefit of U.S. Provisional Patent Application No. 63/634,905, filed Apr. 16, 2024, and U.S. Provisional Patent Application No. 63/709,966, filed Oct. 21, 2024, each of which is incorporated herein by reference in its entirety and for all purposes.

INCORPORATION BY REFERENCE OF SEQUENCE LISTING

The present application is being filed along with a Sequence Listing in electronic format. The Sequence Listing is provided as a file 62668-732301_Sequence_Listing.XML, created Oct. 8, 2025, which is 147,357 bytes in size. The information in the electronic format of the Sequence Listing is incorporated by reference in its entirety.

BACKGROUND

Gene therapy, in which a functional copy of a gene is transfected or otherwise delivered into a cell, has been proposed as a possible method of treating genetic diseases, however many existing gene therapies suffer from significant shortcomings when used to treat subjects due to failure to achieve or maintain therapeutic levels of transgene expression, which often leaves subjects without an effective treatment due to inability to re-dose many such gene therapies. Vectors for transgene delivery which improve gene transfection, expression, or durability could significantly improve gene therapies and patient outcomes. Similarly, transgenes which provide for improved gene expression or durability, or which otherwise provide for an improved therapeutic effect in a gene therapy treatment, could significantly improve gene therapies and patient outcomes.

SUMMARY

Vectors for transgene delivery can be improved by the incorporation of regulatory elements which improve gene delivery and transfection. However, the identification of genetic regulatory elements which tend to have a positive therapeutic effect in improving transgene expression remains a challenge. Disclosed herein are nucleic acid compositions comprising genetic regulatory elements operably linked to therapeutic nucleic acid sequences which improve gene transfection and expression. In some cases, the genetic regulatory elements may include novel nuclear targeting sequences which increase nuclear localization of the nucleic acid composition and resulting gene expression. In some cases, the genetic regulatory elements may also include novel combinations of nuclear targeting sequences, promoters, post-transcriptional elements, nuclear targeting sequences, and other genetic regulatory elements, which increase gene transfection and expression.

In addition to improved vectors, transgenes themselves can be modified to improve their transfection and expression in a subject, and can otherwise be modified to provide an improved therapeutic effect to a subject. However, the identification of transgene elements which tend to have a positive therapeutic effect in improving transgene expression or function remains a challenge, especially in cases of very large transgenes where modifications at any point may disrupt gene expression or degrade transgene performance. Aspects disclosed herein provide a Factor VIII polypeptide comprising: an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. Aspects disclosed herein provide a Factor VIII polypeptide comprising an amino acid sequence having up to 3 amino acid substitutions relative to SEQ ID NO: 24. In some embodiments, the FVIII polypeptide disclosed herein may improve over prior FVIII transgenes by providing for increased gene expression, secretion, and coagulation activity of the FVIII polypeptide, among other benefits described herein.

Aspects disclosed herein provide a nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein: the A1 domain comprises substitution of phenylalanine at position 328 to serine when the Factor VIII polypeptide is aligned with SEQ ID NO: 35; and the A3 domain comprises substitution of cysteine at position 1249 to glycine when the Factor VIII polypeptide is aligned with SEQ ID NO: 35 and substitution of cysteine at position 1253 to glycine when the Factor VIII polypeptide is aligned with SEQ ID NO: 35. In some embodiments, the therapeutic nucleic acid sequence encodes a Factor VIII (FVIII) polypeptide comprising an amino acid sequence having up to 2 amino acid substitutions relative to SEQ ID NO: 24. In some embodiments, the B domain comprises no more than 6 consensus sites for N-linked glycosylation. In some embodiments, the B domain comprises an amino acid sequence of SEQ ID NO: 28, and wherein the FVIII polypeptide is not more than 2300 amino acids in length. In some embodiments, the B domain comprises an amino acid sequence of SEQ ID NO: 34. In some embodiments, the A1 domain comprises an amino sequence of SEQ ID NO: 25. In some embodiments, the A3 domain comprises an amino sequence of SEQ ID NO: 29. In some embodiments, the Factor VIII polypeptide comprises an amino acid sequence of SEQ ID NO: 24. In some embodiments, the nucleic acid composition further includes a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence. In some embodiments, the nucleic acid composition further includes a nucleic acid sequence having at least 96% sequence identity to SEQ ID NO: 45. In some embodiments, the nucleic acid composition further includes a nucleic acid sequence having at least 80% sequence identity to SEQ ID NO: 6. In some embodiments, the nucleic acid sequence having at least 80% sequence identity to SEQ ID NO: 6 increases expression of the therapeutic nucleic acid sequence in a cell by at least 1.25-fold as compared to an otherwise identical control composition lacking the nucleic acid sequence having at least 80% sequence identity to SEQ ID NO: 6. In some embodiments, the first regulatory element comprises a sequence of SEQ ID NO: 9. In some embodiments, the second regulatory element comprises a sequence of SEQ ID NO: 45. In some embodiments, the nucleic acid composition comprises a sequence of SEQ ID NO: 39. Aspects disclosed herein provide a nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 34; and wherein: the A1 domain comprises an amino sequence of SEQ ID NO: 25; and the A3 domain comprises an amino sequence of SEQ ID NO: 29, the nucleic acid composition further comprising: a first regulatory element comprising a sequence of SEQ ID NO: 9; a second regulatory element comprising a second regulatory element comprising a sequence of SEQ ID NO: 45; and a nucleic acid sequence of SEQ ID NO: 6. In some embodiments, the nucleic acid composition comprises a sequence of SEQ ID NO: 39.

Aspects disclosed herein provide the nucleic acid composition disclosed herein for use a method of treating a bleeding disorder in a subject in need thereof, the method comprising administering the nucleic acid composition of any one of the preceding claims to the subject. Aspects disclosed herein provide a method of expressing a nucleic acid payload in a cell, the method comprising administering the nucleic acid composition of any one of the preceding claims to a subject. In some embodiments, the method further includes applying an ultrasonic acoustic energy to the cell. In some embodiments, the method further includes administering to the subject a sonoactive agent. In some embodiments, the nucleic acid composition is administered to the subject as a naked nucleic acid. In some embodiments, the nucleic acid composition encodes a full-length polypeptide, wherein the method induces expression of the full-length polypeptide in-vivo. In some embodiments, the method further includes administering to the subject the nucleic acid composition in at least two treatments at least 48 hours apart, thereby achieving a therapeutic level of the clotting factor in the subject. In some embodiments, the method further includes administering to the subject ultrasound acoustic energy in the treatments. In some embodiments, the method further includes administering to the subject a sonoactive agent in the treatments. In some embodiments, one or both of the nucleic acid composition or the sonoactive agent are administered to the subject intravenously through a peripheral vein. In some embodiments, administering the ultrasound acoustic energy comprises applying the ultrasound energy at a mechanical index (MI) of at least 0.8, 1.3, 1.8, 1.9, or 2.2. In some embodiments, administering the ultrasound acoustic energy further comprises applying the ultrasound energy at a mechanical index (MI) of up to 0.4. In some embodiments, the ultrasound energy is applied at an intensity (ISPTA) of at least 200 mW/cm2. In some embodiments, the ultrasound energy is applied at pulse length of at least 20, 200, or 600 microseconds. In some embodiments, the subject is administered at least three treatments. In some embodiments, the at least three treatments are administered at least 48 hours apart. In some embodiments, the subject is administered at least two cycles, each cycle comprising at least two treatments. In some embodiments, the subject is administered at least three cycles, each cycle comprising at least two treatments. In some embodiments, the subject is administered at least three cycles, each cycle comprising at least three treatments. In some embodiments, each cycle is administered to the subject at least 10 days apart. In some embodiments, each cycle is administered to the subject at least 30 days apart. In some embodiments, each cycle is administered to the subject at least 40 days apart. In some embodiments, the method further includes imaging an organ of the subject with ultrasound acoustic energy. In some embodiments, the imaging the organ of the subject comprises verifying presence of the sonoactive agent in the organ or the targeting of the ultrasound acoustic energy towards to organ. In some embodiments, a therapeutic level of the FVIII polypeptide is maintained for at least 10, 20, 30, 40, 50, 60, 70, 80, 90, 100, 110, 120, 130, 140, 145, or 150 days. In some embodiments, vascular flow is not occluded in the subject. In some embodiments, the subject has a bleeding disorder, wherein the therapeutic nucleic acid sequence encodes FVIII, and wherein the method thereby treats the subject having the bleeding disorder. In some embodiments, the bleeding disorder is hemophilia A.

Aspects disclosed herein provide a nucleic acid composition of any one of the preceding claims, for use a method of treating a bleeding disorder in a subject in need thereof, the method comprising administering the nucleic acid composition of any one of the preceding claims to the subject, administering a sonoactive agent to the subject. Aspects disclosed herein provide a cell comprising the nucleic acid composition of any one of the preceding claims. Aspects disclosed herein provide a nucleic acid composition for use a method of treating a bleeding disorder in a subject in need thereof, the nucleic acid composition comprising: a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 34; and wherein: the A1 domain comprises an amino sequence of SEQ ID NO: 25; and the A3 domain comprises an amino sequence of SEQ ID NO: 29, the nucleic acid composition further comprising: a first regulatory element comprising a sequence of SEQ ID NO: 9; a second regulatory element comprising a second regulatory element comprising a sequence of SEQ ID NO: 45; and a nucleic acid sequence of SEQ ID NO: 6 the method comprising: administering to the subject the nucleic acid composition, a sonoactive agent, and ultrasound acoustic energy in a treatment session; administering a cycle comprising at least three treatment sessions to the subject; administering at least three cycles to the subject each cycle at least 10 days apart, thereby achieving a therapeutic level of the FVIII polypeptide in the subject. In some embodiments, the sonoactive agent comprises lipid-stabilized microstructures. In some embodiments, the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble.

Aspects disclosed herein provide a method of manufacturing the nucleic acid composition disclosed herein. Aspects disclosed herein provide a kit comprising: a sonoactive agent; and means for expressing a Factor VIII polypeptide in vivo at a level that is at least 1.5 fold greater than expression of SEQ ID NO. 3. Aspects disclosed herein provide a kit comprising: a sonoactive agent; and the nucleic acid composition disclosed herein. In some embodiments, further included are instructions for administering ultrasound acoustic energy to a subject to facilitate expression of the FVIII polypeptide in vivo. In some embodiments, further included instructions for administering ultrasound acoustic energy to a subject to facilitate delivery of the nucleic acid composition to a subject. In some embodiments, the sonoactive agent comprises lipid-stabilized microstructures. In some embodiments, the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble.

Aspects disclosed herein provide a nucleic acid composition comprising a nucleic acid sequence having at least 80% sequence identity to SEQ ID NO: 6. Aspects disclosed herein provide a nucleic acid composition comprising a nucleic acid sequence having at least 96% sequence identity to SEQ ID NO: 45. Aspects disclosed herein provide a nucleic acid composition a therapeutic nucleic acid sequence, a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence. Aspects disclosed herein provide a cell comprising the nucleic acid compositions disclosed herein. Aspects disclosed herein provide method of manufacturing the nucleic acid compositions disclosed herein. In some embodiments, the nucleic acid composition includes a nucleic acid sequence having at least 80% sequence identity to SEQ ID NO: 6. In some embodiments, the nucleic acid composition a nuclear targeting sequence that increases expression of the therapeutic nucleic acid sequence in a cell by at least 1.25-fold, as compared to an otherwise identical control nucleic acid composition lacking the nuclear targeting sequence. In some embodiments, the nucleic acid composition includes the nuclear targeting sequence comprises a nucleic acid sequence having at least 80% sequence identity to SEQ ID NO: 6. In some embodiments, the nucleic acid composition includes a first regulatory element comprising an APOE-AAT promoter sequence operably linked to a hBGi sequence, and a second regulatory element comprising a WPRE3 sequence. In some embodiments, the nucleic acid composition includes a therapeutic nucleic acid sequence, wherein the nucleic acid sequence having at least 80% sequence identity to SEQ ID NO: 6 increases expression of the therapeutic nucleic acid sequence in a cell by at least 1.25 fold as compared to an otherwise identical control composition lacking the nucleic acid sequence having at least 80% sequence identity to SEQ ID NO: 6. In some embodiments, the nucleic acid composition includes a first regulatory element comprising an APOE-AAT promoter sequence operably linked to a hBGi sequence, and a second regulatory element comprising a WPRE3 sequence. In some embodiments, the first regulatory element is upstream of the therapeutic nucleic acid sequence. In some embodiments, the second regulatory element is downstream of the therapeutic nucleic acid sequence. In some embodiments, the second regulatory element is downstream of the therapeutic nucleic acid sequence. In some embodiments, each of the first regulatory element and the second regulatory element are operably linked to the therapeutic nucleic acid sequence.

In some embodiments, the first regulatory element is upstream of the therapeutic nucleic acid sequence, and the second regulatory element is downstream of the therapeutic nucleic acid sequence. In some embodiments, the nucleic acid sequence has at least 80% sequence identity to SEQ ID NO: 6 has at least 81, 82, 83, 84, 85, 86, 87, 88, 89, 90, 91, 92, 93, 94, 95, 96, 97, 98, or 99% sequence identity to SEQ ID NO: 6. In some embodiments, the nucleic acid sequence having at least 80% sequence identity to SEQ ID NO: 6 is operably coupled to a second regulatory element comprising a WPRE3 sequence. In some embodiments, the first regulatory element comprises a sequence of SEQ ID NO: 9. In some embodiments, the second regulatory element comprises a sequence of SEQ ID NO: 4. In some embodiments, the nuclear targeting sequence increases expression of the therapeutic nucleic acid sequence in the cell by at least 1.25, 1.5, 2, 3, 4, 5, 6, 7, or 8 fold, as compared to an otherwise identical control composition that lacks the nuclear targeting sequence. In some embodiments, the cell is a liver cell, a kidney cell, a brain cell, a muscle cell, a cardiac cell, a pancreatic cell, a blood cell, or a tumor cell. In some embodiments, the cell is a hepatocyte. In some embodiments, the therapeutic nucleic acid sequence comprises a sequence encoding a therapeutic transgene. In some embodiments, the therapeutic transgene is a FVIII, FIX, COL4A3, COL4A4, COL4A5, PKD1, or a PKD2. In some embodiments, the therapeutic nucleic acid sequence encodes a CRISPR/Cas system, a Cas protein or homolog or variant thereof, a TALEN, a ZFN, or a template DNA molecule suitable for knock-in via homologous end joining (NHEJ) or homology directed repair (HDR). In some embodiments, the nucleic acid composition comprises a miniplasmid backbone. In some embodiments, the miniplasmid backbone is smaller than 1 kb. In some embodiments, the miniplasmid backbone comprises a sequence of SEQ ID NO: 7. In some embodiments, the therapeutic nucleic acid sequence is a therapeutic agent. In some embodiments, the therapeutic nucleic acid sequence encodes a therapeutic agent. In some embodiments, the therapeutic nucleic acid sequence encodes a protein which provides a therapeutic effect to a subject. In some embodiments, the nucleic acid composition is an isolated nucleic acid molecule. In some embodiments, the nucleic acid composition does not comprise an origin of replication, or a bacterial origin of replication. In some embodiments, the nucleic acid composition further comprises one or more Inverted Terminal Repeat (ITR) sequences. In some embodiments, a first ITR sequence is positioned upstream of the therapeutic nucleic acid sequence, promoter sequence, first regulatory element, and/or nuclear targeting sequence. In some embodiments, a second ITR sequence is positioned downstream of the therapeutic nucleic acid sequence, promoter sequence, first regulatory element, and/or nuclear targeting sequence. In some embodiments, the intron sequence comprises a hemoglobin subunit gamma intron (hBGi) sequence. In some embodiments, a nucleic acid composition further comprises a poly-adenylation signal. In some embodiments, the poly-adenylation signal is positioned downstream of the second regulatory element. In some embodiments, the nucleic acid composition comprises the nucleic acid composition comprises a sequence of SEQ ID NO: 45. In some embodiments, the poly-adenylation signal is positioned downstream of the therapeutic nucleic acid sequence. In some embodiments, the poly-adenylation signal is positioned upstream of the nuclear targeting sequence. In some embodiments, the promoter sequence comprises an Apolipoprotein E-Alpha-1-Antitrypsin (APOE-AAT) promoter sequence. In some embodiments, the first regulatory element is positioned upstream and directly coupled to the therapeutic nucleic acid sequence, the second regulatory element is positioned downstream and directly coupled to the therapeutic nucleic acid sequence, the poly-adenylation signal is positioned downstream and directly coupled to the second regulatory element, and wherein the nuclear targeting sequence is positioned downstream and directly coupled to the poly-adenylation signal. In some embodiments, a nucleic acid composition, such as one disclosed herein comprises a therapeutic nucleic acid sequence comprising a nucleic acid sequence of SEQ ID NO: 32. In some embodiments, the nucleic acid composition is a non-viral vector. In some embodiments, the nucleic acid composition is at least 5000, 5500, 6000, 6500, or 7000 bp in length, and wherein the non-viral vector encodes a full-length gene. In some embodiments, the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. Aspects disclosed herein provide a nucleic acid composition, wherein the therapeutic nucleic acid sequence encodes a FVIII polypeptide comprising an amino acid sequence having up to 3 amino acid substitutions relative to SEQ ID NO: 24. In some embodiments, the B domain comprises up to 6 consensus sites for N-linked glycosylation. In some embodiments, the B domain comprises an amino acid sequence of SEQ ID NO: 28. In some embodiments, the B domain comprises an amino acid sequence of SEQ ID NO: 34. In some embodiments, the A1 domain comprises substitution of phenylalanine at position 328 to serine when the Factor VIII polypeptide is aligned with SEQ ID NO: 35. In some embodiments, the A1 domain comprises an amino sequence of SEQ ID NO: 25. In some embodiments, the A3 domain comprises substitution of cysteine at position 1249 to glycine when the Factor VIII polypeptide is aligned with SEQ ID NO: 35. In some embodiments, the A3 domain comprises substitution of cysteine at position 1253 to glycine when the Factor VIII polypeptide is aligned with SEQ ID NO: 35. In some embodiments, the A3 domain comprises an amino sequence of SEQ ID NO: 28. In some embodiments, the therapeutic nucleic acid sequence encodes the amino acid sequence of SEQ ID NO: 24.

Aspects disclosed herein provide a method of expressing a nucleic acid payload in a cell, the method comprising administering the nucleic acid composition disclosed herein to a subject. In some embodiments, the method includes applying ultrasonic acoustic energy to the cell. In some embodiments, the method includes administering to the subject a plurality of sonoactive microstructures. In some embodiments, the method includes contacting the cell with a lipid nanoparticle composition. In some embodiments, the nucleic acid composition is administered to the subject in a viral vector. In some embodiments, the method includes to the subject a plurality of magnetic particles and applying a magnetic field to the cell. In some embodiments, the magnetic particles comprise paramagnetic nanoparticles. In some embodiments, the method includes applying an electrical field to the cell. In some embodiments, the nucleic acid composition is administered to the subject using hydrodynamic injection. In some embodiments, the nucleic acid composition is administered to the subject as a naked nucleic acid. In some embodiments, the nucleic acid composition is administered to the subject as an encapsulated nucleic acid. In some embodiments, the nucleic acid composition is encapsulated in a lipid or a polymer. In some embodiments, the nucleic acid composition encodes a full-length polypeptide, wherein the method induces expression of the full-length polypeptide in-vivo. In some embodiments, the subject has a bleeding disorder, wherein the therapeutic nucleic acid sequence of the polypeptide encodes FVIII or FIX, and wherein the method thereby treats the subject having the bleeding disorder. In some embodiments, the bleeding disorder is hemophilia A.

Aspects disclosed herein provide a Factor VIII polypeptide comprising: an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. A Factor VIII polypeptide comprising an amino acid sequence having up to 3 amino acid substitutions relative to SEQ ID NO: 24. In some embodiments, the FVIII polypeptide has an amino acid sequence having up to 3 amino acid substitutions relative to SEQ ID NO: 24. In some embodiments, the FVIII polypeptide has an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 35; and the A3 domain comprises at least two amino acid substitutions as compared to SEQ ID NO: 36. In some embodiments, the B domain comprises up to 6 consensus sites for N-linked glycosylation. In some embodiments, the B domain comprises an amino acid sequence of SEQ ID NO: 28. In some embodiments, the B domain comprises an amino acid sequence of SEQ ID NO: 34. In some embodiments, the A1 domain comprises substitution of phenylalanine at position 328 to seine when the FVIII polypeptide is aligned with SEQ ID NO: 35. In some embodiments, the A1 domain comprises an amino sequence of SEQ ID NO: 25. In some embodiments, the A3 domain comprises substitution of cysteine at position 1249 to glycine when FVIII polypeptide is aligned with SEQ ID NO: 35. In some embodiments, the A3 domain comprises substitution of cysteine at position 1253 to glycine when FVIII polypeptide is aligned with SEQ ID NO: 35. In some embodiments, the A3 domain comprises an amino sequence of SEQ ID NO: 28. In some embodiments, a FVIII polypeptide disclosed herein comprises the amino acid sequence of SEQ ID NO: 24. Aspects disclosed herein provide a kit comprising: a sonoactive agent; and means for expressing a Factor VIII polypeptide in vivo at a level that is at least 1.5 fold greater than expression of SEQ ID NO: 3. Aspects disclosed herein provide a kit comprising: a sonoactive agent; and the nucleic acid composition of any embodiment described herein. Aspects disclosed herein provide a cell comprising the FVIII polypeptide disclosed herein. Aspects disclosed herein provide a nucleic acid encoding the FVIII polypeptide.

Aspects disclosed herein provide a method of treating a bleeding disorder comprising administering to a subject a nucleic acid encoding a human clotting factor in at least two treatments at least 48 hours apart, thereby achieving a therapeutic level of the clotting factor in the subject. In some embodiments, the therapeutic level of the clotting factor is maintained for at least 10, 20, 30, 40, 50, 60, 70, 80, 90, 100, 110, 120, 130, 140, 145, or 150 days. In some embodiments, the method includes administering to the subject ultrasound acoustic energy in the treatments. In some embodiments, the method includes administering to the subject a sonoactive agent in the treatments. In some embodiments, administering the ultrasound acoustic energy comprises applying the ultrasound energy at a mechanical index (MI) of at least 0.8, 1.3, 1.8, 1.9, or 2.2. In some embodiments, administering the ultrasound acoustic energy comprises applying the ultrasound energy at a mechanical index (MI) of up to 0.4. In some embodiments, administering the ultrasound energy comprises applying an acoustic radiation force to the subject. In some embodiments, the ultrasound energy is applied at an intensity (ISPTA) of at least 200 mW/cm2. In some embodiments, the ultrasound energy is applied at pulse length of at least 20 microseconds. In some embodiments, the subject is administered at least three treatments. In some embodiments, the sonoactive agent comprises protein-stabilized microstructures. In some embodiments, the sonoactive agent comprises a shell filled with a perfluorinated gas. In some embodiments, the sonoactive agent comprises lipid-stabilized microstructures. In some embodiments, the at least three treatments are administered at least 48 hours apart. In some embodiments, the subject is administered at least two cycles, each cycle comprising at least two treatments. In some embodiments, the subject is administered at least three cycles, each cycle comprising at least two treatments. In some embodiments, the subject is administered at least three cycles, each cycle comprising at least three treatments. In some embodiments, each cycle is administered to the subject at least 10 days apart. In some embodiments, each cycle is administered to the subject at least 30 days apart. In some embodiments, each cycle is administered to the subject at least 40 days apart.

BRIEF DESCRIPTION OF THE DRAWINGS

Various features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
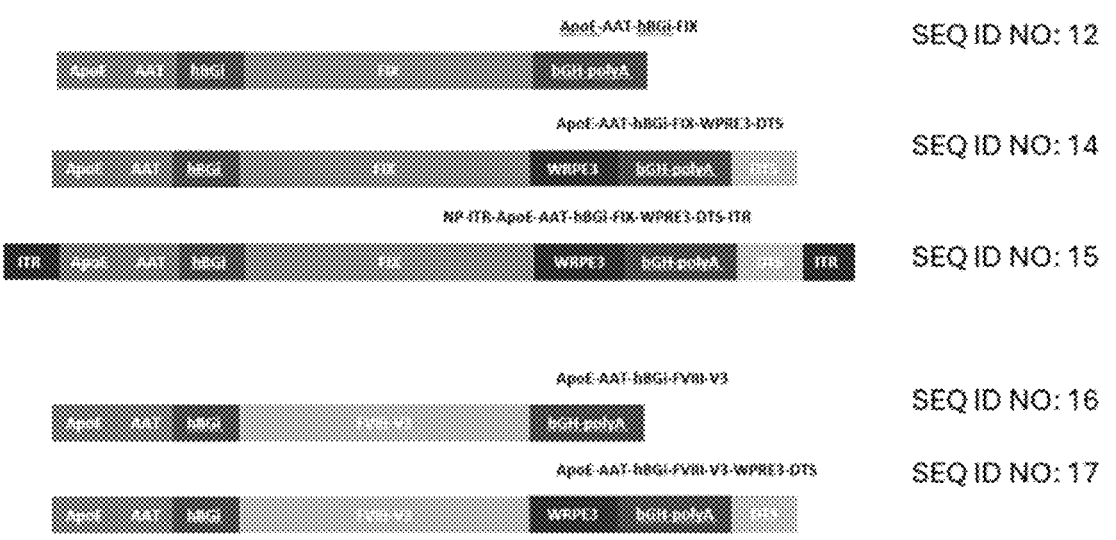
FIG. 1A illustrates vector elements of nucleic acid compositions comprising therapeutic nucleic acid vectors comprising genetic regulatory elements which increase expression of the therapeutic nucleic acid.

Vectors for transgene delivery can be improved by the incorporation of regulatory elements which improve nucleic acid delivery and transfection. However, the identification of genetic regulatory elements which tend to have a positive therapeutic effect in improving transgene expression remains a challenge within the art. Disclosed herein are nucleic acid compositions comprising genetic regulatory elements operably linked to therapeutic nucleic acid sequences which improve nucleic acid delivery and gene expression. In some cases, the genetic regulatory elements may include novel nuclear targeting sequences which increase nuclear localization of the nucleic acid composition and resulting gene expression, and novel combinations of promoters, post-transcriptional elements, nuclear targeting sequences, and other genetic regulatory elements which increase nucleic acid transfection and expression.

In addition to improved vectors, transgenes themselves can be modified to improve their transfection and expression in a subject, and can otherwise be modified to provide an improved therapeutic effect to a subject. However, the identification of transgene elements which tend to have a positive therapeutic effect in improving transgene expression or function remains a challenge, especially in cases of very large transgenes where modifications at any point may disrupt gene expression or degrade transgene performance. Aspects disclosed herein provide a Factor VIII polypeptide comprising: an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. Aspects disclosed herein provide a Factor VIII polypeptide comprising an amino acid sequence having up to 3 amino acid substitutions relative to SEQ ID NO: 24. Aspects disclosed herein provide a nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 34; and wherein: the A1 domain comprises an amino sequence of SEQ ID NO: 25; and the A3 domain comprises an amino sequence of SEQ ID NO: 29, the nucleic acid composition further comprising: a first regulatory element comprising a sequence of SEQ ID NO: 9; a second regulatory element comprising a second regulatory element comprising a sequence of SEQ ID NO: 45; and a nucleic acid sequence of SEQ ID NO: 6. In some embodiments, the nucleic acid composition comprises a sequence of SEQ ID NO: 39. In some embodiments, the FVIII polypeptide disclosed herein may improve over prior FVIII transgenes by providing for increased gene expression, secretion, and coagulation activity of the FVIII polypeptide, among other benefits described herein.

The construction of nucleic acid delivery vectors for transgene delivery involves the incorporation of various genetic regulatory elements to ensure efficient and controlled gene expression. These elements play important roles in modulating the delivery, transfection, expression, and stability of the transgene. Genetic regulatory elements included in the nucleic acid compositions of the presently disclose may include promoters, enhancers, polyadenylation signals, terminator sequences, transcriptional regulatory elements, nuclear targeting sequences, and viral sequences. By carefully selecting and combining genetic regulatory elements, nucleic acid delivery vectors that increase transgene delivery, transfection, and expression to can be designed, as compared to nucleic acid delivery vectors which do not comprise one or more of the selected genetic regulatory elements.

The delivery vectors disclosed herein may comprise DNA nuclear targeting sequences (DTS) that enhance delivery of the nucleic acid composition and/or the therapeutic nucleic acid sequence to a cell. In some cases, the DTS sequences may comprise recognition sequences for endogenous DNA-binding proteins which lead to increased transfection efficiency of non-viral gene delivery by virtue of enhanced nuclear import of the nucleic acid composition, which can lead to enhanced transgene expression. In some cases, the DTS sequences are recognized by nuclear transport proteins, such as importins, bind the DTS sequences and form an import complex which shields the delivery vector from cytoplasmic nucleases during movement toward the nuclear envelope, and facilitate translocation of the delivery vector through the nuclear pore complex. In some cases, the enhanced nuclear import of the nucleic acid composition avoids degradation of the nucleic acid composition in the cytoplasm, brings nucleic acid composition closer in proximity to the transcriptional machinery, thereby promoting efficient transcription of the delivered transgene. In some cases, the DTS sequence minimizes the loss of transgene during cell division, and increases the likelihood of stable inheritance of the transgene by one or more daughter cells. Various DNA nuclear targeting sequences can be operably linked with nucleic acid sequences comprising the transgene of interest in the delivery vectors disclosed herein. In some cases, the nucleic acid composition may comprise a DNA nuclear targeting sequence having at least about 90%, at least about 95%, at least about 96%, at least about 97%, at least about 98%, at least about 99%, or more, sequence identity to SEQ ID NO: 6. In some cases, the nucleic acid composition comprises a DNA nuclear targeting sequence having 100% sequence identity to SEQ ID NO: 6. In some cases, the DNA nuclear targeting sequence may be downstream or 3' of the therapeutic nucleic acid sequence. The identification and selection of nuclear targeting sequences (DTS) that enhance delivery of a nucleic acid composition to a cell remains a challenge, as not all nuclear targeting sequences have been shown to be effective in enhancing delivery of a nucleic acid composition to a cell. See V. B. van Gaal et al., *DNA Nuclear Targeting Sequences for Non-Viral Gene Delivery*, 28 PHARM RES 1707-22 (2011); *Prasad and Rao, The Role of Plasmid Constructs Containing the Sv40 DNA Nuclear-Targeting Sequence in Cationic Lipid-Mediated DNA Delivery*, 10 CELLULAR & MOLECULAR BIOLOGY LETTERS 203-15 (2005).

Aspects disclosed herein provide a nucleic acid composition comprising a therapeutic nucleic acid sequence operably linked to a nuclear targeting sequence that increases expression of the therapeutic nucleic acid in a cell by at least 1.25-fold as compared to an otherwise identical control composition that lacks the nuclear targeting sequence. In some embodiments, the nuclear targeting sequence increases expression of the therapeutic nucleic acid sequence in the cell by at least 1.25, 1.5, 2, 3, 4, 5, 6, 7, or 8-fold, as compared to an otherwise identical control composition that lacks the nuclear targeting sequence. Aspects disclosed herein provide a nucleic acid composition comprising a nucleic acid sequence having at least 80% sequence identity to SEQ ID NO: 6. Aspects disclosed herein provide a nucleic acid composition comprising a nucleic acid sequence having at least 96% sequence identity to SEQ ID NO: 6.

Various promoters can be operably linked with a nucleic acid comprising the transgene of interest in the delivery vectors disclosed herein. In some embodiments, the promoter can drive the expression of the protein of interest in a cell. The promoter can be naturally occurring or non-naturally occurring. In some embodiments the promoter is a synthetic promoter. In one embodiment the synthetic promoter comprises sequences that do not exist in nature and which are designed to regulate the activity of an operably linked gene. In another embodiment the synthetic promoter comprises fragments of natural promoters to form new stretches of DNA sequence that do not exist in nature. Synthetic promoters are typically comprised of regulatory elements, promoters, enhancers, introns, splice donors and acceptors that are designed to produce enhanced tissue specific expression. Examples of promoters include, but are not limited to, viral promoters, plant promoters and mammalian promoters. Examples of promoters contemplated herein include, but are not limited to, e.g., CMV promoter, UbC promoter, CAG promoter, EF-1a promoter, ApoE promoter, ApoE-AAT1 promoter, F8 promoter, 3XSERP promoter, or P3-hybrid promoter. In some embodiments, the nucleic acid construct comprises a promoter sequence comprising CAG. In some embodiments, the nucleic acid construct comprises a promoter sequence comprising ApoE. In some embodiments, the nucleic acid construct comprises a promoter sequence comprising ApoE-AAT. In some embodiments, the nucleic acid construct comprises a promoter sequence comprising SERP. In some embodiments, the nucleic acid construct comprises a promoter sequence comprising P3. In another embodiment the promoter is a liver specific promoter. Examples of liver specific promoters include LP1, HLP, HCR-AAT, ApoE-AAT, LSP, TBG and TTR.

In some embodiments, the promoter comprises the human alpha anti-trypsin (AAT) promoter complex. In some embodiments, the promoter comprises at least a portion of the AAT promoter. In some embodiments, the promoter comprises a liver-specific apolipoprotein E (ApoE) enhancer. In some embodiments, the promoter comprises at least a portion of the ApoE enhancer. In some embodiments, the promoter comprises a liver specific ApoE enhancer coupled to an AAT promoter. The portion of the ApoE-AAT promoter can comprise a nucleic acid sequence having at least about 90%, at least about 95%, at least about 96%, at least about 97%, at least about 98%, at least about 99%, or more (e.g., 100%), sequence identity to SEQ ID NO: 1. In some cases, ApoE-AAT promoter sequence may be 5' (or upstream) of the therapeutic nucleic acid sequence. In some embodiments, the nucleic acid composition includes a first regulatory element comprising an APOE-AAT promoter sequence operably linked to a hBGi sequence. In some embodiments, the promoter comprises an F8 promoter sequence. In some embodiments, the intron sequence comprises a hemoglobin subunit gamma intron (hBGi) sequence.

In some embodiments, the nucleic acid delivery vectors disclosed herein comprise one or more polyadenylation signals. Polyadenylation signals can be utilized in nucleic acid delivery vectors to enhance mRNA stability and ensure proper termination of transcription. For example, the poly-adenylation signal (PolyA) can mark an end of the mRNA coding sequence and signals the RNA polymerase to stop synthesizing the RNA transcript, allowing for production of a functional mRNA molecule encoding the transgene of interest, thereby enhancing transgene expression. In some cases, a poly(A) tail can contribute to mRNA stability, protecting it from enzymatic degradation, and prolonging mRNA half-life within the cell. In some cases, a poly(A) signal can increase nuclear export of mRNA, for example, by forming a polyadenylation binding protein complex (PAC) with poly(A)-binding proteins (PABPs), linkage to nuclear RNA export factor 1 (NXF1) and cofactor p15, interacting with NXF1 (aka Tap, mRNA export factor) marking the transcribed mRNA for export through the nuclear pore complex, thereby increasing cytoplasmic concentration of mRNA encoding the transgene. In some cases, the poly(A) signal is a bovine growth hormone polyade-nylation signal (BGH polyA) and has robust polyade-nylation activity leading to consistent addition of a poly(A) tail to the 3' end of the mRNA transcript, promoting mRNA stability and efficient translation as described herein. In some cases, the BGH polyA regulatory element is active in providing polyadenylation activity across different cell types and species, making it suitable for use in a variety of expression systems, facilitating consistent and reliable transgene expression in different cellular environments. In some cases, the BGH polyA regulatory element provides increased polyadenylation activity across a wider variety of surrounding nucleic acid sequences coupled to the BGH polyA regulatory element, permitting for its incorporation into a wider variety of delivery vectors with greater variations in upstream and downstream sequences. In some cases, BGH polyA regulatory element may be 3' or downstream of the therapeutic nucleic acid sequence. In some embodiments, the nucleic acid composition further comprises a poly-adenylation signal. In some embodiments, the poly-adenylation signal is positioned downstream of the second regulatory element. In some embodiments, the poly-ad-enylation signal is positioned downstream of the therapeutic nucleic acid sequence. In some embodiments, the poly-adenylation signal is positioned upstream of the nuclear targeting sequence.

In some embodiments, the nucleic acid delivery vectors disclosed herein comprise one or more intron sequences. In some cases, inclusion of an intron element may enhance expression compared with expression in the absence of the intron element. For example, introns may facilitate processing of the RNA transcript in mammalian host cells, promote the recruitment of RNA polymerase II and other transcription factors, leading to increased transcription of the transgene, and increased expression of the protein of interest. In some cases, the inclusion of introns may contribute to the stability of mRNA transcripts, protect the mRNA from degradation and enhance its half-life within the cell, leading to prolonged and more sustained transgene expression. In some cases, the inclusion of introns can increase export of transcribed mRNA to the cytoplasm and increase transgene expression.

Non-limiting examples of such an intron are promoters of the fetal globin genes introns (hBGi), β-globin intron, A1AT intron and/or hPAH intron. In some embodiments, the intron is a synthetic intron. In some cases, the intron is a fetal globin gene intron (hBGi). In some cases, the fetal globin genes intron (hBGi) can protect the mRNA from degradation and enhance its half-life within the cell, leading to prolonged and more sustained transgene expression, increase export of transcribed mRNA to the cytoplasm, and increase transgene expression, among other benefits. In some cases, the intron can include a nucleotide sequence having at least about 90%, at least about 95%, at least about 96%, at least about 97%, at least about 98%, at least about 99%, or more (e.g., 100%), sequence identity to SEQ ID NO: 2. The location and size of the intron in the vector can vary. In some embodiments, the intron is located between the promoter and the sequence encoding the therapeutic nucleic acid sequence. In some embodiments, the intron is located 5' of the therapeutic nucleic acid sequence and 3' of the promoter sequence. In some embodiments, the nucleic acid composition includes a first regulatory element comprising an APOE-AAT promoter sequence operably linked to a hBGi sequence.

In some embodiments, the nucleic acid delivery vectors disclosed herein comprise a Woodchuck Hepatitis Virus Posttranscriptional Regulatory Element 3 (WPRE3). In some cases, the WPRE3 element improves ribosomal recruitment to a transcribed mRNA, enhances translation initiation of a transcribed mRNA, and promotes the expression of the therapeutic nucleic acid sequence. In some cases, the WPRE3 element contains sequences which interacts with cellular translation initiation factors, such as eIF4E (eukaryotic translation initiation factor 4E) and eIF4G (eukaryotic translation initiation factor 4G) and enhances the assembly of the translation initiation complex, facilitating the recruitment of ribosomes to the mRNA. In some cases, the WPRE3 element promotes efficient scanning of ribosomes along the mRNA, increasing initiation of translation at the correct site, and promoting the expression of the therapeutic nucleic acid sequence in the cell. In some cases, the translated WPRE3 element contains sequences that are recognized by ribosomal RNA or elements that stabilize the interaction between ribosomal subunits and the mRNA. In some cases, the translated WPRE3 element can reduce secondary mRNA structures such as hairpins and stem-loops, which can hinder ribosomal recruitment and reduce the efficiency of translation. In some cases, the translated WPRE3 element interacts with ribosomal proteins, promoting their binding to the mRNA, and increasing the stability of association between ribosomes and the mRNA. In some cases, the WPRE3 element can include a nucleotide sequence having at least about 90%, at least about 95%, at least about 96%, at least about 97%, at least about 98%, at least about 99%, or more (e.g., 100%), sequence identity to SEQ ID NO: 4. In some embodiments, the WPRE3 element is located 3' of the therapeutic nucleic acid sequence. In some embodiments, the nucleic acid composition includes a second regulatory element comprising a WPRE3 sequence.

In some embodiments, the nucleic acid delivery vectors disclosed herein comprise one or more viral sequences. In some cases, the one or more viral sequences may be adeno-associated viruses (AAVs), Inverted Terminal Repeat (ITR) sequences. In some cases, the inclusion of one or more viral sequences may provide for episomal persistence by facilitating circularization of the vector genome within the nucleus of the cell, and can contribute to durable transgene expression without genomic integration. In some cases, the inclusion of one or more viral sequences may facilitate the production of additional vector copies within the host cell and increase expression of the transgene within the cell. In some cases, the inclusion of one or more viral sequences may enhance the delivery, transfection, or expression of a therapeutic nucleic acid sequence by increasing stability and preventing degradation of the nucleic acid delivery vector in vivo, and increasing the delivery, transfection, and/or expression of the therapeutic nucleic acid sequence in the cell. In some cases, the inclusion of one or more viral sequences may enhance delivery of the therapeutic nucleic acid to a host cell in the liver. The inclusion of one or more viral sequences, such as ITR sequences, in the nucleic acid delivery vectors of the present disclosure can enhance the efficacy, safety, and stability of the nucleic acid delivery vectors disclosed herein. In some embodiments, the delivery vector comprises a plurality of ITR sequences located 5' of the therapeutic nucleic acid sequence and 3' of the promoter sequence. In some embodiments, the delivery vector comprises a plurality of ITR sequences located at the beginning of the nucleic acid delivery vector, and the end of the nucleic acid delivery vector.

In some embodiments, the nucleic acid composition further comprises one or more Inverted Terminal Repeat (ITR) sequences. In some embodiments, a first ITR sequence is positioned upstream of the therapeutic nucleic acid sequence, promoter sequence, first regulatory element, and/ or nuclear targeting sequence. In some embodiments, a second ITR sequence is positioned downstream of the therapeutic nucleic acid sequence, promoter sequence, first regulatory element, and/or nuclear targeting sequence.

The delivery vectors may comprise one or more transgenes. The transgenes may be selected for inducing expression of a therapeutic nucleic acid or therapeutic protein in a cell. Inducing expression of a therapeutic nucleic acid or therapeutic protein may treat one or more genetic diseases in a subject. The transgene is a nucleic acid sequence, heterologous to the vector sequences flanking the transgene, which encodes a polypeptide, protein, or other product of interest. The transgene nucleic acid coding sequence may be operatively linked to regulatory components in a manner which facilitates or enhances transgene delivery, transfection, transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding, green fluorescent protein (GFP), luciferase, β-lactamase, β-galactosidase (LacZ), alkaline phosphatase, thymidine kinase, membrane bound proteins including, for example, CD2, CD4, CD8, fusion proteins comprising a membrane bound protein appropriately fused to an antigen tag domain from, among others, hemagglutinin or Myc. The reporter sequences when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. Where the transgene is green fluorescent protein or luciferase, the vector carrying the signal may be measured visually by color or light production in a luminometer. Where the transgene is green fluorescent protein or luciferase, expression of the transgene may be measured visually by color or light production in a luminometer. Therapeutic delivery vectors may comprise transgenes encoding a therapeutic nucleic acid or therapeutic protein used to correct or ameliorate gene deficiencies, which may include deficiencies in which normal genes are expressed at less than normal levels or deficiencies in which the functional gene product is not expressed. For example, a therapeutic protein or polypeptide which is expressed in a host cell, and, in some cases, secreted from host cell. Suitable transgenes may be readily selected, and selection of the transgene is not considered to be a limitation of the present disclosure. In some embodiments, the transgene is a heterologous protein, and this heterologous protein is a therapeutic protein. Exemplary therapeutic proteins include, but are not limited to, FVIII and FIX. In some embodiments, the therapeutic transgene is a FVIII, FIX, COL4A3, COL4A4, COL4A5, PKD1, or a PKD2. In some embodiments, the therapeutic nucleic acid sequence includes a sequence encoding a therapeutic transgene.

In some embodiments, the therapeutic nucleic acid sequence is a therapeutic cargo other than a transgene. In some embodiments, the therapeutic nucleic acid sequence encodes a CRISPR/Cas system, a Cas protein or homolog or variant thereof, a TALEN, a ZFN, or a template DNA molecule suitable for knock-in via homologous end joining (NHEJ) or homology directed repair (HDR).

The construction of nucleic acid delivery vectors for transgene delivery involves the incorporation of various genetic regulatory elements to ensure efficient and controlled gene expression. These elements play important roles in modulating the delivery, transfection, expression, and stability of the transgene. Genetic regulatory elements included in the nucleic acid compositions of the presently disclosure may include promoters, enhancers, polyadenylation signals, terminator sequences, transcriptional regulatory elements, nuclear targeting sequences, and viral sequences. By carefully selecting and combining genetic regulatory elements, nucleic acid delivery vectors that increase transgene delivery, transfection, and expression to can be designed, as compared to nucleic acid delivery vectors which do not comprise the selected genetic regulatory elements. Further, in addition to the identification of novel sequences of genetic regulatory elements, and the selection of genetic regulatory elements, the combination and arrangement of genetic regulatory elements in a delivery vector can also provide a beneficial technical effect in increasing transgene delivery, transfection, and expression in a host cell.

In some cases, the nucleic acid delivery vectors of the present disclosure may comprise one or more genetic regulatory elements including promoters, enhancers, polyadenylation signals, terminator sequences, transcriptional regulatory elements, nuclear targeting sequences, and viral sequences. In some cases, the nucleic acid delivery vectors or the present disclosure may comprise a promoter sequence operatively linked to a transgene sequence. In some cases, the nucleic acid delivery vectors or the present disclosure may comprise a polyadenylation sequence operatively linked to a transgene sequence. In some cases, the nucleic acid delivery vectors of the present disclosure may comprise an intron sequence operatively linked to a transgene sequence. In some cases, the nucleic acid delivery of vectors of the present disclosure may comprise a post transcriptional regulatory element operatively linked to the transgene sequence. In some cases, the nucleic acid delivery vectors of the present disclosure may comprise a nuclear targeting sequence operatively linked to a transgene sequence. In some cases, the nucleic acid delivery vectors of the present disclosure may comprise one or more viral sequences operatively linked to a transgene sequence.

In some cases, the nucleic acid delivery vectors of the present disclosure may comprise a nuclear targeting sequence positioned downstream of the transgene sequence. In some cases, the nucleic acid delivery vectors of the present disclosure may comprise a nuclear targeting sequence positioned downstream of the transgene and other regulatory elements, for example, a post transcriptional regulatory element, a polyadenylation signal, and/or other regulatory element. In some cases, the nucleic acid delivery vectors may comprise promoter sequences positioned upstream of the transgene sequence. In some embodiments, the nucleic acid delivery vectors may comprise an intron sequence positioned in between a promoter sequence and a transgene sequence. In some cases, the nucleic acid delivery vectors may comprise a post transcriptional regulatory element positioned downstream of a transgene sequence. In some cases, the nucleic acid delivery vectors may comprise polyadenylation sequence positioned downstream of a transgene sequence. In some cases, the nucleic acid delivery vectors may comprise a nuclear targeting sequence positioned downstream of a transgene sequence. In some cases, the nucleic acid delivery vector may comprise one or more viral sequences positioned upstream or downstream of the transgene sequence. In some cases, the nucleic acid delivery vectors may comprise two or more viral sequences, positioned both upstream and downstream of the transgene sequence. In some cases, the nucleic acid delivery of vectors comprise a viral sequence positioned at the beginning and the end of the nucleic acid delivery vector. In some cases, the viral sequences comprise ITR sequences.

In some cases, the nucleic acid delivery vectors comprise a hBGi element positioned in between a promoter sequence and a transgene sequence. In some cases, the hBGi element is operatively linked to the transgene sequence and to the promoter sequence. In some cases, the nucleic acid delivery vectors comprise a WPRE3 element positioned downstream of the transgene. In some cases, the nucleic acid delivery vector comprises a bGH-polyA element position downstream of the WPRE3 element. In some cases, the WPRE3 element is positioned in between the transgene sequence and the bGH-polyA element. In some cases, the WPRE3 element is operably linked to the WPRE3 element and the bGH-polyA element. In some embodiments, a nucleic acid composition further comprises a nucleic acid sequence of SEQ ID NO: 45. Aspects disclosed herein provide a nucleic acid composition comprising a nucleic acid sequence having at least 96% sequence identity to SEQ ID NO: 45. In some cases, SEQ ID NO: 45 provides a beneficial technical effect of improving RNA stability, facilitating attachment to cellular translation initiation factors such as eIF4E (eukaryotic translation initiation factor 4E) and eIF4G (eukaryotic translation initiation factor 4G) and enhances the assembly of the translation initiation complex, facilitating the recruitment of ribosomes to the mRNA, enhancing translation initiation of a transcribed mRNA, and promotes the expression of the therapeutic nucleic acid sequence coupled thereto.

In some cases, the nuclear targeting sequence is positioned downstream of the bGH-polyA element. In some cases, the nuclear targeting sequence is operatively linked to the bGH-polyA element. In some cases, the viral sequences comprise ITR sequences. In some cases, a first ITR sequence is positioned downstream of the nuclear targeting sequence. In some cases, a second ITR sequence is positioned upstream of the promoter sequence. In some cases, the first ITR sequence is operatively linked to the bGH-polyA element, and the second ITR sequence is operatively linked to the nuclear targeting sequence. In some cases, the WPRE3 element and the bGH-polyA element provides a beneficial technical effect of improving RNA stability, facilitating attachment to cellular translation initiation factors such as eIF4E (eukaryotic translation initiation factor 4E) and eIF4G (eukaryotic translation initiation factor 4G) and enhances the assembly of the translation initiation complex, facilitating the recruitment of ribosomes to the mRNA, enhancing translation initiation of a transcribed mRNA, and promotes the expression of the therapeutic nucleic acid sequence coupled thereto.

Aspects disclosed herein provide a nucleic acid composition comprising a therapeutic nucleic acid sequence, a first regulatory element comprising an Apolipoprotein E-Alpha-1-Antitrypsin (APOE-AAT) promoter sequence operably linked to a hemoglobin subunit gamma intron (hBGi) sequence, and a second regulatory element comprising a woodchuck hepatitis posttranscriptional regulatory element (WPRE3) sequence. In some embodiments, the nucleic acid composition includes a nucleic acid sequence having at least 80% sequence identity to SEQ ID NO: 6. In some embodiments, the nucleic acid composition comprises a nuclear targeting sequence that increases expression of the therapeutic nucleic acid sequence in a cell by at least 1.25-fold, as compared to an otherwise identical control nucleic acid composition lacking the nuclear targeting sequence. In some embodiments, the nucleic acid composition includes the nuclear targeting sequence comprises a nucleic acid sequence having at least 80% sequence identity to SEQ ID NO: 6. In some embodiments, the nucleic acid sequence having at least 80% sequence identity to SEQ ID NO: 6 increases expression of the therapeutic nucleic acid sequence in a cell by at least 1.25 fold as compared to an otherwise identical control composition lacking the nucleic acid sequence having at least 80% sequence identity to SEQ ID NO: 6. In some embodiments, the nucleic acid composition includes a first regulatory element comprising an APOE-AAT promoter sequence operably linked to a hBGi sequence, and a second regulatory element comprising a WPRE3 sequence. In some embodiments, the first regulatory element is upstream of the therapeutic nucleic acid sequence. In some embodiments, the second regulatory element is downstream of the therapeutic nucleic acid sequence. In some embodiments, the second regulatory element is downstream of the therapeutic nucleic acid sequence. In some embodiments, each of the first regulatory element and the second regulatory element are operably linked to the therapeutic nucleic acid sequence. In some embodiments, the first regulatory element is upstream of the therapeutic nucleic acid sequence, and the second regulatory element is downstream of the therapeutic nucleic acid sequence. In some embodiments, the nucleic acid sequence has at least 80% sequence identity to SEQ ID NO: 6 has at least 81, 82, 83, 84, 85, 86, 87, 88, 89, 90, 91, 92, 93, 94, 95, 96, 97, 98, or 99% sequence identity (e.g., 100% sequence identity) to SEQ ID NO: 6. In some embodiments, the nucleic acid sequence having at least 80% sequence identity to SEQ ID NO: 6 is operably coupled to a second regulatory element comprising a WPRE3 sequence. In some embodiments, the first regulatory element comprises a sequence of SEQ ID NO: 9. In some embodiments, the second regulatory element comprises a sequence of SEQ ID NO: 4.

Aspects disclosed herein provide a nucleic acid composition a therapeutic nucleic acid sequence, a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence. In some embodiments, the intron sequence comprises a hemoglobin subunit gamma intron (hBGi) sequence. In some embodiments, the nucleic acid composition further comprises a poly-adenylation signal. In some embodiments, the poly-adenylation signal is positioned downstream of the second regulatory element. In some embodiments, the poly-adenylation signal is positioned downstream of the therapeutic nucleic acid sequence. In some embodiments, the poly-adenylation signal is positioned upstream of the nuclear targeting sequence. In some embodiments, the promoter sequence comprises an Apolipoprotein E-Alpha-1-Antitrypsin (APOE-AAT) promoter sequence. In some embodiments, the first regulatory element is positioned upstream and directly coupled to the therapeutic nucleic acid sequence, the second regulatory element is positioned downstream and directly coupled to the therapeutic nucleic acid sequence, the poly-adenylation signal is positioned downstream and directly coupled to the second regulatory element, and wherein the nuclear targeting sequence is positioned downstream and directly coupled to the poly-adenylation signal.

Aspects disclosed herein provide a nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein: the A1 domain comprises substitution of phenylalanine at position 328 to serine when the Factor VIII polypeptide is aligned with SEQ ID NO: 35; and the A3 domain comprises substitution of cysteine at position 1249 to glycine when the Factor VIII polypeptide is aligned with SEQ ID NO: 35 and substitution of cysteine at position 1253 to glycine when the Factor VIII polypeptide is aligned with SEQ ID NO: 35. In some embodiments, the therapeutic nucleic acid sequence encodes a Factor VIII (FVIII) polypeptide comprising an amino acid sequence having up to 2 amino acid substitutions relative to SEQ ID NO: 24. In some cases, the therapeutic nucleic acid sequence encodes a FVIII polypeptide with the combination of a B domain comprises SEQ ID NO: 27; the A1 domain substitution of phenylalanine at position 328 to serine and the A3 domain comprises substitution of cysteine at position 1249 to glycine provides a beneficial technical effect of increasing the coagulation activity of the FVIII protein in a subject. In some cases, the therapeutic nucleic acid sequence encodes a FVIII polypeptide with the combination of a B domain comprising SEQ ID NO: 27; the A1 domain comprising a substitution of phenylalanine at position 328 to serine and the A3 domain comprising a substitution of cysteine at position 1249 to glycine provides a beneficial technical effect of increasing the expression of the FVIII in the subject.

In some embodiments, the B domain comprises no more than 6 consensus sites for N-linked glycosylation. In some embodiments, the B domain comprises an amino acid sequence of SEQ ID NO: 28, and wherein the FVIII polypeptide is not more than 2300 amino acids in length. In some embodiments, the B domain comprises an amino acid sequence of SEQ ID NO: 34. In some embodiments, the A1 domain comprises an amino sequence of SEQ ID NO: 25. In some embodiments, the A3 domain comprises an amino sequence of SEQ ID NO: 29. In some embodiments, the Factor VIII polypeptide comprises an amino acid sequence of SEQ ID NO: 24.

In some embodiments, the nucleic acid composition further includes a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence. In some embodiments, the nucleic acid composition further includes a nucleic acid sequence having at least 96% sequence identity to SEQ ID NO: 45. In some embodiments, the nucleic acid composition further includes a nucleic acid sequence having at least 80% sequence identity to SEQ ID NO: 6. In some embodiments, the nucleic acid sequence having at least 80% sequence identity to SEQ ID NO: 6 increases expression of the therapeutic nucleic acid sequence in a cell by at least 1.25-fold as compared to an otherwise identical control composition lacking the nucleic acid sequence having at least 80% sequence identity to SEQ ID NO: 6. In some embodiments, the first regulatory element comprises a sequence of SEQ ID NO: 9. In some embodiments, the second regulatory element comprises a sequence of SEQ ID NO: 45. In some embodiments, the nucleic acid composition comprises a sequence of SEQ ID NO: 39. In some cases, the combination of the first regulatory element positioned upstream of the therapeutic nucleic acid sequence (e.g., transgene) and the second regulatory element positioned downstream of the therapeutic nucleic acid sequence (e.g., transgene) provides a beneficial technical effect of increasing expression of the therapeutic nucleic acid sequence in a cell. In some cases, the combination of the first regulatory element positioned upstream of the therapeutic nucleic acid sequence (e.g., transgene) and the second regulatory element positioned downstream of the therapeutic nucleic acid sequence (e.g., transgene) and the nuclear targeting sequence having at least 80% sequence identity to SEQ ID NO: 6 provides a beneficial technical effect of increasing delivery of the therapeutic nucleic acid sequence to a nucleus of the cell and resulting expression of the therapeutic nucleic acid sequence in the cell. In some cases, the combination of the first regulatory element positioned upstream of the therapeutic nucleic acid sequence (e.g., transgene) and the second regulatory element positioned downstream of the therapeutic nucleic acid sequence (e.g., transgene) in combination with the post-transcriptional regulatory element of a nucleic acid sequence having at least 96% sequence identity to SEQ ID NO: 45, and the nuclear targeting sequence having at least 80% sequence identity to SEQ ID NO: 6 provides a beneficial technical effect of increasing delivery of the therapeutic nucleic acid sequence to a nucleus of the cell and resulting expression of the therapeutic nucleic acid sequence in the cell.

Aspects disclosed herein provide a nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 34; and wherein: the A1 domain comprises an amino sequence of SEQ ID NO: 25; and the A3 domain comprises an amino sequence of SEQ ID NO: 29, the nucleic acid composition further comprising: a first regulatory element comprising a sequence of SEQ ID NO: 9; a second regulatory element comprising a second regulatory element comprising a sequence of SEQ ID NO: 45; and a nucleic acid sequence of SEQ ID NO: 6. In some embodiments, the nucleic acid composition comprises a sequence of SEQ ID NO: 39. In some cases, the combination of the therapeutic nucleic acid sequence encoding FVIII with a B domain comprising SEQ ID NO: 27; the A1 domain comprising a substitution of phenylalanine at position 328 to serine and the A3 domain comprising a substitution of cysteine at position 1249 to glycine, with the first regulatory element upstream of the therapeutic nucleic acid sequence and the second regulatory element positioned downstream of the therapeutic nucleic acid sequence provides a beneficial technical effect of increasing the activity of the FVIII protein in a subject, and expression of the FVIII protein in the subject. In some cases, the combination of the first regulatory element positioned upstream of the FVIII nucleic acid sequence (e.g., FVIII transgene) and the second regulatory element positioned downstream of the FVIII nucleic acid sequence (e.g., FVIII transgene) in combination with the post-transcriptional regulatory element of a nucleic acid sequence having at least 96% sequence identity to SEQ ID NO: 45, and the nuclear targeting sequence having at least 80% sequence identity to SEQ ID NO: 6 provides a beneficial technical effect of increasing delivery of the FVIII nucleic acid sequence to a nucleus of the cell and resulting expression of FVIII by the cell.

In some embodiments, the therapeutic nucleic acid sequence comprises a nucleic acid sequence of SEQ ID NO: 32. In some embodiments, the nucleic acid composition is a non-viral vector. In some embodiments, the nucleic acid composition is at least 5000, 5500, 6000, 6500, or 7000 bp in length, and wherein the non-viral vector encodes a full-length gene.

In some embodiments, the nucleic acid composition comprises a miniplasmid backbone. In some embodiments, the miniplasmid backbone is smaller than 1 kb. In some embodiments, the miniplasmid backbone comprises a sequence of SEQ ID NO: 7. In some embodiments, the therapeutic nucleic acid sequence is a therapeutic agent. In some embodiments, the therapeutic nucleic acid sequence encodes a therapeutic agent. In some embodiments, the therapeutic nucleic acid sequence encodes a protein which provides a therapeutic effect to a subject.

In some embodiments, the nucleic acid composition is an isolated nucleic acid molecule. In some embodiments, the nucleic acid composition does not comprise an origin of replication, or a bacterial origin of replication. In some embodiments, the nucleic acid composition further comprises one or more Inverted Terminal Repeat (ITR) sequences. In some embodiments, a first ITR sequence is positioned upstream of the therapeutic nucleic acid sequence, promoter sequence, first regulatory element, and/or nuclear targeting sequence. In some embodiments, a second ITR sequence is positioned downstream of the therapeutic nucleic acid sequence, promoter sequence, first regulatory element, and/or nuclear targeting sequence.

In some embodiments, the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. In some embodiments, the nucleic acid composition the therapeutic nucleic acid sequence encodes a FVIII polypeptide comprising an amino acid sequence having up to 3 amino acid substitutions relative to SEQ ID NO: 24. In some embodiments, the B domain comprises up to 6 consensus sites for N-linked glycosylation. In some embodiments, the B domain comprises an amino acid sequence of SEQ ID NO: 28. In some embodiments, the B domain comprises an amino acid sequence of SEQ ID NO: 34. In some embodiments, the A1 domain comprises substitution of phenylalanine at position 328 to serine when the Factor VIII polypeptide is aligned with SEQ ID NO: 35. In some embodiments, the A1 domain comprises an amino sequence of SEQ ID NO: 25. In some embodiments, the A3 domain comprises substitution of cysteine at position 1249 to glycine when the Factor VIII polypeptide is aligned with SEQ ID NO: 35. In some embodiments, the A3 domain comprises substitution of cysteine at position 1253 to glycine when the Factor VIII polypeptide is aligned with SEQ ID NO: 35. In some embodiments, the A3 domain comprises an amino sequence of SEQ ID NO: 28. In some embodiments, the therapeutic nucleic acid sequence encodes the amino acid sequence of SEQ ID NO: 24. In some cases the therapeutic nucleic acid sequence encodes a FVIII polypeptide is a transgene. In some cases, the positioning of a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence, provides a beneficial technical effect of improving transgene delivery and expression. In some cases, the positioning of a nuclear targeting sequence, for example, a nucleic acid sequence having at least 80% sequence identity to SEQ ID NO: 6, provides a beneficial technical effect of improving transgene delivery and expression. In some cases, the poly-adenylation signal positioned downstream of the second regulatory element provides a beneficial technical effect of improving transgene delivery and expression. In some cases, one or more Inverted Terminal Repeat (ITR) sequences provides a beneficial technical effect of improving transgene delivery and expression.

In some cases the where the therapeutic nucleic acid sequence is a FVIII transgene, the first regulatory element is positioned upstream and directly coupled to the therapeutic nucleic acid sequence, the second regulatory element is positioned downstream and directly coupled to the therapeutic nucleic acid sequence, the poly-adenylation signal is positioned downstream and directly coupled to the second regulatory element, and where the nuclear targeting sequence is positioned downstream and directly coupled to the poly-adenylation signal, the combination of elements and relative positioning of elements within the nucleic acid provides a beneficial technical effect of improving transgene delivery and expression.

Methods of Gene Delivery

Aspects disclosed herein provide the nucleic acid composition disclosed herein for use a method of treating a bleeding disorder in a subject in need thereof, the method comprising administering the nucleic acid composition of any one of the preceding claims to the subject. Aspects disclosed herein provide a method of expressing a nucleic acid payload in a cell, the method comprising administering the nucleic acid composition of any one of the preceding claims to a subject. In some embodiments, the method further includes applying an ultrasonic acoustic energy to the cell. In some embodiments, the method further includes administering to the subject a sonoactive agent. In some embodiments, the nucleic acid composition is administered to the subject as a naked nucleic acid. In some embodiments, the nucleic acid composition encodes a full-length polypeptide, wherein the method induces expression of the full-length polypeptide in-vivo. In some embodiments, the method further includes administering to the subject the nucleic acid composition in at least two treatments at least 48 hours apart, thereby achieving a therapeutic level of the clotting factor in the subject. In some embodiments, the method further includes administering to the subject ultrasound acoustic energy in the treatments. In some embodiments, the method further includes administering to the subject a sonoactive agent in the treatments. In some embodiments, one or both of the nucleic acid composition or the sonoactive agent are administered to the subject intravenously through a peripheral vein. In some embodiments, administering the ultrasound acoustic energy comprises applying the ultrasound energy at a mechanical index (MI) of at least 0.8, 1.3, 1.8, 1.9, or 2.2. In some embodiments, administering the ultrasound acoustic energy further comprises applying the ultrasound energy at a mechanical index (MI) of up to 0.4. In some embodiments, the ultrasound energy is applied at an intensity (ISPTA) of at least 200 mW/cm2. In some embodiments, the ultrasound energy is applied at pulse length of at least 20, 200, or 600 microseconds. In some embodiments, the subject is administered at least three treatments. In some embodiments, the at least three treatments are administered at least 48 hours apart. As used herein a "treatment" refers to administration of the nucleic acid composition to the subject in combination with one or more of ultrasound energy, and/or a sonoactive agent.

In some embodiments, the subject is administered at least two cycles, each cycle comprising at least two treatments. In some embodiments, the subject is administered at least three cycles, each cycle comprising at least two treatments. In some embodiments, the subject is administered at least three cycles, each cycle comprising at least three treatments. In some embodiments, each cycle is administered to the subject at least 10 days apart. In some embodiments, each cycle is administered to the subject at least 30 days apart. In some embodiments, each cycle is administered to the subject at least 40 days apart. As used herein a "cycle" refers to a series of two or more (e.g., three) treatments. In some embodiments, the method further includes imaging an organ of the subject with ultrasound acoustic energy. In some embodiments, the imaging the organ of the subject comprises verifying presence of the sonoactive agent in the organ or the targeting of the ultrasound acoustic energy towards to organ. In some embodiments, a therapeutic level of the FVIII polypeptide is maintained for at least 10, 20, 30, 40, 50, 60, 70, 80, 90, 100, 110, 120, 130, 140, 145, or 150 days. In some embodiments, vascular flow is not occluded in the subject. In some embodiments, the subject has a bleeding disorder, wherein the therapeutic nucleic acid sequence encodes FVIII, and wherein the method thereby treats the subject having the bleeding disorder. In some embodiments, the bleeding disorder is hemophilia A. In some embodiments, the sonoactive agent comprises lipid-stabilized microstructures. In some embodiments, the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble. In some cases, administering repeated treatments to the subject in which the nucleic acid composition encoding the FVIII protein delivered using sonoactive agents disrupted with ultrasound energy provides a beneficial technical effect of increasing the delivery of the nucleic acid composition to cells and resulting expression of the FVIII protein, for example, expressing the FVIII protein at therapeutic levels in a subject for extended periods.

Aspects disclosed herein provide a nucleic acid composition of any one of the preceding claims, for use a method of treating a bleeding disorder in a subject in need thereof, the method comprising administering the nucleic acid composition of any one of the preceding claims to the subject, administering a sonoactive agent to the subject. Aspects disclosed herein provide a cell comprising the nucleic acid composition of any one of the preceding claims. Aspects disclosed herein provide a nucleic acid composition for use a method of treating a bleeding disorder in a subject in need thereof, the nucleic acid composition comprising: a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 34; and wherein: the A1 domain comprises an amino sequence of SEQ ID NO: 25; and the A3 domain comprises an amino sequence of SEQ ID NO: 29, the nucleic acid composition further comprising: a first regulatory element comprising a sequence of SEQ ID NO: 9; a second regulatory element comprising a second regulatory element comprising a sequence of SEQ ID NO: 45; and a nucleic acid sequence of SEQ ID NO: 6 the method comprising: administering to the subject the nucleic acid composition, a sonoactive agent, and ultrasound acoustic energy in a treatment session; administering a cycle comprising at least three treatment sessions to the subject; administering at least three cycles to the subject each cycle at least 10 days apart, thereby achieving a therapeutic level of the FVIII polypeptide in the subject. Aspects disclosed herein provide a method of manufacturing the nucleic acid composition disclosed herein. Aspects disclosed herein provide a kit comprising: a sonoactive agent; and means for expressing a Factor VIII polypeptide in vivo at a level that is at least 1.5 fold greater than expression of SEQ ID NO. 3. Aspects disclosed herein provide a kit comprising: a sonoactive agent; and the nucleic acid composition disclosed herein.

Aspects disclosed herein provide a method of treating a bleeding disorder comprising administering to a subject a nucleic acid encoding a human clotting factor in at least two treatments at least 48 hours apart, thereby achieving a therapeutic level of the clotting factor in the subject. In some embodiments, the therapeutic level of the clotting factor is maintained for at least 10, 20, 30, 40, 50, 60, 70, 80, 90, 100, 110, 120, 130, 140, 145, or 150 days. In some embodiments, the subject is administered at least three treatments. In some embodiments, the sonoactive agent comprises protein-stabilized microstructures. In some embodiments, the sonoactive agent comprises a shell filled with a perfluorinated gas. In some embodiments, the sonoactive agent comprises lipid-stabilized microstructures. In some embodiments, the at least three treatments are administered at least 48 hours apart. In some embodiments, the subject is administered at least two cycles, each cycle comprising at least two treatments. In some embodiments, the subject is administered at least three cycles, each cycle comprising at least two treatments. In some embodiments, the subject is administered at least three cycles, each cycle comprising at least three treatments. In some embodiments, each cycle is administered to the subject at least 10 days apart. In some embodiments, each cycle is administered to the subject at least 30 days apart. In some embodiments, each cycle is administered to the subject at least 40 days apart. In some cases, the nucleic acid compositions encoding a human clotting factor disclosed herein are configured to administration to a subject in at least two treatments at least 48 hours apart, thereby achieving a therapeutic level of the clotting factor in the subject. In some cases, the methods of delivery of the nucleic acids encoding human clotting factors disclosed herein provide a beneficial technical effect of increasing expression of the human clotting factor, for example, achieving or maintaining a therapeutic level of the human clotting factor. In some cases, the at least two treatments and at least two cycles of treatments with nucleic acids encoding human clotting factors disclosed herein provide a beneficial technical effect of achieving or maintaining a therapeutic level of the human clotting factor, thereby treating a bleeding disorder. In some cases, the bleeding disorder is hemophilia A and the clotting factor is human FVIII.

In some embodiments, the method includes administering to the subject ultrasound acoustic energy in the treatments. In some embodiments, the method includes administering to the subject a sonoactive agent in the treatments. In some embodiments, administering the ultrasound acoustic energy comprises applying the ultrasound energy at a mechanical index (MI) of at least 0.8, 1.3, 1.8, 1.9, or 2.2. In some embodiments, administering the ultrasound acoustic energy comprises applying the ultrasound energy at a mechanical index (MI) of up to 0.4. In some embodiments, administering the ultrasound energy comprises applying an acoustic radiation force to the subject. In some embodiments, the ultrasound energy is applied at an intensity (ISPTA) of at least 200 mW/cm2. In some embodiments, the ultrasound energy is applied at pulse length of at least 20 microseconds.

In some cases, nucleic acid compositions disclosed herein are administered as naked plasmid DNA. In some cases, nucleic acid compositions disclosed herein are administered using a viral vector, for example, a parvovirus, retrovirus, lentivirus, a herpes simplex virus, or adeno-virus vector (AAV). In some cases, nucleic acid compositions disclosed herein are administered using lipid-based delivery methods, for example, plasmid DNA may be coated with lipids in an organized structure such as a micelle or a liposome (complexed with DNA as a lipoplex). Anionic and neutral lipids may be used for the construction of lipoplexes for synthetic vectors. In one embodiment, cationic lipids, due to their positive charge, may be used to condense negatively charged DNA molecules to facilitate the encapsulation of DNA into liposomes. Alternatively, methods such as sonoporation may be utilized.

Disclosed herein are methods for treating a subject suffering from a genetic disorder comprising administering to the subject a therapeutically effective amount of the delivery vectors comprising a therapeutic transgene, or a pharmaceutical composition comprising the same. In this instance, a "therapeutically effective amount" is an amount of the delivery vector is an amount that after administration results in the expression of the therapeutic protein in a level sufficient to at least partially and preferably fully ameliorate the symptoms of the genetic disorder.

In some embodiments, the cell is a liver cell, a kidney cell, a brain cell, a muscle cell, a cardiac cell, a pancreatic cell, a blood cell, or a tumor cell. In some embodiments, the cell is a hepatocyte.

In some embodiments, the therapeutic nucleic acid sequence encodes a CRISPR/Cas system, a Cas protein or homolog or variant thereof, a TALEN, a ZFN, or a template DNA molecule suitable for knock-in via homologous end joining (NHEJ) or homology directed repair (HDR).

Aspects disclosed herein provide a method of expressing a nucleic acid payload in a cell, the method comprising administering the nucleic acid composition disclosed herein to a subject. In some embodiments, the method includes applying ultrasonic acoustic energy to the cell. In some embodiments, the method includes administering to the subject a plurality of sonoactive microstructures. In some embodiments, the method includes contacting the cell with a lipid nanoparticle composition. In some embodiments, the nucleic acid composition is administered to the subject in a viral vector. In some embodiments, the method includes to the subject a plurality of magnetic particles and applying a magnetic field to the cell. In some embodiments, the magnetic particles comprise paramagnetic nanoparticles. In some embodiments, the method includes applying an electrical field to the cell. In some embodiments, the nucleic acid composition is administered to the subject using hydrodynamic injection. In some embodiments, the nucleic acid composition is administered to the subject as a naked nucleic acid. In some embodiments, the nucleic acid composition is administered to the subject as an encapsulated nucleic acid. In some embodiments, the nucleic acid composition is encapsulated in a lipid or a polymer. In some embodiments, the nucleic acid composition encodes a full-length polypeptide, wherein the method induces expression of the full-length polypeptide in-vivo. In some embodiments, the subject has a bleeding disorder, wherein the therapeutic nucleic acid sequence of the polypeptide encodes FVIII or FIX, and wherein the method thereby treats the subject having the bleeding disorder. In some embodiments, the bleeding disorder is hemophilia A.

Factor VIII (FVIII) is protein which plays an important role in the blood clotting cascade, and is intrinsic to a pathway of coagulation. FVIII is a large multidomain glycoprotein, synthesized in the liver and endothelial cells. Wild-type FVIII is approximately 2,332 amino acids, making it one of the largest proteins involved in the blood clotting cascade. One known function of FVIII is to act as a cofactor for clotting factor IX in the activation of clotting factor X, which ultimately leads to the conversion of prothrombin to thrombin, thereby providing for a coagulation response. The wild-type human FVIII protein consists of several distinct domains: A1-A2-B-A3-C1-C2. Without being bound by theory, the A1 domain is located at the N-terminal end of FVIII and is involved in the binding of FVIII to von Willebrand factor (VWF). The interaction between FVIII and VWF stabilizes FVIII in circulation by protecting it from proteolytic degradation. The A2 domain contains a binding site for activated factor IX (factor IXa). The interaction between the A2 domain of FVIII and factor Ixa is important for the activation of factor X in the coagulation cascade. The wild-type B domain is a large domain of FVIII of about 740 to 800 amino acids, and is not thought to be essential to coagulation function, and separates the A2 and A3 domains. The A3 domain is located adjacent to the A2 domain and is involved in the assembly of the tenase complex, which consists of factor VIIIa, factor IXa, and calcium ions. The C1 domain is located near the C-terminus of FVIII and is important for the binding of FVIII to phospholipid surfaces, which is helpful for the localization of FVIII to the site of vascular injury. The C2 domain is involved in calcium ion binding, which stabilizes the structure of FVIII and is thought to be necessary for its proper FVIII function.

In gene therapy for hemophilia A, various truncated versions of the Factor VIII (FVIII) protein are utilized to address the deficiencies or mutations in the FVIII gene that lead to the disorder, and truncates are usually utilized in order to fit within the carrying capacity of a viral vector, for example, and adenovirus vector. These truncated forms are intended to retain the essential functional domains of FVIII while minimizing the risk of immunogenicity and improving the expression and secretion of the protein, often by deleting the B-domain. For example, the B-domain of FVIII is not essential for its procoagulant function and can be removed without affecting its activity. BDD FVIII lacks this non-essential B-domain, resulting in a smaller protein with improved secretion and stability. BDD FVIII is often used in gene therapy approaches as it is thought to facilitate higher expression levels, may reduce the risk of immune responses compared to full-length FVIII, and provides for packaging within the size of an AAV vector. While B-Domain Deleted (BDD) Factor VIII (FVIII) has been widely used in gene therapy and provides for packaging within viral vectors with small carrying capacities, there may be disadvantages to such BDD FVIII constructs as well, for example, reduced stability, altered pharmacokinetics, functional changes, and reduced overall therapeutic effect. Further, no gene therapy product currently on the market has been able to successfully deliver a full length or FVIII construct, or a FVIII construct which can exceed the carrying capacity of an AAV, and there remains a need for improved FVIII transgenes which provide for improved expression of the therapeutic protein and long-term beneficial effect to patients. Further, modification to other domains of the FVIII protein which can also improve expression of the therapeutic protein and provide a long-term beneficial effect to patients would also represent an improvement over the current FVIII gene therapy products.

Aspects disclosed herein provide a Factor VIII polypeptide comprising: an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 36; and the A3 domain comprises at least two amino acid substitutions as compared to SEQ ID NO: 37. Aspects disclosed herein provide a Factor VIII polypeptide comprising an amino acid sequence having up to 3 amino acid substitutions relative to SEQ ID NO: 24. In some embodiments, the FVIII polypeptide has an amino acid sequence having up to 3 amino acid substitutions relative to SEQ ID NO: 24. In some cases, the non-naturally occurring B domain and one or more amino acid substitution in the A1 and A3 domain may provide for enhanced expression, secretion, and coagulation activity of FVIII. In some cases, the non-naturally occurring B domain and one or more amino acid substitution in the A1 and A3 domain may significantly increase the expression levels of FVIII in host cells by optimizing transcriptional and translational processes leading to increased yields of functional FVIII protein. In some cases, the non-naturally occurring B domain and one or more amino acid substitution in the A1 and A3 domain may provide for increased stability of the FVIII from host cells into the bloodstream, for example, by improving protein folding and trafficking s compared to FVIII protein lacking these modifications. In some cases, the non-naturally occurring B domain and one or more amino acid substitution in the A1 and A3 domain may stabilize the FVIII protein in circulation and protect it from degradation within the cell or in circulation, thereby providing for a longer functional duration, improving its therapeutic efficacy. In some cases, the non-naturally occurring B domain and one or more amino acid substitution in the A1 and A3 domain may provide for proper protein folding in a conformation that mirrors the native conformation of wild-type FVIII.

In some embodiments, the FVIII polypeptide has an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of: the A1 domain comprises at least one amino acid substitution relative to SEQ ID NO: 35; and the A3 domain comprises at least two amino acid substitutions as compared to SEQ ID NO: 36. In some embodiments, the B domain comprises up to 6 consensus sites for N-linked glycosylation. In some embodiments, the B domain comprises an amino acid sequence of SEQ ID NO: 28. In some embodiments, the B domain comprises an amino acid sequence of SEQ ID NO: 34. In some embodiments, the A1 domain comprises substitution of phenylalanine at position 328 to serine when the FVIII polypeptide is aligned with SEQ ID NO: 35. In some embodiments, the A1 domain comprises an amino sequence of SEQ ID NO: 25. In some embodiments, the A3 domain comprises substitution of cysteine at position 1249 to glycine when FVIII polypeptide is aligned with SEQ ID NO: 35. In some embodiments, the A3 domain comprises substitution of cysteine at position 1253 to glycine when FVIII polypeptide is aligned with SEQ ID NO: 35. In some embodiments, the A3 domain comprises an amino sequence of SEQ ID NO: 28. In some embodiments, the FVIII polypeptide comprises the amino acid sequence of SEQ ID NO: 24. Aspects disclosed herein provide a kit comprising: a sonoactive agent; and means for expressing a Factor VIII polypeptide in vivo at a level that is at least 1.5 fold greater than expression of SEQ ID NO. 3. Aspects disclosed herein provide a kit comprising: a sonoactive agent; and the nucleic acid composition disclosed herein. In some embodiments, further included are instructions for administering ultrasound acoustic energy to a subject to facilitate expression of the FVIII polypeptide in vivo. In some embodiments, further included instructions for administering ultrasound acoustic energy to a subject to facilitate delivery of the nucleic acid composition to a subject. In some embodiments, the sonoactive agent comprises lipid-stabilized microstructures. In some embodiments, the lipid-stabilized microstructures comprise a lipid stabilized shell surrounding a perfluorinated gas core. In some embodiments, the lipid stabilized shell comprises a monomolecular membrane of hydrogenated egg yolk phosphatidyl serine, wherein the perfluorinated gas core comprises perfluorobutane gas. In some embodiments, the sonoactive agent is a Sonazoid microbubble. Aspects disclosed herein provide a cell comprising the FVIII polypeptide of any one of the embodiments disclosed herein. Aspects disclosed herein provide a nucleic acid encoding the FVIII polypeptide of any one of the embodiments disclosed herein. In some cases, the combination of the FVIII polypeptide with a B domain comprising SEQ ID NO: 27; the A1 domain comprising a substitution of phenylalanine at position 328 to serine and the A3 domain comprising a substitution of cysteine at position 1249 to glycine provides a beneficial technical effect of increasing the activity of the FVIII protein in a subject, and expression of the FVIII protein in the subject.

Ultrasound refers to the application of electromagnetic energy in the range of greater than 20 kHz up to several gigahertz. Ultrasound is used in many different fields, most commonly in the field of diagnostics and medical imaging for producing images of tissue within the human body. ultrasound acoustic energy can be generated at various frequencies within the 20 kHz up to several gigahertz range, most commonly within the range of about 1 to 10 megahertz when used for diagnostic imaging purposes. Ultrasound is commonly applied using ultrasonic transducers comprising one or more piezoelectric crystals which convert electrical energy into acoustic energy. In addition to imaging applications, ultrasound can also be used for a variety of other diagnostic and therapeutic applications, including determination of tissue elasticity and fibrosis, focused destruction of tissue using ultrasound ablation, and for the delivery of exogenous payloads (e.g., nucleic acids and therapeutic agents) to a cell. Sonoporation refers to the delivery of therapeutic agents, for example nucleic acids, using ultrasound and/or sonoactive microstructures (e.g., sonoactive microstructures) to a cell. Provided in certain embodiments herein are methods of delivering a nucleic acid construct into a target cell or tissue (e.g., of a subject) by applying ultrasonic acoustic energy to a cell, tissue, or organ (e.g., with sonoporation).

B mode ultrasound imaging refers to brightness mode imaging, in which ultrasonic waves are reflected from the tissue of a subject back to the ultrasound probe, and displayed on a 2-dimensional objects that are closer to the ultrasound transducer appear brighter, and objects which are farther away from the ultrasound transducer appear darker. B mode ultrasound imaging generally will focus ultrasonic acoustic energy emitted from a plurality of ultrasound arrays comprising piezoelectric crystals into a focused ultrasound beam which penetrates into the tissue about a vertical axis which is perpendicular to the surface of the ultrasound probe. The focused ultrasound beam reflects off the tissue and back towards the ultrasound transducer, forming a scan line in an ultrasound image. By moving the ultrasound transducer about a surface of tissue, an image of the underlying tissue can be generated using a B mode ultrasound image. B mode ultrasound imaging is the most common form of ultrasound used in the United States for medical imaging, and is what is commonly referred to as diagnostic or imaging ultrasound.

Plane wave imaging refers to an ultrasound imaging technique in which a plurality of ultrasound arrays comprising piezoelectric crystals in an ultrasound transducer are simultaneously fired without directing ultrasonic acoustic energy into a focused ultrasound beam, and which instead direct a large unfocused sheet or wave of ultrasound acoustic energy into a medium or tissue underlying an ultrasound probe. The primary difference between plane wave ultrasound imaging and B mode ultrasound imaging is the number of transducer arrays which are fired. Plain wave imaging typically will fire all arrays within an ultrasound transducer Producing a much larger and less focused wave of ultrasonic energy, while B mode imaging will typically only fire a subset of arrays which focused the ultrasound into a beam producing what is commonly referred to as a scan line. In plane wave imaging, the acoustic radiation pressure is almost uniform over the entire field of view, and lower peak and negative pressures are typically experienced as compared to traditional beam mode focused ultrasound beam imaging.

Acoustic radiation force refers to a static or transient force applied by an acoustic wave on the propagation medium or to an object in the path of the acoustic wave. Acoustic radiation forces can be applied using an ultrasound transducer when applying ultrasonic acoustic energy to a surface of a tissue or a propagation medium with sufficient ultrasound intensity. When applying a sufficient acoustic radiation force to a propagation medium or a tissue, the propagation medium or tissue underlying the ultrasound probe applying the acoustic radiation force may be displaced.

Shear waves, or secondary waves commonly refer to transversely oriented waves which occur in elastic medium that is subjected to a periodic shear. Shear refers to a change in shape without a change of volume of a layer of a propagation medium or tissue produced by a pair of equal forces acting in opposite directions about two faces of the layer or the propagation medium. Shear waves are a type of elastic wave which move through the body of an object or a propagation medium. In an elastic medium, the layer or the tissue will resume its original shape following application of the sheer force, adjacent layers will undergo subsequent shear, and the movement of particles within the medium or tissue will be propagated as a shear wave throughout the propagation medium or tissue. In an elastic medium, shear waves can be produced as a secondary wave following a compressional wave which is transmitted in the propagation medium or tissue. Ultrasound applying an acoustic radiation force can apply a compressional wave to a tissue, which can result in application of shear waves to a tissue when applied with sufficient intensity, at regular intervals, for sufficient periods of time to induce a regular shear in layers of a tissue. A compressional wave displaces tissue in a direction parallel to the propagation of the compressional waves. An ultrasound transducer can induce a compressional wave in a tissue which propagates from the ultrasound transducer about a vector normal to a surface of the ultrasound transducer. In some embodiments, applying the focused acoustic radiation force to the tissue comprises generating a compressional wave in the tissue. As an elastic tissue recovers from displacement due to a compressional wave, shear waves or secondary waves can be generated. In a shear wave, the direction of particle motion is parallel to the direction of propagation of the compressional wave, and the direction of propagation of the shear wave is normal to the direction of propagation of the compressional wave. The direction of particle motion in a shear wave is also normal to the direction of shear wave propagation in an elastic medium. Further, a compressional wave may be followed by a rarefaction wave which is a negative acoustic force in the tissue.

Shear wave elastography refers to a diagnostic technique using ultrasound to determine the elastic modulus of tissue, which is indicative of its fibrotic quality. Diseased tissue with certain fibrotic conditions will result in a significantly reduced elastic modulus of the tissue, as compared to a healthy tissue which is reasonably elastic as compared to diseased tissue in a fibrotic state. Shear wave elastography uses a combination of acoustic radiation force, plane wave imaging, and B mode imaging to provide a clinician with information as to the fibrotic quality of a tissue. Shear wave elastography applies an acoustic radiation force to displace the tissue underlying an ultrasound probe with a compressional wave, thereby generating shear waves in the tissue, applies a plane wave ultrasound to the tissue to monitor the propagation of the shear waves throughout the tissue thereby calculating the elastic modulus, and overlays this data atop a standard B mode ultrasound image to provide a visual representation of tissue stiffness.

Provided in certain embodiments herein are methods of delivering a nucleic acid construct into a target cell or tissue (e.g., of a subject) by applying ultrasonic acoustic energy to a cell, tissue, or organ. Provided in certain embodiments herein are methods of delivering a nucleic acid construct into a target cell or tissue (e.g., of a subject) by delivering an exogenous payload to the subject; and applying a focused acoustic radiation force (ARF) to the subject, thereby generating shear waves in the tissue of the subject, wherein the focused acoustic radiation force enhances delivery of the exogenous payload to the cell in the tissue of an organ of the subject. Disclosed herein are methods of sonoporation in which an exogenous payload is delivered to a cell in a tissue of a subject using a focused acoustic radiation force applied using ultrasound. Aspects of the sonoporation methods disclosed herein may also include inducing displacing the tissue of the subject with the acoustic radiation force to induce propagation of shear waves throughout the tissue of the subject thereby enhancing delivery of a nucleic acid payload to a cell. Disclosed herein are methods of sonoporation in which an exogenous payload is delivered to a cell in a tissue of a subject using a focused acoustic radiation force applied using ultrasound. Aspects of the sonoporation methods disclosed herein may also include inducing displacing the tissue of the subject with the acoustic radiation force to induce propagation of shear waves throughout the tissue of the subject thereby enhancing delivery of a nucleic acid payload to a cell. The method may further include applying the acoustic radiation force to induce propagation of shear waves throughout the tissue in combination with other secondary ultrasound energies such as plane wave ultrasound or focused beam ultrasound in which the secondary ultrasound energy moves sonoactive microstructures endothelial border of a tissue comprising the cell, while applying the focused acoustic radiation force during shear wave propagation induces inertial cavitation of sonoactive microstructures at the endothelial border of the tissue comprising the cell, thereby enhancing delivery of the therapeutic payload to a cell, and, in cases of a nucleic acid payload, resulting gene expression.

In some embodiments, the focused acoustic radiation force is applied using an ultrasound probe applying ultrasound acoustic energy to the tissue. In some embodiments, the ARF displaces the tissue of the subject. In some embodiments, the shear waves displace the tissue of the subject. In some embodiments, a tissue displacement is at least 0.001 mm. In some embodiments, a tissue displacement ranges from at least 0.001 mm to about 5 mm. In some embodiments, a tissue displacement ranges from 0.01 mm to about 1 mm.

In some embodiments, the focused acoustic radiation force is applied using an ultrasound probe applying ultrasound acoustic energy to the tissue. In some embodiments, the ultrasonic acoustic energy is applied at a mechanical index of greater than 0.4. In some embodiments, the ultrasonic acoustic energy is applied at a mechanical index of about 1.4. In some embodiments, the ultrasonic acoustic energy is applied at a mechanical index of at least 1.3. In some embodiments, the ultrasonic acoustic energy is applied at a mechanical index of greater than 0.4 up to about 3.0. In some embodiments, the ultrasonic acoustic energy is applied at a frequency of about 0.1 MHz to about 10 MHz. In some embodiments, the ultrasonic acoustic energy is applied at a frequency of about 2.5 MHz. In some embodiments, the applying ultrasonic acoustic energy to the tissue comprises applying the ultrasound acoustic energy at an ultrasound intensity of at least 100 mW/cm$^2$. In some embodiments, the applying ultrasonic acoustic energy to the tissue comprises applying the ultrasound acoustic energy at an ultrasound intensity of about 100 mW/cm$^2$ to about 10,000 mW/cm$^2$. In some embodiments, the applying ultrasonic acoustic energy to the tissue comprises applying the ultrasound acoustic energy at an ultrasound intensity of about 100 mW/cm$^2$ to about 5,000 mW/cm$^2$. In some embodiments, the applying ultrasonic acoustic energy to the tissue comprises applying the ultrasound acoustic energy at an ultrasound intensity of about 100 mW/cm$^2$ to about 500 mW/cm$^2$. In some embodiments, the applying ultrasonic acoustic energy to the tissue comprises applying the ultrasound acoustic energy at an ultrasound intensity of about 110 mW/cm$^2$ to about 200 mW/cm$^2$. In some embodiments, the applying ultrasonic acoustic energy to the tissue comprises applying the ultrasound acoustic energy at an ultrasound intensity of about 188 mW/cm$^2$. In some embodiments, the ultrasound intensity is a spatial-peak temporal average intensity. In some embodiments, the spatial-peak temporal average intensity is calculated in a focal region of the tissue. In some embodiments, the focused acoustic radiation force is applied in two or more pulses, with an interval between each of the two or more pulses. In some embodiments, a plane wave ultrasound is applied to the tissue during the interval. In some embodiments, the one or more pulses are up to 500 microseconds. In some embodiments, the one or more pulses are at least 100 microseconds. In some embodiments, the one or more pulses are about 100 microseconds to about 500 microseconds. In some embodiments, the interval is up to 500 milliseconds. In some embodiments, the interval is up to 100, 500, 1000, 1500, 2000, 2500, 3000, 4000, or 5000 milliseconds. In some embodiments, the interval is from about 100 milliseconds to about 5000 milliseconds. In some embodiments, the applying the focused acoustic radiation force is performed in one or more sequences, wherein a sequence comprises two or more pulses and interval(s) therebetween. In some embodiments, a time between application of the one or more sequences is at least 5, 10, 20, 30, 60, 120, 180, 240, 300, 360, 420, 480, 540, or 600 seconds. In some embodiments, a time between application of the one or more sequences ranges from about 5 to about 300 seconds. In some embodiments, a time between application of the one or more sequences ranges from about 10 to about 60 seconds. In some embodiments, the focused acoustic radiation force is applied for at least 10, 20, 30, 60, 120, 180, 240, 300, 360, 420, 480, 540, or 600 seconds. In some embodiments, applying ultrasonic acoustic energy to the tissue comprises applying the ultrasound acoustic energy at a focal depth of up to 10, 8, 6, or 4 cm from the ultrasound transducer. In some embodiments, applying ultrasonic acoustic energy to the tissue comprises applying the ultrasound acoustic energy at a focal depth of about 1 to about 10 cm from the ultrasound transducer. In some embodiments, applying ultrasonic acoustic energy to the tissue comprises applying the ultrasound acoustic energy at a focal depth of about 4 to about 10 cm from the ultrasound transducer. In some embodiments, applying ultrasonic acoustic energy to the tissue comprises applying the ultrasound acoustic energy at a focal depth of about 4 cm from the ultrasound transducer. In some embodiments, applying ultrasonic acoustic energy to the tissue comprises applying the ultrasound acoustic energy at a focal depth of about 6 cm from the ultrasound transducer.

In some embodiments, applying the focused wave ultrasound results in moving the sonoactive microstructures towards an endothelial border of the tissue comprising the cell. In some embodiments, the shear waves induce inertial cavitation the sonoactive microstructures at an endothelial border of the tissue comprising the cell, thereby enhancing delivery of the nucleic acid to the cell. In some embodiments, the focused acoustic radiation force increases internalization of the exogenous payload in the cell. In some embodiments, the shear waves increase internalization of the exogenous payload in the cell. In some embodiments, inducing inertial cavitation the sonoactive microstructures increases internalization of the exogenous payload in the cell.

In some embodiments, a process provided herein provides sonoporation at two or more different ultrasonic acoustic energies (e.g., a first and second ultrasonic acoustic energy having a first and second MI, respectively). In certain embodiments, a process provided herein provides a process wherein an ultrasonic acoustic energy is continuously applied (e.g., ultrasonic acoustic energy transitions from the first ultrasonic acoustic energy to the second ultrasonic acoustic energy, without a period of no ultrasonic acoustic energy being applied). In certain embodiments, a transitory (e.g., third, fourth, etc.) ultrasonic acoustic energy is applied between application of the first and second ultrasonic acoustic energies. Provided in certain embodiments herein are methods of delivering a nucleic acid construct into a target cell or tissue (e.g., of a subject) by applying a first ultrasonic acoustic energy to a cell, tissue, or organ, and applying a second ultrasonic acoustic energy to the cell, tissue, or organ. In specific embodiments herein are methods for transfecting a nucleic acid construct into a target cell or tissue by applying a first ultrasonic acoustic energy having a first mechanical index (MI) and applying a second ultrasonic acoustic energy having a second mechanical index (MI). The present disclosure provides methods for enhancing transfection of a nucleic acid construct into the target cell or tissue by applying alternating ultrasonic acoustic energy, the alternating acoustic energy alternating between a first mechanical index (MI) and a second MI. Application of ultrasonic acoustic energy can be repeated several times during sonoporation, such as to increase the efficiency of nucleic acid construct transfection and/or delivery.

In some embodiments, the sonoporation treatment comprises applying an ultrasonic acoustic energy to the target cell (e.g., of a tissue or organ of the subject) (e.g., the ultrasonic acoustic energy having a mechanical index (MI)). In some embodiments, applying an ultrasonic acoustic energy to the target cell comprises applying a first ultrasonic acoustic energy to the target cell and applying a second ultrasonic acoustic energy to the target cell. In some embodiments, the (e.g., first or second) ultrasonic acoustic energy has a first mechanical index (MI). In certain embodiments, (e.g., the other of the first or second) ultrasonic energy has a second mechanical index (MI). In some embodiments, the (e.g., first or second) MI is less than 0.4. In certain embodiments (e.g., the other of the first or second) MI is greater than 0.4 (e.g., and less than 2.0). In specific embodiments, a first ultrasonic acoustic energy and a second ultrasonic acoustic energy are applied sequentially in a repeated manner. In some embodiments, a first MI is a Low MI (e.g., less than 0.4). In certain embodiments, a second MI is a High MI (e.g., 0.4 or greater). In some embodiments, a first MI is a Low MI (e.g., less than 0.4) and a second MI is a High MI (e.g., 0.4 or greater). In some embodiments, a second MI is a Low MI (e.g., less than 0.4). In certain embodiments, a first MI is a High MI (e.g., 0.4 or greater). In specific embodiments, a second MI is a Low MI (e.g., less than 0.4) and a first MI is a High MI (e.g., 0.4 or greater). In some embodiments, a Low MI is less than 0.3. In specific embodiments, a Low MI is less than 0.2. In more specific embodiments, a Low MI is less than 0.1. In still more specific embodiments, a Low MI is about 0.09. In still more specific embodiments, a Low MI is about 0.04. In still more specific embodiments, a Low MI is about 0.03. In some embodiments, a High MI is greater than 0.5. In specific embodiments, a High MI is 0.5 to 2.0 or is between 0.5 and 2.0. In more specific embodiments, a High MI is 0.5 to 1 or is between 0.5 and 2.0. In some embodiments, a High MI is 1.5. In some embodiments, a High MI is 1.8. In some embodiments, a High MI is 2.0. In some embodiments, a High MI is greater than 0.4. In some embodiments, a High MI is greater than 0.5. In more specific embodiments, a High MI is 0.5 to 1 or is between 0.5 and 2.0. In some embodiments, a High MI is 1.5. In some embodiments, a High MI is 1.8. In some embodiments, a High MI is 2.0. In certain embodiments, any process provided herein (e.g., a sonoporation treatment) comprises administering of a continuous ultrasonic acoustic energy (which may have varying energy levels) that alternates (e.g., in identical, similar, or variable periods) between Low MI and High MI. In some embodiments, a low MI (e.g., less than 0.1) (e.g., first) ultrasonic acoustic energy (also referred to herein as a Low MI) is administered to the subject, and a set number pulses (e.g., of less than 30 seconds) of High MI (e.g., second) ultrasonic acoustic energy (also referred to herein as a High MI) is administered to the subject. In some embodiments, a process provided herein comprises administration of a plurality of pulses of high MI (e.g., second) ultrasonic acoustic energy, e.g., during an otherwise continuous administration of a low MI (e.g., first) ultrasonic acoustic energy. In specific embodiments, the number of High MI pulses is about 4 or more, such as up to about 12, or an unlimited number of pulses. In specific embodiments the number of High MI pulses is 6-30. In still more specific embodiments, the number of High MI pulses is between 8, 9, 12, 15, or 18, or any number therebetween. In some embodiments, at least 8, 9, 12, 15, or 18 high MI pulses are administered to the subject in between applications of low MI ultrasound acoustic energy.

In certain embodiments, the first (either High MI or Low MI) ultrasonic acoustic energy is applied before or after administration of any other agent, such as the nucleic acid and/or sonoactive structure. In some embodiments, the first ultrasonic acoustic energy is applied after administration of the sonoactive structure to the subject. In certain embodiments, the first ultrasonic acoustic energy is applied after administration of the nucleic acid to the subject. In some embodiments, the first ultrasonic acoustic energy is applied after administration of both the nucleic acid and the sonoactive structure(s).

In some embodiments, high MI ultrasound acoustic energy is administered in a pulse. In specific embodiments, a pulse length is any suitable length, such as less than 30 seconds. In more specific embodiments, a pulse length is less than 15 seconds. In still more specific embodiments, a pulse length is less than 10 seconds. In yet more specific embodiments, a pulse length is less than 5 seconds. In more specific embodiments, a pulse length is less than 2 seconds. In still more specific embodiments, a pulse length is less than 1 second and/or may be greater than or equal to 1 microsecond. In some embodiments, a pulse length ranges from 100 to 300 microseconds. In some embodiments, a pulse length is up to about 200 microseconds. In some embodiments, a pulse length is up to about 500 microseconds. In some embodiments, a pulse length ranges from 1 to 500 microseconds.

In various embodiments, a High MI ultrasonic acoustic energy is provided first temporally (e.g., first in order). In other embodiments, a Low MI ultrasonic acoustic energy is provided second temporally (e.g., second in order).

In some embodiments, any process provided herein further comprises administering (e.g., systemically administering, such as via infusion) a nucleic acid (e.g., any nucleic acid provided herein) to a subject (e.g., to whom the ultrasonic acoustic energies are applied).

In some embodiments, any process provided herein further comprises administering (e.g., systemically administering, such as via infusion) a sonoactive structure (e.g., any sonoactive structure or microbubble described herein) to a subject (e.g., to whom the ultrasonic acoustic energies are applied).

In certain embodiments, provided herein is a method of delivering a nucleic acid payload in a target cell (e.g., of a tissue or organ) of a subject, the method comprising: (a) administering to the subject a nucleic acid construct comprising the nucleic acid payload; (b) administering to the subject a plurality of sonoactive microstructures; and (c) administering an ultrasound acoustic energy, thereby delivering a sonoporation treatment.

In some embodiments, a sonoporation treatment (e.g., application of a first ultrasonic acoustic energy, a second ultrasonic acoustic energy, a single cycle of a first ultrasonic acoustic energy and a second ultrasonic acoustic energy, or series of cycles comprising a plurality of applications of a first ultrasonic acoustic energy and a plurality of applications of a second acoustic energy) can last for a few seconds (e.g., 1-100 seconds) or more, such as up to a few minutes (e.g., 1-3 minutes). In specific embodiments, a sonoporation treatment lasts for 1-30 seconds. In some specific embodiments, a sonoporation treatment lasts for 5-100 seconds. In certain embodiments, a sonoporation treatment lasts for at least 1 minute (e.g., 1-30 minutes).

In some embodiments, the first ultrasonic acoustic energy is administered within 60 minutes of administration of the nucleic acid and/or sonoactive structure(s). In specific embodiments, the first ultrasonic acoustic energy is administered within 30 minutes of administration of the nucleic acid and/or sonoactive structure(s). In more specific embodiments, the first ultrasonic acoustic energy is administered within 5 minutes of administration of the nucleic acid and/or sonoactive structure(s). In still more specific embodiments, the first ultrasonic acoustic energy is administered within 2 minutes of administration of the nucleic acid and/or sonoactive structure(s). In still more specific embodiments, the first ultrasonic acoustic energy may be applied simultaneously with administration of the nucleic acid and/or sonoactive structure(s).

In specific embodiments, the first (e.g., High MI) ultrasonic acoustic energy is applied immediately upon administration (e.g., infusion) or a period of time after administration (e.g., infusion) of the sonoactive structure(s) and/or nucleic acid.

In some embodiments, either the first or second ultrasonic acoustic energy is an ultrasonic acoustic energy (e.g., Low MI) that when applied to a cell, tissue, or organ of a subject results in stable cavitation (or stable vibrational cavitation) of the sonoactive structure and/or a change in the average diameter of the sonoactive structure(s), for example, due to inherent resonance properties of the microbubbles.

In certain embodiments, the first or second ultrasonic acoustic energy is an ultrasonic acoustic energy (e.g., High MI) that when applied to a cell, tissue, or organ of a subject results in inertial cavitation or the collapse of the sonoactive structures and/or disruption of cell membrane and/or vascular endothelial integrity.

In certain embodiments, either the first or second ultrasonic acoustic energy is an ultrasonic acoustic energy (e.g., Low MI) that when applied to a cell, tissue, or organ of a subject results in stable cavitation (or stable vibrational cavitation) and/or a change in the average diameter of the sonoactive structure(s), and the other of the first or second ultrasonic acoustic energy is an ultrasonic acoustic energy (e.g., High MI) that when applied to a cell, tissue, or organ of a subject results in inertial cavitation or the collapse of the sonoactive structures and/or disruption of cell membrane and/or vascular endothelial integrity.

In some instances, disruption of cell membrane allows target cells to become permeable to circulating agents such as nucleic acid constructs. In certain instances, such circulating agents can then enter the target cells, tissues or organs, such as in a more rapid manner (e.g., relative to either Low MI or High MI ultrasonic acoustic energy application alone, or in the absence of ultrasonic acoustic energy application).

In some embodiments, the methods herein comprise alternating the ultrasonic acoustic energy applied between a first ultrasonic acoustic energy having a first MI and a second ultrasonic acoustic energy having a second MI. In some embodiments, applying alternating ultrasonic acoustic energy administered to a subject between a first MI and a second MI is performed repeatedly over a number of times, such as to enhance gene transfection into the target cells, tissue or organ (e.g., relative to a similar process wherein a first and second ultrasonic acoustic energy are not used and/or are not alternately applied and/or are not alternately applied repeatedly).

In certain embodiments, changing parameters of the ultrasound acoustic energy or MI can be performed to induce and/or enhance an expression of a transgene in a cell or an organ of a subject. In one aspect, provided herein are methods of transfection by alternating the ultrasonic acoustic energy using a first MI and a second MI. In some embodiments, the first MI that results in stable vibrational cavitation is applied prior to the second MI, which results in inertial cavitation. In some embodiments, the ultrasonic acoustic energy using the first MI and the second MI are reapplied a number of times to increase transfection efficiency at the target cell. In some embodiments, during the application of sonoporation, the ultrasonic acoustic energy is applied at the first MI continuously except for when the ultrasonic acoustic energy is applied at the second MI. For example, applying an ultrasonic acoustic energy to the target cell at the first MI then applying an ultrasonic acoustic energy to the target cell at the second MI are repeated between 4 to 18 times. In some embodiments, applying an ultrasonic acoustic energy to the target cell at the first MI then applying an ultrasonic acoustic energy to the target cell at the second MI are repeated an unlimited number of times. In one aspect, during this time, the ultrasonic acoustic energy of the first MI is applied continuously except for when the ultrasonic acoustic energy of the second MI is applied.

In some embodiments, the first MI ranges from about 0.05 to about 0.4. In some embodiments, the first MI ranges from about 0.05 to about 0.3. In some embodiments, the first MI ranges from about 0.05 to about 0.4. In some embodiments, the first MI ranges from about 0.09 to about 0.3.

In some embodiments, the second MI ranges from about 0.5 to about 2.0. In some embodiments, the second MI ranges from greater than 1.4 to about 1.8. In some embodiments, the second MI ranges from greater than 1.4 to about 2.0. In some embodiments, the second MI ranges from about 1.5 to about 2.0.

In some embodiments, applying the ultrasonic acoustic energy at the first MI, and the applying the ultrasonic acoustic energy at the second MI are repeated at least 4, 6, 8, 12, 18, 20, 25, 30, 40, or 50 times. In some embodiments, applying the ultrasonic acoustic energy at the first MI, and the applying the ultrasonic acoustic energy at the second MI are repeated between 4 and 18 times. In some embodiments, applying the ultrasonic acoustic energy at the first MI, and the applying the ultrasonic acoustic energy at the second MI are repeated between 6 and 12 times. In some embodiments, applying the ultrasonic acoustic energy at the first MI, and the applying the ultrasonic acoustic energy at the second MI are repeated between 8 and 10 times. In some embodiments, applying the ultrasonic acoustic energy at the first MI, and the applying the ultrasonic acoustic energy at the second MI are repeated between 8 and 18 times.

In some embodiments, the applying the ultrasound acoustic energy comprises applying the ultrasonic acoustic energy at the first MI, and the applying the ultrasonic acoustic energy at the second MI, without ceasing applying the ultrasonic acoustic energy at the first MI, and the applying the ultrasonic acoustic energy at the second MI. In some embodiments, the applying the ultrasound acoustic energy comprises applying the ultrasonic acoustic energy at the first MI except for when the ultrasonic acoustic energy is applied at the second MI. In some embodiments, an ultrasound probe applying the ultrasonic acoustic energy is in constant contact with the surface of the subject's skin at the location of application (e.g., abdomen, chest wall, skull, etc.). In some embodiments, an ultrasound transducer that applies the ultrasonic acoustic energy to the target cell is continuously in contact with tissue of the subject and is continuously either (1) applying the ultrasound acoustic energy to the subject or (2) receiving reflected ultrasound energy from the subject. In certain embodiments, a transitory (e.g., third, fourth, etc.) ultrasonic acoustic energy is applied between application of the first and second ultrasonic acoustic energies. In certain embodiments, applying the ultrasound acoustic energy comprises applying the ultrasonic acoustic energy without regard to an EKG gating signal regulating the application of the ultrasound acoustic energy. In certain embodiments, applying the ultrasound acoustic energy comprises applying the ultrasonic acoustic energy without turning off power to the ultrasound transducer off. In some embodiments, applying the ultrasound acoustic energy comprises an ultrasound transducer sending ultrasound acoustic energy or receiving reflected ultrasound acoustic energy at least 95% of a period of time in which an ultrasound transducer continuously is contacting the subject.

In some instances, the ultrasonic acoustic energy of the second MI (e.g., high MI) is applied using a pulse. In some instances, a pulse comprises applying the ultrasonic acoustic energy in a short pulse (e.g., microsecond length pulse). In some cases, the high MI is applied with the pulse, results in induces inertial cavitation and destruction of the sonoactive microstructure, resulting in the disruption of cell membrane and vascular endothelial integrity, transducing the nucleic acid payload to the cell. In some instances, the pulse is applied with a duration of about 1 µs to about 200 µs. In some instances, the pulse is applied with a duration of about 1 µs to about 200 µs or greater.

In some embodiments, applying the ultrasonic acoustic energy at the second MI comprises applying the ultrasonic acoustic energy at the second MI using a pulse. In some instances, the duration of the second MI applied ranges from 0.1 µs to about 200 µs. In some instances, the duration of the second MI applied ranges from 1 µs to about 200 µs or greater. In some embodiments, applying the ultrasonic acoustic energy at the second MI comprises applying the ultrasonic acoustic energy at the second MI using a pulse with a duration of about 1 µs to about 200 µs. In some embodiments, applying the ultrasonic acoustic energy at the second MI comprises applying the ultrasonic acoustic energy at the second MI using a pulse with a duration of up to 200 µs. In some embodiments, applying the ultrasonic acoustic energy at the second MI comprises applying the ultrasonic acoustic energy at the second MI using a pulse with a duration of about 1 µs to about 500 µs. In some embodiments, applying the ultrasonic acoustic energy at the second MI comprises applying the ultrasonic acoustic energy at the second MI using a pulse with a duration of up to 500 µs. In some embodiments, applying the ultrasonic acoustic energy at the second MI comprises applying the ultrasonic acoustic energy at the second MI using a pulse with a duration of about 2.3 µs. In some embodiments, applying the ultrasonic acoustic energy at the second MI comprises applying the ultrasonic acoustic energy at the second MI using a pulse with a duration of at least 2.3 µs. In some embodiments, applying the ultrasonic acoustic energy at the second MI comprises applying the ultrasonic acoustic energy at the second MI using a pulse with a duration ranging from 1-500 µs. In some embodiments, applying the ultrasonic acoustic energy at the second MI comprises applying the ultrasonic acoustic energy at the second MI using a pulse with a duration ranging from 0.1-500 µs.

In some cases, alternating the ultrasonic acoustic energy between the first MI and the second MI for a number of times also allows reperfusion of the sonoactive microstructures and the nucleic acid constructs to the target cell, tissue, or organ, following disruption of the sonoactive microstructures within or proximal to the target cell, tissue, or organ.

In some embodiments, the repeating application of ultrasonic acoustic energy between the first MI and the second MI comprises applying the ultrasonic acoustic energy at the first MI for an amount of time sufficient to permit reperfusion of the sonoactive microstructures in a tissue comprising the target cell before reapplying the ultrasonic acoustic energy at the second MI.

In some embodiments, the method comprises applying the ultrasonic acoustic energy at the first MI for 1-30 seconds before repeating the applying the ultrasound acoustic energy of (d). In some embodiments, the method comprises applying the ultrasonic acoustic energy at the first MI for 5-15 seconds before repeating the applying the ultrasound acoustic energy of reapplying the ultrasonic acoustic energy at the second MI. In some embodiments, the method comprises applying the ultrasonic acoustic energy at the first MI for 10 seconds before repeating the applying the ultrasound acoustic energy of reapplying the ultrasonic acoustic energy at the second MI.

In some instances, the duration of the first MI applied ranges from about 2 s to about 30 s. In some embodiments, applying the ultrasonic acoustic energy at the first MI comprises initially applying the ultrasonic acoustic energy at the first MI from about 2 s to about 30 s.

In some embodiments, applying the ultrasonic acoustic energy at the first MI, and the applying the ultrasonic acoustic energy at the second MI are repeated for a total amount of time ranging from about 1 s to about 60 m. In some embodiments, applying the ultrasonic acoustic energy at the first MI, and the applying the ultrasonic acoustic energy at the second MI are repeated for a total amount of time ranging from about 60 s to about 120 s.

In some embodiments, applying the ultrasonic acoustic energy at the first MI induces stable vibration cavitation of the sonoactive microstructures. In some embodiments, applying the ultrasonic acoustic energy at the first MI does not induce substantial disruption of the sonoactive microstructures. In some embodiments, applying the ultrasonic acoustic energy at the first MI does not induce substantial disruption of the sonoactive microstructures in a vasculature space and an extravascular space, or induces stable vibration cavitation of the sonoactive microstructures in a vasculature space and an extravascular space.

In some embodiments, applying the ultrasonic acoustic energy at the first MI induces formation of an intercellular gap or an interendothelial gap or endocytosis. In some embodiments, the intercellular gap or the interendothelial gap ranges from about 10 nm to about 10 um. In some embodiments, the stable vibration cavitation of the sonoactive microstructures moves the nucleic acid construct from an intravenous space into an interstitial space or into cytoplasm.

In some embodiments, applying the ultrasonic acoustic energy at the second MI induces inertial cavitation of the sonoactive microstructures to disrupt the sonoactive microstructures. In some embodiments, applying the ultrasonic acoustic energy at the second MI induces inertial cavitation of the sonoactive microstructures to disrupt the sonoactive microstructures in a vasculature space and an extravascular space. In some embodiments, the extravascular spaces comprise an interstitial space, a subcutaneous space, intramuscular or a lymphatic space. In some embodiments, the extravascular spaces comprise an extravascular tissue. In some embodiments, the extravascular tissue comprises an interstitial space, a cytoplasmic space, a subcutaneous, a lymph tissues, muscular or combinations thereof.

In some embodiments, applying the ultrasonic acoustic energy at the second MI induces formation of a pore in a membrane of the cell. In some embodiments, the formation of a pore in a membrane of the cell ranges from about 10 nm to about 10 um.

In some embodiments, the ultrasound acoustic energy is applied using an ultrasound probe applying ultrasound acoustic energy to the tissue. In some embodiments, the acoustic radiation force is applied using an ultrasound probe applying ultrasound acoustic energy to the tissue. In some embodiments, the ultrasound probe comprises a plurality of piezoelectric elements configured to emit ultrasound acoustic energy. In some embodiments, portions of the plurality of piezoelectric elements are arranged in one or more arrays. In some embodiments, the ultrasound probe is a phased array transducer comprising a plurality of piezoelectric elements configured to emit ultrasound acoustic energy. In some embodiments, the ultrasound probe is a phased array ultrasound probe, a linear ultrasound probe, a curvilinear ultrasound probe, a convex array ultrasound probe, an endocavitary ultrasound probe, a 3D ultrasound probe, a 4D ultrasound probe, a Doppler ultrasound probe, or a color doppler ultrasound probe.

In some embodiments, the nucleic acid construct comprises a miniplasmid backbone. As used herein, the term "miniplasmid (mpDNA)" refers to nucleic acid constructs that are smaller in size (i.e., contain fewer base pairs (bp)) than conventional plasmids or pDNA. In some embodiments, mpDNA constructs comprise a backbone smaller than 1 kb. In some embodiments, mpDNA constructs are smaller than 1000 bp excluding an expression cassette. In some embodiments, mpDNA constructs comprise a backbone smaller than 0.5 kb. In some embodiments, mpDNA constructs are smaller than 500 bp excluding an expression cassette. In some embodiments, the miniplasmid does not comprise a bacterial origin of replication. As used herein, the term "Nanoplasmid™" (e.g., Nanoplasmid sourced from Aldevron, Fargo, South Dakota.) refers to a small mpDNA construct that has a plasmid backbone that is less than 500 bp and does not contain an antibiotic resistance gene.

Miniplasmid DNA nucleic acid constructs can be utilized to deliver an expression cassette, a transgene, or a nonendogenous gene to cells in target cell-types, tissues or organs. In some embodiments, the miniplasmid comprises less than 1000 base pairs excluding an expression cassette. In some embodiments, the miniplasmid comprises less than 500 base pairs excluding an expression cassette. In some embodiments, the miniplasmid does not comprise antibiotic resistant genes. In some embodiments, the miniplasmid does not comprise a bacterial genome. In some embodiments, the miniplasmid comprises a therapeutic transgene and/or a regulatory element. In some embodiments, the miniplasmid is a nanoplasmid. In some embodiments, the miniplasmid construct enhances the expression of the nonendogenous gene or a therapeutic transgene when used in conjunction with the disclosed methods and ultrasound acoustic profiles. In some embodiments, the nanoplasmid construct enhances the expression of the nonendogenous gene or a therapeutic transgene. In some embodiments, durability of expression of a protein encoded by the nucleic acid payload may be increased relative to expression of the same protein in a larger plasmid (e.g., a plasmid of greater than 2 kb in length, excluding the transgene). In some embodiments, durability of expression of a protein encoded by the nucleic acid payload may be increased relative to expression of the same protein in another nucleic acid construct.

In some embodiments, the nucleic acid construct is a miniplasmid e.g., a construct comprising a backbone of less than 1000 bp or less than 500 bp) coupled to a nucleic acid payload.

In some embodiments, the miniplasmid further comprises an expression cassette. As used herein, an expression cassette comprises nucleic acid sequences encoding nucleic acid payload, e.g., an expression cassette comprising a transgene. The expression cassette further comprises a regulatory element such as a promoter, enhancer, ribosome binding site, or transcription termination signal.

In some embodiments, the method further includes inducing expression of the nucleic acid payload and maintaining expression of a protein encoded by the nucleic acid payload for at least 1, 2, 3, 4, 5, 6, or 7 days following administration of the nucleic acid construct, the sonoactive microstructures, and application of the ultrasonic acoustic energy to the target cell. In some embodiments, the method further includes inducing expression of the nucleic acid payload and maintaining expression of a protein encoded by the nucleic acid payload for at least 1, 2, 3, 4, 5, 6, or 7 days following administration of the nucleic acid construct, the sonoactive microstructures, and application of the ultrasonic acoustic energy to the target cell.

In some embodiments, the method further includes increasing expression of the nucleic acid payload by increasing the dosage of the nucleic acid payload administered to the subject. In some embodiments, the method further includes increasing expression of the nucleic acid payload by increasing the dosage of the nucleic acid payload administered to the subject in a linear manner. In some embodiments, the method further includes increasing expression of the nucleic acid payload by administering at least 5, 50, 250, or 500 ug of the nucleic acid payload to the subject.

In some embodiments, the nucleic acid payload comprises an expression cassette. In some embodiments, the expression cassette comprises a transgene. In some embodiments, the nucleic acid payload comprises a transgene (endogenous or non-endogenous). In some embodiments, the transgene comprises a therapeutic transgene. In some embodiments, inducing expression of the nucleic acid payload comprises inducing expression of the therapeutic transgene. In some embodiments, the transgene comprises a detectible marker. In some embodiments, the transgene comprises luciferase. In some embodiments, inducing expression of the nucleic acid payload comprises inducing expression of luciferase.

In some embodiments, a nucleic acid payload comprises a regulatory element such as a promoter, (e.g., APOE-ATT). In some embodiments, a total amount (e.g., dose) of DNA administered to a subject for purposes of sonoporation can range from 100 microgram to 200 mg.

In some embodiments, the therapeutic payload is a non-endogenous gene. In some embodiments, the nucleic acid payload is configured to perform gene augmentation, gene replacement, gene editing, gene knockdown, or gene knock-out.

In some embodiments, the nucleic acid construct comprises one or more regulatory elements, such as a promoter, enhancer, ribosome binding site, or transcription termination signal. Examples of promoters contemplated herein include, but are not limited to, e.g., CMV promoter, UbC promoter, CAG promoter, EF-1α promoter, ApoE promoter, ApoE-AAT1 promoter, 3XSERP promoter, or P3-hybrid promoter.

In some embodiments, the nucleic acid construct comprises a promoter sequence comprising CAG. In some embodiments, the nucleic acid construct comprises a promoter sequence comprising ApoE. In some embodiments, the nucleic acid construct comprises a promoter sequence comprising ApoE-AAT. In some embodiments, the nucleic acid construct comprises a promoter sequence comprising SERP. In some embodiments, the nucleic acid construct comprises a promoter sequence comprising P3.

In some embodiments, inducing expression of the nucleic acid payload comprises inducing production of RNA encoded by the payload. In some embodiments, inducing expression of the nucleic acid payload comprises inducing production of protein encoded by the payload.

In some embodiments, the therapeutic nucleic acid sequence is referred to a payload. In some embodiments, the therapeutic nucleic acid sequence comprises a payload which comprises a therapeutic RNA. In some embodiments, the therapeutic RNA is an mRNA. In some embodiments, the therapeutic RNA is an RNA interference (RNAi) agent, e.g., a double-stranded RNA, a single-stranded RNA, a micro-RNA (miRNA), a short interfering RNA (siRNA), short hairpin RNA (shRNA), or a triplex-forming oligo-nucleotide. In some embodiments, the therapeutic RNA is a catalytically active RNA molecule (ribozyme). In some embodiments, the therapeutic RNA is a transfer RNA (tRNA). In some embodiments, the therapeutic RNA comprises one or more chemical modifications (e.g., one or more modified nucleobases, nucleosides, or nucleotides). In some embodiments, the nucleic acid construct is configured to perform gene augmentation, gene replacement, base editing, base knockdown, gene editing gene knockdown, or gene knockout. In some embodiments, delivering the nucleic acid payload to the target cell of the subject increases or decreases expression of a gene in the target cell.

In some embodiments, the therapeutic nucleic acid sequence is referred to a payload. In some embodiments, the therapeutic nucleic acid sequence comprises a payload which comprises one or more components of a gene editing system. In some embodiments, the payload comprises a nuclease or engineered nuclease suitable for gene editing. In some embodiments, the nuclease is delivered as a polypeptide. In some embodiments, the nuclease is delivered as a nucleic acid encoding the nuclease. In some embodiments, the gene editing system is a CRISPR/Cas system. In some embodiments, the payload comprises a gRNA or a nucleic acid molecule encoding a gRNA (e.g., a plasmid encoding the gRNA). In some embodiments, the payload comprises a Cas protein or homologs or variants thereof, or a nucleic acid molecule encoding the Cas protein or homologs or variants thereof. In some embodiments, the payload comprises a TALEN or a nucleic acid molecule encoding the TALEN. In some embodiments, the payload comprises a zinc-finger nuclease (ZFN) or a nucleic acid encoding the ZFN. In some embodiments, the nuclease is an engineered nuclease. In some embodiments, the engineered nuclease is catalytically inactive. In some embodiments, the engineered nuclease is a fusion protein comprising the engineered nuclease a regulatory protein or an enzyme, or a functional domain thereof (e.g., a nuclease fused to a transcriptional regulatory domain or a nuclease fused to a deaminase) In some embodiments, the payload may further comprise a template DNA molecule suitable for knock-in to the subject's genome via non-homologous end joining (NHEJ) or homology directed repair (HDR).

Sonoactive microstructures (also referred to as acoustic microspheres or "microbubbles") contemplated herein include, but are not limited to, those used as ultrasonic imaging contrast agents. In some embodiments, the sonoactive microstructures comprise a phospholipid stabilized microstructure. In some embodiments, the phospholipid stabilized microstructure comprises a high molecular wight gas core, or a perflutran core. Examples of sonoactive microstructures include, but are not limited to, OPTISON (GE Healthcare), Sonazoid (GE Healthcare), or DEFINITY and Definity RT (Lantheus Medical Imaging, Inc). In some embodiments, the sonoactive microstructures are LUMA-SON (Bracco) (sulfur hexafluoride lipid-type A microspheres). In some embodiments, the sonoactive microstructures are SonoVue (sulfur hexafluoride microbubbles). In some embodiments, the sonoactive microstructures comprise a protein stabilized microstructure. In some embodiments, the sonoactive microstructures are Optison microbubbles.

The sonoactive microstructures can be administered prior to, after, or simultaneous (e.g., co-administered) with the administration of the nucleic acid construct (or nucleic acid payload). In some embodiments, the nucleic acid construct and the sonoactive microstructures are coadministered. In some embodiments, the administering of the nucleic acid construct and the sonoactive microstructures occurs serially, concurrently, sequentially, or continuously. In some embodiments, the administering of the nucleic acid construct and the sonoactive microstructures occurs serially. In some embodiments, the administering of the nucleic acid construct and the sonoactive microstructures occurs concurrently. In some embodiments, the administering of the nucleic acid construct and the sonoactive microstructures occur sequentially. In some embodiments, the administering of the nucleic acid construct and the sonoactive microstructures occurs continuously.

In some embodiments, the nucleic acid construct is administered at a dosage of about 0.5 mg/kg to about 500 mg/kg. In some embodiments, at least $2\times10^{13}$ copies of the nucleic acid construct are administered to the subject. In some embodiments, about $2\times10^{13}$ to about $3\times10^{13}$ copies of the nucleic acid construct are administered to the subject. In some embodiments, each nucleic acid construct comprises a copy of a transgene.

In some embodiments, the sonoactive microstructures are administered at a dosage of about 1-50 mL, for example 1 mL of Optison. The sonoactive microstructures may be administered at a concentration of about 5M to about 8M microstructures per mL. In some embodiments, the sonoactive microstructures are administered at a concentration of about $5\times10^{8}$ to about $1.2\times10^{9}$ microstructures/mL, for example $1\times10^{9}$ of Definity RT. In some embodiments, the sonoactive microstructures are administered at a concentration of about 0.1 to about 0.8 mg/kg. In some embodiments, the sonoactive microstructures are administered at a concentration of about 0.1 to about 1.0 mL/kg. In some embodiments, the sonoactive microstructures are administered at a concentration of about $10^{9}$ microstructures/mL. In some embodiments, the sonoactive microstructures are administered at a concentration of about $5\times10^{8}$ to about $8\times10^{8}$ microstructures/mL.

As used herein, concentrations of microstructures/mL refers to the concentration of the sonoactive microstructures in a pharmaceutical composition immediately prior to administration to the subject. In some embodiments, the sonoactive microstructures are administered at a concentration of about $5\times10^{8}$ to about $1.2\times10^{10}$ microstructures/mL. In some embodiments, the sonoactive microstructures are administered at a dosage of about 1-50 mL, for example 1 mL of a protein-stabilized sonoactive microstructure (e.g., Optison). In some embodiments, the protein-stabilized sonoactive microstructure (e.g., Optison) has a diameter of 3-4.5 micrometers. The sonoactive microstructures may be administered at a concentration of about 5M (million) to about 8M microstructures per mL. In some embodiments, $1\times10^{9}$ of phospholipid stabilized sonoactive microstructures (e.g., Sonazoid) are administered. In some embodiments, the phospholipid stabilized sonoactive microstructures (e.g., Sonazoid) comprise a diameter of 1-5 micrometers. In some embodiments, the sonoactive microstructures are administered at a concentration of about 0.1 to about 0.8 mg/kg. In some embodiments, the sonoactive microstructures are administered at a concentration of about 0.1 to about 1.0 mL/kg. In some embodiments, the sonoactive microstructures are administered at a concentration of about $10^{9}$ microstructures/mL. In some embodiments, the sonoactive microstructures are administered at a concentration of at least $5\times10^{8}$ microstructures per mL. In some embodiments, the sonoactive microstructures are administered at a concentration of up to $1.2\times10^{10}$ microstructures/mL. In some embodiments, the sonoactive microstructures are administered at a concentration of $5\times10^{8}$ to $8\times10^{8}$ microstructures/mL.

In some embodiments, the nucleic acid construct and the sonoactive microstructures are mixed prior to being coadministered. In some instances, the sonoactive microstructures are mixed with the nucleic acid constructs before administering to the subject. In some instances, the sonoactive microstructures are mixed with the nucleic acid constructs along with additional buffers or agents such as saline or other biocompatible solutions with varying electrostatic charges and surface chemistries and ligands before administering to the subject. For example, Optison sonoactive microstructures can be mixed with a Nanoplasmid comprising a promoter operatively linked to a transgene (e.g., APOE-Fluc) and saline and are administered together. In some embodiments, administration of the sonoactive microstructures and nucleic acid constructs occurs simultaneously in that the sonoactive microstructures are mixed with a solution comprising the nucleic acid constructs prior to delivery to the subject. Such mixtures can comprise of 50% v/v of the sonoactive microstructures (e.g., Optison) and 50% v/v of a solution comprising a nucleic acid construct. Such mixtures can comprise varying percentages 5-90% v/v of the sonoactive microstructures.

In some embodiments, the administering of the nucleic acid construct and the sonoactive microstructures is by intravenous administration or subcutaneous or intramuscular or intra-arterial or inter-osseus or direct organ puncture. In some embodiments, administration of the sonoactive microstructures and nucleic acid constructs occurs simultaneously in that the sonoactive microstructures are mixed with a solution comprising the nucleic acid constructs prior to delivery to the subject. Such mixtures can comprise of 50% v/v of the sonoactive microstructures (e.g., Optison) and 50% v/v of a solution comprising a nucleic acid construct. Such mixtures can comprise varying percentages 5-90% v/v of the sonoactive microstructures. In some cases, mixtures may comprise a ratio of one part solution comprising the nucleic acid constructs to four or more parts solution comprising the sonoactive microstructures.

In some embodiments, after administering of the nucleic acid construct and sonoactive microstructures, the ultrasound acoustic energy is applied at the target cell, tissue, or organ.

In some embodiments, inducing expression of the nucleic acid payload comprises inducing expression within about 3 to about 12 hours of administering the payload. In some embodiments, inducing expression of the nucleic acid payload comprises inducing expression within about 3 hours of administration. In some embodiments, inducing expression of the nucleic acid payload comprises inducing expression within about 6 hours of administration. In some embodiments, inducing expression of the nucleic acid payload comprises inducing expression within about 12 hours of administration.

Undesirable effects on living cells or tissues can occur due to ultrasound applications. In some embodiments, the present disclosure provides methods for improvement of gene transfection and not result in substantial DNA or cell damage in the target cells, tissues, or organs, using sonoporation by alternating ultrasonic acoustic energy between the first MI and the second MI. In some embodiments, the method does not result in substantial cellular damage to the target cell. In some embodiments, the method results in less than 1%, 5%, or 10% of target cells undergoing apoptosis.

Cellular damage can be detected using apoptotic biomarkers. For example, in liver, detection of released hepatocellular transaminases, e.g., serum alanine aminotransferase (ALT) or aspartate aminotransferase (AST), can be an indicator of apoptotic hepatocytes. Additional apoptotic biomarkers comprise interleukin 6 (IL6) or B-cell lymphoma 2 (BCL2 or BCL2 apoptosis regulator). In some embodiments, the following biomarkers for cellular damage are not detected at apoptotic levels following delivering the nucleic acid payload to the target cell of the subject: ALT, AST, IL6, BCL2, or combinations thereof. In some embodiments, the following biomarkers for cellular damage are not clinically elevated following delivering the nucleic acid payload to the target cell of the subject: ALT, AST, IL6, BCL2, or combinations thereof. In some embodiments, the following biomarkers for cellular damage are not detected at apoptotic levels following delivering the nucleic acid payload to the target cell of the subject: ALT, AST, IL6, BCL2, or combinations thereof, and, optionally wherein the target cell is in a liver. In some embodiments, the following biomarkers for cellular damage are not clinically elevated following delivering the nucleic acid payload to the target cell of the subject: ALT, AST, 1L6, BCL2, or combinations thereof, and, optionally wherein the target cell is in a liver. In some embodiments, the following biomarkers for cellular damage are not clinically elevated following delivering the nucleic acid payload to the target cell of the subject: creatinine levels in urine, albumin to creatine ratio in urine, creatinine levels in blood, a glomerular filtration rate, blood in urine, protein levels in urine, or an osmolality of urine, and, optionally wherein the target cell is in a kidney. In some embodiments, the following biomarkers for cellular damage are not clinically elevated following delivering the nucleic acid payload to the target cell of the subject: troponin levels in blood, or creatinine phosphokinase, and, optionally wherein the target cell is in a heart or skeletal muscle. In some embodiments, ALT is not detected at levels exceeding 60, 65, 70, 75, 80, 85, 90, 95, 100, 125, 150, 175, or 200 U/L following delivering the nucleic acid payload to the target cell of the subject. In some embodiments, AST is not detected at levels exceeding 225, 250, 275, or 300 U/L following delivering the nucleic acid payload to the target cell of the subject. In some embodiments, IL6 is not detected at levels exceeding 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 4.2, 4.4, 4.6, 4.8, 5, 5.2, 5.4, 5.6, 5.8, or 6 pg/mL following delivering the nucleic acid payload to the target cell of the subject.

A sonoporation treatment using the methods described herein can be used to induce expression of a nucleic acid payload in a cell in a liver or a cell in a kidney.

In another aspect, the present disclosure provides a kit to perform the methods described herein. In some embodiments, the kit comprises: (a) a first container comprising microbubbles for sonoporation; and (b) a second container comprising nucleic acids (e.g., miniplasmids) comprising a transgene and a mixture chamber (reservoir, syringe, Y-port, etc.). In some embodiments, the kit further comprises instructions for administration of ultrasound acoustic energy in connection with administration of the microbubbles and the nucleic acids.

In some embodiments, the first container and second container are configured to induce the expression of the transgene in the target cell of the subject within 20 hours after the transfection.

In some embodiments, the kit further comprises instructions for software and hardware directions for the safe and effective operation of an ultrasound machine sufficient to disrupt the sonoactive microstructures to generate the sonoporation processes which include but are not limited to the following: disrupting the microstructures, inducing inertial and stable cavitation, promoting endocytosis and inter-endothelial gap formation, microstreaming at cell surfaces, thereby increasing transfection of a nucleic acid payload to a cell. In some embodiments, the instructions described methods for improvement of gene transfection using sonoporation by applying alternating ultrasonic acoustic energy applying an acoustic radiation force to a subject and inducing a shear wave in a tissue comprising the target cell. In some embodiments, the instructions described methods for improvement of gene transfection using sonoporation by applying alternating ultrasonic acoustic energy between a first MI then a second MI. In some embodiments, the kit further comprises instructions for administration of the first container and the second container. Aspects disclosed herein provide a kit comprising: a sonoactive agent; and means for expressing a Factor VIII polypeptide in vivo at a level that is at least 1.5 fold greater than expression of SEQ ID NO. 3 Aspects disclosed herein provide a kit comprising: a sonoactive agent; and the nucleic acid composition of any embodiment disclosed herein. Aspects disclosed herein provide a cell comprising the FVIII polypeptide of any embodiment disclosed herein. Aspects disclosed herein provide a nucleic acid encoding the FVIII polypeptide. In some cases, the means for increasing expression of a Factor VIII polypeptide in vivo, for example, at a level that is at least 1.5 fold greater than expression of SEQ ID NO. 3, includes: a nucleic acid sequence having at least 80% sequence identity to SEQ ID NO: 6; a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence; a first regulatory element positioned upstream and directly coupled to the therapeutic nucleic acid sequence, a second regulatory element positioned downstream and directly coupled to the therapeutic nucleic acid sequence, the poly-adenylation signal positioned downstream and directly coupled to the second regulatory element, and the nuclear targeting sequence is positioned downstream and directly coupled to the poly-adenylation signal, one or more Inverted Terminal Repeat (ITR) sequences; a nucleic acid sequence comprising a sequence of any one of SEQ ID NO: 38, 39, or 44; and combinations thereof.

Exemplary Embodiments

Among the exemplary embodiments are:

1. A nucleic acid composition comprising a nucleic acid sequence having at least 80% sequence identity to SEQ ID NO: 6.

2. A nucleic acid composition comprising a therapeutic nucleic acid sequence, a first regulatory element comprising a promoter sequence operably linked to an intron sequence comprising a hemoglobin subunit gamma intron (hBGi) sequence positioned upstream of the therapeutic nucleic acid sequence, and a second regulatory element comprising a woodchuck hepatitis posttranscriptional regulatory element 3 (WPRE3) sequence positioned downstream of the therapeutic nucleic acid sequence.

3. A nucleic acid composition comprising a nucleic acid sequence having at least 96% sequence identity to SEQ ID NO: 45.

4. The nucleic acid composition of embodiment 2, further comprising a nucleic acid sequence having at least 80% sequence identity to SEQ ID NO: 6.

5. The nucleic acid composition of embodiment 1, further comprising a therapeutic nucleic acid sequence, wherein the nucleic acid sequence having at least 80% sequence identity to SEQ ID NO: 6 increases expression of the therapeutic nucleic acid sequence in a cell by at least 1.25-fold as compared to an otherwise identical control composition lacking the nucleic acid sequence having at least 80% sequence identity to SEQ ID NO: 6.

6. The nucleic acid composition of embodiment 1 or embodiment 4, further comprising a first regulatory element comprising a promoter sequence operably linked to an intron sequence, and a second regulatory element comprising a WPRE3 sequence.

7. The nucleic acid composition of any one of embodiments 2 or 6, wherein the first regulatory element is upstream of the therapeutic nucleic acid sequence.

8. The nucleic acid composition of any one of embodiments 2, 6, or 7, wherein the second regulatory element is downstream of the therapeutic nucleic acid sequence.

9. The nucleic acid composition of embodiment 8, wherein the each of the first regulatory element and the second regulatory element are operably linked to the therapeutic nucleic acid sequence.

10. The nucleic acid composition of any one of embodiments 1 or 4, wherein the nucleic acid sequence having at least 80% sequence identity to SEQ ID NO: 6 has at least 81, 82, 83, 84, 85, 86, 87, 88, 89, 90, 91, 92, 93, 94, 95, 96, 97, 98, or 99% sequence identity or has 100% sequence identity to SEQ ID NO: 6.

11. The nucleic acid composition of any one of embodiments 1, 4 or 10, wherein the nucleic acid sequence having at least 80% sequence identity to SEQ ID NO: 6 is operably coupled to a second regulatory element comprising a WPRE3 sequence.

12. The nucleic acid composition of any one of embodiments 2, or 6-9, wherein the first regulatory element comprises a sequence of SEQ ID NO: 9.

13. The nucleic acid composition of any one of embodiments 2, or 6-10, wherein the second regulatory element comprises a sequence of SEQ ID NO: 4.

14. The nucleic acid composition of any one of embodiments 1, 4, or 10-11, wherein the nucleic acid sequence having at least 80% sequence identity to SEQ ID NO: 6 comprises a nuclear targeting sequence, wherein the nuclear targeting sequence increases expression of the therapeutic nucleic acid sequence in a cell by at least 1.25, 1.5, 2, 3, 4, 5, 6, 7, or 8-fold, as compared to an otherwise identical control composition that lacks the nuclear targeting sequence.

15. The nucleic acid composition of any one of embodiments 5 or 14, wherein the cell is a liver cell, a kidney cell, a brain cell, a muscle cell, a cardiac cell, a pancreatic cell, a blood cell, or a tumor cell.

16. The nucleic acid composition of embodiment 15, wherein the cell is a hepatocyte.

17. The nucleic acid composition of any one of embodiments 2, 5, or 7-9, or 14 wherein the therapeutic nucleic acid sequence comprises a sequence encoding a therapeutic transgene.

18. The nucleic acid composition of embodiment 17, wherein the therapeutic transgene encodes a FVIII, FIX, COL4A3, COL4A4, COL4A5, PKD1, or a PKD2 protein.

19. The nucleic acid composition of any one of embodiments 2, 5, or 7-9, or 14, wherein the therapeutic nucleic acid sequence comprises a CRISPR/Cas system, a DNA molecule suitable for knock-in via homologous end joining (NHEJ), a DNA molecule suitable for homology directed repair (HDR), a gRNA, an RNA interference (RNAi) agent, a micro-RNA (miRNA), a short interfering RNA (siRNA), short hairpin RNA (shRNA), or a triplex-forming oligo-nucleotide, a catalytically active RNA molecule, a transfer RNA (tRNA), a base editor, a prime editor, a recombinase, an integrase, a transposase, a reverse transcriptase, a spliceosomal RNA, an adenosine deaminase, or combinations thereof.

20. The nucleic acid composition of any one of embodiments 2, 5, or 7-9, or 14, wherein the therapeutic nucleic acid sequence encodes a therapeutic agent comprising a Cas protein or homolog or variant thereof, a TALEN, a ZFN, or combinations thereof.

21. The nucleic acid composition of any one of the preceding embodiments, wherein the nucleic acid composition comprises a miniplasmid backbone.

22. The nucleic acid composition of embodiment 21, wherein the miniplasmid backbone is smaller than 1 kb.

23. The nucleic acid composition of embodiment 21, wherein the miniplasmid backbone comprises a sequence of SEQ ID NO: 7.

24. The nucleic acid composition of any one of embodiments 2, 5, or 7-9, or 14, wherein the therapeutic nucleic acid sequence encodes a protein which provides a therapeutic effect to a subject.

25. The nucleic acid composition of any one of the preceding embodiments, wherein the nucleic acid composition is an isolated nucleic acid molecule.

26. The nucleic acid composition of any one of the preceding embodiments, wherein the nucleic acid composition does not comprise an origin of replication or a bacterial origin of replication.

27. The nucleic acid composition of any one of embodiments 2 or 6, wherein the intron sequence comprises a hemoglobin subunit gamma intron (hBGi) sequence.

28. The nucleic acid composition of any one of the preceding embodiments, further comprising a poly-adenylation signal.

29. The nucleic acid composition of embodiment 28, wherein the poly-adenylation signal is positioned downstream of the second regulatory element.

30. The nucleic acid composition of embodiment 28, wherein the poly-adenylation signal is positioned downstream of the therapeutic nucleic acid sequence.

31. The nucleic acid composition of embodiment 28, wherein the poly-adenylation signal is positioned upstream of a nuclear targeting sequence.

32. The nucleic acid composition of any one of embodiments 2 or 6, wherein the promoter sequence comprises an Apolipoprotein E-Alpha-1-Antitrypsin (APOE-AAT) promoter sequence.

33. The nucleic acid composition of embodiment 31, wherein the first regulatory element is positioned upstream and directly coupled to the therapeutic nucleic acid sequence, the second regulatory element is positioned downstream and directly coupled to the therapeutic nucleic acid sequence, the poly-adenylation signal is positioned downstream and directly coupled to the second regulatory element, and wherein the nuclear targeting sequence is positioned downstream and directly coupled to the poly-adenylation signal.

34. The nucleic acid composition of any one of the preceding embodiments, wherein the nucleic acid composition further comprises one or more Inverted Terminal Repeat (ITR) sequences.

35. The nucleic acid composition of embodiment 34, wherein a first ITR sequence is positioned upstream of the therapeutic nucleic acid sequence, promoter sequence, first regulatory element, and/or nuclear targeting sequence.

36. The nucleic acid composition of embodiment 35, wherein a second ITR sequence is positioned downstream of the therapeutic nucleic acid sequence, promoter sequence, first regulatory element, and/or nuclear targeting sequence.

37. The nucleic acid composition of any one of the preceding embodiments, wherein the therapeutic nucleic acid sequence comprises a nucleic acid sequence of SEQ ID NO: 32, or of SEQ ID NO: 33.

38. The nucleic acid composition of any one of the preceding embodiments, wherein the nucleic acid composition is a non-viral vector.

39. The nucleic acid composition of embodiment 37, wherein the nucleic acid composition is at least 5000, 5500, 6000, 6500, or 7000 bp in length.

40. The nucleic acid composition of any one of the preceding embodiments, wherein the nucleic acid composition encodes a full-length gene.

41. The nucleic acid composition of any one of the preceding embodiments, wherein the nucleic acid composition encodes a nucleic acid sequence of SEQ ID NO: 38 or SEQ ID NO: 44.

42. The nucleic acid composition of any one of the preceding embodiments, wherein the nucleic acid composition encodes a nucleic acid sequence of SEQ ID NO: 43.

43. The nucleic acid composition of any one of the preceding embodiments, wherein the nucleic acid composition comprises a sequence of SEQ ID NO: 45.

44. The nucleic acid composition of any one of the preceding embodiments, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2, wherein the B domain comprises SEQ ID NO: 27; and wherein one or both of:
(a) the A1 domain comprises at least one amino acid substitution relative to SEQ ID NO: 36; and
(b) the A3 domain comprises at least two amino acid substitutions as compared to SEQ ID NO: 37.

45. A nucleic acid composition comprising a therapeutic nucleic acid sequence, wherein the therapeutic nucleic acid sequence encodes a FVIII polypeptide having an A1 domain, and A2 domain, a non-naturally occurring B domain (B), an A3 domain, a C1 domain, and a C2 domain, positioned from N- to C-terminus as A1-A2-B-A3-C1-C2,
wherein the B domain comprises SEQ ID NO: 27; and
wherein one or both of:
(a) the A1 domain comprises at least one amino acid substitution relative to SEQ ID NO: 36; and
(b) the A3 domain comprises at least two amino acid substitutions as compared to SEQ ID NO: 37.

46. The nucleic acid composition of embodiment 44 or 45, wherein the therapeutic nucleic acid sequence encodes a Factor VIII (FVIII) polypeptide comprising an amino acid sequence having up to 2 amino acid substitutions relative to SEQ ID NO: 24.

47. The nucleic acid composition of any one of embodiments 44-46, wherein the B domain comprises no more than 6 consensus sites for N-linked glycosylation.

48. The nucleic acid composition of any one of embodiments 44-47, wherein the B domain comprises an amino acid sequence of SEQ ID NO: 28, and wherein the FVIII polypeptide is not more than 2300 amino acids in length.

49. The nucleic acid composition of any one of embodiments 44-48, wherein the B domain comprises an amino acid sequence of SEQ ID NO: 34.

50. The nucleic acid composition of any one of embodiments 44-49, wherein the A1 domain comprises substitution of phenylalanine at position 328 to serine when the Factor VIII polypeptide is aligned with SEQ ID NO: 35.

51. The nucleic acid composition of any one of embodiments 44-50, wherein the A1 domain comprises an amino acid sequence of SEQ ID NO: 25.

52. The nucleic acid composition of any one of embodiments 44-51, wherein the A3 domain comprises substitution of cysteine at position 1249 to glycine when the Factor VIII polypeptide is aligned with SEQ ID NO: 35.

53. The nucleic acid composition of any one of embodiments 44-52, wherein the A3 domain comprises substitution of cysteine at position 1253 to glycine when the Factor VIII polypeptide is aligned with SEQ ID NO: 35.

54. The nucleic acid composition of any one of embodiments 44-53, wherein the A3 domain comprises an amino sequence of SEQ ID NO: 29.

55. The nucleic acid composition of any one of embodiments 44-54, comprising an amino acid sequence of SEQ ID NO: 24.

56. The nucleic acid composition of any one of embodiments 44-55, for use a method of treating a genetic disorder requiring a gene therapy or a protein replacement therapy in a subject in need thereof, the method comprising administering the nucleic acid composition of any one of embodiments 44-55 to the subject.

57. The nucleic acid composition of any one of embodiments 44-55, for use a method of treating a bleeding disorder in a subject in need thereof, the method comprising administering the nucleic acid composition of any one of embodiments 44-55 to the subject.

58. The nucleic acid composition of embodiment 57, wherein the bleeding disorder is hemophilia A.

59. A cell comprising the nucleic acid composition of any one of the preceding embodiments.

60. A method of expressing a nucleic acid payload in a cell, the method comprising administering the nucleic acid composition of any one of the preceding embodiments to a subject.

61. The method of embodiment 60, further comprising applying an ultrasonic acoustic energy to the cell.

62. The method of any one of embodiments 61, further comprising administering to the subject a sonoactive agent.

63. The method of any one of embodiments 60, wherein the nucleic acid composition is administered to the subject as a naked nucleic acid.

64. The method of embodiment 60, further comprising contacting the cell with a lipid nanoparticle composition.

65. The method of embodiment 60, wherein the nucleic acid composition is administered to the subject as an encapsulated nucleic acid.

66. The method of embodiment 65, wherein the nucleic acid composition is encapsulated in a lipid or a polymer.

67. The method of embodiment 60, wherein the nucleic acid composition is administered to the subject as cationic polymer.

68. The method of embodiment 60, wherein the nucleic acid composition is administered to the subject in a viral vector.

69. The method of embodiment 61, further comprising administering to the subject a plurality of magnetic particles and applying a magnetic field to the cell.

70. The method of embodiment 69, wherein the magnetic particles comprise paramagnetic nanoparticles.

71. The method of any one of embodiments 60, or 68-69, further comprising applying an electrical field to the cell.

72. The method of any one of embodiments 60-71, wherein the nucleic acid composition is administered to the subject using a hydrodynamic injection.

73. The method of any one of embodiments 60-72, wherein the nucleic acid composition encodes a full-length polypeptide, wherein the method induces expression of the full-length polypeptide in-vivo.

74. The method of any one of embodiments 60-73, wherein the subject has a bleeding disorder, wherein the therapeutic nucleic acid sequence encodes FVIII or FIX, and wherein the method thereby treats the subject having the bleeding disorder.

75. The method of embodiment 74, wherein the bleeding disorder is hemophilia A.

76. A method of manufacturing the nucleic acid composition of any one of embodiments 1-55.

77. A Factor VIII polypeptide comprising:
   an A1 domain, and A2 domain, a non-naturally occurring B domain (B), an A3 domain, a C1 domain, and a C2 domain, positioned from N- to C-terminus as A1-A2-B-A3-C1-C2,
   wherein the B domain comprises SEQ ID NO: 27; and
   wherein one or both of:
   (a) the A1 domain comprises at least one amino acid substitution relative to SEQ ID NO: 36; and
   (b) the A3 domain comprises at least two amino acid substitutions as compared to SEQ ID NO: 37.

78. A Factor VIII polypeptide comprising an amino acid sequence having no more than 2 amino acid substitutions relative to SEQ ID NO: 24.

79. The FVIII polypeptide of embodiment 77, comprising an amino acid sequence having no more than 2 amino acid substitutions relative to SEQ ID NO: 24.

80. The FVIII polypeptide of embodiment 78, comprising:
   an A1 domain, and A2 domain, a non-naturally occurring B domain (B), an A3 domain, a C1 domain, and a C2 domain, positioned from N- to C-terminus as A1-A2-B-A3-C1-C2,
   wherein the B domain comprises SEQ ID NO: 27; and
   wherein one or both of:

(a) the A1 domain comprises at least one amino acid substitution relative to SEQ ID NO: 35; and
   (b) the A3 domain comprises at least two amino acid substitutions as compared to SEQ ID NO: 36.

81. The FVIII polypeptide of any one of embodiments 77-80, wherein the B domain comprises no more than 6 consensus sites for N-linked glycosylation.

82. The FVIII polypeptide of any one of embodiments 77-81, wherein the B domain comprises an amino acid sequence of SEQ ID NO: 28 and wherein the FVIII polypeptide is not more than 2300 amino acids in length.

83. The FVIII polypeptide of any one of embodiments 77-82, wherein the B domain comprises an amino acid sequence of SEQ ID NO: 34.

84. The FVIII polypeptide of any one of embodiments 77-83, wherein the A1 domain comprises substitution of phenylalanine at position 328 to serine when the FVIII polypeptide is aligned with SEQ ID NO: 35.

85. The FVIII polypeptide of any one of embodiments 77-84, wherein the A1 domain comprises an amino sequence of SEQ ID NO: 25.

86. The FVIII polypeptide of any one of embodiments 77-85, wherein the A3 domain comprises substitution of cysteine at position 1249 to glycine when the FVIII polypeptide is aligned with SEQ ID NO: 35.

87. The FVIII polypeptide of any one of embodiments 77-86, wherein the A3 domain comprises substitution of cysteine at position 1253 to glycine when the FVIII polypeptide is aligned with SEQ ID NO: 35.

88. The FVIII polypeptide of any one of embodiments 77-87, wherein the A3 domain comprises an amino sequence of SEQ ID NO: 29.

89. The FVIII polypeptide of any one of embodiments 77-88, comprising the amino acid sequence of SEQ ID NO: 24.

89A. The FVIII polypeptide of any one of embodiments 77-89, wherein the FVIII polypeptide comprises an improved coagulation activity as compared to a FVIII polypeptide lacking one or more of: a B domain other than SEQ ID NO: 27, an A1 domain lacking substitution of phenylalanine at position 328 to serine, or an A3 domain lacking substitution of cysteine at position 1249 to glycine.

90. The FVIII polypeptide of any one of embodiments 77-89A, for use a method of treating a bleeding disorder in a subject in need thereof, the method comprising administering the FVIII polypeptide to the subject.

91. A kit comprising:
   a. a sonoactive agent; and
   b. means for expressing a Factor VIII polypeptide in vivo at a level that is at least 1.5 fold greater than expression of SEQ ID NO: 3.

92. A kit comprising:
   a. a sonoactive agent; and
   b. the nucleic acid composition of any one of embodiments 1-55.

93. A cell comprising the FVIII polypeptide of any one of the preceding embodiments.

94. A nucleic acid encoding the FVIII polypeptide of any one of the preceding embodiments.

95. The nucleic acid composition of any one of the preceding embodiments, wherein the therapeutic nucleic acid sequence encodes the FVIII polypeptide of any one of the preceding embodiments.

96. A cell comprising the nucleic acid of any one of embodiments 94-95.

97. A method of treating a bleeding disorder comprising administering to a subject a nucleic acid encoding a human clotting factor in at least two treatments at least 48 hours apart, thereby achieving a therapeutic level of the clotting factor in the subject.

98. The method of embodiment 97, wherein the therapeutic level of the clotting factor is maintained for at least 10, 20, 30, 40, 50, 60, 70, 80, 90, 100, 110, 120, 130, 140, 145, or 150 days.

99. The method of any one of embodiments 97-98, further comprising administering to the subject ultrasound acoustic energy in the treatments.

100. The method of any one of embodiments 97-99, further comprising administering to the subject a sonoactive agent in the treatments.

101. The method of embodiment 99, wherein administering the ultrasound acoustic energy comprises applying the ultrasound energy at a mechanical index (MI) of at least 0.8, 1.3, 1.8, 1.9, or 2.2.

102. The method of embodiment 99, wherein administering the ultrasound acoustic energy comprises applying the ultrasound energy at a mechanical index (MI) of up to 0.4.

103. The method of embodiment 99, wherein administering the ultrasound energy comprises applying an acoustic radiation force to the subject.

104. The method of embodiment 103, wherein the ultrasound energy is applied at an intensity (ISPTA) of at least 200 mW/cm2.

105. The method of embodiment 103, wherein the ultrasound energy is applied at pulse length of at least 20 microseconds.

106. The method of embodiment 100, wherein the subject is administered at least three treatments.

107. The method of embodiment 100, wherein the sonoactive agent comprises protein-stabilized microstructures.

108. The method of embodiment 100, wherein the sonoactive agent comprises a shell filled with a perfluorinated gas.

109. The method of embodiment 100, wherein the sonoactive agent comprises lipid-stabilized microstructures.

110. The method of embodiment 106, wherein the at least three treatments are administered at least 48 hours apart.

111. The method of embodiment 100, wherein the subject is administered at least two cycles, each cycle comprising at least two treatments.

112. The method of embodiment 100, wherein the subject is administered at least three cycles, each cycle comprising at least two treatments.

113. The method of embodiment 100, wherein the subject is administered at least three cycles, each cycle comprising at least three treatments.

114. The method of any one of embodiments 111-113, wherein each cycle is administered to the subject at least 10 days apart.

115. The method of any one of embodiments 111-113, wherein each cycle is administered to the subject at least 30 days apart.

116. The method of any one of embodiments 111-113, wherein each cycle is administered to the subject at least 40 days apart.

EXAMPLES

Example 1. In Vitro Expression of FVIII and FIX Coding Plasmids in HepG2 Cell Lines In this example, in-vitro expression of therapeutic nucleic acids encoding FIX and FVIII coding nucleic acid sequences in vectors comprising genetic regulatory elements which increase expression transfected to Human Liver Hepatocellular Cell Line HepG2 were evaluated. Plasmid DNA (pDNA) encoding FIX and FVIII coupled to promoters and genetic regulatory elements were produced. Circular DNA sequences encoding the sequence of SEQ ID NO: 12 (APOE-AAT-hbGi-FIX), SEQ ID NO: 14 (APOE-AAT-hbGi-FIX-WPRE3-bGH-polyA-DTS), SEQ ID NO: 15 (APOE-AAT-hbGi-FIX WPRE3-bGH-polyA-DTS-ITR), SEQ ID NO: 16 (APOE-AAT-hbGi-FVIII-v3-bGH-polyA), and SEQ ID NO: 17 (APOE-AAT-hbGi-FVIII-v3-WPRE3-bGH-polyA-DTS) were manufactured. Vector maps of nucleic acid sequences encoding the therapeutic nucleic acid in vectors comprising genetic regulatory elements which increase expression of the therapeutic nucleic acid were illustrated in FIG. 1A. Parts of the DNA vectors were synthesized (GeneScript) and combined in final pDNA vectors by NEBuilder® HiFi DNA Assembly (NEB) following manufacture's protocol. In brief, DNA fragments were amplified by PCR reaction utilized Phusion® High-Fidelity DNA Polymerase and primers designed with NEBuilder Assembly Tool. PCR fragments were purified from agarose gel utilizing NED Monarch Gel Extraction kit (NEB) and assembled in HiFi DNA assembly reaction. pDNA sequence integrity was confirmed by next generation sequencing methods.

Following confirmation of the correct pDNA sequences, the pDNA constructs were transfected to HepG2 cell lines using a lipid-nanoparticle based Lipofectamine® P3000 transfection reagent. 100 ng of pDNA, with 5 uL of Opti-MEM™ Reduced-Serum Medium 0.1 uL, and 0.1 of P3000 transfection reagent were combined in a 96 well plate and incubating at room temperature for 5 min. Negative controls were prepared by combining 5 uL of Opti-MEM™ Reduced-Serum Medium 0.1 uL, and 0.15 of P3000 transfection reagent, and incubating at room temperature for 5 min. The HepG2 cell were then added, were cultured, and media collected at 72 hours post transfection and frozen at −80 C.

FIX samples were later defrosted, diluted 5-fold, and analyzed using ELISA Green Mountain Antibodies for detection of human FIX. Concentration of secreted transgenic human FIX in culture media 72 hours post transfection was measured by ELISA utilizing Green Mountain Antibodies. Approximately 100 uL of capture antibody (GMA-102) was incubated at 4 C overnight. The stock solution of the capture antibody was diluted to 2 ug/mL antibody solution. A 96 well plate was washed three times with 300 uL of wash buffer, and 300 uL of block buffer was added, and incubated at room temperature for 30 min. A standard serial dilutions were prepared using a recombinant FIX (Abcam 1.8 mg/mL). 100 uL samples were 5-fold. A 96 well plate was washed three times with 300 uL of wash buffer, and 100 uL of block buffer and FIX standard were added, and incubated at room temperature for 60 min. The 96 well plate was again washed three times with 300 uL of wash buffer, and 100 uL of detection antibody (GMA-184) per well was added and incubated at room temperature for 60 minutes. The 96 well plate was washed three times with 300 uL of wash buffer, and 100 uL of streptavidin peroxidase per well was added, an incubated at room temperature for 30 minutes. The 96 well plate was washed three times with 300 uL of wash buffer, and 100 uL of o-Phenylenediamine (OPD) substrate (dissolved 1 tablet (5 mg) in 12 mL citrate buffer, then added 5 ul 30% $H_2O_2$) was added and incubated at room temperature for 15 min. 50 uL of 2N H2SO4 was added, and absorbance measurements were taken on the SpectraMax at 490 nm and 570 nm. An asymmetric sigmoidal, 5PL, x=concentration analysis was used to interpolate sample values based on the standard curves, and a limit of detection of 0.8 ng/mL of FIX was established for this ELISA plate.

FVIII samples were later defrosted, diluted 5-fold, and analyzed using ELISA Green Mountain Antibodies for detection of human FVIII. Concentration of secreted trans- genic human FVIII in culture media 72 hours post transfec- tion was measured by ELISA utilizing Green Mountain Antibodies. Approximately 100 uL of capture antibody (GMA-8024) was incubated at 4 C overnight. The stock solution of the capture antibody was diluted to 2 ug/mL antibody solution. A 96 well plate was washed three times with 300 uL of wash buffer, and 300 uL of block buffer was added, and incubated at room temperature for 30 min. A standard serial dilutions were prepared using a recombinant FVIII (Syd Labs 200 IU/mL). 100 uL samples were diluted 5-fold. A 96 well plate was washed three times with 300 uL of wash buffer, and 100 uL of block buffer and FVIII standard were added, and incubated at room temperature for 60 min. The 96 well plate was again washed three times with 300 uL of wash buffer, and 100 uL of detection antibody (GMA-8023) per well was added and incubated at room temperature for 60 minutes. The 96 well plate was washed three times with 300 uL of wash buffer, and 100 uL of streptavidin peroxidase per well was added, an incubated at room temperature for 30 minutes. The 96 well plate was washed three times with 300 uL of wash buffer, and 100 uL of o-Phenylenediamine (OPD) substrate (dissolved 1 tablet (5 mg) in 12 mL citrate buffer, then added 5 ul 30% H2O2) was added and incubated at room temperature for 15 min. 50 uL of 2N H2SO4 was added, and absorbance measurements were taken on the SpectraMax at 490 nm and 570 nm. An asymmetric sigmoidal, 5PL, x=concentration analysis was used to interpolate sample values based on the standard curves, and a limit of detection of 0.000994 IU/mL of FVIII with a limit of quantification of 0.14 IU/ML was established for this ELISA plate.

Figure 1B:
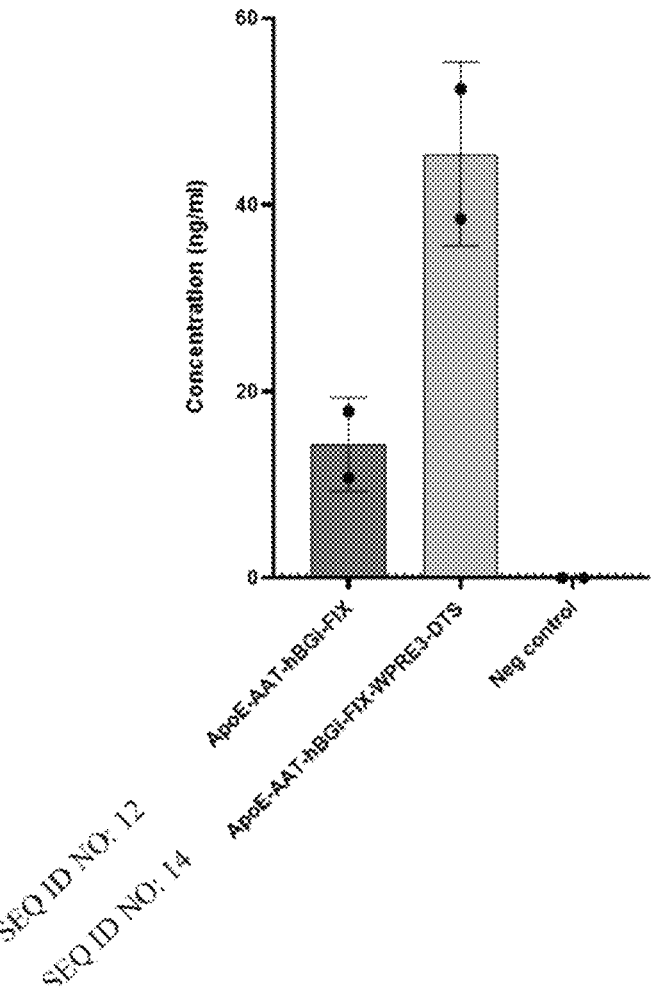
FIG. 1B provides data illustrating improved expression of the therapeutic nucleic acid in vectors in-vitro.
Figure 1C:
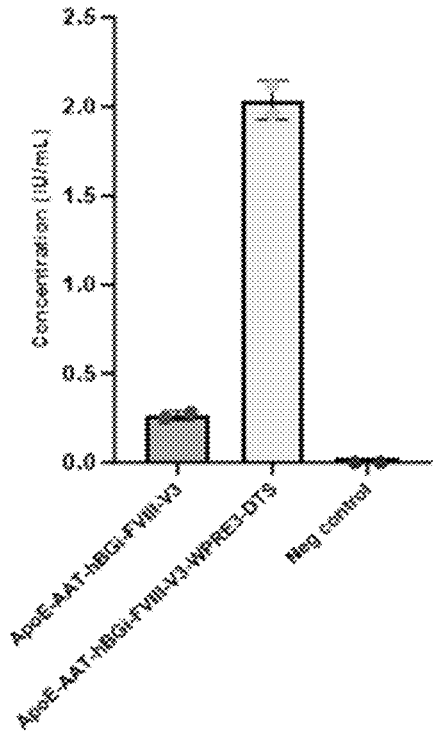
FIG. 1C provides data illustrating improved expression of the therapeutic nucleic acid in vectors comprising improved genetic regulatory elements in-vitro.
Figure 1D:
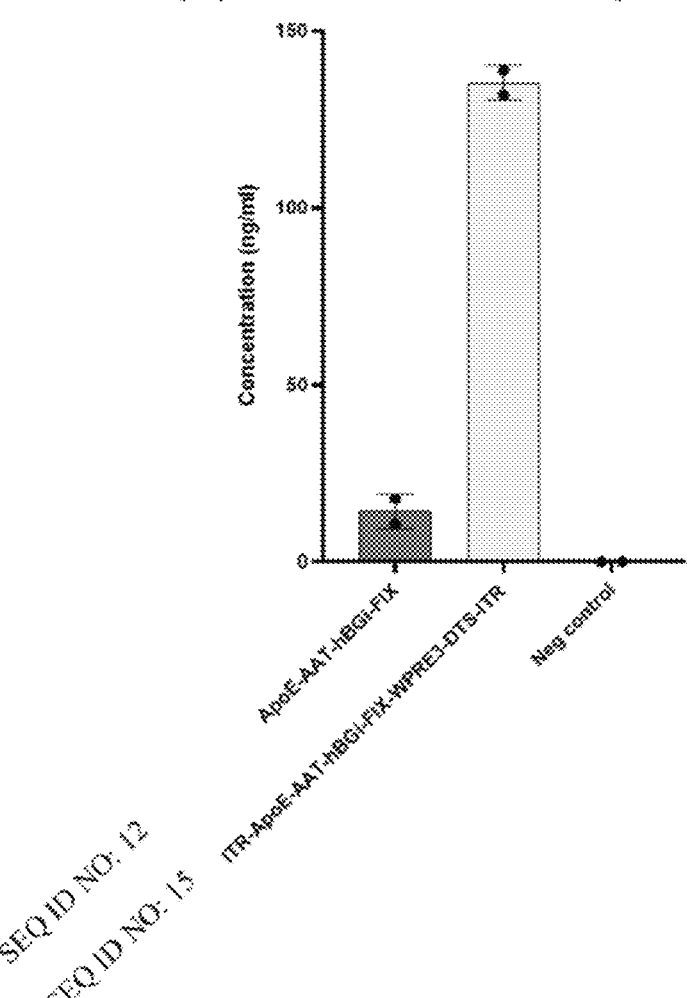
FIG. 1D provides data illustrating improved expression of the therapeutic nucleic acid in vectors in-vitro.

As is shown in FIGS. 1B-1D, the combination of the genetic regulatory element SEQ ID NO: 4 (WPRE3) and the nuclear targeting sequence SEQ ID NO: 6 (DTS) enhances the expression of FVIII and FIX in-vitro, in HepG2 cell lines. Cells transfected with the pDNA comprising the sequence of SEQ ID NO: 12 (APOE-AAT-hbGi-FIX) encoding FIX coupled to an APOE-AAT promoter sequence produced FIX at a concentration of about 15 ng/mL, while cells transfected with pDNA comprising the sequence of SEQ ID NO. 14 (APOE-AAT-hbGi-FIX-WPRE3-bGH-polyA-DTS) encod- ing FIX 5' coupled to the same APOE-AAT promoter sequence but further being coupled to the WPRE3 and DTS elements expressed FIX at nearly 3x the levels at a concen- tration of about 45 ng/mL.

Cells transfected with the pDNA comprising the sequence of SEQ ID NO: 16 (APOE-AAT-hbGi-FVIII-v3-bGH- polyA) encoding FVIII coupled to an APOE-AAT promoter sequence produced FVIII at a concentration of about 0.25 ng/mL, while cells transfected with pDNA comprising the sequence of SEQ ID NO. 17 (APOE-AAT-hbGi-FVIII-v3- WPRE3-bGH-polyA-DTS) encoding FVIII coupled to the same APOE-AAT promoter sequence but further being coupled to the DTS nuclear targeting sequence of SEQ ID NO: 6 expressed FVIII at nearly 8x the levels at a concen- tration of about 2.0 ng/mL.

In FIG. 1D, cells that were transfected with the pDNA comprising the sequence of SEQ ID NO: 15 (APOE-AAT- hbGi-FIX WPRE3-bGH-polyA-DTS-ITR) encoding FIX 5' coupled to the same APOE-AAT promoter sequence but further being coupled to the WPRE3 and DTS and ITR elements expressed FIX at approximately 12x the levels at a concentration of about 130 ng/mL, when compared to cells transfected with the pDNA comprising the sequence of SEQ ID NO: 12 (APOE-AAT-hbGi-FIX).

Example 2. In-Vivo Expression of FIX in Murine Models Via Sonoporation

In this example, in-vivo expression of FIX transfected in vectors comprising genetic regulatory elements which increase expression of the therapeutic nucleic acid to the murine liver in C57 mice were evaluated. Prior to the experiment, each mouse was implanted with a jugular vein catheter (JVC), through which the sonoactive microstruc- tures and nucleic acid constructs were administered. Circu- lar DNA encoding FIX coupled to promoters and genetic regulatory elements were produced. Parts of the DNA vec- tors were synthesized (GeneScript) and combined in final circular DNA vectors by NEBuilder® HiFi DNA Assembly (NEB) following manufacture's protocol. In brief, DNA fragments were amplified by PCR reaction utilized Phu- sion® High-Fidelity DNA Polymerase and primers designed with NEBuilder Assembly Tool. PCR fragments were puri- fied from agarose gel utilizing NED Monarch Gel Extraction kit (NEB) and assembled in HiFi DNA assembly reaction. Circular DNA comprising the sequence of SEQ ID NO: 12 (APOE-AAT-hbGi-FIX), SEQ ID NO: 18 (APOE-AAT- hbGi-FIX-WPRE3-DTS) were manufactured, and their sequences confirmed using Sanger sequencing, and next generation sequencing: methods. Following confirmation of the correct pDNA sequences, transfection of the nucleic acid constructs to the C57 mice was performed and evaluated in three experimental groups of 5 C57 mice: a first negative control in which no nucleic acids were administered; a second experimental group transfected with a pDNA sequence comprising the sequence of SEQ ID NO: 12 (APOE-AAT-hbGi-FIX); and a third experimental group transfected with a DNA sequence comprising the sequence of SEQ ID NO: 18 (APOE-AAT-hbGi-FIX-WPRE3-DTS).

A dose of sonoactive microstructure and DNA solution was readied by first preparing the sonoactive microstructures (Optison) as instructed on the label: remove from 4 C storage and roll between the palms for 20 seconds; removing protective plastic and aluminum covering from Optison vial; placing 25G needle through the rubber gasket to provide a pressure vent; and using 1.5 inch 18G needle to draw up 200 uL of Optison into a syringe (dead space of the needle (about 50 microliters (uL)) included in the calculations). With the same needle and syringe, 50 uL of solution comprising 250 ug of pDNA payload was drawn into the syringe to combine the DNA and Optison. The Optison microbubbles and DNA payload were mixed in the syringe by rolling the syringe between the fingers until the solution was homogenous at a 1:4 volumetric ratio of DNA to microbubble solution. The DNA+Optison solution was drawn out of the needle dead space. Then the 18G needle was exchanged for a 25G blunt needle for injection into a subject JVC.

Approximately one-third of the microbubble-DNA solu- tion were administered to the subject in a bolus injection over about 10 seconds through the jugular vein catheter, and ultrasound energy was applied to the subject over the liver using an alternating mechanical index protocol. Ultrasound energy was transcutaneously applied to the liver region of the subject with a L6-24 ultrasound probe, alternating between a first MI of 0.07, and a second MI of 1.5, at a focal depth of 2 cm, and a gain of 28. Nine flashes of high MI ultrasound energy were delivered at an MI of 1.5 with an interval of 4 seconds between each flash with the administration of the 9 pulses being repeated three times over a single liver location. The high MI pulse duration was about 0.82 microseconds. Following administration of ultrasound energy, the second one-third dose of the microbubble-DNA solution was administered to the subject in a bolus injection, and ultrasound energy was transcutaneously applied to a second region liver using the same ultrasound parameters. Following completion of the second administration of ultrasound energy, the final one-third dose of the microbubble-DNA solution was administered to the subject in a bolus injection, and ultrasound energy was transcutaneously applied to a third region liver using the same ultrasound parameters. Plasma samples were collected from the subject 72 hours following administration of the sonoporation treatment.

FIX samples were later defrosted, diluted 5-fold, and analyzed using ELISA Green Mountain Antibodies for detection of human FIX. Concentration of secreted transgenic human FIX in culture media 72 hours post transfection was measured by ELISA utilizing Green Mountain Antibodies. Approximately 100 uL of capture antibody (GMA-102) was incubated at 4 C overnight. The stock solution of the capture antibody was diluted to 2 ug/mL antibody solution. A 96 well plate was washed three times with 300 uL of wash buffer, and 300 uL of block buffer was added, and incubated at room temperature for 30 min. A standard serial dilutions were prepared using a recombinant FIX (Abcam 1.8 mg/mL). 100 uL samples were 5-fold. A 96 well plate was washed three times with 300 uL of wash buffer, and 100 uL of block buffer and FIX standard were added, and incubated at room temperature for 60 min. The 96 well plate was again washed three times with 300 uL of wash buffer, and 100 uL of detection antibody (GMA-184) per well was added and incubated at room temperature for 60 minutes. The 96 well plate was washed three times with 300 uL of wash buffer, and 100 uL of streptavidin peroxidase per well was added, an incubated at room temperature for 30 minutes. The 96 well plate was washed three times with 300 uL of wash buffer, and 100 uL of o-Phenylenediamine (OPD) substrate (dissolved 1 tablet (5 mg) in 12 mL citrate buffer, then added 5 ul 30% H2O2) was added and incubated at room temperature for 15 min. 50 uL of 2N H2SO4 was added, and absorbance measurements were taken on the SpectraMax at 490 nm and 570 nm. An asymmetric sigmoidal, 5PL, x=concentration analysis was used to interpolate sample values based on the standard curves, and a limit of detection of 0.8 ng/mL of FIX was established for this ELISA plate.

Figure 3:
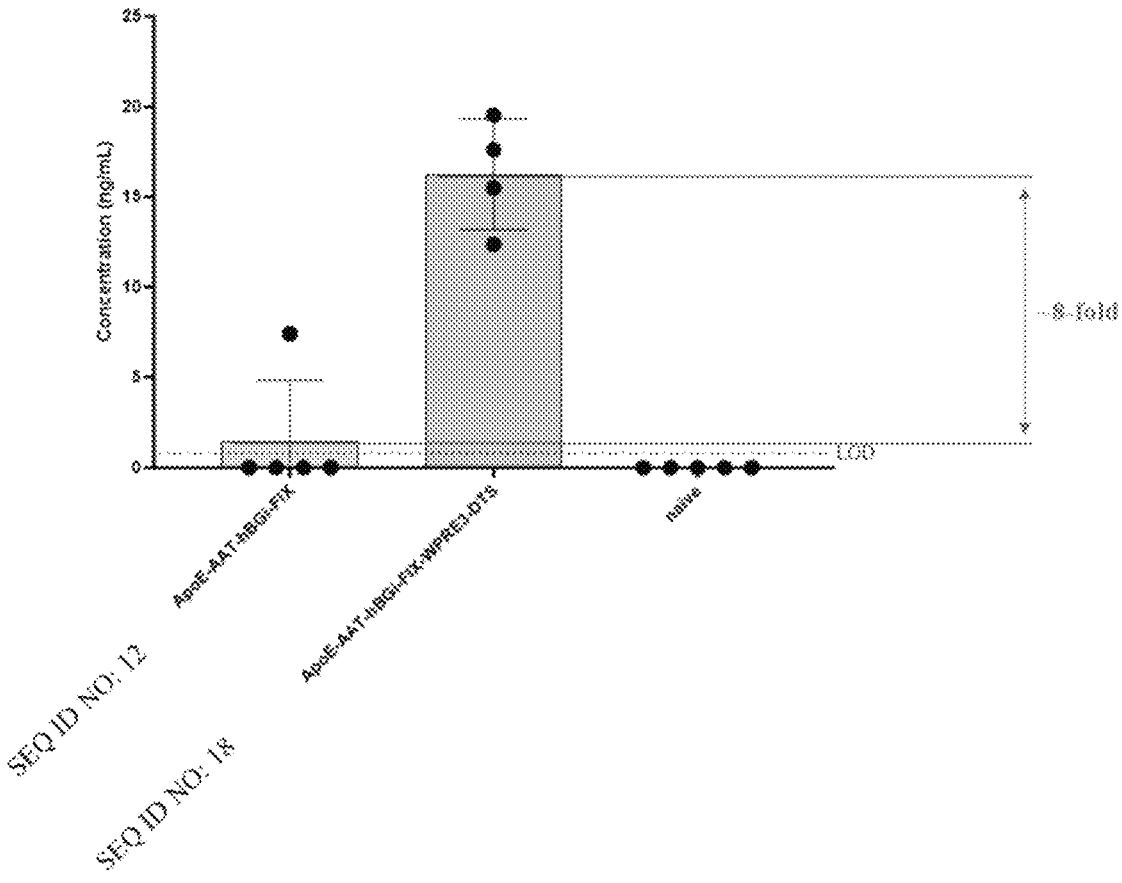
FIG. 3 provides data illustrating improved expression of the therapeutic nucleic acid in vectors comprising improved genetic regulatory elements in-vivo.

Results are shown in FIG. 3, in which it is shown that the control group of naïve mice administered no nucleic acids exhibited no FIX expression, the second experimental group administered a pDNA sequence comprising the sequence of SEQ ID NO: 12 (APOE-AAT-hbGi-FIX) exhibited FIX expression at about 2.0 ng/mL, while the third experimental group administered a pDNA sequence comprising the sequence of SEQ ID NO: 18 (APOE-AAT-hbGi-FIX-WPRE3-DTS) exhibited FIX expression at about 16.0 ng/mL—an eight fold expression increase over the second experimental group administered the FIX plasmid not comprising the DTS nuclear targeting sequence of SEQ ID NO: 6.

Example 3. In-Vivo Expression of FIX in Murine Models Via Sonoporation

Figure 2A:
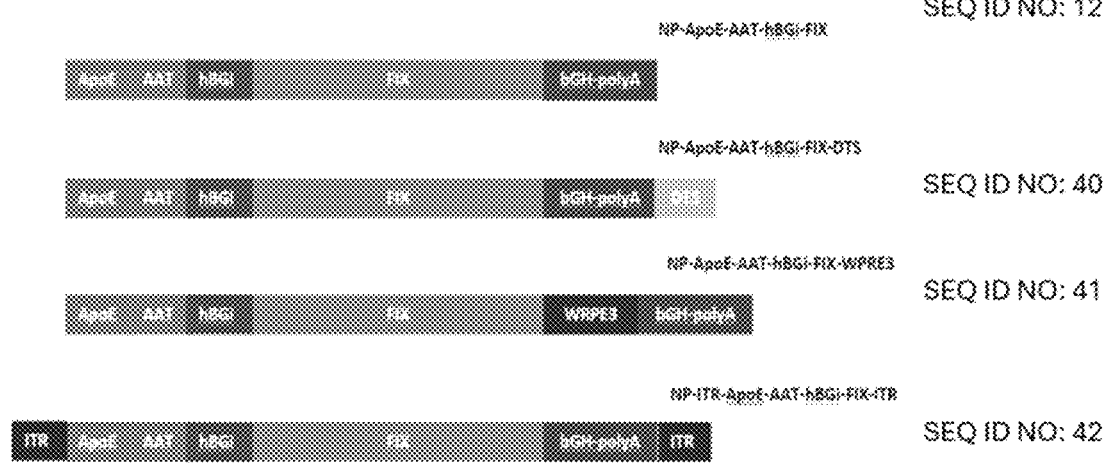
FIG. 2A illustrates vector elements of nucleic acid compositions comprising a therapeutic nucleic acid in vectors comprising genetic regulatory elements which increase expression of the therapeutic nucleic acid.

In this example, in-vivo expression FIX transfected in vectors comprising genetic regulatory elements which increase expression of the therapeutic nucleic acid to the murine liver in C57 mice was evaluated. Prior to the experiment, each mouse was implanted with a jugular vein catheter (JVC), through which the sonoactive microstructures and nucleic acid constructs were administered. Circular DNA encoding FIX coupled to promoters and genetic regulatory elements were produced. Parts of the DNA vectors were synthesized (GeneScript) and combined in final circular DNA vectors by NEBuilder® HiFi DNA Assembly (NEB) following manufacture's protocol. In brief, DNA fragments were amplified by PCR reaction utilized Phusion® High-Fidelity DNA Polymerase and primers designed with NEBuilder Assembly Tool. PCR fragments were purified from agarose gel utilizing NED Monarch Gel Extraction kit (NEB) and assembled in HiFi DNA assembly reaction. Circular DNA comprising the sequence of SEQ ID NO: 13 (APOE-AAT-hBGi-FIX-bGH-polyA), SEQ ID NO: 40 (APOE-AAT-hBGi-FIX-bGH-polyA-DTS), SEQ ID NO: 41 (APOE-AAT-hBGi-FIX WPRE3-bGH-polyA), and SEQ ID NO: 42 (ITR-APOE-AAT-hBGi-FIX-bGH-polyA-ITR), were manufactured, and their sequences confirmed using Sanger sequencing, and next generation sequencing. Vector maps of nucleic acid sequences comprising the therapeutic nucleic acid in vectors comprising genetic regulatory elements which increase expression of the therapeutic nucleic acid are illustrated in FIG. 2A.

Following confirmation of the correct circular DNA sequences, transfection of the nucleic acid constructs to the C57 mice was performed and evaluated in five experimental groups of three C57 mice: a first negative control in which no nucleic acids were administered; a second experimental group serving as a positive control transfected with a circular DNA sequence comprising the sequence of SEQ ID NO: 13 (APOE-AAT-hBGi-FIX-bGH-polyA), a third experimental group transfected with a circular DNA sequence comprising the sequence of SEQ ID NO: 40 (APOE-AAT-hBGi-FIX-bGH-polyA-DTS), a fourth experimental group transfected with a circular DNA sequence comprising the sequence of SEQ ID NO: 41 (APOE-AAT-hBGi-FIX WPRE3-bGH-polyA), and a fifth experimental group transfected with a circular DNA sequence comprising the sequence of SEQ ID NO: 42 (ITR-APOE-AAT-hBGi-FIX-bGH-polyA-ITR).

A dose of sonoactive microstructure and DNA solution was readied by first preparing the sonoactive microstructures (Optison) as instructed on the label: remove from 4 C storage and roll between the palms for 20 seconds; removing protective plastic and aluminum covering from Optison vial; placing 25G needle through the rubber gasket to provide a pressure vent; and using 1.5 inch 18G needle to draw up 200 uL of Optison into a syringe (dead space of the needle (about 50 microliters (uL)) included in the calculations). With the same needle and syringe, 50 uL of solution comprising 250 ug of pDNA payload was drawn into the syringe to combine the DNA and Optison. The Optison microbubbles and DNA payload were mixed in the syringe by rolling the syringe between the fingers until the solution was homogenous at a 1:4 volumetric ratio of DNA to microbubble solution. The DNA+Optison solution was drawn out of the needle dead space. Then the 18G needle was exchanged for a 25G blunt needle for injection into a subject JVC.

Approximately one-third of the microbubble-DNA solution were administered to the subject in a bolus injection over about 10 seconds through the jugular vein catheter, and ultrasound energy was applied to the subject over the liver using an alternating mechanical index protocol. Ultrasound energy was transcutaneously applied to the liver region of the subject with a L6-24 ultrasound probe, alternating between a first MI of 0.07, and a second MI of 1.5, at a focal depth of 2 cm, and a gain of 28. Nine flashes of high MI ultrasound energy were delivered at an MI of 1.5 with an interval of 4 seconds between each flash with the administration of the 9 pulses being repeated three times over a single liver location. The high MI pulse duration was about 0.82 microseconds. Following administration of ultrasound energy, the second one-third dose of the microbubble-DNA solution was administered to the subject in a bolus injection, and ultrasound energy was transcutaneously applied to a second region liver using the same ultrasound parameters. Following completion of the second administration of ultrasound energy, the final one-third dose of the microbubble-DNA solution was administered to the subject in a bolus injection, and ultrasound energy was transcutaneously applied to a third region liver using the same ultrasound parameters. Blood samples were collected from the subjects 72 hours following administration of the sonoporation treatment.

FIX samples were later defrosted, diluted 5-fold, and analyzed using ELISA Green Mountain Antibodies for detection of human FIX. Concentration of secreted transgenic human FIX in culture media 72 hours post transfection was measured by ELISA utilizing Green Mountain Antibodies. Approximately 100 uL of capture antibody (GMA-102) was incubated at 4 C overnight. The stock solution of the capture antibody was diluted to 2 ug/mL antibody solution. A 96 well plate was washed three times with 300 uL of wash buffer, and 300 uL of block buffer was added, and incubated at room temperature for 30 min. A standard serial dilutions were prepared using a recombinant FIX (Abcam 1.8 mg/mL). 100 uL samples were 5-fold. A 96 well plate was washed three times with 300 uL of wash buffer, and 100 uL of block buffer and FIX standard were added, and incubated at room temperature for 60 min. The 96 well plate was again washed three times with 300 uL of wash buffer, and 100 uL of detection antibody (GMA-184) per well was added and incubated at room temperature for 60 minutes. The 96 well plate was washed three times with 300 uL of wash buffer, and 100 uL of streptavidin peroxidase per well was added, an incubated at room temperature for 30 minutes. The 96 well plate was washed three times with 300 uL of wash buffer, and 100 uL of o-Phenylenediamine (OPD) substrate (dissolved 1 tablet (5 mg) in 12 mL citrate buffer, then added 5 ul 30% H2O2) was added and incubated at room temperature for 15 min. 50 uL of 2N H2SO4 was added, and absorbance measurements were taken on the SpectraMax at 490 nm and 570 nm. An asymmetric sigmoidal, 5PL, x=concentration analysis was used to interpolate sample values based on the standard curves, and a limit of detection of 0.8 ng/mL of FIX was established for this ELISA plate.

Figure 2B:
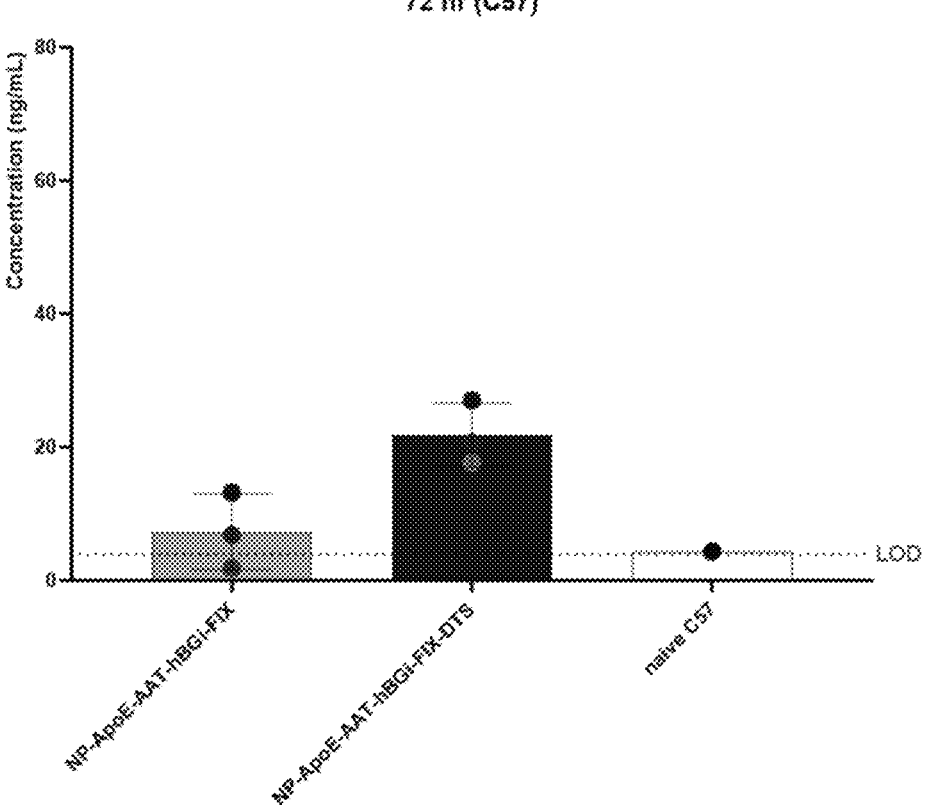
FIG. 2B provides data illustrating improved expression of the therapeutic nucleic acid in the vectors comprising improved genetic regulatory elements in-vivo.
Figure 2C:
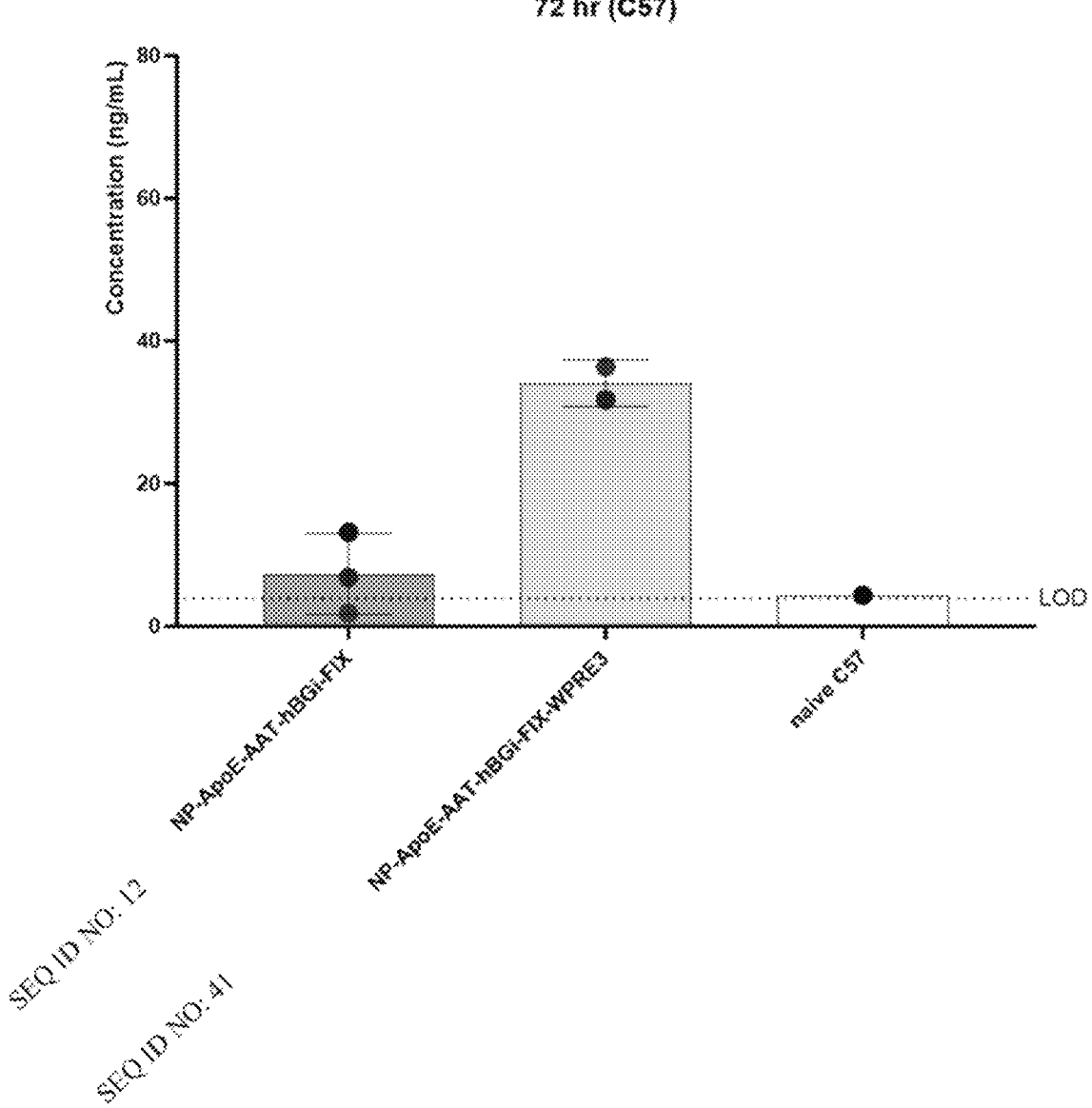
FIG. 2C provides data illustrating improved expression of the therapeutic nucleic acid in the vectors comprising improved genetic regulatory elements in-vivo.
Figure 2D:
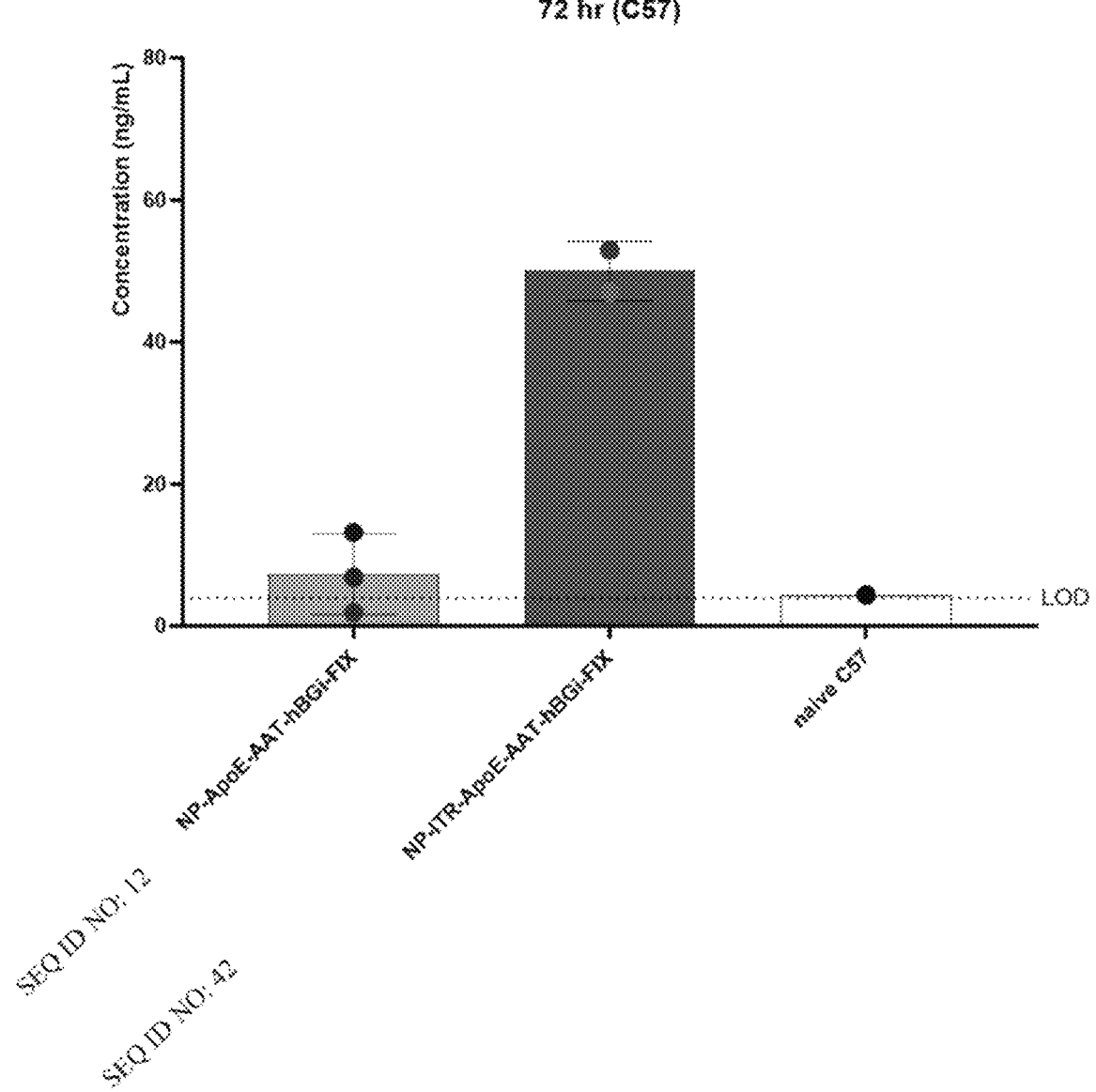
FIG. 2D provides data illustrating improved expression of the therapeutic nucleic acid in the vectors comprising improved genetic regulatory elements in-vivo.

Results are shown in FIGS. 2B-2D, in which it is shown that the control group of naïve mice administered no nucleic acids exhibited no detectable FIX expression, that the second experimental group serving as a positive control transfected with nucleic acid composition comprising the sequence of SEQ ID NO: 13 (APOE-AAT-hBGi-FIX-bGH-polyA) exhibited low levels of FIX expression of about 5 ng/mL, while experimental groups 3-5 exhibited increased FIX expression ranging from about 25 ng/mL up to about 50 ng/mL.

In FIG. 2B, it is illustrated that the third experimental group transfected with nucleic acid composition comprising the sequence of SEQ ID NO: 40 (APOE-AAT-hBGi-FIX-bGH-polyA-DTS) including the nuclear target sequence described herein exhibited increased FIX levels of about 25 ng/mL, a 5× increase over the second experimental group serving as a positive control transfected with nucleic acid composition comprising the sequence of SEQ ID NO: 13 (APOE-AAT-hBGi-FIX-bGH-polyA), indicating that the DTS nuclear targeting sequence (SEQ ID NO: 6) provided a beneficial technical effect in increasing expression of the therapeutic transgene.

In FIG. 2C, it is illustrated that the fourth experimental group transfected with a circular DNA sequence comprising the sequence of SEQ ID NO: 41 (APOE-AAT-hBGi-FIX WPRE3-bGH-polyA) comprising the WPRE3 post-transcriptional regulatory element exhibited increased FIX levels of about 35 ng/mL, a 7× increase over the second experimental group serving as a positive control transfected with nucleic acid composition comprising the sequence of SEQ ID NO: 13 (APOE-AAT-hBGi-FIX-bGH-polyA), indicating that the combination of the hemoglobin subunit gamma intron (hBGi) sequence upstream of the therapeutic nucleic acid sequence and WPRE3 post-transcriptional regulatory element (SEQ ID NO: 4) downstream of the therapeutic nucleic acid sequence provided a beneficial technical effect in increasing expression of the therapeutic transgene.

In FIG. 2C, it is illustrated that the fourth experimental group transfected with a circular DNA sequence comprising the sequence of SEQ ID NO: 41 (APOE-AAT-hBGi-FIX WPRE3-bGH-polyA) comprising the WPRE3 post-transcriptional regulatory element exhibited increased FIX levels of about 35 ng/mL, a 7× increase over the second experimental group serving as a positive control transfected with nucleic acid composition comprising the sequence of SEQ ID NO: 13 (APOE-AAT-hBGi-FIX-bGH-polyA), indicating that the post-transcriptional regulatory element of SEQ ID NO: 45 provided a beneficial technical effect in increasing expression of the therapeutic transgene.

In FIG. 2D, it is illustrated that the fifth experimental group transfected with a circular DNA sequence comprising the sequence of SEQ ID NO: 42 (ITR-APOE-AAT-hBGi-FIX-bGH-polyA-ITR) comprising the ITR sequences exhibited increased FIX levels of about 50 ng/mL, a 10× increase over the second experimental group serving as a positive control transfected with nucleic acid composition comprising the sequence of SEQ ID NO: 13 (APOE-AAT-hBGi-FIX-bGH-polyA), indicating that the ITR sequences (SEQ ID NO: 4) provided a beneficial technical effect in increasing expression of the therapeutic transgene.

Example 4. In-Vitro Expression of Novel FVIII Transgenes in HepG2 and Hepa1-6 Cell Lines In this example, in-vitro expression of therapeutic nucleic acids encoding FVIII coding nucleic acid sequences in vectors comprising genetic regulatory elements which increase expression transfected to Human Liver Hepatocellular Cell Line HepG2 and Murine (C57L) Hepatocellular Cell Line Hepa1-6 were evaluated. Each cell line was tested using two experimental groups. A first experimental group was administered a nucleic acid composition comprising the sequence of SEQ ID NO: 43 (ApoE-AAT-hBGi-FVIII-v3-WPRE3-DTS), a FVIII sequence known within the art. A second experimental group was administered a nucleic acid composition comprising the sequence of SEQ ID NO:39 (ApoE-AAT-hBGi-FVIII-N6-F309S-DM-WPRE3-DTS), a novel and modified version of the FVIII transgene disclosed herein.

Circular DNA encoding the differing FVIII variants were coupled to a same combination of promoters and genetic regulatory elements were produced using methods known within the art. Circular DNA sequences comprising the sequence of SEQ ID NO: 39 (ApoE-AAT-hBGi-FVIII-N6-F309S-DM-WPRE3-DTS), and SEQ ID NO: 43 (ApoE-AAT-hBGi-FVIII-v3-WPRE3-DTS), were manufactured. Parts of the DNA vectors were synthesized (GeneScript) and combined in final pDNA vectors by NEBuilder® HiFi DNA Assembly (NEB) following manufacture's protocol. In brief, DNA fragments were amplified by PCR reaction utilized Phusion® High-Fidelity DNA Polymerase and primers designed with NEBuilder Assembly Tool. PCR fragments were purified from agarose gel utilizing NED Monarch Gel Extraction kit (NEB) and assembled in HiFi DNA assembly reaction. Circular DNA sequence integrity was confirmed by next generation sequencing methods.

Following confirmation of the correct circular DNA sequences, the nucleic acid compositions were transfected to Human Liver Hepatocellular Cell Line HepG2, and Murine (C57L) Hepatocellular Cell Line Hepa1-6 using a lipid-nanoparticle based Lipofectamine® P3000 transfection reagent. 100 ng of DNA, with 5 uL of Opti-MEM™ Reduced-Serum Medium 0.1 uL, and 0.1 of P3000 trans-fection reagent were combined in a 96 well plate and incubating at room temperature for 5 min. Negative controls were prepared by combining 5 uL of Opti-MEM™ Reduced-Serum Medium 0.1 uL, and 0.15 of P3000 trans-fection reagent, and incubating at room temperature for 5 min. The HepG2 cell were then added, were cultured, and media collected at 72 hours post transfection and frozen at −80 C.

FVIII samples were later defrosted, diluted 5-fold, and analyzed using ELISA Green Mountain Antibodies for detection of human FVIII. Concentration of secreted trans-genic human FVIII in culture media 72 hours post transfec-tion was measured by ELISA utilizing Green Mountain Antibodies. Approximately 100 uL of capture antibody (GMA-8024) was incubated at 4 C overnight. The stock solution of the capture antibody was diluted to 2 ug/mL antibody solution. A 96 well plate was washed three times with 300 uL of wash buffer, and 300 uL of block buffer was added, and incubated at room temperature for 30 min. A standard serial dilutions were prepared using a recombinant FVIII (Syd Labs 200 IU/mL). 100 uL samples were diluted 5-fold. A 96 well plate was washed three times with 300 uL of wash buffer, and 100 uL of block buffer and FVIII standard were added, and incubated at room temperature for 60 min. The 96 well plate was again washed three times with 300 uL of wash buffer, and 100 uL of detection antibody (GMA-8023) per well was added and incubated at room temperature for 60 minutes. The 96 well plate was washed three times with 300 uL of wash buffer, and 100 uL of streptavidin peroxidase per well was added, an incubated at room temperature for 30 minutes. The 96 well plate was washed three times with 300 uL of wash buffer, and 100 uL of o-Phenylenediamine (OPD) substrate (dissolved 1 tablet (5 mg) in 12 mL citrate buffer, then added 5 ul 30% $H_2O_2$) was added and incubated at room temperature for 15 min. 50 uL of 2N H2SO4 was added, and absorbance measurements were taken on the SpectraMax at 490 nm and 570 nm. An asymmetric sigmoidal, 5PL, x=concentration analysis was used to interpolate sample values based on the standard curves, and a limit of detection of 0.000994 IU/mL of FVIII with a limit of quantification of 0.14 IU/ML was established for this ELISA plate.

Figure 4A:
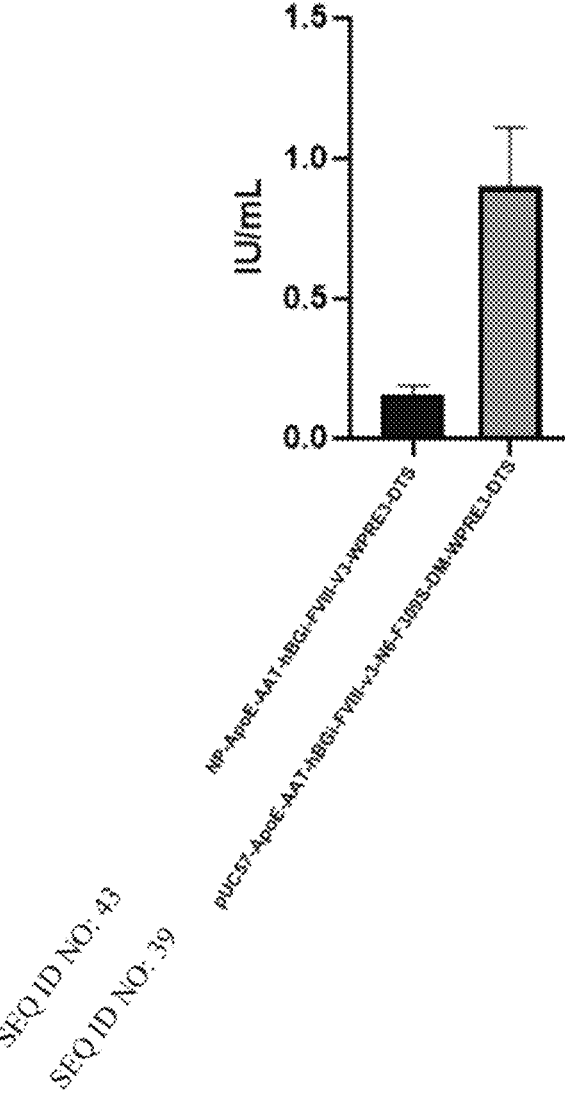
FIG. 4A provides data illustrating improved expression of a therapeutic nucleic acid comprising a modified transgene in a vector comprising improved genetic regulatory elements in-vitro.
Figure 4B:
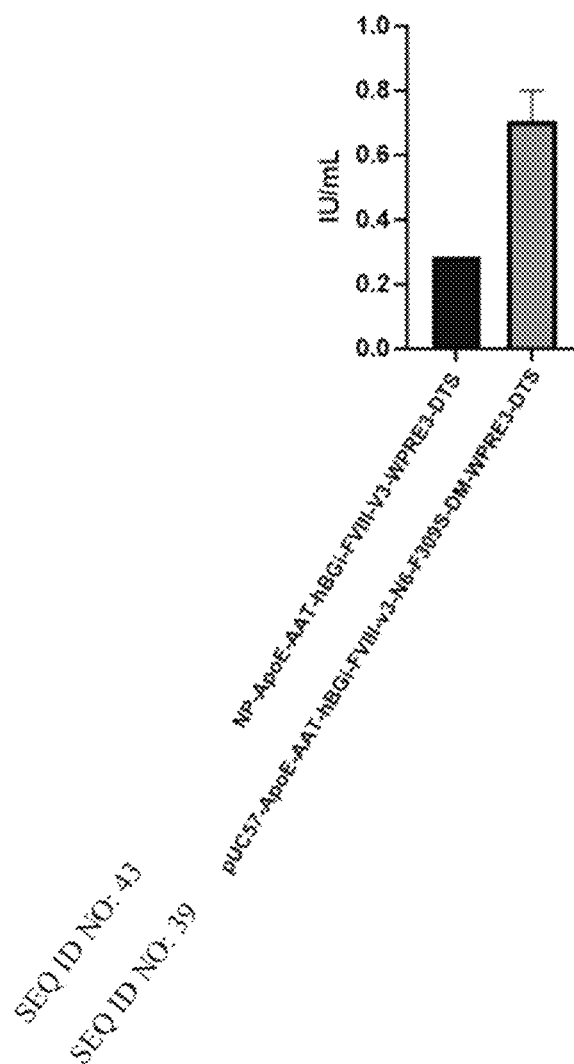
FIG. 4B provides data illustrating improved expression of a therapeutic nucleic acid comprising a modified transgene in a vector comprising improved genetic regulatory elements in-vitro.

As is shown in FIGS. 4A-4B, the modifications to the FVIII polypeptide sequence increase expression of FVIII in both the Human Liver Hepatocellular Cell Line HepG2 and Murine (C57L) Hepatocellular Hepa1-6 Cell Line.

In FIG. 4A, it illustrated that expression in the Murine (C57L) Hepatocellular Hepa1-6 Cell Line is increased. The first experimental group administered the nucleic acid com-position comprising the sequence of SEQ ID NO: 43 (ApoE-AAT-hBGi-FVIII-v3-WPRE3-DTS), a FVIII sequence known within the art, exhibits FVIII levels of about 0.15 IU/mL. The second experimental group administered the nucleic acid composition comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), exhibits FVIII levels of about 0.9 IU/mL, a 6-fold (6×) increase over the first experimental group, indicating that the modifications to the FVIII transgene disclosed herein in SEQ ID NO:39 provide a beneficial technical effect in increasing expression of FVIII.

In FIG. 4B, it illustrated that expression in the Human Liver Hepatocellular Cell Line HepG2 is increased. The first experimental group administered the nucleic acid composi-tion comprising the sequence of SEQ ID NO: 43 (ApoE-AAT-hBGi-FVIII-v3-WPRE3-DTS), a FVIII sequence known within the art, exhibits FVIII levels of about 0.3 IU/mL. The second experimental group administered the nucleic acid composition comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), exhibits FVIII levels of about 0.7 IU/mL, a 2.3-fold (2.3×) increase over the first experimental group, indicating that the modifications to the FVIII transgene disclosed herein in SEQ ID NO:39 provide a beneficial technical effect in increasing expression of FVIII.

Example 5. In-Vivo Expression of FVIII in Murine Models Via Sonoporation

In this example, in-vivo expression FVIII transfected to Rag2 mice was evaluated. Prior to the experiment, each mouse was implanted with a jugular vein catheter (JVC), through which the sonoactive microstructures and nucleic acid constructs were administered. Circular DNA encoding FVIII coupled to promoters and genetic regulatory elements were produced: circular DNA comprising the sequence of SEQ ID NO: 43 (ApoE-AAT-hBGi-FVIII-v3-WPRE3-DTS), a FVIII sequence known within the art; and circular DNA comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24).

Parts of the DNA vectors were synthesized (GeneScript) and combined in final circular DNA vectors by NEBuilder® HiFi DNA Assembly (NEB) following manufacture's pro-tocol. In brief, DNA fragments were amplified by PCR reaction utilized Phusion® High-Fidelity DNA Polymerase and primers designed with NEBuilder Assembly Tool. PCR fragments were purified from agarose gel utilizing NED Monarch Gel Extraction kit (NEB) and assembled in HiFi DNA assembly reaction.

Sequences were confirmed using Sanger sequencing, and next-generation sequencing methods. Following confirma-tion of the correct pDNA sequences, transfection of the nucleic acid constructs to the Rag2 mice was performed and evaluated in four experimental groups of three or four Rag2 mice each: a first experimental group was administered 250 ug of a nucleic acid composition comprising the sequence of SEQ ID NO: 43 (ApoE-AAT-hBGi-FVIII-v3-WPRE3-DTS); and a second experimental group was administered 250 ug of a nucleic acid composition comprising the sequence of SEQ ID NO:39 (ApoE-AAT-hBGi-FVIII-N6-F309S-DM-WPRE3-DTS), a nucleic acid expression vector encoding a modified version of the FVIII transgene; a third experimental group was administered 100 ug of a nucleic acid composition comprising the sequence of SEQ ID NO: 43 (ApoE-AAT-hBGi-FVIII-v3-WPRE3-DTS); and a fourth experimental group was administered 100 ug of a nucleic acid composition comprising the sequence of SEQ ID NO:39 (ApoE-AAT-hBGi-FVIII-N6-F309S-DM-WPRE3-DTS), a modified FVIII transgene.

A dose of sonoactive microstructure and DNA solution was readied by first preparing the sonoactive microstructures (Optison) as instructed on the label: remove from 4 C storage and roll between the palms for 20 seconds; removing protective plastic and aluminum covering from Optison vial; placing 25G needle through the rubber gasket to provide a pressure vent; and using 1.5 inch 18G needle to draw up 200 uL of Optison into a syringe (dead space of the needle (about 50 microliters (uL)) included in the calculations). With the same needle and syringe, 50 uL of solution comprising either 250 ug or 100 ug (depending on experimental group) of pDNA payload was drawn into the syringe to combine the DNA and Optison. The Optison microbubbles and DNA payload were mixed in the syringe by rolling the syringe between the fingers until the solution was homogenous at a 1:4 volumetric ratio of DNA to microbubble solution. The DNA+Optison solution was drawn out of the needle dead space. Then the 18G needle was exchanged for a 25G blunt needle for injection into a subject JVC.

The microbubble-DNA solution was administered to the subject in a single bolus injection over about 30 seconds through the jugular vein catheter, and ultrasound energy was applied to the subject over the liver. Ultrasound energy was transcutaneously applied to the liver region of the subject with a C1-6 ultrasound probe, and scans liver of each mouse were performed with a GE LOGIQ e10 ultrasound system equipped with a C1-6 probe, and use of the "ELASTO" software, Shear Wave, using shear wave elastography parameters: GE LOGIQe10 probe C1-6, Abdomen, CHI, Frame rate 55, MI 1.4, Frequency 2.5 MHz, Gain 44, Depth 4 cm, AO %100, Gain 55, T 8, SVD 6.0, AO %100%, +50-400 Hz, GEN. 100% push output and 100% Track output. Mice were administered 150 μL of protein stabilized Optison sonoactive microstructures and 250 pg of nucleic acid in 50 uL of solution, for a total injection volume of about 200 uL, and an acoustic radiation force protocol was applied for 10 seconds, followed by 20 seconds with no application of ultrasound during which the ultrasound probe was removed from the subject, followed again by 10 seconds of an acoustic radiation force protocol, up to the amount of total time of radiation force protocol application indicated in the below table. The shear wave ultrasound acoustic radiation force protocol was applied at an ultrasound intensity of 117.5 to 187.9 mW/cm$^2$ ($I_{SPTA}$) (spatial-peak temporal average intensity), at a mechanical index of 1.4, and a frequency of 2.5 MHz. Ultrasound energy was applied using an alternating imaging technique applying focused ultrasound and generating a B-mode ultrasound image at a mechanical index of 1.4, and a frequency of 2.5 MHz with the ultrasound probe removed from contacting the subject as indicated.

After the administration of the sonoporation treatment, FVIII expression and secretion was measured in subject plasma samples collected at 72 hours following the sonoporation treatment and frozen at −80 C.

Transgenic FVIII level in mouse plasma was measured by MSD assay. Briefly capture antibody (GMA-8024) was loaded to the 96-well plate overnight at 4 C. Next the plate was washed three times with wash buffer and incubated with blocking buffer for 30 min at room temperature. 8 point serial dilution standard were prepared using Xinta® ranging from 0.921U/ml to 0.01 IU/ml. 2-fold diluted samples and standards were added to the wells in 96-well plate. Incubated 2 hours at room temperature and washed 3 times. The detection was performed by incubating samples with GMA-8023 antibody during 2 hours following triple wash. Signal was developed by Sulfo-TAG and detected by MSD machine.

Figure 5:
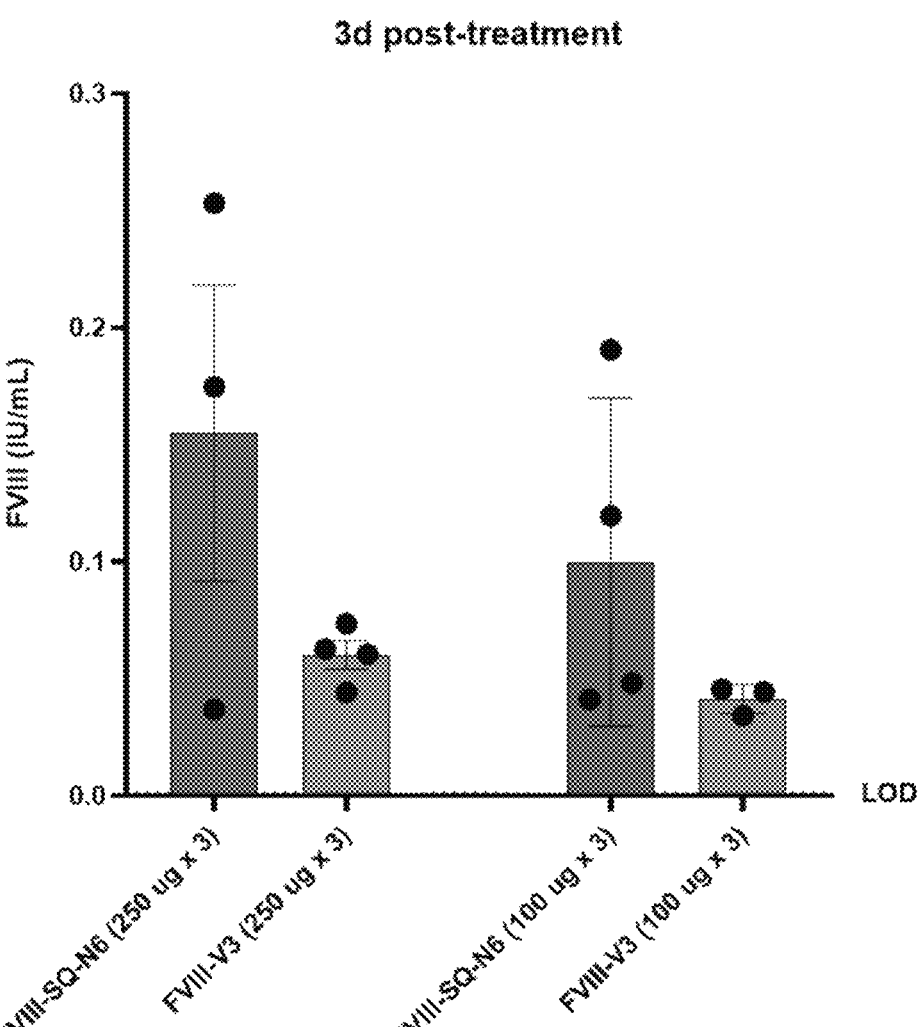
FIG. 5 provides data illustrating improved expression of a therapeutic nucleic acid comprising a modified transgene in a vector comprising improved genetic regulatory elements in-vivo.

Results are shown in FIG. 5, in which it is shown that the first experimental group administered 250 ug of a nucleic acid composition comprising the sequence of SEQ ID NO: 43 (ApoE-AAT-hBGi-FVIII-v3-WPRE3-DTS) exhibits FVIII levels of about 0.06 IU/mL; the second experimental group was administered 250 ug of a nucleic acid composition comprising the sequence of SEQ ID NO:39 (ApoE-AAT-hBGi-FVIII-N6-F309S-DM-WPRE3-DTS), a modified FVIII transgene, exhibits FVIII levels of about 1.5 IU/mL; the third experimental group administered 100 ug of a nucleic acid composition comprising the sequence of SEQ ID NO: 43 (ApoE-AAT-hBGi-FVIII-v3-WPRE3-DTS) exhibits FVIII levels of about 0.04 IU/mL; and the fourth experimental group administered 100 ug of a nucleic acid composition comprising the sequence of SEQ ID NO:39 (ApoE-AAT-hBGi-FVIII-N6-F309S-DM-WPRE3-DTS), a modified FVIII transgene exhibits FVIII levels of about 0.1 IU/mL. Comparing the 250 ug dose groups, it was observed that the second experimental group administered 250 ug of the novel and modified version FVIII transgene of SEQ ID NO: 39 exhibited approximately 3-fold (3x) higher expression levels of FVIII as compared to the second experimental group administered 250 ug of the FVIII sequence of SEQ ID NO: 43, indicating that the modifications to the FVIII transgene disclosed herein in SEQ ID NO:39 provide a beneficial technical effect in increasing expression of FVIII in-vivo. Comparing the 100 ug dose groups, it was observed that the fourth experimental group administered 100 ug of the novel and modified version of the FVIII transgene disclosed herein (SEQ ID NO: 39) exhibited approximately 2.5-fold (2.5x) higher expression levels of FVIII as compared to the third experimental group administered 100 ug of the FVIII sequence of SEQ ID NO: 43, indicating that the modifications to the FVIII transgene disclosed herein in SEQ ID NO:39 provide a beneficial technical effect in increasing expression of FVIII in-vivo.

Example 6. In-Vivo Expression of FVIII in Murine Models Via Sonoporation

In this example, in-vivo expression of a modified FVIII transgene transfected to Rag2 mice was evaluated. Prior to the experiment, each mouse was implanted with a jugular vein catheter (JVC), through which the sonoactive microstructures and nucleic acid constructs were administered. Circular DNA encoding FVIII coupled to promoters and genetic regulatory elements were produced: circular DNA comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), was evaluated in for long term expression in a triple repeated treatment administration protocol.

Parts of the DNA vectors were synthesized (GeneScript) and combined in final circular DNA vectors by NEBuilder® HiFi DNA Assembly (NEB) following manufacture's protocol. In brief, DNA fragments were amplified by PCR reaction using Phusion® High-Fidelity DNA Polymerase and primers were designed with NEBuilder Assembly Tool. PCR fragments were purified from agarose gel utilizing NED Monarch Gel Extraction kit (NEB) and assembled in HiFi DNA assembly reaction.

Sequences were confirmed using Sanger sequencing, and next-generation sequencing methods. Following confirmation of the correct pDNA sequences, transfection of the nucleic acid constructs to the Rag2 mice was performed and evaluated in four experimental groups of three or four Rag2 mice each: an experimental group was administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified version of the FVIII transgene.

The treatment protocol is described in the following paragraphs. Each subject was administered three treatments constituting a cycle, each treatment administered 48 hours apart. Each subject was administered a second cycle 40 days following the completion of the third treatment in the first cycle. Then, each subject was administered a third cycle, 50 days following the completion of the third treatment in the second cycle.

A dose of sonoactive microstructure and DNA solution was readied by first preparing the sonoactive microstructures (Optison) as instructed on the label: remove from 4 C storage and roll between the palms for 20 seconds; removing protective plastic and aluminum covering from Optison vial; placing 25G needle through the rubber gasket to provide a pressure vent; and using 1.5 inch 18G needle to draw up 200 uL of Optison into a syringe. With the same needle and syringe, 50 uL of solution comprising 50 ug of DNA payload was drawn into the syringe to combine the DNA and Optison. The Optison microbubbles and DNA payload were mixed in the syringe by rolling the syringe between the fingers until the solution was homogenous at a 1:4 volumetric ratio of DNA to microbubble solution. The DNA+ Optison solution was drawn out of the needle dead space. Then the 18G needle was exchanged for a 25G blunt needle for injection into a subject JVC.

The microbubble-DNA solution was administered to the subject in a single bolus injection over about 30 seconds through the jugular vein catheter, and ultrasound energy was applied to the subject over the liver. Ultrasound energy was transcutaneously applied to the liver region of the subject with a C1-6 ultrasound probe, and scans liver of each mouse were performed with a GE LOGIQ e10 ultrasound system equipped with a C1-6 probe, and use of the "ELASTO" software, Shear Wave, using shear wave elastography parameters: GE LOGIQe10 probe C1-6, Abdomen, CHI, Frame rate 55, MI 1.4, Frequency 2.5 MHz, Gain 44, Depth 4 cm, AO %100, Gain 55, T 8, SVD 6.0, AO %100%, +50-400 Hz, GEN. 100% push output 100% and Track output 0%. Mice were administered 150 μL of protein stabilized Optison sonoactive microstructures and 50 pg of nucleic acid in 50 uL of solution, for a total injection volume of about 200 uL, and an acoustic radiation force protocol was applied for 10 seconds, followed by 20 seconds with no application of ultrasound during which the ultrasound probe was removed from the subject, followed again by 10 seconds of an acoustic radiation force protocol, for 40 seconds of total ultrasound application. The shear wave ultrasound acoustic radiation force protocol was applied at an ultrasound intensity of 117.5 to 187.9 mW/cm$^2$ ($I_{SPTA}$) (spatial-peak temporal average intensity), at a mechanical index of 1.4, and a frequency of 2.5 MHz. Ultrasound energy was applied using an alternating imaging technique applying focused ultrasound and generating a B-mode ultrasound image at a mechanical index of 0.4, and a frequency of 2.5 MHz with the ultrasound probe removed from contacting the subject as indicated.

After the administration of the sonoporation treatment, FVIII expression and secretion was measured in subject plasma samples collected approximately every 7 days following the sonoporation treatment and frozen at −80 C.

Transgenic FVIII level in mouse plasma was measured by immunoassay (MESO SCALE DIAGNOSTICS, LLC). Briefly capture antibody (GMA-8024) was loaded to the 96-well plate overnight at 4 C. Next the plate was washed three times with wash buffer and incubated with blocking buffer for 30 min at room temperature. 8 point serial dilution standard were prepared using Xinta® ranging from 0.921U/ ml to 0.01 IU/ml. 2-fold diluted samples and standards were added to the wells in 96-well plate. The plate was incubated 2 hours at room temperature and washed 3 times. The detection was performed by incubating samples with GMA-8023 antibody during 2 hours following triple wash. Signal was developed by Sulfo-TAG and detected by MSD machine.

Figure 6:
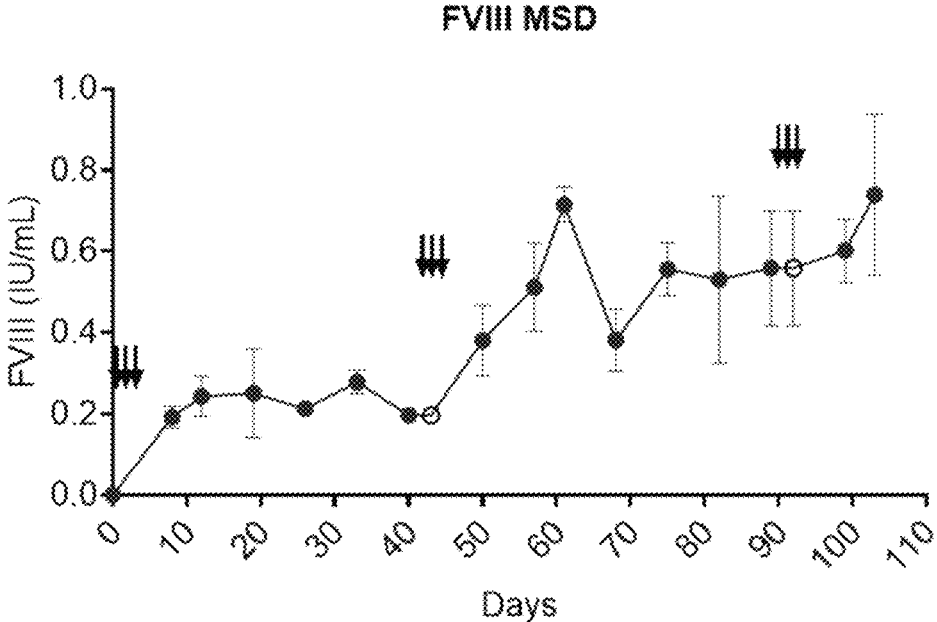
FIG. 6 provides data illustrating improved expression of a therapeutic nucleic acid comprising a modified transgene in a vector comprising improved genetic regulatory elements in-vivo.

Results are shown in FIG. 6, in which it is shown that the experimental group administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified FVIII transgene, exhibits: FVIII levels of about 0.2 IU/mL following the administration of the first cycle with expression levels maintained at this level up to administration of the second cycle; FVIII levels of about 0.5 IU/mL (ranging from 0.2 to 0.7 IU/mL) following the administration of the second cycle with expression levels maintained at about 0.5 IU/mL up to administration of the third cycle; and FVIII levels of about 0.7 IU/mL following the administration of the third cycle with expression levels maintained at about 0.7 IU/mL past 100 days of the study. The results shown herein indicate that the modifications to the nucleic acid expression vector disclosed herein encoding the modified FVIII transgene disclosed herein in SEQ ID NO:39 provide a beneficial technical effect in increasing expression of FVIII in-vivo and maintaining a stable level of FVIII expression in-vivo following a multiple treatment protocol.

Example 7. In-Vivo Expression of FVIII in Murine Models Via Sonoporation

In this example, in-vivo expression of FVIII transfected to Rag2 mice was evaluated. Prior to the experiment, each mouse was implanted with a jugular vein catheter (JVC), through which the sonoactive microstructures and nucleic acid constructs were administered. Circular DNA encoding FVIII coupled to promoters and genetic regulatory elements were produced: circular DNA comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), was evaluated in for short term expression in a triple repeated treatment administration protocol with a lipid stabilized sonoactive agent.

Parts of the DNA vectors were synthesized (GeneScript) and combined in final circular DNA vectors by NEBuilder® HiFi DNA Assembly (NEB) following manufacture's protocol. In brief, DNA fragments were amplified by PCR reaction using Phusion® High-Fidelity DNA Polymerase and primers were designed with NEBuilder Assembly Tool. PCR fragments were purified from agarose gel utilizing NED Monarch Gel Extraction kit (NEB) and assembled in HiFi DNA assembly reaction.

Sequences were confirmed using Sanger sequencing, and next-generation sequencing methods. Following confirmation of the correct pDNA sequences, transfection of the nucleic acid constructs to the Rag2 mice was performed and evaluated in four experimental groups of three or four Rag2 mice each: an experimental group was administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified version of the FVIII transgene.

The treatment protocol is described in the following paragraphs. Each subject was administered three treatments constituting a cycle.

A dose of sonoactive microstructure and DNA solution was readied by first preparing the sonoactive microstructures (Sonazoid, phospholipid stabilized perfluorobutane microbubbles) as instructed on the label. In brief sterile water was drawn up into a syringe, and the vial was penetrated under aseptic conditions. The sterile water was gently injected into the vial, avoiding forceful handling that could damage the microbubbles. Next, the vial was swirled in a gentle, circular motion for several seconds, ensuring the Sonazoid powder dissolves and forms a uniform suspension without creating excess foam or bubbles. Once reconstituted, the suspension is visually inspected for clarity and absence of particulate matter or discoloration. With the same needle and syringe, 50 uL of solution comprising 50 ug of DNA payload was drawn into the syringe to combine the DNA and Sonazoid. The Sonazoid microbubbles and DNA payload were mixed in the syringe by rolling the syringe between the fingers until the solution was homogenous. The DNA+Sonazoid solution was drawn out of the needle dead space in preparation for injection into a subject JVC.

The microbubble-DNA solution was administered to the subject in a single bolus injection over about 30 seconds through the jugular vein catheter, and ultrasound energy was applied to the subject over the liver. Ultrasound energy was transcutaneously applied to the liver region of the subject with a C1-6 ultrasound probe, and scans liver of each mouse were performed with a GE LOGIQ e10 ultrasound system equipped with a C1-6 probe, and use of the "ELASTO" software, Shear Wave, using shear wave elastography parameters: GE LOGIQe10 probe C1-6, Abdomen, CHI, Frame rate 55, MI 1.4, Frequency 2.5 MHz, Gain 44, Depth 4 cm, AO %100, Gain 55, T 8, SVD 6.0, AO %100%, +50-400 Hz, GEN. 100% push output 100% and Track output 0%. Mice were administered the sonoactive agent and DNA suspension, and an acoustic radiation force protocol was applied for 10 seconds, followed by 20 seconds with no application of ultrasound during which the ultrasound probe was removed from the subject, followed again by 10 seconds of an acoustic radiation force protocol, for 40 seconds of total ultrasound application. The shear wave ultrasound acoustic radiation force protocol was applied at an ultrasound intensity of 117.5 to 187.9 mW/cm$^2$ ($I_{SPTA}$) (spatial-peak temporal average intensity), at a mechanical index of 1.4, and a frequency of 2.5 MHz. Ultrasound energy was applied using an alternating imaging technique applying focused ultrasound and generating a B-mode ultrasound image at a mechanical index of 0.4, and a frequency of 2.5 MHz with the ultrasound probe removed from contacting the subject as indicated.

After the administration of the sonoporation treatment, FVIII expression and secretion was measured in subject plasma samples collected approximately at days 9 and 13 following the sonoporation treatment and frozen at −80 C.

Transgenic FVIII level in mouse plasma was measured by immunoassay (MESO SCALE DIAGNOSTICS, LLC). Briefly capture antibody (GMA-8024) was loaded to the 96-well plate overnight at 4 C. Next the plate was washed three times with wash buffer and incubated with blocking buffer for 30 min at room temperature. 8 point serial dilution standard were prepared using Xinta® ranging from 0.921U/ml to 0.01 IU/ml. 2-fold diluted samples and standards were added to the wells in 96-well plate. Incubated 2 hours at room temperature and washed 3 times. The detection was performed by incubating samples with GMA-8023 antibody for 2 hours following triple wash. Signal was developed by Sulfo-TAG and detected by MSD machine.

Figure 7:
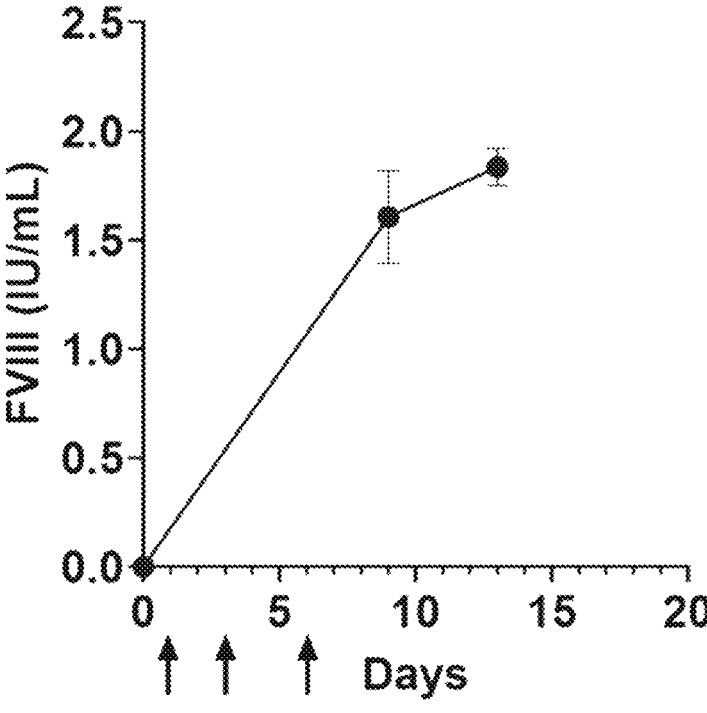
FIG. 7 provides data illustrating improved expression of a therapeutic nucleic acid comprising a modified transgene in a vector comprising improved genetic regulatory elements in-vivo.
Figure 8:
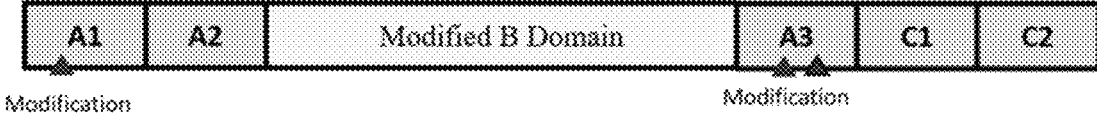
FIG. 8 illustrates a modified FVIII transgene disclosed herein.

Results are shown in FIG. 7, in which it is shown that the experimental group administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified FVIII transgene, exhibits: FVIII levels of about 1.37 IU/mL at day 9 and 1.72 IU/mL at day 13 following the administration of the first cycle. The results shown herein indicate that the modifications to the nucleic acid expression vector disclosed herein encoding the modified FVIII transgene disclosed herein in SEQ ID NO:39 provide a beneficial technical effect in increasing expression of FVIII in-vivo and maintaining a stable level of FVIII expression in-vivo following a multiple treatment protocol.

Example 8. Chromogenic Assay Evaluating Clotting Activity of FVIII in a Murine Model of Hemophilia A In this example, in-vivo expression of FVIII transgenes of the present disclosure transfected to 129S-F8 mice (a FVIII knock out mouse which is used as a murine model of Hemophilia A) were evaluated, and the clotting activity of secreted FVIII protein was evaluated using a chromogenic assay. Circular DNA encoding FVIII coupled to promoters and genetic regulatory elements were produced: circular DNA comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), was evaluated in for short term expression and clotting activity of the FVIII protein as compared to a clinically validated FVIII protein control.

Parts of the DNA vectors were synthesized (GeneScript) and combined in final circular DNA vectors by NEBuilder® HiFi DNA Assembly (NEB) following manufacture's protocol. In brief, DNA fragments were amplified by PCR reaction using Phusion® High-Fidelity DNA Polymerase and primers were designed with NEBuilder Assembly Tool. PCR fragments were purified from agarose gel utilizing NED Monarch Gel Extraction kit (NEB) and assembled in HiFi DNA assembly reaction.

Sequences were confirmed using Sanger sequencing, and next-generation sequencing methods. Following confirmation of the correct pDNA sequences, transfection of the nucleic acid constructs to the 129S-F8 mice was performed and evaluated in three experimental groups of one (for the naive control group) or four 129S-F8 mice each: Group 1 was a naive control not administered any ultrasound or nucleic acids; Group 2 was administered 50 ug of a nucleic acid composition comprising the sequence of SEQ ID NO:39 (ApoE-AAT-hBGi-FVIII-N6-F309S-DM-WPRE3-DTS) which encodes a FVIII polypeptide having a sequence of SEQ ID NO: 24; and Group 3 was administered 50 ug of a nucleic acid composition encoding a clinically validated FVIII transgene (FVIII v3) having a sequence of SEQ ID NO: 46. The 50 ug dose of the nucleic acid composition was administered to the mice through tail vein injection using a hydrodynamic delivery technique in which a solution of 50 uL of the nucleic acid composition and 1950 uL of saline were rapidly injected into the tail vein over about 1 second to drive delivery into the liver.

After the administration of the sonoporation treatment, FVIII expression and secretion was measured in subject plasma samples collected approximately 24 hours following the hydrodynamic delivery.

Transgenic FVIII level in mouse plasma was measured by immunoassay (MESO SCALE DIAGNOSTICS, LLC). Briefly capture antibody (GMA-8024) was loaded to the 96-well plate overnight at 4 C. Next the plate was washed three times with wash buffer and incubated with blocking buffer for 30 min at room temperature. 8 point serial dilution standard were prepared using Xinta® ranging from 0.921U/ ml to 0.01 IU/ml. 2-fold diluted samples and standards were added to the wells in 96-well plate. Incubated 2 hours at room temperature and washed 3 times. The detection was performed by incubating samples with GMA-8023 antibody for 2 hours following triple wash. Signal was developed by Sulfo-TAG and detected by MSD machine.

Figure 9A:
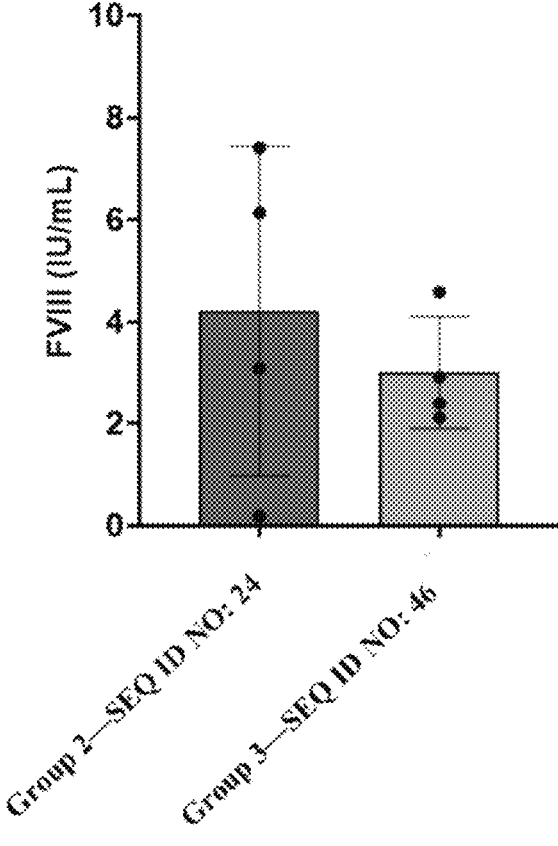
FIG. 9A provides data illustrating improved expression of a modified FVIII polypeptide and its clotting activity measured by chromogenic assay.

Results are shown in FIG. 9A, in which it is shown that the experimental Group 2 administered 50 ug of a nucleic acid composition comprising the sequence of SEQ ID NO:39 (ApoE-AAT-hBGi-FVIII-N6-F309S-DM-WPRE3-DTS) and encoding a FVIII polypeptide of SEQ ID NO: 24, a nucleic acid expression vector encoding a modified FVIII transgene, exhibits average FVIII levels of about 4 IU/mL; experimental Group 3 administered 50 ug of a nucleic acid composition encoding a clinically validated FVIII transgene (FVIII v3) having a sequence of SEQ ID NO: 46 exhibits FVIII levels of about 3.25 IU/mL.

The FVIII chromogenic assay is a laboratory method used to measure the functional activity of Factor VIII through a two-stage process: first, patient plasma is incubated with activated Factor IX, Factor X, phospholipids, and calcium, allowing active Factor VIII to facilitate the conversion of Factor X to Factor Xa; second, the amount of Factor Xa produced is quantified by adding a chromogenic substrate that releases a colored product upon cleavage by Factor Xa, with the color intensity being directly proportional to the Factor VIII activity in the sample.

Next, the FVIII chromogenic assay was performed on remaining plasma samples to assess the clotting activity of the novel transgenic FVIII protein. Initially, all required reagents and consumables are prepared, ensuring that if the assay kit is brand new, all components are reconstituted correctly to yield sufficient material for two full plates. Prior to commencing the assay, the $CaCl_2$) and S-2765+I-2581 solutions are pre-warmed to 37° C., and the shaking incubator is set to the same temperature. Standard curves are established using several control materials: stock FACT plasma (from George King Bio-Medical, lot 7662) standardized at 100% with a CoA chromogenic FVIII activity of 92%, naive C57 plasma collected with $K_2$-EDTA, and stock Xyntha (lot GX0072) at 62 IU/mL. For sample preparation, 5 µL of each sample or standard is diluted into 400 µL of 1× Buffer Solution in a deep-well plate, and the mixtures are briefly agitated using the shaking incubator set to a short mixing cycle. Next, 25 µL of the diluted sample or standard is transferred into the wells of a 96-well plate, followed by the addition of 50 µL of the IXa/X/Phospholipid reagent.

The plate is then sealed and incubated at 37° C. for 5 minutes. Subsequently, 25 µL of $CaCl_2$ is added, the plate is resealed, and the incubation at 37° C. continues for another 5 minutes. Thereafter, 50 µL of the combined S-2765+I-2581 solution is introduced, and following sealing, the incubation at 37° C. is maintained for an additional 5 minutes. To terminate the enzymatic reaction, 25 µL of 20% acetic acid (serving as the stop buffer) is added, the plate is sealed once more, and a brief shake using the "Short" button ensures thorough mixing. Finally, the plate is immediately read on a SpectraMax Plate Reader at wavelengths of 405 nm and 490 nm to determine the chromogenic response, which correlates with the Factor VIII activity in the tested samples.

Figure 9B:
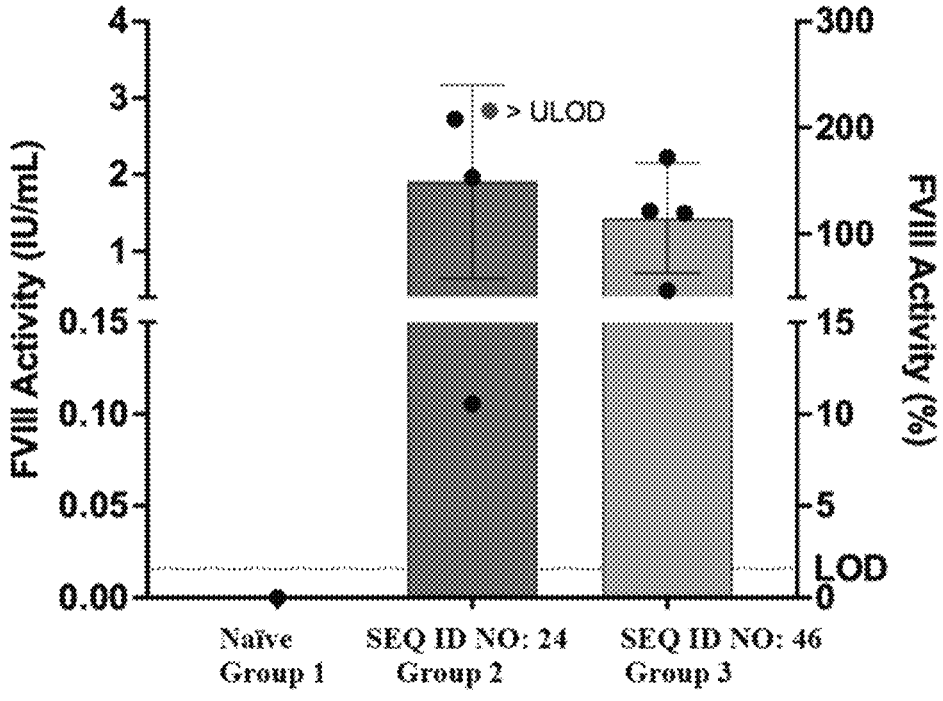
FIG. 9B provides data illustrating improved expression of a modified FVIII polypeptide and its clotting activity measured by chromogenic assay.
Figure 9C:
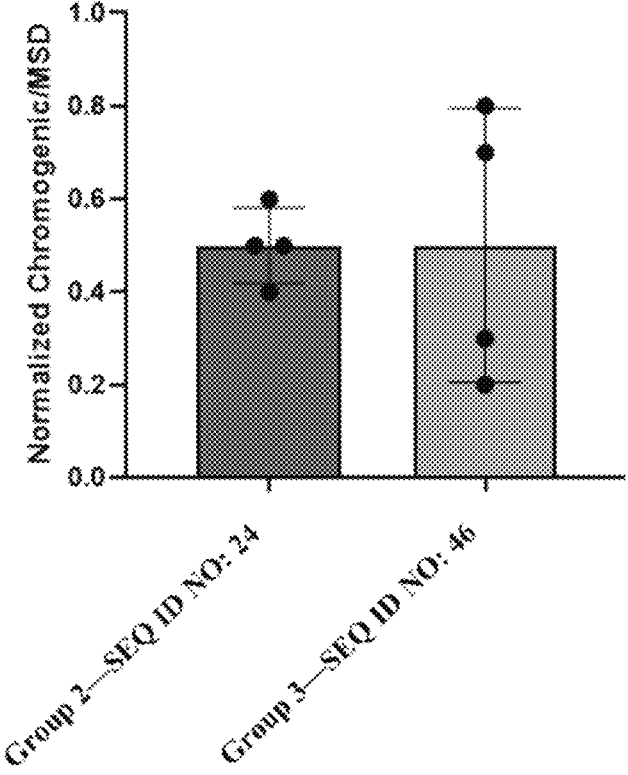
FIG. 9C provides data illustrating improved expression of a modified FVIII polypeptide and its clotting activity measured by chromogenic assay.

Results are shown in FIG. 9B, where it is shown that experimental Group 2 administered 50 ug of a nucleic acid composition comprising the sequence of SEQ ID NO:39 (ApoE-AAT-hBGi-FVIII-N6-F309S-DM-WPRE3-DTS) and encoding a FVIII polypeptide of SEQ ID NO: 24, a nucleic acid expression vector encoding a modified FVIII transgene, exhibits average FVIII activity levels of about 2 IU/mL and 175% FVIII activity; and experimental Group 3 administered 50 ug of a nucleic acid composition encoding a clinically validated FVIII transgene (FVIII v3) having a sequence of SEQ ID NO: 46 exhibits average FVIII activity levels of about 1.25 IU/mL and 110% FVIII activity. Additional results are shown in FIG. 9C where the FVIII activity levels are normalized to the FVIII plasma levels to show the relative clotting activity of each FVIII polypeptide to allow for assessment of the specific activity of the protein, distinguishing whether differences in the coagulation function was due to a reduced quantity of Factor VIII or to qualitative defects in the protein's functionality. As can be shown in FIG. 9C, the FVIII polypeptide of SEQ ID NO: 24 exhibits a normalized FVIII activity level (normalized to MSD FVIII plasma protein level) of about 0.5, which is approximate equivalent to clinically validated FVIII transgene (FVIII v3) having a sequence of SEQ ID NO: 46. The results shown herein indicate that the modifications to the modified FVIII transgene disclosed herein in SEQ ID NO:24 maintains coagulation activity of FVIII.

Example 9. In-Vivo Expression of FVIII in Murine Models Via Sonoporation

In this example, in-vivo expression of a modified FVIII transgene transfected to Rag2 mice was evaluated. Prior to the experiment, each mouse was implanted with a jugular vein catheter (JVC), through which the sonoactive microstructures and nucleic acid constructs were administered. Circular DNA encoding FVIII coupled to promoters and genetic regulatory elements were produced: circular DNA comprising the sequence of SEQ ID NO:39 (ApoE-AAT-hBGi-FVIII-N6-F309S-DM-WPRE3-DTS), encoding a modified version of the FVIII transgene disclosed herein (SEQ ID NO: 24), and was evaluated in for long term expression in a triple treatment administration protocol.

Parts of the DNA vectors were synthesized (GeneScript) and combined in final circular DNA vectors by NEBuilder® HiFi DNA Assembly (NEB) following manufacture's protocol. In brief, DNA fragments were amplified by PCR reaction using Phusion® High-Fidelity DNA Polymerase and primers were designed with NEBuilder Assembly Tool. PCR fragments were purified from agarose gel utilizing NED Monarch Gel Extraction kit (NEB) and assembled in HiFi DNA assembly reaction.

Sequences were confirmed using Sanger sequencing, and next-generation sequencing methods. Following confirmation of the correct pDNA sequences, transfection of the nucleic acid constructs to the Rag2 mice was performed and evaluated in four experimental groups of five Rag2 mice each: an experimental group was administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified version of the FVIII transgene (SEQ ID NO: 24).

A dose of sonoactive microstructure and DNA solution was readied by first preparing the sonoactive microstructures (Sonazoid, phospholipid stabilized perfluorobutane microbubbles) as instructed on the label. In brief sterile water was drawn up into a syringe, and the vial was penetrated under aseptic conditions. The sterile water was gently injected into the vial, avoiding forceful handling that could damage the microbubbles. Next, the vial was swirled in a gentle, circular motion for several seconds, ensuring the Sonazoid powder dissolves and forms a uniform suspension without creating excess foam or bubbles. Once reconstituted, the suspension is visually inspected for clarity and absence of particulate matter or discoloration. With the same needle and syringe, 20 uL of solution comprising 50 ug of DNA payload was drawn into the syringe to combine the DNA and Sonazoid microbubbles. The Sonazoid microbubbles and DNA payload were mixed in the syringe by rolling the syringe between the fingers until the solution was homogenous at a 1:4 volumetric ratio of DNA to microbubble solution. The DNA+Optison solution was drawn out of the needle dead space. Then the 18G needle was exchanged for a 25G blunt needle for injection into a subject JVC.

The microbubble-DNA solution was administered to the subject in a single bolus injection over about 30 seconds through the jugular vein catheter, and ultrasound energy was applied to the subject over the liver. Ultrasound energy was transcutaneously applied to the liver region of the subject with a C1-6 ultrasound probe, and scans liver of each mouse were performed with a GE LOGIQ e10 ultrasound system equipped with a C1-6 probe, and use of the "ELASTO" software, Shear Wave, using shear wave elastography parameters: GE LOGIQe10 probe C1-6, Abdomen, CHI, Frame rate 55, MI 1.4, Frequency 2.5 MHz, Gain 44, Depth 4 cm, AO %100, Gain 55, T 8, SVD 6.0, AO %100%, +50-400 Hz, GEN. 100% push output 100% and Track output 0%. Mice were administered 150 μL of protein stabilized Optison sonoactive microstructures and 50 pg of nucleic acid in 50 uL of solution, for a total injection volume of about 200 uL, and an acoustic radiation force protocol was applied for 10 seconds, followed by 20 seconds with no application of ultrasound during which the ultrasound probe was removed from the subject, followed again by 10 seconds of an acoustic radiation force protocol, for 40 seconds of total ultrasound application. The shear wave ultrasound acoustic radiation force protocol was applied at an ultrasound intensity of 117.5 to 187.9 mW/cm$^2$ ($I_{SPTA}$) (spatial-peak temporal average intensity), at a mechanical index of 1.4, and a frequency of 2.5 MHz. Ultrasound energy was applied using an alternating imaging technique applying focused ultrasound and generating a B-mode ultrasound image at a mechanical index of 0.4, and a frequency of 2.5 MHz with the ultrasound probe removed from contacting the subject as indicated.

After the administration of the sonoporation treatment, FVIII expression and secretion was measured in subject plasma samples collected and frozen at −80 C approximately every 10 days following the sonoporation treatment for the first forty days, and then every forty days for the next 3 sample collections.

Transgenic FVIII level in mouse plasma was measured by immunoassay (MESO SCALE DIAGNOSTICS, LLC). Briefly capture antibody (GMA-8024) was loaded to the 96-well plate overnight at 4 C. Next the plate was washed three times with wash buffer and incubated with blocking buffer for 30 min at room temperature. 8 point serial dilution standard were prepared using Xinta® ranging from 0.921U/ml to 0.01 IU/ml. 2-fold diluted samples and standards were added to the wells in 96-well plate. The plate was incubated 2 hours at room temperature and washed 3 times. The detection was performed by incubating samples with GMA-8023 antibody during 2 hours following triple wash. Signal was developed by Sulfo-TAG and detected by MSD machine.

Figure 10:
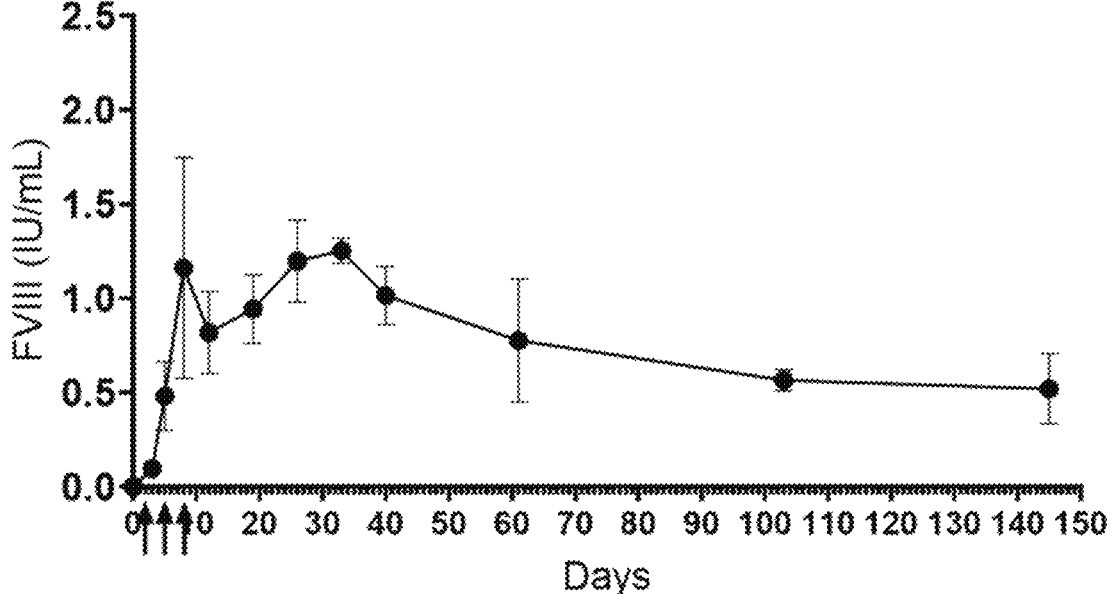
FIG. 10 provides data illustrating improved expression of a modified FVIII polypeptide delivered in a vector comprising improved genetic regulatory elements in-vivo.

Results are shown in FIG. 10, in which it is shown that the experimental group administered 50 ug of a nucleic acid composition comprising the sequence of SEQ ID NO:39 (ApoE-AAT-hBGi-FVIII-N6-F309S-DM-WPRE3-DTS), a nucleic acid expression vector encoding a modified FVIII transgene (SEQ ID NO: 24), exhibits: FVIII levels of about 1.16 IU/mL following the administration of the cycle of three doses with expression levels maintained from a range of 0.8 to 1.25 IU/mL through day 40, with FVIII levels of 0.77, 0.56, 0.52 IU/mL being observed at days 61, 103, and 145 respectively.

The results shown herein indicate that the modifications to the nucleic acid expression vector (SEQ ID NO:39) disclosed herein encoding the modified FVIII transgene (SEQ ID NO: 24) disclosed herein in provide a beneficial technical effect in increasing expression of FVIII in-vivo and maintaining a stable level of FVIII expression in-vivo following a multiple treatment protocol for at least 145 days.

Definitions

As used herein, the term "effective amount" refers to an amount sufficient to affect beneficial or desirable biological and/or clinical results.

As used herein, the term "full-length" as applied to a gene, transgene, or polypeptide refers to an amino acid sequence (or a nucleic acid that encodes an amino acid sequence) that comprises all domains of the polypeptide that are needed for functional biological activity. Thus, a full-length sequence may refer to a truncated or modified version of a protein (or a nucleic acid that directly encodes the protein) so long as the resulting protein retains functional biological activity. However, neither a non-functional protein nor a nucleic acid that encodes that encodes only non-functional portions of a polypeptide are full-length proteins.

As used herein, the term "sonoactive agent" or "sonoactive microstructure" refers to ultrasound agents which undergo cavitation when exposed to ultrasound acoustic energy and which may be used to deliver a sonoporation treatment to a subject.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The term "isolated" when used in relation to a nucleic acid molecule of the present disclosure typically refers to a nucleic acid sequence that is identified and separated from at least one contaminant nucleic acid with which it is ordinarily associated in its natural source. Isolated nucleic acid may be present in a form or setting that is different from that in which it is found in nature. Isolated nucleic acid molecules therefore are distinguished from the nucleic acid molecule as they exist in natural cells.

The term "identity," and grammatical variations thereof, mean that two or more referenced entities are the same, when they are "aligned" sequences. Thus, by way of example, when two polypeptide sequences are identical, they have the same amino acid sequence, at least within the referenced region or portion. Where two polynucleotide sequences are identical, they have the same polynucleotide sequence, at least within the referenced region or portion. The identity can be over a defined area (region or domain) of the sequence. An "area" or "region" of identity refers to a portion of two or more referenced entities that are the same. Thus, where two protein or nucleic acid sequences are identical over one or more sequence areas or regions, they share identity within that region. An "aligned" sequence refers to multiple polynucleotide or protein (amino acid) sequences, often containing corrections for missing or additional bases or amino acids (gaps) as compared to a reference sequence.

As used herein the term "sequence identity" refers to the percentage identity calculated as the matching residues divided by the total number of residues in the total alignment when performing a consensus alignment of two sequences, with gaps in the alignment scored as a mismatching residue.

As used herein "therapeutic protein" refers to a polypeptide that has a biological activity that replaces or compensates for the loss or reduction of activity of an endogenous protein. For example, functional human factor VIII is a therapeutic protein for hemophilia A.

As used herein "FVIII polypeptide" refers to a full length FVIII polypeptide or any biologically active fragment or variant of a FVIII polypeptide.

What has been described and illustrated herein is an example along with some of its variations. The terms, descriptions and figures used herein are set forth by way of illustration only and are not meant as limitations.

SEQUENCE LISTING

| Element | Sequence | # |
|---|---|---|
| ApoE-AAT promoter | CGCGTCTGCAGGCTCAGAGGCACACAGGAGTTTCTGGGCTCACCCTGCCCCCTTCCAACCCCTCA GTTCCCATCCTCCAGCAGCTGTTTGTGTGCTGCCTCTGAAGTCCACACTGAACAAACTTCAGCCT ACTCATGTCCCTAAAATGGGCAAACATTGCAAGCAGCAAACAGCAAACACACAGCCCTCCCTGC CTGCTGACCTTGGAGCTGGGGCAGAGGTCAGAGACCTCTCTGGGCCCATGCCACCTCCAACATC CACTCGACCCCTTGGAATTTCGGTGGAGAGGAGCAGAGGTTGTCCTGGCGTGGTTTAGGTAGTG TGAGAGGGGTCGACTGGACACAGGACGCTGTGGTTTCTGAGCCAGGGGGCGACTCAGATCCCAG CCAGTGGACTTAGCCCCTGTTTGCTCCTCCGATAACTGGGGTGACCTTGGTTAATATTCACCAGC AGCCTCCCCCGTTGCCCC | 1 |
| hBGi intron | TCTGGATCCACTGCTTAAATACGGACGAGGACAGGGCCCTGTCTCCTCAGCTTCAGGCACCACC ACTGACCTGGGACAGTGAATCGTAAGTACTAGCAGCTACAATCCAGCTACCATTCTGCTTTTATT TTATGGTTGGGATAAGGCTGGATTATTCTGAGTCCAAGCTAGGCCCTTTTGCTAATCATGTTCAT ACCTCTTATCTTCCTCCCACAGCTCCTGGGCAACGTGCTGGTCTGTGTGCTGGCCCATCACTTTGG CAAAGAATTGCGATCGCCACC | 2 |
| FVIII-v3 ORF | ATGCAGATTGAGCTGAGCACCTGCTTCTTCCTGTGCCTGCTGAGGTTCTGCTTCTCTGCCACCAG GAGATACTACCTGGGGGCTGTGGAGCTGAGCTGGGACTACATGCAGTCTGACCTGGGGGAGCTG CCTGTGGATGCCAGGTTCCCCCCCAGAGTGCCCAAGAGCTTCCCCTTCAACACCTCTGTGGTGTA CAAGAAGACCCTGTTTGTGGAGTTCACTGACCACCTGTTCAACATTGCCAAGCCCAGGCCCCCCT GGATGGGCCTGCTGGGCCCCACCATCCAGGCTGAGGTGTATGACACTGTGGTGATCACCCTGAA GAACATGGCCAGCCACCCTGTGAGCCTGCATGCTGTGGGGGTGAGCTACTGGAAGGCCTCTGAG GGGGCTGAGTATGATGACCAGACCAGCCAGAGGGAGAAGGAGGATGACAAGGTGTTCCCTGGG GGCAGCCACACCTATGTGTGGCAGGTGCTGAAGGAGAATGGCCCCATGGCCTCTGACCCCCTGT GCCTGACCTACAGCTACCTGAGCCATGTGGACCTGGTGAAGGACCTGAACTCTGGCCTGATTGG GGCCCTGCTGGTGTGCAGGGAGGGCAGCCTGGCCAAGGAGAAGACCCAGACCCTGCACAAGTT CATCCTGCTGTTTGCTGTGTTTGATGAGGGCAAGAGCTGGCACTCTGAAACCAAGAACAGCCTG ATGCAGGACAGGGATGCTGCCTCTGCCAGGGCCTGGCCCAAGATGCACACTGTGAATGGCTATG TGAACAGGAGCCTGCCTGGCCTGATTGGCTGCCACAGGAAGTCTGTGTACTGGCATGTGATTGG CATGGGCACCACCCCTGAGGTGCACAGCATCTTCCTGGAGGGCCACACCTTCCTGGTCAGGAAC CACAGGCAGGCCAGCCTGGAGATCAGCCCCATCACCTTCCTGACTGCCCAGACCCTGCTGATGG ACCTGGGCCAGTTCCTGCTGTTCTGCCACATCAGCAGCCACCAGCATGATGGCATGGAGGCCTA TGTGAAGGTGGACAGCTGCCCTGAGGAGCCCCAGCTGAGGATGAAGAACAATGAGGAGGCTGA GGACTATGATGATGACCTGACTGACTCTGAGATGGATGTGGTGAGGTTTGATGATGACAACAGC CCCAGCTTCATCCAGATCAGGTCTGTGGCCAAGAAGCACCCCAAGACCTGGGTGCACTACATTG CTGCTGAGGAGGAGGACTGGGACTATGCCCCCCTGGTGCTGGCCCCTGATGACAGGAGCTACAA GAGCCAGTACCTGAACAATGGCCCCCAGAGGATTGGCAGGAAGTACAAGAAGGTCAGGTTCAT GGCCTACACTGATGAAACCTTCAAGACCAGGGAGGCCATCCAGCATGAGTCTGGCATCCTGGGC CCCCTGCTGTATGGGGAGGTGGGGGACACCCTGCTGATCATCTTCAAGAACCAGGCCAGCAGGC CCTACAACATCTACCCCCATGGCATCACTGATGTGAGGCCCCTGTACAGCAGGAGGCTGCCCAA GGGGGTGAAGCACCTGAAGGACTTCCCCATCCTGCCTGGGGAGATCTTCAAGTACAAGTGGACT GTGACTGTGGAGGATGGCCCCACCAAGTCTGACCCCAGGTGCCTGACCAGATACTACAGCAGCT TTGTGAACATGGAGAGGGACCTGGCCTCTGGCCTGATTGGCTGCCCCCTGCTGATCTGCTACAAGGA GTCTGTGGACCAGAGGGGCAACCAGATCATGTCTGACAAGAGGAATGTGATCCTGTTCTCTGTG TTTGATGAGAACAGGAGCTGGTACCTGACTGAGAACATCCAGAGGTTCCTGCCCAACCCTGCTG GGGTGCAGCTGGAGGACCCTGAGTTCCAGGCCAGCAACATCATGCACAGCATCAATGGCTATGT GTTTGACAGCCTGCAGCTGTCTGTGTGCCTGCATGAGGTGGCCTACTGGTACATCCTGAGCATTG | 3 |

| SEQUENCE LISTING | | |
| --- | --- | --- |
| Element | Sequence | # |

```
         GGGCCCAGACTGACTTCCTGTCTGTGTTCTTCTCTGGCTACACCTTCAAGCACAAGATGGTGTAT
         GAGGACACCCTGACCCTGTTCCCCTTCTCTGGGGAGACTGTGTTCATGAGCATGGAGAACCCTG
         GCCTGTGGATTCTGGGCTGCCACAACTCTGACTTCAGGAACAGGGGCATGACTGCCCTGCTGAA
         AGTCTCCAGCTGTGACAAGAACACTGGGGACTACTATGAGGACAGCTATGAGGACATCTCTGCC
         TACCTGCTGAGCAAGAACAATGCCATTGAGCCCAGGGACTTCAGCCAGAATGCCACTAATGTGT
         CTAACAACAGCAACACCAGCAATGACAGCAATGTGTCTCCCCCAGTGCTGAAGAGGCACCAGA
         GGGAGATCACCAGGACCACCCTGCAGTCTGACCAGGAGGAGATTGACTATGATGACACCATCTC
         TGTGGAGATGAAGAAGGAGGACTTTGACATCTACGACGAGGACGAGAACCAGAGCCCCAGGAG
         CTTCCAGAAGAAGACCAGGCACTACTTCATTGCTGCTGTGGAGAGGCTGTGGGACTATGGCATG
         AGCAGCAGCCCCCATGTGCTGAGGAACAGGGCCCAGTCTGGCTCTGTGCCCCAGTTCAAGAAGG
         TGGTGTTCCAGGAGTTCACTGATGGCAGCTTCACCCAGCCCCTGTACAGAGGGGAGCTGAATGA
         GCACCTGGGCCTGCTGGGCCCCTACATCAGGGCTGAGGTGGAGGACAACATCATGGTGACCTTC
         AGGAACCAGGCCAGCAGGCCCTACAGCTTCTACAGCAGCCTGATCAGCTATGAGGAGGACCAG
         AGGCAGGGGGCTGAGCCCAGGAAGAACTTTGTGAAGCCCAATGAAACCAAGACCTACTTCTGG
         AAGGTGCAGCACCACATGGCCCCCACCAAGGATGAGTTTGACTGCAAGGCCTGGGCCTACTTCT
         CTGATGTGGACCTGGAGAAGGATGTGCACTCTGGCCTGATTGGCCCCCTGCTGGTGTGCCACAC
         CAACACCCTGAACCCTGCCCATGGCAGGCAGGTGACTGTGCAGGAGTTTGCCCTGTTCTTCACCA
         TCTTTGATGAAACCAAGAGCTGGTACTTCACTGAGAACATGGAGAGGAACTGCAGGGCCCCCTG
         CAACATCCAGATGGAGGACCCCACCTTCAAGGAGAACTACAGGTTCCATGCCATCAATGGCTAC
         ATCATGGACACCCTGCCTGGCCTGGTGATGGCCCAGGACCAGAGGATCAGGTGGTACCTGCTGA
         GCATGGGCAGCAATGAGAACATCCACAGCATCCACTTCTCTGGCCATGTGTTCACTGTGAGGAA
         GAAGGAGGAGTACAAGATGGCCCTGTACAACCTGTACCCTGGGGTGTTTGAGACTGTGGAGATG
         CTGCCCAGCAAGGCTGGCATCTGGAGGGTGGAGTGCCTGATTGGGGAGCACCTGCATGCTGGCA
         TGAGCACCCTGTTCCTGGTGTACAGCAACAAGTGCCAGACCCCCCTGGGCATGGCCTCTGGCCA
         CATCAGGGACTTCCAGATCACTGCCTCTGGCCAGTATGGCCAGTGGGCCCCCAAGCTGGCCAGG
         CTGCACTACTCTGGCAGCATCAATGCCTGGAGCACCAAGGAGCCCTTCAGCTGGATCAAGGTGG
         ACCTGCTGGCCCCCATGATCATCCATGGCATCAAGACCCAGGGGGCCAGGCAGAAGTTCAGCAG
         CCTGTACATCAGCCAGTTCATCATCATGTACAGCCTGGATGGCAAGAAGTGGCAGACCTACAGG
         GGCAACAGCACTGGCACCCTGATGGTGTTCTTTGGCAATGTGGACAGCTCTGGCATCAAGCACA
         ACATCTTCAACCCCCCCATCATTGCCAGATACATCAGGCTGCACCCCACCCACTACAGCATCAGG
         AGCACCCTGAGGATGGAGCTGATGGGCTGTGACCTGAACAGCTGCAGCATGCCCCTGGGCATGG
         AGAGCAAGGCCATCTCTGATGCCCAGATCACTGCCAGCAGCTACTTCACCAACATGTTTGCCAC
         CTGGAGCCCCAGCAAGGCCAGGCTGCACCTGCAGGGCAGGAGCAATGCCTGGAGGCCCCAGGT
         CAACAACCCCAAGGAGTGGCTGCAGGTGGACTTCCAGAAGACCATGAAGGTGACTGGGGTGAC
         CACCCAGGGGGTGAAGAGCCTGCTGACCAGCATGTATGTGAAGGAGTTCCTGATCAGCAGCAGC
         CAGGATGGCCACCAGTGGACCCTGTTCTTCCAGAATGGCAAGGTGAAGGTGTTCCAGGGCAACC
         AGGACAGCTTCACCCCTGTGGTGAACAGCCTGGACCCCCCCCCTGCTGACCAGATACCTGAGGAT
         TCACCCCCAGAGCTGGGTGCACCAGATTGCCCTGAGGATGGAGGTGCTGGGCTGTGAGGCCCAG
         GACCTGTACTGA
```

| WPRE3 | AATCAACCTCTGGATTACAAAATTTGTGAAAGATTGACTGGTATTCTTAACTATGTTGCTCCTTTT<br>ACGCTATGTGGATACGCTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTGGCCCGTTGTCAGGCAA<br>CGTGGCGTGGTGTGCACTGTGTTTGCTGACGCAACCCCCACTGGTTGGGGCATTGCCACCACCTG<br>TCAGCTCCTTTCCGGGACTTTCGCTTTCCCCCTCCCTATTGCCACGGCGGAACTCATCGCCGCCTG<br>CCTTGCCCGCTGCTGGACAGGGGCTCGGCTGTTGGGCACTGACAATTCCGTGG | 4 |

| bGH poly A | TGTGCCTTCTAGTTGCCAGCCATCTGTTGTTTGCCCCTCCCCCGTGCCTTCCTTGACCCTGGAAGG<br>TGCCACTCCCACTGTCCTTTCCTAATAAAATGAGGAAATTGCATCGCATTGTCTGAGTAGGTGTC<br>ATTCTATTCTGGGGGGTGGGGTGGGGCAGGACAGCAAGGGGGAGGATTGGGAAGACAATAGCA<br>GGCATGCTGGGGATGCGGTGGGCTCTATGG | 5 |

| DTS | GAGCTGTGCGATCCCTGCTGGGGACTTTCCGCTGGGGACTTTCCGCTGGGGACTTTCCGCCTTCA<br>GCTAAGGAAGCTACCAATATTTAGAGGTACATTTTGTTCTAGAACAAAATGTACCGGTACATTTT<br>GTTCTGGTACATTTTGTTCT | 6 |

| NP<br>Backbone | TGGCTTGTTGTCCACAACCATTAAACCTTAAAAGCTTTAAAAGCCTTATATATTCTTTTTTTTCTT<br>ATAAAACTTAAAACCTTAGAGGCTATTTAAGTTGCTGATTTATATTAATTTTATTGTTCAAACAT<br>GAGAGCTTAGTACGTGAAACATGAGAGCTTAGTACATTAGCCATGAGAGCTTAGTACATTAAA<br>ATGAGGGTTTAGTTCATTAAACATGAGAGCTTAGTACATTAAACATGAGAGCTTAGTACATTAA<br>ACATGAGAGCTTAGTACATACTATCAACAGGTTGAACTGCTGATCTGTACAGTAGAATTGGTAA<br>AGAGAGTTGTGTAAAATATTGAGTTCGCACATCTTGTTGTCTGATTATTGATTTTTGGCGAAACC<br>ATTTGATCATATGACAAGATGTGTATCTACCTTAACTTAATGATTTTGATAAAAATCATTA | 7 |

| FVIII-v3<br>AA<br>sequence | MQIELSTCFFLCLLRFCFSATRRYYLGAVELSWDYMQSDLGELPVDARFPPRVPKSFPFNTSVVYKKT<br>LFVEFTDHLFNIAKPRPPWMGLLGPTIQAEVYDTVVITLKNMASHPVSLHAVGVSYWKASEGAEYD<br>DQTSQREKEDDKVFPGGSHTYVWQVLKENGPMASDPLCLTYSYLSHVDLVKDLNSGLIGALLVCRE<br>GSLAKEKTQTLHKFILLFAVFDEGKSWHSETKNSLMQDRDAASARAWPKMHTVNGYVNRSLPGLIG<br>CHRKSVYWHVIGMGTTPEVHSIFLEGHTFLVRNHRQASLEISPITFLTAQTLLMDLGQFLLFCHISSHQ<br>HDGMEAYVKVDSCPEEPQLRMKNNEEAEDYDDDLTDSEMDVVRFDDDNSPSFIQIRSVAKKHPKT<br>WVHYIAAEEEDWDYAPLVLAPDDRSYKSQYLNNGPQRIGRKYKKVRFMAYTDETFKTREAIQHESG<br>ILGPLLYGEVGDTLLIIFKNQASRPYNIYPHGITDVRPLYSRRLPKGVKHLKDFPILPGEIFKYKWTVTV<br>EDGPTKSDPRCLTRYYSSFVNMERDLASGLIGPLLICYKESVDQRGNQIMSDKRNVILFSVFDENRSW<br>YLTENIQRFLPNPAGVQLEDPEFQASNIMHSINGYVFDSLQLSVCLHEVAYWYILSIGAQTDFLSVFFS<br>GYTFKHKMVYEDTLTLFPFSGETVFMSMENPGLWILGCHNSDFRNRGMTALLKVSSCDKNTGDYYE | 8 |

SEQUENCE LISTING

| Element | Sequence | # |
| --- | --- | --- |

DSYEDISAYLLSKNNAIEPRSFSQNATNVSNNSNTSNDSNVSPPVLKRHQREITRTTLQSDQEEIDYDD
TISVEMKKEDFDIYDEDENQSPRSFQKKTRHYFIAAVERLWDYGMSSSPHVLRNRAQSGSVPQFKKV
VFQEFTDGSFTQPLYRGELNEHLGLLGPYIRAEVEDNIMVTFRNQASRPYSFYSSLISYEEDQRQGAEP
RKNFVKPNETKTYFWKVQHHMAPTKDEFDCKAWAYFSDVDLEKDVHSGLIGPLLVCHTNTLNPAH
GRQVTVQEFALFFTIFDETKSWYFTENMERNCRAPCNIQMEDPTFKENYRFHAINGYIMDTLPGLVM
AQDQRIRWYLLSMGSNENIHSIHFSGHVFTVRKKEEYKMALYNLYPGVFETVEMLPSKAGIWRVEC
LIGEHLHAGMSTLFLVYSNKCQTPLGMASGHIRDFQITASGQYGQWAPKLARLHYSGSINAWSTKEP
FSWIKVDLLAPMIIHGIKTQGARQKFSSLYISQFIIMYSLDGKKWQTYRGNSTGTLMVFFGNVDSSGI
KHNIFNPPIIARYIRLHPTHYSIRSTLRMELMGCDLNSCSMPLGMESKAISDAQITASSYFTNMFATWS
PSKARLHLQGRSNAWRPQVNNPKEWLQVDFQKTMKVTGVTTQGVKSLLTSMYVKEFLISSSQDGH
QWTLFFQNGKVKVFQGNQDSFTPVVNSLDPPLLTRYLRIHPQSWVHQIALRMEVLGCEAQDLY*

| ApoE-AAT-hbGi | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACC | 9 |
| FIX NA sequence | ATGCAGCGCGTGAACATGATCATGGCAGAATCACCAGGCCTCATCACCATCTGCCTTTTAGGAT<br>ATCTACTCAGTGCTGAATGTACAGTTTTTCTTGATCATGAAAACGCCAACAAAATTCTGAATCGG<br>CCAAAGAGGTATAATTCAGGTAAATTGGAAGAGTTTGTTCAAGGGAACCTTGAGAGAGAATGTA<br>TGGAAGAAAGTGTAGTTTTGAAGAAGCACGAGAAGTTTTTGAAAACACTGAAAGAACAACTG<br>AATTTTGGAAGCAGTATGTTGATGGAGATCAGTGTGAGTCCAATCCATGTTTAAATGGCGGCAG<br>TTGCAAGGATGACATTAATTCCTATGAATGTTGGTGTCCCTTTGGATTTGAAGGAAAGAACTGTG<br>AATTAGATGTAACATGTAACATTAAGAATGGCAGATGCGAGCAGTTTTGTAAAAATAGTGCTGA<br>TAACAAGGTGGTTTGCTCCTGTACTGAGGGATATCGACTTGCAGAAAACCAGAAGTCCTGTGAA<br>CCAGCAGTGCCATTTCCATGTGGAAGAGTTTCTGTTTCACAAACTTCTAAGCTCACCCGTGCTGA<br>GACTGTTTTTCCTGATGTGGACTATGTAAATTCTACTGAAGCTGAAACCATTTTGGATAACATCA<br>CTCAAAGCACCCAATCATTTAATGACTTCACTCGGGTTGTTGGTGGAGAAGATGCCAAACCAGG<br>TCAATTCCCTTGGCAGGTTGTTTTGAATGGTAAAGTTGATGCATTCTGTGGAGGCTCTATCGTTA<br>ATGAAAAATGGATTGTAACTGCTGCCCCACTGTGTTGAAACTGGTGTTAAAATTACAGTTGTCGCA<br>GGTGAACATAATATTGAGGAGACAGAACATACAGAGCAAAAGCGAAATGTGATTCGAATTATT<br>CCTCACCACAACTACAATGCAGCTATTAATAAGTACAACCATGACATTGCCCTTCTGGAACTGG<br>ACGAACCCTTAGTGCTAAACAGCTACGTTACACCTATTTGCATTGCTGACAAGGAATACACGAA<br>CATCTTCCTCAAATTTGGATCTGGCTATGTAAGTGGCTGGGGAAGAGTCTTCCACAAAGGGAGA<br>TCAGCTTTAGTTCTTCAGTACCTTAGAGTTCCACTTGTTGACCGAGCCACATGTCTTCGATCTACA<br>AAGTTCACCATCTATAACAACATGTTCTGTGCTGGCTTCCATGAAGGAGGTAGAGATTCATGTCA<br>AGGAGATAGTGGGGGACCCCATGTTACTGAAGTGGAAGGGACCAGTTTCTTAACTGGAATTATT<br>AGCTGGGGTGAAGAGTGTGCAATGAAAGGCAAATATGGAATATATACCAAGGTATCCCGGTAT<br>GTCAACTGGATTAAGGAAAAAACAAAGCTCACTTAATGA | 10 |
| 5'ITR | CCTGCAGGCAGCTGCGCGCTCGCTCGCTCACTGAGGCCGCCCGGGCGTCGGGCGACCTTTGGTC<br>GCCCGGCCTCAGTGAGCGAGCGCGCAGAGAGGGAGTGGCCAACTCCATCACTAGGGGTTCCT | 11 |
| APOE-AAT-hBGi-FIX | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGCGCGTGAACATGATCATGGC<br>AGAATCACCAGGCCTCATCACCATCTGCCTTTTAGGATATCTACTCAGTGCTGAATGTACAGTTT<br>TTCTTGATCATGAAAACGCCAACAAAATTCTGAATCGGCCAAAGAGGTATAATTCAGGTAAATT<br>GGAAGAGTTTGTTCAAGGGAACCTTGAGAGAGAATGTATGGAAGAAAGTGTAGTTTTGAAGA<br>AGCACGAGAAGTTTTTGAAAACACTGAAAGAACAACTGAATTTTGGAAGCAGTATGTTGATGGA<br>GATCAGTGTGAGTCCAATCCATGTTTAAATGGCGGCAGTTGCAAGGATGACATTAATTCCTATG<br>AATGTTGGTGTCCCTTTGGATTTGAAGGAAAGAACTGTGAATTAGATGTAACATGTAACATTAA<br>GAATGGCAGATGCGAGCAGTTTTGTAAAAATAGTGCTGATAACAAGGTGGTTTGCTCCTGTACT<br>GAGGGATATCGACTTGCAGAAAACCAGAAGTCCTGTGAACCAGCAGTGCCATTTCCATGTGGAA<br>GAGTTTCTGTTTCACAAACTTCTAAGCTCACCCGTGCTGAGACTGTTTTTCCTGATGTGGACTATG<br>TAAATTCTACTGAAGCTGAAACCATTTTGGATAACATCACTCAAAGCACCCAATCATTTAATGAC<br>TTCACTCGGGTTGTTGGTGGAGAAGATGCCAAACCAGGTCAATTCCCTTGGCAGGTTGTTTTGAA<br>TGGTAAAGTTGATGCATTCTGTGGAGGCTCTATCGTTAATGAAAAATGGATTGTAACTGCTGCCC | 12 |

SEQUENCE LISTING

| Element | Sequence | # |
|---|---|---|
| | ACTGTGTTGAAACTGGTGTTAAAATTACAGTTGTCGCAGGTGAACATAATATTGAGGAGACAGA<br>ACATACAGAGCAAAAGCGAAATGTGATTCGAATTATTCCTCACCACAACTACAATGCAGCTATT<br>AATAAGTACAACCATGACATTGCCCTTCTGGAACTGGACGAACCCTTAGTGCTAAACAGCTACG<br>TTACACCTATTTGCATTGCTGACAAGGAATACACGAACATCTTCCTCAAATTTGGATCTGGCTAT<br>GTAAGTGGCTGGGGAAGAGTCTTCCACAAAGGGAGATCAGCTTTTAGTTCTTCAGTACCTTAGAG<br>TTCCACTTGTTGACCGAGCCACATGTCTTCGATCTACAAAGTTCACCATCTATAACAACATGTTC<br>TGTGCTGGCTTCCATGAAGGAGGTAGAGATTCATGTCAAGGAGATAGTGGGGGACCCCATGTTA<br>CTGAAGTGGAAGGGACCAGTTTCTTAACTGGAATTATTAGCTGGGGTGAAGAGTGTGCAATGAA<br>AGGCAAATATGGAATATATACCAAGGTATCCCGGTATGTCAACTGGATTAAGGAAAAACAAA<br>GCTCACTTAATGA | |
| APOE-<br>AAT-hBGi-<br>FIX-bGH-<br>poly A | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGCGCGTGAACATGATCATGGC<br>AGAATCACCAGGCCTCATCACCATCTGCCTTTTAGGATATCTACTCAGTGCTGAATGTACAGTTT<br>TTCTTGATCATGAAAACGCCAACAAAATTCTGAATCGGCCAAAGAGGTATAATTCAGGTAAATT<br>GGAAGAGTTTGTTCAAGGGAACCTTGAGAGAGAATGTATGGAAGAAAAGTGTAGTTTTGAAGA<br>AGCACGAGAAGTTTTTGAAAACACTGAAAGAACAACTGAATTTTGGAAGCAGTATGTTGATGGA<br>GATCAGTGTGAGTCCAATCCATGTTTAAATGGCGGCAGTTGCAAGGATGACATTAATTCCTATG<br>AATGTTGGTGTCCCTTTGGATTTGAAGGAAAGAACTGTGAATTAGATGTAACATGTAACATTAA<br>GAATGGCAGATGCGAGCAGTTTTGTAAAAATAGTGCTGATAACAAGGTGGTTTGCTCCTGTACT<br>GAGGGATATCGACTTGCAGAAAAACCAGAAGTCCTGTGAACCAGCAGTGCCATTTCCATGTGGAA<br>GAGTTTCTGTTTCACAAACTTCTAAGCTCACCCGTGCTGAGACTGTTTTTCCTGATGTGGACTATG<br>TAAATTCTACTGAAGCTGAAACCATTTTGGATAACATCACTCAAAGCACCCAATCATTTAATGAC<br>TTCACTCGGGTTGTTGGTGGAGAAGATGCCAAACCAGGTCAATTCCCTTGGCAGGTTGTTTTGAA<br>TGGTAAAGTTGATGCATTCTGTGGAGGCTCTATCGTTAATGAAAAATGGATTGTAACTGCTGCCC<br>ACTGTGTTGAAACTGGTGTTAAAATTACAGTTGTCGCAGGTGAACATAATATTGAGGAGACAGA<br>ACATACAGAGCAAAAGCGAAATGTGATTCGAATTATTCCTCACCACAACTACAATGCAGCTATT<br>AATAAGTACAACCATGACATTGCCCTTCTGGAACTGGACGAACCCTTAGTGCTAAACAGCTACG<br>TTACACCTATTTGCATTGCTGACAAGGAATACACGAACATCTTCCTCAAATTTGGATCTGGCTAT<br>GTAAGTGGCTGGGGAAGAGTCTTCCACAAAGGGAGATCAGCTTTAGTTCTTCAGTACCTTAGAG<br>TTCCACTTGTTGACCGAGCCACATGTCTTCGATCTACAAAGTTCACCATCTATAACAACATGTTC<br>TGTGCTGGCTTCCATGAAGGAGGTAGAGATTCATGTCAAGGAGATAGTGGGGGACCCCATGTTA<br>CTGAAGTGGAAGGGACCAGTTTCTTAACTGGAATTATTAGCTGGGGTGAAGAGTGTGCAATGAA<br>AGGCAAATATGGAATATATACCAAGGTATCCCGGTATGTCAACTGGATTAAGGAAAAACAAA<br>GCTCACTTAATGACCTCGAGGTGTGCCTTCTAGTTGCCAGCCATCTGTTGTTTGCCCCTCCCCCGT<br>GCCTTCCTTGACCCTGGAAGGTGCCACTCCCACTGTCCTTTCCTAATAAAATGAGGAAATTGCAT<br>CGCATTGTCTGAGTAGGTGTCATTCTATTCTGGGGGGTGGGGTGGGGCAGGACAGCAAGGGGGA<br>GGATTGGGAAGACAATAGCAGGCATGCTGGGGATGCGGTGGGCTCTATGG | 13 |
| APOE-<br>AAT-hBGi-<br>FIX<br>WPRE3-<br>bGH-<br>poly A-DTS | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGCGCGTGAACATGATCATGGC<br>AGAATCACCAGGCCTCATCACCATCTGCCTTTTAGGATATCTACTCAGTGCTGAATGTACAGTTT<br>TTCTTGATCATGAAAACGCCAACAAAATTCTGAATCGGCCAAAGAGGTATAATTCAGGTAAATT<br>GGAAGAGTTTGTTCAAGGGAACCTTGAGAGAGAATGTATGGAAGAAAAGTGTAGTTTTGAAGA<br>AGCACGAGAAGTTTTTGAAAACACTGAAAGAACAACTGAATTTTGGAAGCAGTATGTTGATGGA<br>GATCAGTGTGAGTCCAATCCATGTTTAAATGGCGGCAGTTGCAAGGATGACATTAATTCCTATG<br>AATGTTGGTGTCCCTTTGGATTTGAAGGAAAGAACTGTGAATTAGATGTAACATGTAACATTAA<br>GAATGGCAGATGCGAGCAGTTTTGTAAAAATAGTGCTGATAACAAGGTGGTTTGCTCCTGTACT<br>GAGGGATATCGACTTGCAGAAAAACCAGAAGTCCTGTGAACCAGCAGTGCCATTTCCATGTGGAA<br>GAGTTTCTGTTTCACAAACTTCTAAGCTCACCCGTGCTGAGACTGTTTTTCCTGATGTGGACTATG<br>TAAATTCTACTGAAGCTGAAACCATTTTGGATAACATCACTCAAAGCACCCAATCATTTAATGAC<br>TTCACTCGGGTTGTTGGTGGAGAAGATGCCAAACCAGGTCAATTCCCTTGGCAGGTTGTTTTGAA<br>TGGTAAAGTTGATGCATTCTGTGGAGGCTCTATCGTTAATGAAAAATGGATTGTAACTGCTGCCC<br>ACTGTGTTGAAACTGGTGTTAAAATTACAGTTGTCGCAGGTGAACATAATATTGAGGAGACAGA<br>ACATACAGAGCAAAAGCGAAATGTGATTCGAATTATTCCTCACCACAACTACAATGCAGCTATT | 14 |

| SEQUENCE LISTING | | |
|---|---|---|
| Element | Sequence | # |

|  | AATAAGTACAACCATGACATTGCCCTTCTGGAACTGGACGAACCCTTAGTGCTAAACAGCTACG | |
|  | TTACACCTATTTGCATTGCTGACAAGGAATACACGAACATCTTCCTCAAATTTGGATCTGGCTAT | |
|  | GTAAGTGGCTGGGGAAGAGTCTTCCACAAAGGGAGATCAGCTTTAGTTCTTCAGTACCTTAGAG | |
|  | TTCCACTTGTTGACCGAGCCACATGTCTTCGATCTACAAAGTTCACCATCTATAACAACATGTTC | |
|  | TGTGCTGGCTTCCATGAAGGAGGTAGAGATTCATGTCAAGGAGATAGTGGGGGACCCCATGTTA | |
|  | CTGAAGTGGAAGGGACCAGTTTCTTAACTGGAATTATTAGCTGGGGTGAAGAGTGTGCAATGAA | |
|  | AGGCAAATATGGAATATATACCAAGGTATCCCGGTATGTCAACTGGATTAAGGAAAAACAAA | |
|  | GCTCACTTAATGACCCTCGAGAATCAACCTCTGGATTACAAAATTTGTGAAAGATTGACTGGTAT | |
|  | TCTTAACTATGTTGCTCCTTTTACGCTATGTGGATACGCTGCTTTAATGCCTTTGTATCATGCTAT | |
|  | TGCTTCCCGTATGGCTTTCATTTTCTCCTCCTTGTATAAATCCTGGTTGCTGTCTCTTTATGAGGA | |
|  | GTTGTGGCCCGTTGTCAGGCAACGTGGCGTGGTGTGCACTGTGTTTGCTGACGCAACCCCCACTG | |
|  | GTTGGGGCATTGCCACCACCTGTCAGCTCCTTTCCGGGACTTTCGCTTTCCCCCTCCCTATTGCCA | |
|  | CGGCGGAACTCATCGCCGCCTGCCTTGCCCGCTGCTGGACAGGGGCTCGGCTGTTGGGCACTGA | |
|  | CAATTCCGTGGGGTGTGCCTTCTAGTTGCCAGCCATCTGTTGTTTGCCCCTCCCCCGTGCCTTCCT | |
|  | TGACCCTGGAAGGTGCCACTCCCACTGTCCTTTCCTAATAAAATGAGGAAATTGCATCGCATTGT | |
|  | CTGAGTAGGTGTCATTCTATTCTGGGGGGTGGGGTGGGGCAGGACAGCAAGGGGGAGGATTGG | |
|  | GAAGACAATAGCAGGCATGCTGGGGATGCGGTGGGCTCTATGGGAAGATGTCTACTGAGCTGTG | |
|  | CGATCCCTGCTGGGGACTTTCCGCTGGGGACTTTCCGCTGGGGACTTTCCGCCTTCAGCTAAGGA | |
|  | AGCTACCAATATTTAGAGGTACATTTTGTTCTAGAACAAAATGTACCGGTACATTTTGTTCTGGT | |
|  | ACATTTTGTTCT | |

| ITR-APOE-<br>AAT-hBGi-<br>FIX-<br>WPRE3-<br>bGH-<br>poly A-DTS-<br>ITR | CCTGCAGGCAGCTGCGCGCTCGCTCGCTCACTGAGGCCGCCCGGGCGTCGGGCGACCTTTGGTC<br>GCCCGGCCTCAGTGAGCGAGCGCGCAGAGAGGGAGTGGCCAACTCCATCACTAGGGGTTCCTGC<br>GGCCGCACGCGTCTAGTTATTAATAGTAATCGAATTCGCGTCTGCAGGCTCAGAGGCACACAGG<br>AGTTTCTGGGCTCACCCTGCCCCCTTCCAACCCCTCAGTTCCCATCCTCCAGCAGCTGTTTGTGTG<br>CTGCCTCTGAAGTCCACACTGAACAAACTTCAGCCTACTCATGTCCCTAAAATGGGCAAACATTG<br>CAAGCAGCAAACAGCAAACACACAGCCCTCCCTGCCTGCTGACCTTGGAGCTGGGGCAGAGGTC<br>AGAGACCTCTCTGGGCCCATGCCACCTCCAACATCCACTCGACCCCTTGGAATTTCGGTGGAGA<br>GGAGCAGAGGTTGTCCTGGCGTGGTTTAGGTAGTGTGAGAGGGGTCGACTGGACACAGGACGCT<br>GTGGTTTCTGAGCCAGGGGGCGACTCAGATCCCAGCCAGTGGACTTAGCCCCTGTTTGCTCCTCC<br>GATAACTGGGGTGACCTTGGTTAATATTCACCAGCAGCCTCCCCCGTTGCCCCTCTGGATCCACT<br>GCTTAAATACGGACGAGGACAGGGCCCTGTCTCCTCAGCTTCAGGCACCACCACTGACCTGGGA<br>CAGTGAATCGTAAGTACTAGCAGCTACAATCCAGCTACCATTCTGCTTTTATTTTATGGTTGGGA<br>TAAGGCTGGATTATTCTGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTTTGGCAAAGAATTGCG<br>ATCGCCACCATGCAGCGCGTGAACATGATCATGGCAGAATCACCAGGCCTCATCACCATCTGCC<br>TTTTAGGATATCTACTCAGTGCTGAATGTACAGTTTTTCTTGATCATGAAAACGCCAACAAAATT<br>CTGAATCGGCCAAAGAGGTATAATTCAGGTAAATTGGAAGAGTTTGTTCAAGGGAACCTTGAGA<br>GAGAATGTATGGAAGAAAAGTGTAGTTTTGAAGAAGCACGAGAAGTTTTTGAAAACACTGAAA<br>GAACAACTGAATTTTGGAAGCAGTATGTTGATGGAGATCAGTGTGAGTCCAATCCATGTTTAAA<br>TGGCGGCAGTTGCAAGGATGACATTAATTCCTATGAATGTTGGTGTCCCTTTGGATTTGAAGGAA<br>AGAACTGTGAATTAGATGTAACATGTAACATTAAGAATGGCAGATGCGAGCAGTTTTGTAAAAA<br>TAGTGCTGATAACAAGGTGGTTTGCTCCTGTACTGAGGGATATCGACTTGCAGAAAACCAGAAG<br>TCCTGTGAACCAGCAGTGCCATTTCCATGTGGAAGAGTTTCTGTTTCACAAACTTCTAAGCTCAC<br>CCGTGCTGAGACTGTTTTTCCTGATGTGGACTATGTAAATTCTACTGAAGCTGAAACCATTTTGG<br>ATAACATCACTCAAAGCACCCAATCATTTAATGACTTCACTCGGGTTGTTGGTGGAGAAGATGC<br>CAAACCAGGTCAATTCCCTTGGCAGGTTGTTTTGAATGGTAAAGTTGATGCATTCTGTGGAGGCT<br>CTATCGTTAATGAAAAATGGATTGTAACTGCTGCCCACTGTGTTGAAACTGGTGTTAAAATTACA<br>GTTGTCGCAGGTGAACATAATATTGAGGAGCAGAACATACAGAGCAAAAGCGAAATGTGATT<br>CGAATTATTCCTCACCACAACTACAATGCAGCTATTAATAAGTACAACCATGACATTGCCCTTCT<br>GGAACTGGACGAACCCTTAGTGCTAAACAGCTACGTTACACCTATTTGCATTGCTGACAAGGAA<br>TACACGAACATCTTCCTCAAATTTGGATCTGGCTATGTAAGTGGCTGGGGAAGAGTCTTCCACAA<br>AGGGAGATCAGCTTTAGTTCTTCAGTACCTTAGAGTTCCACTTGTTGACCGAGCCACATGTCTTC<br>GATCTACAAAGTTCACCATCTATAACAACATGTTCTGTGCTGGCTTCCATGAAGGAGGTAGAGA<br>TTCATGTCAAGGAGATAGTGGGGGACCCCATGTTACTGAAGTGGAAGGGACCAGTTTCTTAACT<br>GGAATTATTAGCTGGGGTGAAGAGTGTGCAATGAAAGGCAAATATGGAATATATACCAAGGTAT<br>CCCGGTATGTCAACTGGATTAAGGAAAAACAAAGCTCACTTAATGACCCTCGAGAATCAACCT<br>CTGGATTACAAAATTTGTGAAAGATTGACTGGTATTCTTAACTATGTTGCTCCTTTTACGCTATGT<br>GGATACGCTGCTTTAATGCCTTTGTATCATGCTATTGCTTCCCGTATGGCTTTCATTTTCTCCTCCT<br>TGTATAAATCCTGGTTGCTGTCTCTTTATGAGGAGTTGTGGCCCGTTGTCAGGCAACGTGGCGTG<br>GTGTGCACTGTGTTTGCTGACGCAACCCCCACTGGTTGGGGCATTGCCACCACCTGTCAGCTCCT<br>TTCCGGGACTTTCGCTTTCCCCCTCCCTATTGCCACGGCGGAACTCATCGCCGCCTGCCTTGCCCG<br>CTGCTGGACAGGGGCTCGGCTGTTGGGCACTGACAATTCCGTGGGGTGTGCCTTCTAGTTGCCAG<br>CCATCTGTTGTTTGCCCCTCCCCCGTGCCTTCCTTGACCCTGGAAGGTGCCACTCCCACTGTCCTT<br>TCCTAATAAAATGAGGAAATTGCATCGCATTGTCTGAGTAGGTGTCATTCTATTCTGGGGGGTGG<br>GGTGGGGCAGGACAGCAAGGGGGAGGATTGGGAAGACAATAGCAGGCATGCTGGGGATGCGGT<br>GGGCTCTATGGGACGTGCGGAGCTGTGCGATCCCTGCTGGGGACTTTCCGCTGGGGACTTTCCG<br>CTGGGGACTTTCCGCCTTCAGCTAAGGAAGCTACCAATATTTAGAGGTACATTTTGTTCTAGAAC<br>AAAATGTACCGGTACATTTTGTTCTGGTACATTTTGTTCATCGATCGAGCGGCCGCAGGAACCC<br>CTAGTGATGGAGTTGGCCACTCCCTCTCTGCGCGCTCGCTCGCTCACTGAGGCCGGGCGACCAA<br>AGGTCGCCCGACGCCCGGGCTTTGCCCGGGCGGCCTCAGTGAGCGAGCGAGCGCGCAGCTGCCT<br>GCAGG | 15 |

| APOE-<br>AAT-hBGi- | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT | 16 |

-continued

| SEQUENCE LISTING | | |
|---|---|---|
| Element | Sequence | # |
| FVIII-v3-<br>bGH-poly A | ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGATTGAGCTGAGCACCTGCTTC<br>TTCCTGTGCCTGCTGAGGTTCTGCTTCTCTGCCACCAGGAGATACTACCTGGGGGCTGTGGAGCT<br>GAGCTGGGACTACATGCAGTCTGACCTGGGGGAGCTGCCTGTGGATGCCAGGTTCCCCCCCAGA<br>GTGCCCAAGAGCTTCCCCTTCAACACCTCTGTGGTGTACAAGAAGACCCTGTTTGTGGAGTTCAC<br>TGACCACCTGTTCAACATTGCCAAGCCCAGGCCCCCCTGGATGGGCCTGCTGGGCCCCACCATCC<br>AGGCTGAGGTGTATGACACTGTGGTGATCACCCTGAAGAACATGGCCAGCCACCCTGTGAGCCT<br>GCATGCTGTGGGGGTGAGCTACTGGAAGGCCTCTGAGGGGGCTGAGTATGATGACCAGACCAGC<br>CAGAGGGAGAAGGAGGATGACAAGGTGTTCCCTGGGGGCAGCCACACCTATGTGTGGCAGGTG<br>CTGAAGGAGAATGGCCCCATGGCCTCTGACCCCCTGTGCCTGACCTACAGCTACCTGAGCCATG<br>TGGACCTGGTGAAGGACCTGAACTCTGGCCTGATTGGGGCCCTGCTGGTGTGCAGGGAGGGCAG<br>CCTGGCCAAGGAGAAGACCCAGACCCTGCACAAGTTCATCCTGCTGTTTGCTGTGTTTGATGAG<br>GGCAAGAGCTGGCACTCTGAAACCAAGAACAGCCTGATGCAGGACAGGGATGCTGCCTCTGCC<br>AGGGCCTGGCCCAAGATGCACACTGTGAATGGCTATGTGAACAGGAGCCTGCCTGGCCTGATTG<br>GCTGCCACAGGAAGTCTGTGTACTGGCATGTGATTGGCATGGGCACCACCCCTGAGGTGCACAG<br>CATCTTCCTGGAGGGCCACACCTTCCTGGTCAGGAACCACAGGCAGGCCAGCCTGGAGATCAGC<br>CCCATCACCTTCCTGACTGCCCAGACCCTGCTGATGGACCTGGGCCAGTTCCTGCTGTTCTGCCA<br>CATCAGCAGCCACCAGCATGATGGCATGGAGGCCTATGTGAAGGTGGACAGCTGCCCTGAGGA<br>GCCCCAGCTGAGGATGAAGAACAATGAGGAGGCTGAGGACTATGATGATGACCTGACTGACTCT<br>GAGATGGATGTGGTGAGGTTTGATGATGACAACAGCCCCAGCTTCATCCAGATCAGGTCTGTGG<br>CCAAGAAGCACCCCAAGACCTGGGTGCACTACATTGCTGCTGAGGAGGAGGACTGGGACTATGC<br>CCCCCTGGTGCTGGCCCCTGATGACAGGAGCTACAAGAGCCAGTACCTGAACAATGGCCCCCAG<br>AGGATTGGCAGGAAGTACAAGAAGGTCAGGTTCATGGCCTACACTGATGAAACCTTCAAGACCA<br>GGGAGGCCATCCAGCATGAGTCTGGCATCCTGGGCCCCCTGCTGTATGGGGAGGTGGGGGACAC<br>CCTGCTGATCATCTTCAAGAACCAGGCCAGCAGGCCCTACAACATCTACCCCCATGGCATCACT<br>GATGTGAGGCCCCTGTACAGCAGGAGGCTGCCCAAGGGGGTGAAGCACCTGAAGGACTTCCCC<br>ATCCTGCCTGGGGAGATCTTCAAGTACAAGTGGACTGTGACTGTGGAGGATGGCCCCACCAAGT<br>CTGACCCCAGGTGCCTGACCAGATACTACAGCAGCTTTGTGAACATGGAGAGGGACCTGGCCTC<br>TGGCCTGATTGGCCCCCTGCTGATCTGCTACAAGGAGTCTGTGGACCAGAGGGGCAACCAGATC<br>ATGTCTGACAAGAGGAATGTGATCCTGTTCTCTGTGTTTGATGAGAACAGGAGCTGGTACCTGA<br>CTGAGAACATCCAGAGGTTCCTGCCCAACCCTGCTGGGGTGCAGCTGGAGGACCCTGAGTTCCA<br>GGCCAGCAACATCATGCACAGCATCAATGGCTATGTGTTTGACAGCCTGCAGCTGTCTGTGTGCC<br>TGCATGAGGTGGCCTACTGGTACATCCTGAGCATTGGGGCCCAGACTGACTTCCTGTCTGTGTTC<br>TTCTCTGGCTACACCTTCAAGCACAAGATGGTGTATGAGGACACCCTGACCCTGTTCCCCTTCTC<br>TGGGGAGACTGTGTTCATGAGCATGGAGAACCCTGGCCTGTGGATTCTGGGCTGCCACAACTCT<br>GACTTCAGGAACAGGGGCATGACTGCCCTGCTGAAAGTCTCCAGCTGTGACAAGAACACTGGGG<br>ACTACTATGAGGACAGCTATGAGGACATCTCTGCCTACCTGCTGAGCAAGAACAATGCCATTGA<br>GCCCAGGAGCTTCAGCCAGAATGCCACTAATGTGTCTAACAACAGCAACACCAGCAATGACAGC<br>AATGTGTCTCCCCCAGTGCTGAAGAGGCACCAGAGGGAGATCACCAGGACCACCCTGCAGTCTG<br>ACCAGGAGGAGATTGACTATGATGACACCATCTCTGTGGAGATGAAGAAGGAGGACTTTGACAT<br>CTACGACGAGGACGAGAACCAGAGCCCCAGGAGCTTCCAGAAGAAGACCAGGCACTACTTCAT<br>TGCTGCTGTGGAGAGGCTGTGGGACTATGGCATGAGCAGCAGCCCCCATGTGCTGAGGAACAGG<br>GCCCAGTCTGGCTCTGTGCCCCAGTTCAAGAAGGTGGTGTTCCAGGAGTTCACTGATGGCAGCTT<br>CACCCAGCCCCTGTACAGAGGGGAGCTGAATGAGCACCTGGGCCTGCTGGGCCCCTACATCAGG<br>GCTGAGGTGGAGGACAACATCATGGTGACCTTCAGGAACCAGGCCAGCAGGCCCTACAGCTTCT<br>ACAGCAGCCTGATCAGCTATGAGGAGGACCAGAGGCAGGGGCTGAGCCCAGGAAGAACTTTG<br>TGAAGCCCAATGAAACCAAGACCTACTTCTGGAAGGTGCAGCACCACATGGCCCCCACCAAGGA<br>TGAGTTTGACTGCAAGGCCTGGGCCTACTTCTCTGATGTGGACCTGGAGAAGGATGTGCACTCTG<br>GCCTGATTGGCCCCCTGCTGGTGTGCCACACCAACACCCTGAACCCTGCCCATGGCAGGCAGGT<br>GACTGTGCAGGAGTTTGCCCTGTTCTTCACCATCTTTGATGAAACCAAGAGCTGGTACTTCACTG<br>AGAACATGGAGAGGAACTGCAGGGCCCCCTGCAACATCCAGATGGAGGACCCCACCTTCAAGG<br>AGAACTACAGGTTCCATGCCATCAATGGCTACATCATGGACACCCTGCCTGGCCTGGTGATGGC<br>CCAGGACCAGAGGATCAGGTGGTACCTGCTGAGCATGGGCAGCAATGAGAACATCCACAGCAT<br>CCACTTCTCTGGCCATGTGTTCACTGTGAGGAAGAAGGAGGAGTACAAGATGGCCCTGTACAAC<br>CTGTACCCTGGGGTGTTTGAGACTGTGGAGATGCTGCCCAGCAAGGCTGGCATCTGGAGGGTGG<br>AGTGCCTGATTGGGGAGCACCTGCATGCTGGCATGAGCACCCTGTTCCTGGTGTACAGCAACAA<br>GTGCCAGACCCCCCTGGGCATGGCCTCTGGCCACATCAGGGACTTCCAGATCACTGCCTCTGGCC<br>AGTATGGCCAGTGGGCCCCCAAGCTGGCCAGGCTGCACTACTCTGGCAGCATCAATGCCTGGAG<br>CACCAAGGAGCCCTTCAGCTGGATCAAGGTGGACCTGCTGGCCCCCATGATCATCCATGGCATC<br>AAGACCCAGGGGGCCAGGCAGAAGTTCAGCAGCCTGTACATCAGCCAGTTCATCATCATGTACA<br>GCCTGGATGGCAAGAAGTGGCAGACCTACAGGGGCAACAGCACTGGCACCCTGATGGTGTTCTT<br>TGGCAATGTGGACAGCTCTGGCATCAAGCACAACATCTTCAACCCCCCCATCATTGCCAGATAC<br>ATCAGGCTGCACCCCACCCACTACAGCATCAGGAGCACCCTGAGGATGGAGCTGATGGGCTGTG<br>ACCTGAACAGCTGCAGCATGCCCCTGGGCATGGAGAGCAAGGCCATCTCTGATGCCCAGATCAC<br>TGCCAGCAGCTACTTCACCAACATGTTTGCCACCTGGAGCCCCAGCAAGGCCAGGCTGCACCTG<br>CAGGGCAGGAGCAATGCCTGGAGGCCCCAGGTCAACAACCCCAAGGAGTGGCTGCAGGTGGAC<br>TTCCAGAAGACCATGAAGGTGACTGGGGTGACCACCCAGGGGGTGAAGAGCCTGCTGACCAGC | |

-continued

| SEQUENCE LISTING | | |
|---|---|---|
| Element | Sequence | # |
| | ATGTATGTGAAGGAGTTCCTGATCAGCAGCAGCCAGGATGGCCACCAGTGGACCCTGTTCTTCC<br>AGAATGGCAAGGTGAAGGTGTTCCAGGGCAACCAGGACAGCTTCACCCCTGTGGTGAACAGCCT<br>GGACCCCCCCCTGCTGACCAGATACCTGAGGATTCACCCCCAGAGCTGGGTGCACCAGATTGCC<br>CTGAGGATGGAGGTGCTGGGCTGTGAGGCCCAGGACCTGTACTGATAACTCGAGAATCAACCTC<br>TGGATTACAAAATTTGTGAAAGATTGACTGGTATTCTTAACTATGTTGCTCCTTTTACGCTATGTG<br>GATACGCTGCTTTAATGCCTTTGTATCATGCTATTGCTTCCCGTATGGCTTTCATTTTCTCCTCCTT<br>GTATAAATCCTGGTTGCTGTCTCTTTATGAGGAGTTGTGGCCCGTTGTCAGGCAACGTGGCGTGG<br>TGTGCACTGTGTTTGCTGACGCAACCCCCACTGGTTGGGGCATTGCCACCACCTGTCAGCTCCTT<br>TCCGGGACTTTCGCTTTCCCCCTCCCTATTGCCACGGCGGAACTCATCGCCGCCTGCCTTGCCCG<br>CTGCTGGACAGGGGCTCGGCTGTTGGGCACTGACAATTCCGTGGGGTGTGCCTTCTAGTTGCCAG<br>CCATCTGTTGTTTGCCCCTCCCCCGTGCCTTCCTTGACCCTGGAAGGTGCCACTCCCACTGTCCTT<br>TCCTAATAAAATGAGGAAATTGCATCGCATTGTCTGAGTAGGTGTCATTCTATTCTGGGGGGTGG<br>GGTGGGGCAGGACAGCAAGGGGGAGGATTGGGAAGACAATAGCAGGCATGCTGGGGATGCGGT<br>GGGCTCTATGGGAAGATGTCTACTGAGCTGTGCGATCCCTGCTGGGGACTTTCCGCTGGGGACTT<br>TCCGCTGGGGACTTTCCGCCTTCAGCTAAGGAAGCTACCAATATTTAGAGGTACATTTTGTTCTA<br>GAACAAAATGTACCGGTACATTTTGTTCTGGTACATTTTGTTCT | |
| APOE-<br>AAT-hBGi-<br>FVIII-v3-<br>WPRE3-<br>bGH-<br>poly A-DTS | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGATTGAGCTGAGCACCTGCTTC<br>TTCCTGTGCCTGCTGAGGTTCTGCTTCTCTGCCACCAGGAGTACTACCTGGGGGCTGTGGAGCT<br>GAGCTGGGACTACATGCAGTCTGACCTGGGGGAGCTGCCTGTGGATGCCAGGTTCCCCCCCAGA<br>GTGCCCAAGAGCTTCCCCTTCAACACCTCTGTGGTGTACAAGAAGACCCTGTTTGTGGAGTTCAC<br>TGACCACCTGTTCAACATTGCCAAGCCCAGGCCCCCCTGGATGGGCCTGCTGGGCCCCACCATCC<br>AGGCTGAGGTGTATGACACTGTGGTGATCACCCTGAAGAACATGGCCAGCCACCCTGTGAGCCT<br>GCATGCTGTGGGGGTGAGCTACTGGAAGGCCTCTGAGGGGGCTGAGTATGATGACCAGACCAGC<br>CAGAGGGAGAAGGAGGATGACAAGGTGTTCCCTGGGGGCAGCCACACCTATGTGTGGCAGGTG<br>CTGAAGGAGAATGGCCCCATGGCCTCTGACCCCCTGTGCCTGACCTACAGCTACCTGAGCCATG<br>TGGACCTGGTGAAGGACCTGAACTCTGGCCTGATTGGGGCCCTGCTGGTGTGCAGGGAGGGCAG<br>CCTGGCCAAGGAGAAGACCCAGACCCTGCACAAGTTCATCCTGCTGTTTGCTGTGTTTGATGAG<br>GGCAAGAGCTGGCACTCTGAAACCAAGAACAGCCTGATGCAGGACAGGGATGCTGCCTCTGCC<br>AGGGCCTGGCCCAAGATGCACACTGTGAATGGCTATGTGAACAGGAGCCTGCCTGGCCTGATTG<br>GCTGCCACAGGAAGTCTGTGTACTGGCATGTGATTGGCATGGGCACCACCCCTGAGGTGCACAG<br>CATCTTCCTGGAGGGCCACACCTTCCTGGTCAGGAACCACAGGCAGGCCAGCCTGGAGATCAGC<br>CCCATCACCTTCCTGACTGCCCAGACCCTGCTGATGGACCTGGGCCAGTTCCTGCTGTTCTGCCA<br>CATCAGCAGCCACCAGCATGATGGCATGGAGGCCTATGTGAAGGTGGACAGCTGCCCTGAGGA<br>GCCCCAGCTGAGGATGAAGAACAATGAGGAGGCTGAGGACTATGATGATGACCTGACTGACTCT<br>GAGATGGATGTGGTGAGGTTTGATGATGACAACAGCCCCAGCTTCATCCAGATCAGGTCTGTGG<br>CCAAGAAGCACCCCAAGACCTGGGTGCACTACATTGCTGCTGAGGAGGAGGACTGGGACTATGC<br>CCCCCTGGTGCTGGCCCCTGATGACAGGAGCTACAAGAGCCAGTACCTGAACAATGGCCCCCAG<br>AGGATTGGCAGGAAGTACAAGAAGGTCAGGTTCATGGCCTACACTGATGAAACCTTCAAGACCA<br>GGGAGGCCATCCAGCATGAGTCTGGCATCCTGGGCCCCCTGCTGTATGGGGAGGTGGGGGACAC<br>CCTGCTGATCATCTTCAAGAACCAGGCCAGCAGGCCCTACAACATCTACCCCCATGGCATCACT<br>GATGTGAGGCCCCTGTACAGCAGGAGGCTGCCCAAGGGGGTGAAGCACCTGAAGGACTTCCCC<br>ATCCTGCCTGGGGAGATCTTCAAGTACAAGTGGACTGTGACTGTGGAGGATGGCCCCACCAAGT<br>CTGACCCCAGGTGCCTGACCAGATACTACAGCAGCTTTGTGAACATGGAGAGGGACCTGGCCTC<br>TGGCCTGATTGGCCCCCTGCTGATCTGCTACAAGGAGTCTGTGGACCAGAGGGGCAACCAGATC<br>ATGTCTGACAAGAGGAATGTGATCCTGTTCTCTGTGTTTGATGAGAACAGGAGCTGGTACCTGA<br>CTGAGAACATCCAGAGGTTCCTGCCCAACCCTGCTGGGGTGCAGCTGGAGGACCCTGAGTTCCA<br>GGCCAGCAACATCATGCACAGCATCAATGGCTATGTGTTTGACAGCCTGCAGCTGTCTGTGTGCC<br>TGCATGAGGTGGCCTACTGGTACATCCTGAGCATTGGGGCCCAGACTGACTTCCTGTCTGTGTTC<br>TTCTCTGGCTACACCTTCAAGCACAAGATGGTGTATGAGGACACCCTGACCCTGTTCCCCTTCTC<br>TGGGGAGACTGTGTTCATGAGCATGGAGAACCCTGGCCTGTGGATTCTGGGCTGCCACAACTCT<br>GACTTCAGGAACAGGGGCATGACTGCCCTGCTGAAAGTCTCCAGCTGTGACAAGAACACTGGGG<br>ACTACTATGAGGACAGCTATGAGGACATCTCTGCCTACCTGCTGAGCAAGAACAATGCCATTGA<br>GCCCAGGAGCTTCAGCCAGAATGCCACTAATGTGTCTAACAACAGCAACACCAGCAATGACAGC<br>AATGTGTCTCCCCCAGTGCTGAAGAGGCACCAGAGGGAGATCACCAGGACCACCCTGCAGTCTG<br>ACCAGGAGGAGATTGACTATGATGACACCATCTCTGTGGAGATGAAGAAGGAGGACTTTGACAT<br>CTACGACGAGGACGAGAACCAGAGCCCCAGGAGCTTCCAGAAGAAGACCAGGCACTACTTCAT<br>TGCTGCTGTGGAGAGGCTGTGGGACTATGGCATGAGCAGCAGCCCCCATGTGCTGAGGAACAGG<br>GCCCAGTCTGGCTCTGTGCCCCAGTTCAAGAAGGTGGTGTTCCAGGAGTTCACTGATGGCAGCTT<br>CACCCAGCCCCTGTACAGAGGGGAGCTGAATGAGCACCTGGGCCTGCTGGGCCCCTACATCAGG<br>GCTGAGGTGGAGGACAACATCATGGTGACCTTCAGGAACCAGGCCAGCAGGCCCTACAGCTTCT<br>ACAGCAGCCTGATCAGCTATGAGGAGGACCAGAGGCAGGGGCTGAGCCCAGGAAGAACTTTG<br>TGAAGCCCAATGAAACCAAGACCTACTTCTGGAAGGTGCAGCACCACATGGCCCCCACCAAGGA<br>TGAGTTTGACTGCAAGGCCTGGGCCTACTTCTCTGATGTGGACCTGGAGAAGGATGTGCACTCTG | 17 |

| SEQUENCE LISTING | | |
|---|---|---|
| Element | Sequence | # |
| | GCCTGATTGGCCCCCTGCTGGTGTGCCACACCAACACCCTGAACCCTGCCCATGGCAGGCAGGT | |
| | GACTGTGCAGGAGTTTGCCCTGTTCTTCACCATCTTTGATGAAACCAAGAGCTGGTACTTCACTG | |
| | AGAACATGGAGAGGAACTGCAGGGCCCCCTGCAACATCCAGATGGAGGACCCCACCTTCAAGG | |
| | AGAACTACAGGTTCCATGCCATCAATGGCTACATCATGGACACCCTGCCTGGCCTGGTGATGGC | |
| | CCAGGACCAGAGGATCAGGTGGTACCTGCTGAGCATGGGCAGCAATGAGAACATCCACAGCAT | |
| | CCACTTCTCTGGCCATGTGTTCACTGTGAGGAAGAAGGAGGAGTACAAGATGGCCCTGTACAAC | |
| | CTGTACCCTGGGGTGTTTGAGACTGTGGAGATGCTGCCCAGCAAGGCTGGCATCTGGAGGGTGG | |
| | AGTGCCTGATTGGGGAGCACCTGCATGCTGGCATGAGCACCCTGTTCCTGGTGTACAGCAACAA | |
| | GTGCCAGACCCCCCTGGGCATGGCCTCTGGCCACATCAGGGACTTCCAGATCACTGCCTCTGGCC | |
| | AGTATGGCCAGTGGGCCCCCAAGCTGGCCAGGCTGCACTACTCTGGCAGCATCAATGCCTGGAG | |
| | CACCAAGGAGCCCTTCAGCTGGATCAAGGTGGACCTGCTGGCCCCCATGATCATCCATGGCATC | |
| | AAGACCCAGGGGGCCAGGCAGAAGTTCAGCAGCCTGTACATCAGCCAGTTCATCATCATGTACA | |
| | GCCTGGATGGCAAGAAGTGGCAGACCTACAGGGGCAACAGCACTGGCACCCTGATGGTGTTCTT | |
| | TGGCAATGTGGACAGCTCTGGCATCAAGCACAACATCTTCAACCCCCCCCATCATTGCCAGATAC | |
| | ATCAGGCTGCACCCCACCCACTACAGCATCAGGAGCACCCTGAGGATGGAGCTGATGGGCTGTG | |
| | ACCTGAACAGCTGCAGCATGCCCCTGGGCATGGAGAGCAAGGCCATCTCTGATGCCCAGATCAC | |
| | TGCCAGCAGCTACTTCACCAACATGTTTGCCACCTGGAGCCCCAGCAAGGCCAGGCTGCACCTG | |
| | CAGGGCAGGAGCAATGCCTGGAGGCCCCAGGTCAACAACCCCAAGGAGTGGCTGCAGGTGGAC | |
| | TTCCAGAAGACCATGAAGGTGACTGGGGTGACCACCCAGGGGGTGAAGAGCCTGCTGACCAGC | |
| | ATGTATGTGAAGGAGTTCCTGATCAGCAGCAGCCAGGATGGCCACCAGTGGACCCTGTTCTTCC | |
| | AGAATGGCAAGGTGAAGGTGTTCCAGGGCAACCAGGACAGCTTCACCCCTGTGGTGAACAGCCT | |
| | GGACCCCCCCCTGCTGACCAGATACCTGAGGATTCACCCCCAGAGCTGGGTGCACCAGATTGCC | |
| | CTGAGGATGGAGGTGCTGGGCTGTGAGGCCCAGGACCTGTACTGATAACTCGAGAATCAACCTC | |
| | TGGATTACAAAATTTGTGAAAGATTGACTGGTATTCTTAACTATGTTGCTCCTTTTACGCTATGTG | |
| | GATACGCTGCTTTAATGCCTTTGTATCATGCTATTGCTTCCCGTATGGCTTTCATTTTCTCCTCCTT | |
| | GTATAAATCCTGGTTGCTGTCTCTTTATGAGGAGTTGTGGCCCGTTGTCAGGCAACGTGGCGTGG | |
| | TGTGCACTGTGTTTGCTGACGCAACCCCCACTGGTTGGGGCATTGCCACCACCTGTCAGCTCCTT | |
| | TCCGGGACTTTCGCTTTCCCCCTCCCTATTGCCACGGCGGAACTCATCGCCGCCTGCCTTGCCCG | |
| | CTGCTGGACAGGGGCTCGGCTGTTGGGCACTGACAATTCCGTGGGGTGTGCCTTCTAGTTGCCAG | |
| | CCATCTGTTGTTTGCCCCTCCCCCGTGCCTTCCTTGACCCTGGAAGGTGCCACTCCCACTGTCCTT | |
| | TCCTAATAAAATGAGGAAATTGCATCGCATTGTCTGAGTAGGTGTCATTCTATTCTGGGGGGTGG | |
| | GGTGGGGCAGGACAGCAAGGGGGAGGATTGGGAAGACAATAGCAGGCATGCTGGGGATGCGGT | |
| | GGGCTCTATGGGAAGATGTCTACTGAGCTGTGCGATCCCTGCTGGGGACTTTCCGCTGGGGACTT | |
| | TCCGCTGGGGACTTTCCGCCTTCAGCTAAGGAAGCTACCAATATTTAGAGGTACATTTTGTTCTA | |
| | GAACAAAATGTACCGGTACATTTTGTTCTGGTACATTTTGTTCT | |
| APOE- AAT-hBGi- FIX- WPRE3- bGH-poly A DTS | CGCGTCTGCAGGCTCAGAGGCACACAGGAGTTTCTGGGCTCACCCTGCCCCCTTCCAACCCCTCA GTTCCCATCCTCCAGCAGCTGTTTGTGTGCTGCCTCTGAAGTCCACACTGAACAAACTTCAGCCT ACTCATGTCCCTAAAATGGGCAAACATTGCAAGCAGCAAACAGCAAACACACAGCCCTCCCTGC CTGCTGACCTTGGAGCTGGGGCAGAGGTCAGAGACCTCTCTGGGCCCATGCCACCTCCAACATC CACTCGACCCCTTGGAATTTCGGTGGAGAGGAGCAGAGGTTGTCCTGGCGTGGTTTAGGTAGTG TGAGAGGGGTCGACTGGACACAGGACGCTGTGGTTTCTGAGCCAGGGGGCGACTCAGATCCCAG CCAGTGGACTTAGCCCCTGTTTGCTCCTCCGATAACTGGGGTGACCTTGGTTAATATTCACCAGC AGCCTCCCCCGTTGCCCCTCTGGATCCACTGCTTAAATACGGACGAGGACAGGGCCCTGTCTCCT CAGCTTCAGGCACCACCACTGACCTGGGACAGTGAATCGTAAGTACTAGCAGCTACAATCCAGC TACCATTCTGCTTTTATTTTATGGTTGGGATAAGGCTGGATTATTCTGAGTCCAAGCTAGGCCCTT TTGCTAATCATGTTCATACCTCTTATCTTCCTCCCACAGCTCCTGGGCAACGTGCTGGTCTGTGTG CTGGCCCATCACTTTGGCAAAGAATTGCGATCGCCACCATGCAGCGCGTGAACATGATCATGGC AGAATCACCAGGCCTCATCACCATCTGCCTTTTAGGATATCTACTCAGTGCTGAATGTACAGTTT TTCTTGATCATGAAAACGCCAACAAAATTCTGAATCGGCCAAAGAGGTATAATTCAGGTAAATT GGAAGAGTTTGTTCAAGGGAACCTTGAGAGAGAATGTATGGAAGAAAAGTGTAGTTTTGAAGA AGCACGAGAAGTTTTTGAAAACACTGAAAGAACAACTGAATTTTGGAAGCAGTATGTTGATGGA GATCAGTGTGAGTCCAATCCATGTTTAAATGGCGGCAGTTGCAAGGATGACATTAATTCCTATG AATGTTGGTGTCCCTTTGGATTTGAAGGAAAGAACTGTGAATTAGATGTAACATGTAACATTAA GAATGGCAGATGCGAGCAGTTTTGTAAAAATAGTGCTGATAACAAGGTGGTTTGCTCCTGTACT GAGGGATATCGACTTGCAGAAAACCAGAAGTCCTGTGAACCAGCAGTGCCATTTCCATGTGGAA GAGTTTCTGTTTCACAAACTTCTAAGCTCACCCGTGCTGAGACTGTTTTTCCTGATGTGGACTATG TAAATTCTACTGAAGCTGAAACCATTTTGGATAACATCACTCAAAGCACCCAATCATTTAATGAC TTCACTCGGGTTGTTGGTGGAGAAGATGCCAAACCAGGTCAATTCCCTTGGCAGGTTGTTTTGAA TGGTAAAGTTGATGCATTCTGTGGAGGCTCTATCGTTAATGAAAAATGGATTGTAACTGCTGCCC ACTGTGTTGAAACTGGTGTTAAAATTACAGTTGTCGCAGGTGAACATAATATTGAGGAGACAGA ACATACAGAGCAAAAGCGAAATGTGATTCGAATTATTCCTCACCACAACTACAATGCAGCTATT AATAAGTACAACCATGACATTGCCCTTCTGGAACTGGACGAACCCTTAGTGCTAAACAGCTACG TTACACCTATTTGCATTGCTGACAAGGAATACACGAACATCTTCCTCAAATTTGGATCTGGCTAT GTAAGTGGCTGGGGAAGAGTCTTCCACAAAGGGAGATCAGCTTTAGTTCTTCAGTACCTTAGAG TTCCACTTGTTGACCGAGCCACATGTCTTCGATCTACAAAGTTCACCATCTATAACAACATGTTC TGTGCTGGCTTCCATGAAGGAGGTAGAGATTCATGTCAAGGAGATAGTGGGGGACCCCATGTTA CTGAAGTGGAAGGGACCAGTTTCTTAACTGGAATTATTAGCTGGGGTGAAGAGTGTGCAATGAA AGGCAAATATGGAATATATACCAAGGTATCCCGGTATGTCAACTGGATTAAGGAAAAAACAAA GCTCACTTAATGACCCTCGAGAATCAACCTCTGGATTACAAAATTTGTGAAAGATTGACTGGTAT TCTTAACTATGTTGCTCCTTTTACGCTATGTGGATACGCTGCTTTAATGCCTTTGTATCATGCTAT TGCTTCCCGTATGGCTTTCATTTTCTCCTCCTTGTATAAATCCTGGTTGCTGTCTCTTTATGAGGA GTTGTGGCCCGTTGTCAGGCAACGTGGCGTGGTGTGCACTGTGTTTGCTGACGCAACCCCCACTG GTTGGGGCATTGCCACCACCTGTCAGCTCCTTTCCGGGACTTTCGCTTTCCCCCTCCCTATTGCCA CGGCGGAACTCATCGCCGCCTGCCTTGCCCGCTGCTGGACAGGGGCTCGGCTGTTGGGCACTGA | 18 |

-continued

| Element | Sequence | # |
|---|---|---|
| | CAATTCCGTGGGGTGTGCCTTCTAGTTGCCAGCCATCTGTTGTTTGCCCCTCCCCCGTGCCTTCCT<br>TGACCCTGGAAGGTGCCACTCCCACTGTCCTTTCCTAATAAAATGAGGAAATTGCATCGCATTGT<br>CTGAGTAGGTGTCATTCTATTCTGGGGGGTGGGGTGGGGCAGGACAGCAAGGGGGAGGATTGG<br>GAAGACAATAGCAGGCATGCTGGGGATGCGGTGGGCTCTATGGGAAGATGTCTACTGAGCTGTG<br>CGATCCCTGCTGGGGACTTTCCGCTGGGGACTTTCCGCTGGGGACTTTCCGCCTTCAGCTAAGGA<br>AGCTACCAATATTTAGAGGTACATTTTGTTCTAGAACAAAATGTACCGGTACATTTTGTTCTGGT<br>ACATTTTGTTCT | |
| APOE-<br>AAT-hbGi-<br>FVIIIv3- | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGATTGAGCTGAGCACCTGCTTC<br>TTCCTGTGCCTGCTGAGGTTCTGCTTCTCTGCCACCAGGAGATACTACCTGGGGGCTGTGGAGCT<br>GAGCTGGGACTACATGCAGTCTGACCTGGGGGAGCTGCCTGTGGATGCCAGGTTCCCCCCCAGA<br>GTGCCCAAGAGCTTCCCCTTCAACACCTCTGTGGTGTACAAGAAGACCCTGTTTGTGGAGTTCAC<br>TGACCACCTGTTCAACATTGCCAAGCCCAGGCCCCCCTGGATGGGCCTGCTGGGCCCCACCATCC<br>AGGCTGAGGTGTATGACACTGTGGTGATCACCCTGAAGAACATGGCCAGCCACCCTGTGAGCCT<br>GCATGCTGTGGGGGTGAGCTACTGGAAGGCCTCTGAGGGGGCTGAGTATGATGACCAGACCAGC<br>CAGAGGGAGAAGGAGGATGACAAGGTGTTCCCTGGGGGCAGCCACACCTATGTGTGGCAGGTG<br>CTGAAGGAGAATGGCCCCATGGCCTCTGACCCCCTGTGCCTGACCTACAGCTACCTGAGCCATG<br>TGGACCTGGTGAAGGACCTGAACTCTGGCCTGATTGGGGCCCTGCTGGTGTGCAGGGAGGGCAG<br>CCTGGCCAAGGAGAAGACCCAGACCCTGCACAAGTTCATCCTGCTGTTTGCTGTGTTTGATGAG<br>GGCAAGAGCTGGCACTCTGAAACCAAGAACAGCCTGATGCAGGACAGGGATGCTGCCTCTGCC<br>AGGGCCTGGCCCAAGATGCACACTGTGAATGGCTATGTGAACAGGAGCCTGCCTGGCCTGATTG<br>GCTGCCACAGGAAGTCTGTGTACTGGCATGTGATTGGCATGGGCACCACCCCTGAGGTGCACAG<br>CATCTTCCTGGAGGGCCACACCTTCCTGGTCAGGAACCACAGGCAGGCCAGCCTGGAGATCAGC<br>CCCATCACCTTCCTGACTGCCCAGACCCTGCTGATGGACCTGGGCCAGTTCCTGCTGTTCTGCCA<br>CATCAGCAGCCACCAGCATGATGGCATGGAGGCCTATGTGAAGGTGGACAGCTGCCCTGAGGA<br>GCCCCAGCTGAGGATGAAGAACAATGAGGAGGCTGAGGACTATGATGATGACCTGACTGACTCT<br>GAGATGGATGTGGTGAGGTTTGATGATGACAACAGCCCCAGCTTCATCCAGATCAGGTCTGTGG<br>CCAAGAAGCACCCCAAGACCTGGGTGCACTACATTGCTGCTGAGGAGGAGGACTGGGACTATGC<br>CCCCCTGGTGCTGGCCCCTGATGACAGGAGCTACAAGAGCCAGTACCTGAACAATGGCCCCCAG<br>AGGATTGGCAGGAAGTACAAGAAGGTCAGGTTCATGGCCTACACTGATGAAACCTTCAAGACCA<br>GGGAGGCCATCCAGCATGAGTCTGGCATCCTGGGCCCCCTGCTGTATGGGGAGGTGGGGGACAC<br>CCTGCTGATCATCTTCAAGAACCAGGCCAGCAGGCCCTACAACATCTACCCCCATGGCATCACT<br>GATGTGAGGCCCCTGTACAGCAGGAGGCTGCCCAAGGGGGTGAAGCACCTGAAGGACTTCCCC<br>ATCCTGCCTGGGGAGATCTTCAAGTACAAGTGGACTGTGACTGTGGAGGATGGCCCCACCAAGT<br>CTGACCCCAGGTGCCTGACCAGATACTACAGCAGCTTTGTGAACATGGAGAGGGACCTGGCCTC<br>TGGCCTGATTGGCCCCCTGCTGATCTGCTACAAGGAGTCTGTGGACCAGAGGGGCAACCAGATC<br>ATGTCTGACAAGAGGAATGTGATCCTGTTCTCTGTGTTTGATGAGAACAGGAGCTGGTACCTGA<br>CTGAGAACATCCAGAGGTTCCTGCCCAACCCTGCTGGGGTGCAGCTGGAGGACCCTGAGTTCCA<br>GGCCAGCAACATCATGCACAGCATCAATGGCTATGTGTTTGACAGCCTGCAGCTGTCTGTGTGCC<br>TGCATGAGGTGGCCTACTGGTACATCCTGAGCATTGGGGCCCAGACTGACTTCCTGTCTGTGTTC<br>TTCTCTGGCTACACCTTCAAGCACAAGATGGTGTATGAGGACACCCTGACCCTGTTCCCCTTCTC<br>TGGGGAGACTGTGTTCATGAGCATGGAGAACCCTGGCCTGTGGATTCTGGGCTGCCACAACTCT<br>GACTTCAGGAACAGGGGCATGACTGCCCTGCTGAAAGTCTCCAGCTGTGACAAGAACACTGGGG<br>ACTACTATGAGGACAGCTATGAGGACATCTCTGCCTACCTGCTGAGCAAGAACAATGCCATTGA<br>GCCCAGGAGCTTCAGCCAGAATGCCACTAATGTGTCTAACAACAGCAACACCAGCAATGACAGC<br>AATGTGTCTCCCCCAGTGCTGAAGAGGCACCAGAGGGAGATCACCAGGACCACCCTGCAGTCTG<br>ACCAGGAGGAGATTGACTATGATGACACCATCTCTGTGGAGATGAAGAAGGAGGACTTTGACAT<br>CTACGACGAGGACGAGAACCAGAGCCCCAGGAGCTTCCAGAAGAAGACCAGGCACTACTTCAT<br>TGCTGCTGTGGAGAGGCTGTGGGACTATGGCATGAGCAGCAGCCCCCATGTGCTGAGGAACAGG<br>GCCCAGTCTGGCTCTGTGCCCCAGTTCAAGAAGGTGGTGTTCCAGGAGTTCACTGATGGCAGCTT<br>CACCCAGCCCCTGTACAGAGGGGAGCTGAATGAGCACCTGGGCCTGCTGGGCCCCTACATCAGG<br>GCTGAGGTGGAGGACAACATCATGGTGACCTTCAGGAACCAGGCCAGCAGGCCCTACAGCTTCT<br>ACAGCAGCCTGATCAGCTATGAGGAGGACCAGAGGCAGGGGGCTGAGCCCAGGAAGAACTTTG<br>TGAAGCCCAATGAAACCAAGACCTACTTCTGGAAGGTGCAGCACCACATGGCCCCCACCAAGGA<br>TGAGTTTGACTGCAAGGCCTGGGCCTACTTCTCTGATGTGGACCTGGAGAAGGATGTGCACTCTG<br>GCCTGATTGGCCCCCTGCTGGTGTGCCACACCAACACCCTGAACCCTGCCCATGGCAGGCAGGT<br>GACTGTGCAGGAGTTTGCCCTGTTCTTCACCATCTTTGATGAAACCAAGAGCTGGTACTTCACTG<br>AGAACATGGAGAGGAACTGCAGGGCCCCCTGCAACATCCAGATGGAGGACCCCACCTTCAAGG<br>AGAACTACAGGTTCCATGCCATCAATGGCTACATCATGGACACCCTGCCTGGCCTGGTGATGGC<br>CCAGGACCAGAGGATCAGGTGGTACCTGCTGAGCATGGGCAGCAATGAGAACATCCACAGCAT<br>CCACTTCTCTGGCCATGTGTTCACTGTGAGGAAGAAGGAGGAGTACAAGATGGCCCTGTACAAC<br>CTGTACCCTGGGGTGTTTGAGACTGTGGAGATGCTGCCCAGCAAGGCTGGCATCTGGAGGGTGG<br>AGTGCCTGATTGGGGAGCACCTGCATGCTGGCATGAGCACACCTGTTCCTGGTGTACAGCAACAA<br>GTGCCAGACCCCCCTGGGCATGGCCTCTGGCCACATCAGGGACTTCCAGATCACTGCCTCTGGCC | 19 |

SEQUENCE LISTING

| Element | Sequence | # |
|---|---|---|
| | AGTATGGCCAGTGGGCCCCCAAGCTGGCCAGGCTGCACTACTCTGGCAGCATCAATGCCTGGAG<br>CACCAAGGAGCCCTTCAGCTGGATCAAGGTGGACCTGCTGGCCCCCATGATCATCCATGGCATC<br>AAGACCCAGGGGGCCAGGCAGAAGTTCAGCAGCCTGTACATCAGCCAGTTCATCATCATGTACA<br>GCCTGGATGGCAAGAAGTGGCAGACCTACAGGGGCAACAGCACTGGCACCCTGATGGTGTTCTT<br>TGGCAATGTGGACAGCTCTGGCATCAAGCACAACATCTTCAACCCCCCCATCATTGCCAGATAC<br>ATCAGGCTGCACCCCACCCACTACAGCATCAGGAGCACCCTGAGGATGGAGCTGATGGGCTGTG<br>ACCTGAACAGCTGCAGCATGCCCCTGGGCATGGAGAGCAAGGCCATCTCTGATGCCCAGATCAC<br>TGCCAGCAGCTACTTCACCAACATGTTTGCCACCTGGAGCCCCAGCAAGGCCAGGCTGCACCTG<br>CAGGGCAGGAGCAATGCCTGGAGGCCCCAGGTCAACAACCCCAAGGAGTGGCTGCAGGTGGAC<br>TTCCAGAAGACCATGAAGGTGACTGGGGTGACCCACCCAGGGGGTGAAGAGCCTGCTGACCAGC<br>ATGTATGTGAAGGAGTTCCTGATCAGCAGCAGCCAGGATGGCCACCAGTGGACCCTGTTCTTCC<br>AGAATGGCAAGGTGAAGGTGTTCCAGGGCAACCAGGACAGCTTCACCCCTGTGGTGAACAGCCT<br>GGACCCCCCCCTGCTGACCAGATACCTGAGGATTCACCCCCAGAGCTGGGTGCACCAGATTGCC<br>CTGAGGATGGAGGTGCTGGGCTGTGAGGCCCAGGACCTGTACTGA | |
| APOE-<br>AAT-hBGi-<br>FVIIIv3-<br>WPRE3-<br>bGH-poly A<br>DTS | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGATTGAGCTGAGCACCTGCTTC<br>TTCCTGTGCCTGCTGAGGTTCTGCTTCTCTGCCACCAGGAGATACTACCTGGGGGCTGTGGAGCT<br>GAGCTGGGACTACATGCAGTCTGACCTGGGGGAGCTGCCTGTGGATGCCAGGTTCCCCCCCAGA<br>GTGCCCAAGAGCTTCCCCTTCAACACCTCTGTGGTGTACAAGAAGACCCTGTTTGTGGAGTTCAC<br>TGACCACCTGTTCAACATTGCCAAGCCCAGGCCCCCCTGGATGGGCCTGCTGGGCCCCACCATCC<br>AGGCTGAGGTGTATGACACTGTGGTGATCACCCTGAAGAACATGGCCAGCCACCCTGTGAGCCT<br>GCATGCTGTGGGGGTGAGCTACTGGAAGGCCTCTGAGGGGGCTGAGTATGATGACCAGACCAGC<br>CAGAGGGAGAAGGAGGATGACAAGGTGTTCCCTGGGGGCAGCCACCTATGTGTGGCAGGTG<br>CTGAAGGAGAATGGCCCCATGGCCTCTGACCCCCTGTGCCTGACCTACAGCTACCTGAGCCATG<br>TGGACCTGGTGAAGGACCTGAACTCTGGCCTGATTGGGGCCCTGCTGGTGTGCAGGGAGGGCAG<br>CCTGGCCAAGGAGAAGACCCAGACCCTGCACAAGTTCATCCTGCTGTTTGCTGTGTTTGATGAG<br>GGCAAGAGCTGGCACTCTGAAACCAAGAACAGCCTGATGCAGGACAGGGATGCTGCCTCTGCC<br>AGGGCCTGGCCCAAGATGCACACTGTGAATGGCTATGTGAACAGGAGCCTGCCTGGCCTGATTG<br>GCTGCCACAGGAAGTCTGTGTACTGGCATGTGATTGGCATGGGCACCACCCCTGAGGTGCACAG<br>CATCTTCCTGGAGGGCCACACCTTCCTGGTCAGGAACCACAGGCAGGCCAGCCTGGAGATCAGC<br>CCCATCACCTTCCTGACTGCCCAGACCCTGCTGATGGACCTGGGCCAGTTCCTGCTGTTCTGCCA<br>CATCAGCAGCCACCAGCATGATGGCATGGAGGCCTATGTGAAGGTGGACAGCTGCCCTGAGGA<br>GCCCCAGCTGAGGATGAAGAACAATGAGGAGGCTGAGGACTATGATGATGACCTGACTGACTCT<br>GAGATGGATGTGGTGAGGTTTGATGATGACAACAGCCCCAGCTTCATCCAGATCAGGTCTGTGG<br>CCAAGAAGCACCCCAAGACCTGGGTGCACTACATTGCTGCTGAGGAGGAGGACTGGGACTATGC<br>CCCCCTGGTGCTGGCCCCTGATGACAGGAGCTACAAGAGCCAGTACCTGAACAATGGCCCCCAG<br>AGGATTGGCAGGAAGTACAAGAAGGTCAGGTTCATGGCCTACACTGATGAAACCTTCAAGACCA<br>GGGAGGCCATCCAGCATGAGTCTGGCATCCTGGGCCCCCTGCTGTATGGGGAGGTGGGGGACAC<br>CCTGCTGATCATCTTCAAGAACCAGGCCAGCAGGCCCTACAACATCTACCCCCATGGCATCACT<br>GATGTGAGGCCCCTGTACAGCAGGAGGCTGCCCAAGGGGGTGAAGCACCTGAAGGACTTCCCC<br>ATCCTGCCTGGGGAGATCTTCAAGTACAAGTGGACTGTGACTGTGGAGGATGGCCCCACCAAGT<br>CTGACCCCAGGTGCCTGACCAGATACTACAGCAGCTTTGTGAACATGGAGAGGGACCTGGCCTC<br>TGGCCTGATTGGCCCCCTGCTGATCTGCTACAAGGAGTCTGTGGACCAGAGGGGCAACCAGATC<br>ATGTCTGACAAGAGGAATGTGATCCTGTTCTCTGTGTTTGATGAGACAGGAGCTGGTACCTGA<br>CTGAGAACATCCAGAGGTTCCTGCCCAACCCTGCTGGGGTGCAGCTGGAGGACCCTGAGTTCCA<br>GGCCAGCAACATCATGCACAGCATCAATGGCTATGTGTTTGACAGCCTGCAGCTGTCTGTGTGCC<br>TGCATGAGGTGGCCTACTGGTACATCCTGAGCATTGGGGCCCAGACTGACTTCCTGTCTGTGTTC<br>TTCTCTGGCTACACCTTCAAGCACAAGATGGTGTATGAGGACACCCTGACCCTGTTCCCCTTCTC<br>TGGGGAGACTGTGTTCATGAGCATGGAGAACCCTGGCCTGTGGATTCTGGGCTGCCACAACTCT<br>GACTTCAGGAACAGGGGCATGACTGCCCTGCTGAAAGTCTCCAGCTGTGACAAGAACACTGGGG<br>ACTACTATGAGGACAGCTATGAGGACATCTCTGCCTACCTGCTGAGCAAGAACAATGCCATTGA<br>GCCCAGGAGCTTCAGCCAGAATGCCACTAATGTGTCTAACAACAGCAACACCAGCAATGACAGC<br>AATGTGTCTCCCCCAGTGCTGAAGAGGCACCAGAGGGAGATCACCAGGACCACCCTGCAGTCTG<br>ACCAGGAGGAGATTGACTATGATGACACCATCTCTGTGGAGATGAAGAAGGAGGACTTTGACAT<br>CTACGACGAGGACGAGAACCAGAGCCCCAGGAGCTTCCAGAAGAAGACCAGGCACTACTTCAT<br>TGCTGCTGTGGAGAGGCTGTGGGACTATGGCATGAGCAGCAGCCCCCATGTGCTGAGGAACAGG<br>GCCCAGTCTGGCTCTGTGCCCCAGTTCAAGAAGGTGGTGTTCCAGGAGTTCACTGATGGCAGCTT<br>CACCCAGCCCCTGTACAGAGGGGAGCTGAATGAGCACCTGGGCCTGCTGGGCCCCTACATCAGG<br>GCTGAGGTGGAGGACAACATCATGGTGACCTTCAGGAACCAGGCCAGCAGGCCCTACAGCTTCT<br>ACAGCAGCCTGATCAGCTATGAGGAGGACCAGAGGCAGGGGGCTGAGCCCAGGAAGAACTTTG<br>TGAAGCCCAATGAAACCAAGACCTACTTCTGGAAGGTGCAGCACCACATGGCCCCCACCAAGGA<br>TGAGTTTGACTGCAAGGCCTGGGCCTACTTCTCTGATGTGGACCTGGAGAAGGATGTGCACTCTG<br>GCCTGATTGGCCCCCTGCTGGTGTGCCACACCAACACCCTGAACCCTGCCCATGGCAGGCAGGT<br>GACTGTGCAGGAGTTTGCCCTGTTCTTCACCATCTTTGATGAAACCAAGAGCTGGTACTTCACTG | 20 |

| SEQUENCE LISTING | | |
| --- | --- | --- |
| Element | Sequence | # |

```
AGAACATGGAGAGGAACTGCAGGGCCCCCTGCAACATCCAGATGGAGGACCCCACCTTCAAGG
AGAACTACAGGTTCCATGCCATCAATGGCTACATCATGGACACCCTGCCTGGCCTGGTGATGGC
CCAGGACCAGAGGATCAGGTGGTACCTGCTGAGCATGGGCAGCAATGAGAACATCCACAGCAT
CCACTTCTCTGGCCATGTGTTCACTGTGAGGAAGAAGGAGGAGTACAAGATGGCCCTGTACAAC
CTGTACCCTGGGGTGTTTGAGACTGTGGAGATGCTGCCCAGCAAGGCTGGCATCTGGAGGGTGG
AGTGCCTGATTGGGGAGCACCTGCATGCTGGCATGAGCACCCTGTTCCTGGTGTACAGCAACAA
GTGCCAGACCCCCCTGGGCATGGCCTCTGGCCACATCAGGGACTTCCAGATCACTGCCTCTGGCC
AGTATGGCCAGTGGGCCCCCAAGCTGGCCAGGCTGCACTACTCTGGCAGCATCAATGCCTGGAG
CACCAAGGAGCCCTTCAGCTGGATCAAGGTGGACCTGCTGGCCCCCATGATCATCCATGGCATC
AAGACCCAGGGGGCCAGGCAGAAGTTCAGCAGCCTGTACATCAGCCAGTTCATCATCATGTACA
GCCTGGATGGCAAGAAGTGGCAGACCTACAGGGGCAACAGCACTGGCACCCTGATGGTGTTCTT
TGGCAATGTGGACAGCTCTGGCATCAAGCACAACATCTTCAACCCCCCCATCATTGCCAGATAC
ATCAGGCTGCACCCCACCCACTACAGCATCAGGAGCACCCTGAGGATGGAGCTGATGGGCTGTG
ACCTGAACAGCTGCAGCATGCCCCTGGGCATGGAGAGCAAGGCCATCTCTGATGCCCAGATCAC
TGCCAGCAGCTACTTCACCAACATGTTTGCCACCTGGAGCCCCAGCAAGGCCAGGCTGCACCTG
CAGGGCAGGAGCAATGCCTGGAGGCCCCAGGTCAACAACCCCAAGGAGTGGCTGCAGGTGGAC
TTCCAGAAGACCATGAAGGTGACTGGGGTGACCACCCAGGGGGTGAAGAGCCTGCTGACCAGC
ATGTATGTGAAGGAGTTCCTGATCAGCAGCAGCCAGGATGGCCACCAGTGGACCCTGTTCTTCC
AGAATGGCAAGGTGAAGGTGTTCCAGGGCAACCAGGACAGCTTCACCCCTGTGGTGAACAGCCT
GGACCCCCCCCTGCTGACCAGATACCTGAGGATTCACCCCCAGAGCTGGGTGCACCAGATTGCC
CTGAGGATGGAGGTGCTGGGCTGTGAGGCCCAGGACCTGTACTGATAACTCGAGAATCAACCTC
TGGATTACAAAATTTGTGAAAGATTGACTGGTATTCTTAACTGTTGCTCCTTTTACGCTATGTG
GATACGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGCGTGG
TGTGCACTGTGTTTGCTGACGCAACCCCCACTGGTTGGGGCATTGCCACCACCTGTCAGCTCCTT
TCCGGGACTTTCGCTTTCCCCCTCCCTATTGCCACGGCGGAACTCATCGCCGCCTGCCTTGCCCG
CTGCTGGACAGGGGCTCGGCTGTTGGGCACTGACAATTCCGTGGGGTGTGCCTTCTAGTTGCCAG
CCATCTGTTGTTTGCCCCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGATGCGGT
GGGCTCTATGGGAAGATGTCTACTGAGCTGTGCGATCCCTGCTGGGGACTTTCCGCTGGGGACTT
TCCGCTGGGGACTTTCCGCCTTCAGCTAAGGAAGCTACCAATATTTAGAGGTACATTTTGTTCTA
GAACAAAATGTACCGGTACATTTTGTTCTGGTACATTTTGTTCT
```

| FIX AA Sequence | MQRVNMIMAESPGLITICLLGYLLSAECTVFLDHENANKILNRPKRYNSGKLEEFVQGNLERECMEE<br>KCSFEEAREVFENTERTTEFWKQYVDGDQCESNPCLNGGSCKDDINSYECWCPFGFEGKNCELDVT<br>CNIKNGRCEQFCKNSADNKVVSCSCTEGYRLAENQKSCEPAVPFPCGRVSVSQTSKLTRAETVFPDVD<br>YVNSTEAETILDNITQSTQSFNDFTRVVGGEDAKPGQFPWQVVLNGKVDAFCGGSIVNEKWIVTAAH<br>CVETGVKITVVAGEHNIEETEHTEQKRNVIRIIPHHNYNAAINKYNHDIALLELDEPLVLNSYVTPICIA<br>DKEYTNIFLKFGSGYVSGWGRVFHKGRSALVLQYLRVPLVDRATCLRSTKFTIYNNMFCAGFHEGG<br>RDSCQGDSGGPHVTEVEGTSFLTGIISWGEECAMKGKYGIYTKVSRYVNWIKEKTKLT** | 21 |
| 3'ITR | AGGAACCCCTAGTGATGGAGTTGGCCACTCCCTCTCTGCGCGCTCGCTCGCTCACTGAGGCCGG<br>GCGACCAAAGGTCGCCCGACGCCCGGGCTTTGCCCGGGCGGCCTCAGTGAGCGAGCGAGCGCG<br>CAGCTGCCTGCAGG | 22 |
| NP Backbone | TGGCTTGTTGTCCACAACCATTAAACCTTAAAAGCTTTAAAAGCCTTATATATTCTTTTTTTTCTT<br>ATAAAACTTAAAAACCTTAGAGGCTATTTAAGTTGCTGATTTATATTAATTTTATTGTTCAAACAT<br>GAGAGCTTAGTACGTGAAACATGAGAGCTTAGTACATTAGCCATGAGAGCTTAGTACATTAGCC<br>ATGAGGGTTTAGTTCATTAAACATGAGAGCTTAGTACATTAAACATGAGAGCTTAGTACATTAA<br>ACATGAGAGCTTAGTACATACTATCAACAGGTTGAACTGCTGATCTGTACAGTAGAATTGGTAA<br>AGAGAGTTGTGTAAAATATTGAGTTCGCACATCTTGTTGTCTGATTATTGATTTTTGGCGAAACC<br>ATTTGATCATATGACAAGATGTGTATCTACCTTAACTTAATGATTTTGATAAAAATCATTA | 23 |
| FVIII-SQ-N6-F309S-DM | MQIELSTCFFLCLLRFCFSATRRYYLGAVELSWDYMQSDLGELPVDARFPPRVPKSFPFNTSVVYKKT<br>LFVEFTDHLFNIAKPRPPWMGLLGPTIQAEVYDTVVITLKNMASHPVSLHAVGVSYWKASEGAEYD<br>DQTSQREKEDDKVFPGGSHTYVWQVLKENGPMASDPLCLTYSYLSHVDLVKDLNSGLIGALLVCRE<br>GSLAKEKTQTLHKFILLFAVFDEGKSWHSETKNSLMQDRDAASARAWPKMHTVNGYVNRSLPGLIG<br>CHRKSVYWHVIGMGTTPEVHSIFLEGHTFLVRNHRQASLEISPITFLTAQTLLMDLGQFLLSCHISSHQ<br>HDGMEAYVKVDSCPEEPQLRMKNNEEAEDYDDDLTDSEMDVVRFDDDNSPSFIQIRSVAKKHPKT<br>WVHYIAAEEEDWDYAPLVLAPDDRSYKSQYLNNGPQRIGRKYKKVRFMAYTDETFKTREAIQHESG<br>ILGPLLYGEVGDTLLIIFKNQASRPYNIYPHGITDVRPLYSRRLPKGVKHLKDFPILPGEIFKYKWTVTV<br>EDGPTKSDPRCLTRYYSSFVNMERDLASGLIGPLLICYKESVDQRGNQIMSDKRNVILFSVFDENRSW<br>YLTENIQRFLPNPAGVQLEDPEFQASNIMHSINGYVFDSLQLSVCLHEVAYWYILSIGAQTDFLSVFFS<br>GYTFKHKMVYEDTLTLFPFSGETVFMSMENPGLWILGCHNSDFRNRGMTALLKVSSCDKNTGDYYE<br>DSYEDISAYLLSKNNAIEPRSFSQNPPVLTRSFSQNSRHPSTRQKQFNATTIPENDIEKTDPWFAHRTP<br>MPKIQNVSSSDLLMLLRQSPTPHGLSLSDLQEAKYETFSDDPSPGAIDSNNSLSEMTHFRPQLHHSGD<br>MVFTPESGLQLRLNEKLGTTAATELKKLDFKVSSTSNNLISTIPSDNLAAGTDNTSSLGPPSMPVHYD<br>SQLDTTLFGKKSSPLTESGGPLSLSEENNDSKLLESGLMNSQESSWGKNVSSTREITRTTLQSDQEEID<br>YDDTISVEMKKEDFDIYDEDENQSPRSFQKKTRHYFIAAVERLWDYGMSSSPHVLRNRAQSGSVPQF<br>KKVVFQEFTDGSFTQPLYRGELNEHLGLLGPYIRAEVEDNIMVTFRNQASRPYSFYSSLISYEEDQRQ<br>GAEPRKNFVKPNETKTYFWKVQHHMAPTKDEFDCKAWAYFSDVDLEKDVHSGLIGPLLVCHTNTL<br>NPAHGRQVTVQEFALFFTIFDETKSWYFTENMERNGRAPGNIQMEDPTFKENYRFHAINGYIMDTLP<br>GLVMAQDQRIRWYLLSMGSNENIHSIHFSGHVFTVRKKEEYKMALYNLYPGVFETVEMLPSKAGIW<br>RVECLIGEHLHAGMSTLFLVYSNKCQTPLGMASGHIRDFQITASGQYGQWAPKLARLHYSGSINAWS | 24 |

| SEQUENCE LISTING | | |
|---|---|---|
| Element | Sequence | # |

| | TKEPFS WIKVDLLAPMIIHGIKTQGARQKFSSLYISQFIIMYSLDGKKWQTYRGNSTGTLMVFFGNVD | |
| | SSGIKHNIFNPPIIARYIRLHPTHYSIRSTLRMELMGCDLNSCSMPLGMESKAISDAQITASSYFTNMFA | |
| | TWSPSKARLHLQGRSNAWRPQVNNPKEWLQVDFQKTMKVTGVTTQGVKSLLTSMYVKEFLISSSQ | |
| | DGHQWTLFFQNGKVKVFQGNQDSFTPVVNSLDPPLLTRYLRIHPQSWVHQIALRMEVLGCEAQDLY | |

| FVIII-SQ-N6-F309S-DM: A1 domain | MQIELSTCFFLCLLRFCFSATRRYYLGAVELSWDYMQSDLGELPVDARFPPRVPKSFPFNTSVVYKKT LFVEFTDHLFNIAKPRPPWMGLLGPTIQAEVYDTVVITLKNMASHPVSLHAVGVSYWKASEGAEYD DQTSQREKEDDKVFPGGSHTYVWQVLKENGPMASDPLCLTYSYLSHVDLVKDLNSGLIGALLVCRE GSLAKEKTQTLHKFILLFAVFDEGKSWHSETKNSLMQDRDAASARAWPKMHTVNGYVNRSLPGLIG CHRKSVYWHVIGMGTTPEVHSIFLEGHTFLVRNHRQASLEISPITFLTAQTLLMDLGQFLLSCHISSHQ HDGMEAYVKVDSCPEEPQLRMKNNEEAEDYDDDLTDSEMDVVRFDDDNSPSFIQIR | 25 |

| FVIII-SQ-N6-F309S-DM: A2 domain | SVAKKHPKTWVHYIAAEEEDWDYAPLVLAPDDRSYKSQYLNNGPQRIGRKYKKVRFMAYTDETFK TREAIQHESGILGPLLYGEVGDTLLIIFKNQASRPYNIYPHGITDVRPLYSRRLPKGVKHLKDFPILPGE IPKYKWTVTVEDGPTKSDPRCLTRYYSSFVNMERDLASGLIGPLLICYKESVDQRGNQIMSDKRNVIL FSVFDENRSWYLTENIQRFLPNPAGVQLEDPEFQASNIMHSINGYVFDSLQLSVCLHEVAYWYILSIG AQTDFLSVFFSGYTFKHKMVYEDTLTLFPFSGETVFMSMENPGLWILGCHNSDFRNRGMTALLKVSS CDKNTGDYYEDSYEDISAYLLSKNNAIEPR | 26 |

| FVIII-SQ-N6-F309S-DM: SQ domain | SFSQNPPVLTR | 27 |

| FVIII-SQ-N6-F309S-DM: N6 domain | SFSQNSRHPSTRQKQFNATTIPENDIEKTDPWFAHRTPMPKIQNVSSSDLLMLLRQSPTPHGLSLSDLQ EAKYETFSDDPSPGAIDSNNSLSEMTHFRPQLHHSGDMVFTPESGLQLRLNEKLGTTAATELKKLDF KVSSTSNNLISTIPSDNLAAGTDNTSSLGPPSMPVHYDSQLDTTLFGKKSSPLTESGGPLSLSEENNDS KLLESGLMNSQESSWGKNVSST | 28 |

| FVIII-SQ-N6-F309S-DM: A3 domain | REITRTTLQSDQEEIDYDDTISVEMKKEDFDIYDEDENQSPRSFQKKTRHYFIAAVERLWDYGMSSSP HVLRNRAQSGSVPQFKKVVFQEFTDGSFTQPLYRGELNEHLGLLGPYIRAEVEDNIMVTFRNQASRP YSFYSSLISYEEDQRQGAEPRKNFVKPNETKTYFWKVQHHMAPTKDEFDCKAWAYFSDVDLEKDV HSGLIGPLLVCHTNTLNPAHGRQVTVQEFALFFTIFDETKSWYFTENMERNGRAPGNIQMEDPTFKE NYRFHAINGYIMDTLPGLVMAQDQRIRWYLLSMGSNENIHSIHFSGHVFTVRKKEEYKMALYNLYP GVFETVEMLPSKAGIWRVECLIGEHLHAGMSTLFLVYSNK | 29 |

| FVIII-SQ-N6-F309S-DM: C1 domain | CQTPLGMASGHIRDFQITASGQYGQWAPKLARLHYSGSINAWSTKEPFSWIKVDLLAPMIIHGIKTQG ARQKFSSLYISQFIIMYSLDGKKWQTYRGNSTGTLMVFFGNVDSSGIKHNIFNPPIIARYIRLHPTHYSI RSTLRMELMGCDLNS | 30 |

| FVIII-SQ-N6-F309S-DM: C1 domain | CSMPLGMESKAISDAQITASSYFTNMFATWSPSKARLHLQGRSNAWRPQVNNPKEWLQVDFQKTM KVTGVTTQGVKSLLTSMYVKEFLISSSQDGHQWTLFFQNGKVKVFQGNQDSFTPVVNSLDPPLLTRY LRIHPQSWVHQIALRMEVLGCEAQDLY | 31 |

| FVIII-SQ-N6-F309S-DM: NA Coding Sequence 1 | ATGCAGATCGAGCTGTCTACCTGCTTCTTCCTGTGCCTGCTGCGGTTCTGCTTCAGCGCCACCAG AAGATATTACCTGGGCGCCGTGGAACTGAGCTGGGACTACATGCAGTCTGACCTGGGAGAGCTG CCCGTGGACGCTAGATTTCCTCCAAGAGTGCCCAAGAGCTTCCCCTTCAACACCTCCGTGGTGTA CAAGAAAACCCTGTTCGTGGAATTCACCGACCACCTGTTCAATATCGCCAAGCCTCGGCCTCCTT GGATGGGACTGCTGGGACCTACAATTCAGGCCGAGGTGTACGACACCGTGGTCATCACCCTGAA GAACATGGCCAGCCATCCTGTGTCTCTGCACGCCGTGGGAGTGTCTTACTGGAAGGCTTCTGAG GGCGCCGAGTACGACGATCAGACAAGCCAGAGAGAGAAAGAGGACGACAAGGTTTTCCCTGGC GGCAGCCACACCTATGTCTGGCAGGTCCTGAAAGAAAACGGCCCTATGGCCTCCGATCCTCTGT GCCTGACATACAGCTACCTGAGCCACGTGGACCTGGTCAAGGACCTGAATTCTGGCCTGATCGG AGCCCTGCTCGTGTGTAGAGAAGGCAGCCTGGCCAAAGAGAAACCCAGACACTGCACAAGTT CATCCTGCTGTTCGCCGTGTTCGACGAGGGCAAGAGCTGGCACAGCGAGACAAAGAACAGCCTG ATGCAGGACAGGGATGCCGCCTCTGCTAGAGCTTGGCCTAAGATGCACACCGTGAACGGCTACG TGAACGAAGCCTGCCTGGACTGATCGGCTGCCACAGAAAGTCCGTGTACTGGCACGTGATCGG CATGGGCACAACACCTGAGGTGCACAGCATCTTTCTGGAAGGACACACCTTCCTCGTGCGGAAC CATAGACAGGCCAGCCTGGAAATCAGCCCTATCACCTTCCTGACCGCTCAGACCCTGCTGATGG ATCTGGGCCAGTTTCTGCTGAGCTGCCACATCAGCTCCCACCAGCACGATGGCATGGAAGCCTA CGTGAAGGTGGACAGCTGCCCCGAAGAACCCCAGCTGCGGATGAAGAACAACGAGGAAGCCGA GGACTACGACGACGACCTGACCGACTCTGAGATGGACGTCGTCAGATTCGACGACGATAACAGC CCCAGCTTCATCCAGATCAGAAGCGTGGCCAAGAAGCACCCCAAGACCTGGGTGCACTATATCG CCGCCGAGGAAGAGGACTGGGATTACGCTCCTCTGGTGCTGGCCCCTGACGACAGAAGCTACAA GAGCCAGTACCTGAACAACGGCCCTCAGCGGATCGGCCGAAGTATAAGAAAGTGCGGTTCAT GGCCTACACCGACGAGACATTCAAGACCAGAGAGGCCATCCAGCACGAGAGCGGAATTCTGGG CCCTCTGCTGTATGGCGAAGTGGGCGATACACTGCTGATCATCTTCAAGAACCAGGCCAGCAGA CCCTACAACATCTACCCTCACGGCATCACCGATGTGCGGCCCCTGTATTCTAGAAGGCTGCCCAA GGGCGTGAAGCACCTGAAGGACTTCCCTATCCTGCCTGGCGAGATCTTCAAGTACAAGTGGACC GTGACCGTGGAAGATGGCCCCACCAAGAGCGACCCTAGATGTCTGACACGGTACTACAGCAGCT TCGTGAACATGGAACGCGACCTGGCCAGCGGCCTGATTGGACCTCTGCTGATCTGCTACAAAGA AAGCGTGGACCAGCGGGGCAACCAGATCATGAGCGACAAGCGGAACGTGATCCTGTTTAGCGT GTTCGATGAGAACCGGTCCTGGTATCTGACCGAGAACATCCAGCGGTTTCTGCCCAATCCTGCTG | 32 |

SEQUENCE LISTING

| Element | Sequence | # |
|---|---|---|
| | GCGTGCAGCTGGAAGATCCTGAGTTCCAGGCCTCCAACATCATGCACTCCATCAATGGCTATGT<br>GTTCGACAGCCTGCAGCTGAGCGTGTGCCTGCACGAAGTGGCCTACTGGTACATCCTGAGCATT<br>GGCGCCCAGACCGACTTCCTGTCCGTGTTCTTTAGCGGCTACACCTTCAAGCACAAGATGGTGTA<br>CGAGGATACCCTGACACTGTTCCCATTCAGCGGCGAGACAGTGTTCATGAGCATGGAAAACCCC<br>GGCCTGTGGATCCTGGGCTGTCACAACAGCGACTTCCGGAACAGAGGCATGACAGCCCTGCTGA<br>AGGTGTCCAGCTGCGACAAGAACACCGGCGACTACTACGAGGACAGCTATGAGGACATCAGCG<br>CCTACCTGCTGAGCAAGAACAATGCCATCGAGCCCAGAAGCTTCTCCCAAAATCCTCCGGTCCT<br>CACACGTTCCTTCAGCCAGAATAGCAGACACCCCTCCACCAGACAGAAGCAGTTCAACGCCACA<br>ACAATCCCCGAGAACGACATCGAGAAAACCGATCCTTGGTTTGCCCACAGAACCCCTATGCCTA<br>AGATCCAGAACGTGTCCTCCAGCGATCTGCTGATGCTCCTGAGACAGAGCCCTACACCTCACGG<br>ACTGAGCCTGTCCGATCTGCAAGAGGCCAAATACGAAACCTTCAGCGACGACCCTTCTCCTGGC<br>GCCATCGACAGCAACAATAGCCTGAGCGAGATGACCCACTTCAGACCACAGCTGCACCACAGCG<br>GCGACATGGTGTTTACACCTGAGAGCGGCCTCCAGCTGAGACTGAATGAGAAGCTGGGAACCAC<br>CGCCGCCACCGAGCTGAAGAAACTGGACTTCAAGGTGTCCTCTACCAGCAACAACCTGATCAGC<br>ACAATCCCCTCCGACAACCTGGCTGCCGGCACCGACAACACATCTTCTCTGGGCCCCACCTAGCAT<br>GCCCGTGCACTACGATAGCCAGCTGGATACCACACTGTTCGGCAAGAAGTCTAGCCCTCTGACA<br>GAGTCTGGCGGCCCTCTGTCTCTGAGCGAGGAAAACAACGACAGCAAGCTGCTGGAATCCGGCC<br>TGATGAACAGCCAAGAGTCCTCCTGGGGCAAGAATGTGTCCAGCACCAGAGAAATCACCCGGA<br>CCACACTGCAGAGCGACCAAGAAGAGATCGATTACGACGATACCATCAGCGTCGAGATGAAGA<br>AGAAGATTTCGACATCTACGACGAGGACGAGAATCAGAGCCCTCGGAGCTTCCAGAAGAAAA<br>CCAGGCACTACTTTATTGCCGCCGTCGAGCGGCTGTGGGACTACGGAATGTCTAGCTCTCCTCAC<br>GTGCTGCGGAATAGAGCCCAGTCTGGTAGCGTGCCCCAGTTCAAAAAGGTCGTGTTCCAAGAGT<br>TCACCGACGGCAGCTTCACCCAGCCACTGTATAGAGGCGAGCTGAACGAGCATCTGGGCCTGCT<br>GGGCCCTTATATCAGAGCCGAAGTGGAAGATAACATCATGGTCACCTTCCGGAATCAGGCCTCT<br>CGGCCCTACAGCTTCTACAGCTCCCTGATCTCCTACGAAGAGGACCAGAGACAGGGCGCAGAGC<br>CCCGGAAGAATTTCGTGAAGCCCAACGAGACTAAGACCTACTTTTGGAAGGTGCAGCACCATAT<br>GGCCCCTACAAAGGACGAGTTCGACTGCAAAGCCTGGGCCTACTTCTCCGATGTGGACCTTGAG<br>AAGGATGTGCACAGCGGACTCATCGGCCCACTGCTTGTGTGCCACACCAACACACTGAACCCCG<br>CTCACGGCAGACAAGTGACAGTGCAAGAATTCGCCCTGTTTTTCACCATCTTCGACGAAACGAA<br>GTCCTGGTACTTCACCGAAAACATGGAAAGAAACGGACGCGCGCCTGGCAACATTCAGATGGA<br>AGATCCCACCTTCAAAGAGAACTACCGGTTCCACGCCATCAACGGCTACATCATGGACACACTG<br>CCCGGCCTGGTTATGGCTCAGGATCAGAGAATCCGGTGGTATCTGCTGTCCATGGGCTCCAACG<br>AGAATATCCACTCCATCCACTTCAGCGGCCACGTGTTCACCGTCCGCAAGAAAGAAGAGTACAA<br>GATGGCCCTGTACAATCTGTACCCCGGCGTTTTCGAAACCGTTGAGATGCTGCCTAGCAAGGCC<br>GGAATTTGGAGAGTGGAATGTCTGATTGGAGAGCACCTCCACGCCGGGATGAGCACCCTGTTTC<br>TGGTGTACTCCAACAAGTGTCAGACCCCTCTCGGCATGGCCTCTGGCCACATTAGAGACTTCCAG<br>ATCACCGCCAGCGGACAGTATGGACAGTGGGCCCCTAAACTGGCCAGACTGCACTACTCCGGCA<br>GCATCAATGCCTGGTCCACCAAAGAGCCTTTCAGCTGGATCAAAGTGGACCTGCTGGCTCCCAT<br>GATCATCCACGGAATCAAGACCCAGGGCGCCAGACAAAAGTTCAGCAGCCTGTACATCAGCCA<br>GTTCATCATCATGTACAGCCTGGACGGAAAGAAGTGGCAGACCTACCGGGGCAATAGCACCGGC<br>ACACTGATGGTGTTCTTCGGCAACGTGGACTCCAGCGGCATTAAGCACAACATCTTCAACCCTCC<br>AATCATTGCCCGGTACATCCGGCTGCACCCCACACACTACAGCATCAGGTCTACCCTGAGAATG<br>GAACTGATGGGCTGCGACCTGAACAGCTGCAGCATGCCCCTCGGAATGGAAAGCAAGGCCATC<br>AGCGACGCCCAGATCACAGCCTCTAGCTACTTCACCAACATGTTCGCCACTTGGAGCCCCTCTAA<br>GGCCCGGCTTCATCTGCAAGGCAGAAGCAACGCTTGGAGGCCCCAAGTGAACAACCCCAAAGA<br>ATGGCTGCAGGTCGACTTTCAGAAAACCATGAAAGTGACAGGCGTGACCACACAGGGCGTCAA<br>GTCCCTGCTGACCTCTATGTACGTGAAAGAGTTTCTGATCAGCTCCAGCCAGGACGGCCACCAGT<br>GGACCCTGTTCTTCCAGAACGGCAAAGTGAAAGTGTTCCAGGGAAATCAGGACAGCTTCACACC<br>CGTGGTCAACTCCCTGGATCCTCCACTGCTGACAAGATACCTGCGGATTCACCCTCAGTCTTGGG<br>TGCACCAGATTGCCCTGCGGATGGAAGTGCTGGGCTGTGAAGCTCAGGACCTCTACTGATAG | |
| FVIII-SQ-<br>N6-F309S-<br>DM: NA<br>Coding<br>Sequence 2 | ATGCAGATTGAGCTGAGCACCTGCTTCTTCCTGTGCCTGCTGAGGTTCTGCTTCTCTGCCACCAG<br>GAGATACTACCTGGGGGCTGTGGAGCTGAGCTGGGACTACATGCAGTCTGACCTGGGGGAGCTG<br>CCTGTGGATGCCAGGTTCCCCCCCCAGAGTGCCCAAGAGCTTCCCCTTCAACACCTCTGTGGTGTA<br>CAAGAAGACCCTGTTTGTGGAGTTCACTGACCACCTGTTCAACATTGCCAAGCCCAGGCCCCCCT<br>GGATGGGCCTGCTGGGCCCCACCATCCAGGCTGAGGTGTATGACACTGTGGTGATCACCCTGAA<br>GAACATGGCCAGCCACCCTGTGAGCCTGCATGCTGTGGGGGTGAGCTACTGGAAGGCCTCTGAG<br>GGGGCTGAGTATGATGACCAGACCAGCCAGAGGGAGAAGGAGGATGACAAGGTGTTCCCTGGG<br>GGCAGCCACACCTATGTGTGGCAGGTGCTGAAGGAGAATGGCCCCATGGCCTCTGACCCCCTGT<br>GCCTGACCTACAGCTACCTGAGCCATGTGGACCTGGTGAAGGACCTGAACTCTGGCCTGATTGG<br>GGCCCTGCTGGTGTGCAGGGAGGGCAGCCTGGCCAAGGAGAAGACCCAGACCCTGCACAAGTT<br>CATCCTGCTGTTTGCTGTGTTTGATGAGGGCAAGAGCTGGCACTCTGAAACCAAGAACAGCCTG<br>ATGCAGGACAGGGATGCTGCCTCTGCCAGGGCCTGGCCCAAGATGCACACTGTGAATGGCTATG<br>TGAACAGGAGCCTGCCTGGCCTGATTGGCTGCCACAGGAAGTCTGTGTACTGGCATGTGATTGG<br>CATGGGCACCACCCCTGAGGTGCACAGCATCTTCCTGGAGGGCCACACCTTCCTGGTCAGGAAC<br>CACAGGCAGGCCAGCCTGGAGATCAGCCCCATCACCTTCCTGACTGCCCAGACCCTGCTGATGG<br>ACCTGGGCCAGTTCCTGCTGAGCTGCCACATCAGCAGCCACCAGCATGATGGCATGGAGGCCTA<br>TGTGAAGGTGGACAGCTGCCCTGAGGAGCCCCAGCTGAGGATGAAGAACAATGAGGAGGCTGA<br>GGACTATGATGATGACCTGACTGACTCTGAGATGGATGTGGTGAGGTTTGATGATGACAACAGC<br>CCCAGCTTCATCCAGATCAGGTCTGTGGCCAAGAAGCACCCCAAGACCTGGGTGCACTACATTG<br>CTGCTGAGGAGGAGGACTGGGACTATGCCCCCCTGGTGCTGGCCCCTGATGACAGGAGCTACAA<br>GAGCCAGTACCTGAACAATGGCCCCCAGAGGATTGGCAGGAAGTACAAGAAGGTCAGGTTCAT<br>GGCCTACACTGATGAAACCTTCAAGACCAGGGAGGCCATCCAGCATGAGTCTGGCATCCTGGGC<br>CCCCTGCTGTATGGGGAGGTGGGGGACACCCTGCTGATCATCTTCAAGAACCAGGCCAGCAGGC<br>CCTACAACATCTACCCCCATGGCATCACTGATGTGAGGCCCCTGTACAGCAGGAGGCTGCCCAA | 33 |

SEQUENCE LISTING

| Element | Sequence | # |
|---------|----------|---|
| | GGGGGTGAAGCACCTGAAGGACTTCCCCATCCTGCCTGGGGAGATCTTCAAGTACAAGTGGACT | |
| | GTGACTGTGGAGGATGGCCCCACCAAGTCTGACCCCAGGTGCCTGACCAGATACTACAGCAGCT | |
| | TTGTGAACATGGAGAGGGACCTGGCCTCTGGCCTGATTGGCCCCCTGCTGATCTGCTACAAGGA | |
| | GTCTGTGGACCAGAGGGGCAACCAGATCATGTCTGACAAGAGGAATGTGATCCTGTTCTCTGTG | |
| | TTTGATGAGAACAGGAGCTGGTACCTGACTGAGAACATCCAGAGGTTCCTGCCCAACCCTGCTG | |
| | GGGTGCAGCTGGAGGACCCTGAGTTCCAGGCCAGCAACATCATGCACAGCATCAATGGCTATGT | |
| | GTTTGACAGCCTGCAGCTGTCTGTGTGCCTGCATGAGGTGGCCTACTGGTACATCCTGAGCATTG | |
| | GGGCCCAGACTGACTTCCTGTCTGTGTTCTTCTCTGGCTACACCTTCAAGCACAAGATGGTGTAT | |
| | GAGGACACCCTGACCCTGTTCCCCTTCTCTGGGGAGACTGTGTTCATGAGCATGGAGAACCCTG | |
| | GCCTGTGGATTCTGGGCTGCCACAACTCTGACTTCAGGAACAGGGGCATGACTGCCCTGCTGAA | |
| | AGTCTCCAGCTGTGACAAGAACACTGGGGACTACTATGAGGACAGCTATGAGGACATCTCTGCC | |
| | TACCTGCTGAGCAAGAACAATGCCATTGAGCCCAGGAGCTTCAGCCAGAATCCCCCAGTGCTCA | |
| | CCCGGTCCTTTAGCCAGAATTCTCGCCATCCCTCCACCCGGCAAAAGCAGTTCAACGCCACTACC | |
| | ATCCCAGAGAACGACATCGAAAAAACCGACCCCTGGTTCGCCCACAGAACTCCCATGCCCAAAGA | |
| | TTCAGAATGTTTCCAGTTCTGACCTCCTTATGTTGCTGCGCCAGTCTCCGACCCCTCATGGACTGT | |
| | CCCTGAGTGACTTGCAGGAGGCCAAGTACGAGACGTTCTCTGATGACCCCAGCCCAGGCGCGAT | |
| | TGACTCAAATAACTCCCTGTCTGAGATGACACATTTTCGCCCTCAGCTCCATCACAGCGGGGACA | |
| | TGGTGTTCACTCCAGAGTCCGGACTTCAGCTGCGCCTCAACGAGAAACTCGGTACTACAGCCGC | |
| | GACAGAACTCAAAAAGCTGGATTTCAAGGTTTCCAGCACCAGCAATAACCTGATCTCTACAATT | |
| | CCCAGCGATAACCTGGCGGCTGGAACCGACAACACTTCCAGCCTGGGACCTCCGTCCATGCCTG | |
| | TGCACTACGACTCCCAGCTCGACACCACTCTGTTCGGCAAGAAAAGTAGCCCCCTGACCGAATC | |
| | CGGCGGTCCGCTGTCCCTCTCGAAGAGAATAACGATAGCAAGCTCCTGGAATCTGGGCTTATG | |
| | AACTCTCAAGAGTCATCCTGGGGCAAGAACGTTTCATCAACTAGGGAGATCACCAGGACCACCC | |
| | TGCAGTCTGACCAGGAGGAGATTGACTATGATGACACCATCTCTGTGGAGATGAAGAAGGAGG | |
| | ACTTTGACATCTACGACGAGGACGAGAACCAGAGCCCCAGGAGCTTCCAGAAGAAGACCAGGC | |
| | ACTACTTCATTGCTGCTGTGGAGAGGCTGTGGGACTATGGCATGAGCATGGCAGCAGCCCCCATGTGCT | |
| | GAGGAACAGGGCCCAGTCTGGCTCTGTGCCCCAGTTCAAGAAGGTGGTGTTCCAGGAGTTCACT | |
| | GATGGCAGCTTCACCCAGCCCCTGTACAGAGGGGAGCTGAATGAGCACCTGGGCCTGCTGGGCC | |
| | CCTACATCAGGGCTGAGGTGGAGGACAACATCATGGTGACCTTCAGGAACCAGGCCAGCAGGC | |
| | CCTACAGCTTCTACAGCAGCCTGATCAGCTATGAGGAGGACCAGAGGCAGGGGGCTGAGCCCA | |
| | GGAAGAACTTTGTGAAGCCCAATGAAACCAAGACCTACTTCTGGAAGGTGCAGCACCACATGGC | |
| | CCCCACCAAGGATGAGTTTGACTGCAAGGCCTGGGCCTACTTCTCTGATGTGGACCTGGAGAAG | |
| | GATGTGCACTCTGGCCTGATTGGCCCCCTGCTGGTGTGCCACACCAACACCCTGAACCCTGCCCA | |
| | TGGCAGGCAGGTGACTGTGCAGGAGTTTGCCCTGTTCTTCACCATCTTTGATGAAACCAAGAGCT | |
| | GGTACTTCACTGAGAACATGGAGAGGAACGGCAGGGCCCCCGGCAACATCCAGATGGAGGACC | |
| | CCACCTTCAAGGAGAACTACAGGTTCCATGCCATCAATGGCTACATCATGGACACCCTGCCTGG | |
| | CCTGGTGATGGCCCAGGACCAGAGGATCAGGTGGTACCTGCTGAGCATGGGCAGCAATGAGAA | |
| | CATCCACAGCATCCACTTCTCTGGCCATGTGTTCACTGTGAGGAAGAAGGAGGAGTACAAGATG | |
| | GCCCTGTACAACCTGTACCCTGGGGTGTTTGAGACTGTGGAGATGCTGCCCAGCAAGGCTGGCA | |
| | TCTGGAGGGTGGAGTGCCTGATTGGGGAGCACCTGCATGCTGGCATGAGCACCCTGTTCCTGGT | |
| | GTACAGCAACAAGTGCCAGACCCCCCTGGGCATGGCCTCTGGCCACATCAGGGACTTCCAGATC | |
| | ACTGCCTCTGGCCAGTATGGCCAGTGGGCCCCCAAGCTGGCCAGGCTGCACTACTCTGGCAGCA | |
| | TCAATGCCTGGAGCACCAAGGAGCCCTTCAGCTGGATCAAGGTGGACCTGCTGGCCCCCATGAT | |
| | CATCCATGGCATCAAGACCCAGGGGGCCAGGCAGAAGTTCAGCAGCCTGTACATCAGCCAGTTC | |
| | ATCATCATGTACAGCCTGGATGGCAAGAAGTGGCAGACCTACAGGGGCAACAGCACTGGCACC | |
| | CTGATGGTGTTCTTTGGCAATGTGGACAGCTCTGGCATCAAGCACAACATCTTCAACCCCCCCAT | |
| | CATTGCCAGATACATCAGGCTGCACCCCACCCACTACAGCATCAGGAGCACCCTGAGGATGGAG | |
| | CTGATGGGCTGTGACCTGAACAGCTGCAGCATGCCCCTGGGCATGGAGAGCAAGGCCATCTCTG | |
| | ATGCCCAGATCACTGCCAGCAGCTACTTCACCAACATGTTTGCCACCTGGAGCCCCAGCAAGGC | |
| | CAGGCTGCACCTGCAGGGCAGGAGCAATGCCTGGAGGCCCCAGGTCAACAACCCCAAGGAGTG | |
| | GCTGCAGGTGGACTTCCAGAAGACCATGAAGGTGACTGGGGTGACCACCCAGGGGGTGAAGAG | |
| | CCTGCTGACCAGCATGTATGTGAAGGAGTTCCTGATCAGCAGCAGCCAGGATGGCCACCAGTGG | |
| | ACCCTGTTCTTCCAGAATGGCAAGGTGAAGGTGTTCCAGGGCAACCAGGACAGCTTCACCCCTG | |
| | TGGTGAACAGCCTGGACCCCCCCCTGCTGACCAGATACCTGAGGATTCACCCCCAGAGCTGGGT | |
| | GCACCAGATTGCCCTGAGGATGGAGGTGCTGGGCTGTGAGGCCCAGGACCTGTACTGA | |
| N6-SQ domain | SFSQNPPVLTRSFSQNSRHPSTRQKQFNATTIPENDIEKTDPWFAHRTPMPKIQNVSSSDLLMLLRQSP TPHGLSLSDLQEAKYETFSDDPSPGAIDSNNSLSEMTHFRPQLHHSGDMVFTPESGLQLRLNEKLGTT AATELKKLDFKVSSTSNNLISTIPSDNLAAGTDNTSSLGPPSMPVHYDSQLDTTLFGKKSSPLTESGGP LSLSEENNDSKLLESGLMNSQESSWGKNVSST | 34 |
| FVIII (SQ + N6) | MQIELSTCFFLCLLRFCFSATRRYYLGAVELSWDYMQSDLGELPVDARFPPRVPKSFPFNTSVVYKKT LFVEFTDHLFNIAKPRPPWMGLLGPTIQAEVYDTVVITLKNMASHPVSLHAVGVSYWKASEGAEYD DQTSQREKEDDKVFPGGSHTYVWQVLKENGPMASDPLCLTYSYLSHVDLVKDLNSGLIGALLVCRE GSLAKEKTQTLHKFILLFAVFDEGKSWHSETKNSLMQDRDAASARAWPKMHTVNGYVNRSLPGLIG CHRKSVYWHVIGMGTTPEVHSIFLEGHTFLVRNHRQASLEISPITFLTAQTLLMDLGQFLLFCHISSHQ HDGMEAYVKVDSCPEEPQLRMKNNEEAEDYDDDLTDSEMDVVRFDDDNSPSFIQIRSVAKKHPKT WVHYIAAEEEDWDYAPLVLAPDDRSYKSQYLNNGPQRIGRKYKKVRFMAYTDETFKTREAIQHESG ILGPLLYGEVGDTLLIIFKNQASRPYNIYPHGITDVRPLYSRRLPKGVKHLKDFPILPGEIFKYKWTVTV EDGPTKSDPRCLTRYYSSFVNMERDLASGLIGPLLICYKESVDQRGNQIMSDKRNVILFSVFDENRSW YLTENIQRFLPNPAGVQLEDPEFQASNIMHSINGYVFDSLQLSVCLHEVAYWYILSIGAQTDFLSVFFS GYTFKHKMVYEDTLTLFPFSGETVFMSMENPGLWILGCHNSDFRNRGMTALLKVSSCDKNTGDYYE DSYEDISAYLLSKNNAIEPRSFSQNPPVLTRSFSQNSRHPSTRQKQFNATTIPENDIEKTDPWFAHRTP MPKIQNVSSSDLLMLLRQSPTPHGLSLSDLQEAKYETFSDDPSPGAIDSNNSLSEMTHFRPQLHHSGD MVFTPESGLQLRLNEKLGTTAATELKKLDFKVSSTSNNLISTIPSDNLAAGTDNTSSLGPPSMPVHYD | 35 |

SEQUENCE LISTING

| Element | Sequence | # |
|---|---|---|
| | SQLDTTLFGKKSSPLTESGGPLSLSEENNDSKLLESGLMNSQESSWGKNVSSTREITRTTLQSDQEEID YDDTISVEMKKEDFDIYDEDENQSPRSFQKKTRHYFIAAVERLWDYGMSSSPHVLRNRAQSGSVPQF KKVVFQEFTDGSFTQPLYRGELNEHLGLLGPYIRAEVEDNIMVTFRNQASRPYSFYSSLISYEEDQRQ GAEPRKNFVKPNETKTYFWKVQHHMAPTKDEFDCKAWAYFSDVDLEKDVHSGLIGPLLVCHTNTL NPAHGRQVTVQEFALFFTIFDETKSWYFTENMERNCRAPCNIQMEDPTFKENYRFHAINGYIMDTLP GLVMAQDQRIRWYLLSMGSNENIHSIHFSGHVFTVRKKEEYKMALYNLYPGVFETVEMLPSKAGIW RVECLIGEHLHAGMSTLFLVYSNKCQTPLGMASGHIRDFQITASGQYGQWAPKLARLHYSGSINAWS TKEPFSWIKVDLLAPMIIHGIKTQGARQKFSSLYISQFIIMYSLDGKKWQTYRGNSTGTLMVFFGNVD SSGIKHNIFNPPIIARYIRLHPTHYSIRSTLRMELMGCDLNSCSMPLGMESKAISDAQITASSYFTNMFA TWSPSKARLHLQGRSNAWRPQVNNPKEWLQVDFQKTMKVTGVTTQGVKSLLTSMYVKEFLISSSQ DGHQWTLFFQNGKVKVFQGNQDSFTPVVNSLDPPLLTRYLRIHPQSWVHQIALRMEVLGCEAQDLY | |
| FVIII A1 | MQIELSTCFFLCLLRFCFSATRRYYLGAVELSWDYMQSDLGELPVDARFPPRVPKSFPFNTSVVYKKT LFVEFTDHLFNIAKPRPPWMGLLGPTIQAEVYDTVVITLKNMASHPVSLHAVGVSYWKASEGAEYD DQTSQREKEDDKVFPGGSHTYVWQVLKENGPMASDPLCLTYSYLSHVDLVKDLNSGLIGALLVCRE GSLAKEKTQTLHKFILLFAVFDEGKSWHSETKNSLMQDRDAASARAWPKMHTVNGYVNRSLPGLIG CHRKSVYWHVIGMGTTPEVHSIFLEGHTFLVRNHRQASLEISPITFLTAQTLLMDLGQFLLFCHISSHQ HDGMEAYVKVDSCPEEPQLRMKNNEEAEDYDDDLTDSEMDVVRFDDDNSPSFIQIR | 36 |
| FVIII A3 | REITRTTLQSDQEEIDYDDTISVEMKKEDFDIYDEDENQSPRSFQKKTRHYFIAAVERLWDYGMSSSP HVLRNRAQSGSVPQFKKVVFQEFTDGSFTQPLYRGELNEHLGLLGPYIRAEVEDNIMVTFRNQASRP YSFYSSLISYEEDQRQGAEPRKNFVKPNETKTYFWKVQHHMAPTKDEFDCKAWAYFSDVDLEKDV HSGLIGPLLVCHTNTLNPAHGRQVTVQEFALFFTIFDETKSWYFTENMERNCRAPCNIQMEDPTFKEN YRFHAINGYIMDTLPGLVMAQDQRIRWYLLSMGSNENIHSIHFSGHVFTVRKKEEYKMALYNLYPG VFETVEMLPSKAGIWRVECLIGEHLHAGMSTLFLVYSNK | 37 |
| NP-ITR-ApoE-AAT-hBGi-FVIII-SQ-N6-F309S-DM-WPRE3-DTS-ITR | GAATCAACCTCTGGATTACAAAATTTGTGAAAGATTGACTGGTATTCTTAACTATGTTGCTCCTT TTACGCTATGTGGATACGCTGCTTTAATGCCTTTGTATCATGCTATTGCTTCCCGTATGGCTTTCA TTTTCTCCTCCTTGTATAAATCCTGGTTGCTGTCTCTTTATGAGGAGTTGTGGCCCGTTGTCAGGC AACGTGGCGTGGTGTGCACTGTGTTTGCTGACGCAACCCCCACTGGTTGGGGCATTGCCACCACC TGTCAGCTCCTTTCCGGGACTTTCGCTTTCCCCCTCCCTATTGCCACGGCGGAACTCATCGCCGCC TGCCTTGCCCGCTGCTGGACAGGGGCTCGGCTGTTGGGCACTGACAATTCCGTGGGGTGTGCCTT CTAGTTGCCAGCCATCTGTTGTTTGCCCCTCCCCCGTGCCTTCCTTGACCCTGGAAGGTGCCACTC CCACTGTCCTTTCCTAATAAAATGAGGAAATTGCATCGCATTGTCTGAGTAGGTGTCATTCTATT CTGGGGGGTGGGGTGGGGCAGGACAGCAAGGGGGAGGATTGGGAAGACAATAGCAGGCATGCT GGGGATGCGGTGGGCTCTATGGGCACGTGCGGAGCTGTGCGATCCCTGCTGGGGACTTTCCGCT GGGGACTTTCCGCTGGGGACTTTCCGCCTTCAGCTAAGGAAGCTACCAATATTTAGAGGTACATT TTGTTCTAGAACAAAATGTACCGGTACATTTTGTTCTGGTACATTTTGTTCTATCGATCGAGCGG CCGCAGGAACCCCTAGTGATGGAGTTGGCCACTCCCTCTCTGCGCGCTCGCTCGCTCACTGAGGC CGGGCGACCAAAGGTCGCCCGACGCCCGGGCTTTGCCCGGGCGGCCTCAGTGAGCGAGCGAGC GCGCAGCTGCCTGCAGGGGCTTGTTGTCCACAACCATTAAAACCTTAAAAGCTTTAAAAGCCTTAT ATATTCTTTTTTTTCTTATAAAACTTAAAACCTTAGAGGCTATTTAAGTTGCTGATTTATATTAAT TTTATTGTTCAAACATGAGAGCTTAGTACGTGAAACATGAGAGCTTAGTACATTAGCCATGAGA GCTTAGTACATTAGCCATGAGGGTTTAGTTCATTAAACATGAGAGCTTAGTACATTAAACATGA GAGCTTAGTACATTAAACATGAGAGCTTAGTACATACTATCAACAGGTTGAACTGCTGATCTGT ACAGTAGAATTGGTAAAGAGAGTTGTGTAAAATATTGAGTTCGCACATCTTGTTGTCTGATTATT GATTTTTGGCGAAACCATTTGATCATATGACAAGATGTGTATCTACCTTAACTTAATGATTTTGA TAAAAATCATTACCTGCAGGCAGCTGCGCGCTCGCTCGCTCACTGAGGCCGCCCGGGCGTCGGG CGACCTTTGGTCGCCCGGCCTCAGTGAGCGAGCGCGCAGAGAGGGAGTGGCCAACTCCATCACT AGGGGTTCCTGCGGCCGCACGCGTCTAGTTATTAATAGTAATCGAATTCGCGTCTGCAGGCTCAG AGGCACACAGGAGTTTCTGGGCTCACCTGCCCCCTTCCAACCCCTCAGTTCCCATCCTCCAGCA GCTGTTTGTGTGCTGCCTCTGAAGTCCACACTGAACAAACTTCAGCCTACTCATGTCCCTAAAAT GGGCAAACATTGCAAGCAGCAAACAGCAAACACACAGCCCTCCCTGCCTGCTGACCTTGGAGCT GGGGCAGAGGTCAGAGACCTCTCTGGGCCCATGCCACCTCCAACATCCACTCGACCCCTTGGAA TTTCGGTGGAGAGGAGCAGAGGTTGTCCTGGCGTGGTTTAGGTAGTGTGAGAGGGGTCGACTGG ACACAGGACGCTGTGGTTTCTGAGCCAGGGGCGACTCAGATCCCAGCCAGTGGACTTAGCCCC TGTTTGCTCCTCCGATAACTGGGGTGACCTTGGTTAATATTCACCAGCAGCCTCCCCCGTTGCCC CTCTGGATCCACTGCTTAAATACGGACGAGGACAGGGCCCTGTCTCCTCAGCTTCAGGCACCAC CACTGACCTGGGACAGTGAATCGTAAGTACTAGCAGCTACAATCCAGCTACCATTCTGCTTTTAT TTTATGGTTGGGATAAGGCTGGATTATTCTGAGTCCAAGCTAGGCCCTTTTGCTAATCATGTTCA TACCTCTTATCTTCCTCCCACAGCTCCTGGGCAACGTGCTGGTCTGTGTGCTGGCCCATCACTTTG GCAAAGAATTGCGATCGCCACCATGCAGATTGAGCTGAGCACCTGCTTCTTCCTGTGCCTGCTGA GGTTCTGCTTCTCTGCCACCAGGAGATACTACCTGGGGGCTGTGGAGCTGAGCTGGGACTACAT GCAGTCTGACCTGGGGGAGCTGCCTGTGGATGCCAGGTTCCCCCCCAGAGTGCCCAAGAGCTTC CCCTTCAACACCTCTGTGGTGTACAAGAAGACCCTGTTTGTGGAGTTCACTGACCACCTGTTCAA CATTGCCAAGCCCAGGCCCCCCTGGATGGGCCTGCTGGGCCCCACCATCCAGGCTGAGGTGTAT GACACTGTGGTGATCACCCTGAAGAACATGGCCAGCCACCCTGTGAGCCTGCATGCTGTGGGGG TGAGCTACTGGAAGGCCTCTGAGGGGGCTGAGTATGATGACCAGACCAGCCAGAGGGAGAAGG AGGATGACAAGGTGTTCCCTGGGGGCAGCCACACCTATGTGTGGCAGGTGCTGAAGGAGAATG GCCCCATGGCCTCTGACCCCCTGTGCCTGACCTACAGCTACCTGAGCCATGTGGACCTGGTGAAG GACCTGAACTCTGGCCTGATTGGGGCCCTGCTGGTGTGCAGGGAGGGCAGCCTGGCCAAGGAGA AGACCCAGACCCTGCACAAGTTCATCCTGCTGTTTGCTGTGTTTGATGAGGGCAAGAGCTGGCA CTCTGAAACCAAGAACAGCCTGATGCAGGACAGGGATGCTGCCTCTGCCAGGGCCTGGCCCAAG ATGCACACTGTGAATGGCTATGTGAACAGGAGCCTGCCTGGCCTGATTGGCTGCCACAGGAAGT CTGTGTACTGGCATGTGATTGGCATGGGCACCACCCCTGAGGTGCACAGCATCTTCCTGGAGGG | 38 |

SEQUENCE LISTING

| Element | Sequence | # |
|---------|----------|---|
| | CCACACCTTCCTGGTCAGGAACCACAGGCAGGCCAGCCTGGAGATCAGCCCCATCACCTTCCTG<br>ACTGCCCAGACCCTGCTGATGGACCTGGGCCAGTTCCTGCTGAGCTGCCACATCAGCAGCCACC<br>AGCATGATGGCATGGAGGCCTATGTGAAGGTGGACAGCTGCCCTGAGGAGCCCCAGCTGAGGA<br>TGAAGAACAATGAGGAGGCTGAGGACTATGATGATGACCTGACTGACTCTGAGATGGATGTGGT<br>GAGGTTTGATGATGACAACAGCCCCAGCTTCATCCAGATCAGGTCTGTGGCCAAGAAGCACCCC<br>AAGACCTGGGTGCACTACATTGCTGCTGAGGAGGAGGACTGGGACTATGCCCCCCTGGTGCTGG<br>CCCCTGATGACAGGAGCTACAAGAGCCAGTACCTGAACAATGGCCCCCAGAGGATTGGCAGGA<br>AGTACAAGAAGGTCAGGTTCATGGCCTACACTGATGAAACCTTCAAGACCAGGGAGGCCATCCA<br>GCATGAGTCTGGCATCCTGGGCCCCCTGCTGTATGGGGAGGTGGGGGACACCCTGCTGATCATC<br>TTCAAGAACCAGGCCAGCAGGCCCTACAACATCTACCCCCATGGCATCACTGATGTGAGGCCCC<br>TGTACAGCAGGAGGCTGCCCAAGGGGGTGAAGCACCTGAAGGACTTCCCCATCCTGCCTGGGGA<br>GATCTTCAAGTACAAGTGGACTGTGACTGTGGAGGATGGCCCCACCAAGTCTGACCCCAGGTGC<br>CTGACCAGATACTACAGCAGCTTTGTGAACATGGAGAGGGACCTGGCCTCTGGCCTGATTGGCC<br>CCCTGCTGATCTGCTACAAGGAGTCTGTGGACCAGAGGGGCAACCAGATCATGTCTGACAAGAG<br>GAATGTGATCCTGTTCTCTGTGTTTGATGAGAACAGGAGCTGGTACCTGACTGAGAACATCCAG<br>AGGTTCCTGCCCAACCCTGCTGGGGTGCAGCTGGAGGACCCTGAGTTCCAGGCCAGCAACATCA<br>TGCACAGCATCAATGGCTATGTGTTTGACAGCCTGCAGCTGTCTGTGTGCCTGCATGAGGTGGCC<br>TACTGGTACATCCTGAGCATTGGGGCCCAGACTGACTTCCTGTCTGTGTTCTTCTCTGGCTACAC<br>CTTCAAGCACAAGATGGTGTATGAGGACACCCTGACCCTGTTCCCCTTCTCTGGGGAGACTGTGT<br>TCATGAGCATGGAGAACCCTGGCCTGTGGATTCTGGGCTGCCACAACTCTGACTTCAGGAACAG<br>GGGCATGACTGCCCTGCTGAAAGTCTCCAGCTGTGACAAGAACACTGGGGACTACTATGAGGAC<br>AGCTATGAGGACATCTCTGCCTACCTGCTGAGCAAGAACAATGCCATTGAGCCCAGGAGCTTCA<br>GCCAGAATCCCCCAGTGCTCACCCGGTCCTTTAGCCAGAATTCTCGCCATCCCTCCACCCGGCAA<br>AAGCAGTTCAACGCCACTACCATCCCAGAGAACGACATCGAAAAAACCGACCCCTGGTTCGCCC<br>ACAGAACTCCCATGCCAAAGATTCAGAATGTTTCCAGTTCTGACCTCCTTATGTTGCTGCGCCAG<br>TCTCCGACCCCTCATGGACTGTCCCTGAGTGACTTGCAGGAGGCCAAGTACGAGACGTTCTCTGA<br>TGACCCCAGCCCCAGGCGCGATTGACTCAAATAACTCCCTGTCTGAGATGACACATTTTCGCCCTC<br>AGCTCCATCACAGCGGGGACATGGTGTTCACTCCAGAGTCCGGACTTCAGCTGCGCCTCAACGA<br>GAAACTCGGTACTACAGCCGCGACAGAACTCAAAAAGCTGGATTTCAAGGTTTCCAGCACCAGC<br>AATAACCTGATCTCTACAATTCCCAGCGATAACCTGGCGGCTGGAACCGACAACACTTCCAGCC<br>TGGGACCTCCGTCCATGCCTGTGCACTACGACTCCCAGCTCGACACCACTCTGTTCGGCAAGAAA<br>AGTAGCCCCTGACCGAATCCGGCGGTCCGCTGTCCCTCTCCAAGAGAATAACGATAGCAAGC<br>TCCTGGAATCTGGGCTTATGAACTCTCAAGAGTCATCCTGGGGCAAGAACGTTTCATCAACTAG<br>GGAGATCACCAGGACCACCCTGCAGTCTGACCAGGAGGAGATTGACTATGATGACACCATCTCT<br>GTGGAGATGAAGAAGGAGGACTTTGACATCTACGACGAGGACGAGAACCAGAGCCCCAGGAGC<br>TTCCAGAAGAAGACCAGGCACTACTTCATTGCTGCTGTGGAGAGGCTGTGGGACTATGGCATGA<br>GCAGCAGCCCCCATGTGCTGAGGAACAGGGCCCAGTCTGGCTCTGTGCCCCAGTTCAAGAAGGT<br>GGTGTTCCAGGAGTTCACTGATGGCAGCTTCACCCAGCCCCTGTACAGAGGGGAGCTGAATGAG<br>CACCTGGGCCTGCTGGGCCCCTACATCAGGGCTGAGGTGGAGGACAACATCATGGTGACCTTCA<br>GGAACCAGGCCAGCAGGCCCTACAGCTTCTACAGCAGCCTGATCAGCTATGAGGAGGACCAGA<br>GGCAGGGGGCTGAGCCCAGGAAGAACTTTGTGAAGCCCAATGAAACCAAGACCTACTTCTGGA<br>AGGTGCAGCACCACATGGCCCCCACCAAGGATGAGTTTGACTGCAAGGCCTGGGCCTACTTCTC<br>TGATGTGGACCTGGAGAAGGATGTGCACTCTGGCCTGATTGGCCCCCTGCTGGTGTGCCACACC<br>AACACCCTGAACCCTGCCCATGGCAGGCAGGTGACTGTGCAGGAGTTTGCCCTGTTCTTCACCAT<br>CTTTGATGAAACCAAGAGCTGGTACTTCACTGAGAACATGGAGAGGAACGGCAGGGCCCCCGG<br>CAACATCCAGATGGAGGACCCCACCTTCAAGGAGAACTACAGGTTCCATGCCATCAATGGCTAC<br>ATCATGGACACCCTGCCTGGCCTGGTGATGGCCCAGGACCAGAGGATCAGGTGGTACCTGCTGA<br>GCATGGGCAGCAATGAGAACATCCACAGCATCCACTTCTCTGGCCATGTGTTCACTGTGAGGAA<br>GAAGGAGGAGTACAAGATGGCCCTGTACAACCTGTACCCTGGGGTGTTTGAGACTGTGGAGATG<br>CTGCCCAGCAAGGCTGGCATCTGGAGGGTGGAGTGCCTGATTGGGGAGCACCTGCATGCTGGCA<br>TGAGCACCCTGTTCCTGGTGTACAGCAACAAGTGCCAGACCCCCCTGGGCATGGCCTCTGGCCA<br>CATCAGGGACTTCCAGATCACTGCCTCTGGCCAGTATGGCCAGTGGGCCCCCAAGCTGGCCAGG<br>CTGCACTACTCTGGCAGCATCAATGCCTGGAGCACCAAGGAGCCCTTCAGCTGGATCAAGGTGG<br>ACCTGCTGGCCCCCATGATCATCCATGGCATCAAGACCCAGGGGGCCAGGCAGAAGTTCAGCAG<br>CCTGTACATCAGCCAGTTCATCATCATGTACAGCCTGGATGGCAAGAAGTGGCAGACCTACAGG<br>GGCAACAGCACTGGCACCCTGATGGTGTTCTTTGGCAATGTGGACAGCTCTGGCATCAAGCACA<br>ACATCTTCAACCCCCCCATCATTGCCAGATACATCAGGCTGCACCCCACCCACTACAGCATCAGG<br>AGCACCCTGAGGATGGAGCTGATGGGCTGTGACCTGAACAGCTGCAGCATGCCCCTGGGCATGG<br>AGAGCAAGGCCATCTCTGATGCCCAGATCACTGCCAGCAGCTACTTCACCAACATGTTTGCCAC<br>CTGGAGCCCCAGCAAGGCCAGGCTGCACCTGCAGGGCAGGAGCAATGCCTGGAGGCCCCAGGT<br>CAACAACCCCAAGGAGTGGCTGCAGGTGGACTTCCAGAAGACCATGAAGGTGACTGGGGTGAC<br>CACCCAGGGGGTGAAGAGCCTGCTGACCAGCATGTATGTGAAGGAGTTCCTGATCAGCAGCAGC<br>CAGGATGGCCACCAGTGGACCCTGTTCTTCCAGAATGGCAAGGTGAAGGTGTTCCAGGGCAACC<br>AGGACAGCTTCACCCCTGTGGTGAACAGCCTGGACCCCCCCCTGCTGACCAGATACCTGAGGAT<br>TCACCCCCAGAGCTGGGTGCACCAGATTGCCCTGAGGATGGAGGTGCTGGGCTGTGAGGCCCAG<br>GACCTGTACTGACTCGA | |
| ApoE-AAT-<br>hBGi-<br>FVIII-N6-<br>F309S-DM-<br>WPRE3-<br>DTS | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCGTAAGTACTAGCAGCTACAATCCAGCTACCATTCTGCTTTTATTTTAT | 39 |

| Element | Sequence | # |
|---------|----------|---|
| | GGTTGGGATAAGGCTGGATTATTCTGAGTCCAAGCTAGGCCCTTTTGCTAATCATGTTCATACCT | |
| | CTTATCTTCCTCCCACAGATGCAGATTGAGCTGAGCACCTGCTTCTTCCTGTGCCTGCTGAGGTTC | |
| | TGCTTCTCTGCCACCAGGAGATACTACCTGGGGGCTGTGGAGCTGAGCTGGGACTACATGCAGT | |
| | CTGACCTGGGGGAGCTGCCTGTGGATGCCAGGTTCCCCCCCAGAGTGCCCAAGAGCTTCCCCTTC | |
| | AACACCTCTGTGGTGTACAAGAAGACCCTGTTTGTGGAGTTCACTGACCACCTGTTCAACATTGC | |
| | CAAGCCCAGGCCCCCCTGGATGGGCCTGCTGGGCCCCACCATCCAGGCTGAGGTGTATGACACT | |
| | GTGGTGATCACCCTGAAGAACATGGCCAGCCACCCTGTGAGCCTGCATGCTGTGGGGGTGAGCT | |
| | ACTGGAAGGCCTCTGAGGGGGCTGAGTATGATGACCAGACCAGCCAGAGGGAGAAGGAGGATG | |
| | ACAAGGTGTTCCCTGGGGGCAGCCACACCTATGTGTGGCAGGTGCTGAAGGAGAATGGCCCCCAT | |
| | GGCCTCTGACCCCCTGTGCCTGACCTACAGCTACCTGAGCCATGTGGACCTGGTGAAGGACCTG | |
| | AACTCTGGCCTGATTGGGGCCCTGCTGGTGTGCAGGGAGGGCAGCCTGGCCAAGGAGAAGACCC | |
| | AGACCCTGCACAAGTTCATCCTGCTGTTTGCTGTGTTTGATGAGGGCAAGAGCTGGCACTCTGAA | |
| | ACCAAGAACAGCCTGATGCAGGACAGGGATGCTGCCTCTGCCAGGGCCTGGCCCAAGATGCAC | |
| | ACTGTGAATGGCTATGTGAACAGGAGCCTGCCTGGCCTGATTGGCTGCCACAGGAAGTCTGTGT | |
| | ACTGGCATGTGATTGGCATGGGCACCACCCCTGAGGTGCACAGCATCTTCCTGGAGGGCCACAC | |
| | CTTCCTGGTCAGGAACCACAGGCAGGCCAGCCTGGAGATCAGCCCCATCACCTTCCTGACTGCC | |
| | CAGACCCTGCTGATGGACCTGGGCCAGTTCCTGCTGAGCTGCCACATCAGCAGCCACCAGCATG | |
| | ATGGCATGGGAGGCCTATGTGAAGGTGGACAGCTGCCCTGAGGAGCCCCAGCTGAGGATGAAGA | |
| | ACAATGAGGAGGCTGAGGACTATGATGATGACCTGACTGACTCTGAGATGGATGTGGTGAGGTT | |
| | TGATGATGACAACAGCCCCAGCTTCATCCAGATCAGGTCTGTGGCCAAGAAGCACCCCAAGACC | |
| | TGGGTGCACTACATTGCTGCTGAGGAGGAGGACTGGGACTATGCCCCCCTGGTGCTGGCCCCTG | |
| | ATGACAGGAGCTACAAGAGCCAGTACCTGAACAATGGCCCCCAGAGGATTGGCAGGAAGTACA | |
| | AGAAGGTCAGGTTCATGGCCTACACTGATGAAACCTTCAAGACCAGGGAGGCCATCCAGCATGA | |
| | GTCTGGCATCCTGGGCCCCCTGCTGTATGGGGAGGTGGGGGACACCCTGCTGATCATCTTCAAG | |
| | AACCAGGCCAGCAGGCCCTACAACATCTACCCCCATGGCATCACTGATGTGAGGCCCCTGTACA | |
| | GCAGGAGGCTGCCCAAGGGGGTGAAGCACCTGAAGGACTTCCCCATCCTGCCTGGGGAGATCTT | |
| | CAAGTACAAGTGGACTGTGACTGTGGAGGATGGCCCCACCAAGTCTGACCCCAGGTGCCTGACC | |
| | AGATACTACAGCAGCTTTGTGAACATGGAGAGGGACCTGGCCTCTGGCCTGATTGGCCCCCTGC | |
| | TGATCTGCTACAAGGAGTCTGTGGACCAGAGGGGCAACCAGATCATGTCTGACAAGAGGAATGT | |
| | GATCCTGTTCTCTGTGTTTGATGAGAACAGGAGCTGGTACCTGACTGAGAACATCCAGAGGTTCC | |
| | TGCCCAACCCTGCTGGGGTGCAGCTGGAGGACCCTGAGTTCCAGGCCAGCAACATCATGCACAG | |
| | CATCAATGGCTATGTGTTTGACAGCCTGCAGCTGTCTGTGTGCCTGCATGAGGTGGCCTACTGGT | |
| | ACATCCTGAGCATTGGGGCCCAGACTGACTTCCTGTCTGTGTTCTTCTCTGGCTACACCTTCAAG | |
| | CACAAGATGGTGTATGAGGACACCCTGACCCTGTTCCCCTTCTCTGGGGAGACTGTGTTCATGAG | |
| | CATGGAGAACCCTGGCCTGTGGATTCTGGGCTGCCACAACTCTGACTTCAGGAACAGGGGCATG | |
| | ACTGCCCTGCTGAAAGTCTCCAGCTGTGACAAGAACACTGGGGACTACTATGAGGACAGCTATG | |
| | AGGACATCTCTGCCTACCTGCTGAGCAAGAACAATGCCATTGAGCCCAGGAGCTTCAGCCAGAA | |
| | TCCCCCAGTGCTCACCCGGTCCTTTAGCCAGAATTCTCGCCATCCCTCCACCCGGCAAAAGCAGT | |
| | TCAACGCCACTACCATCCCAGAGAACGACATCGAAAAAACCGACCCCTGGTTCGCCCACAGAAC | |
| | TCCCATGCCAAAGATTCAGAATGTTTCCAGTTCTGACCTCCTTATGTTGCTGCGCCAGTCTCCGA | |
| | CCCCTCATGGACTGTCCCTGAGTGACTTGCAGGAGGCCAAGTACGAGACGTTCTCTGATGACCC | |
| | CAGCCCAGGCGCGATTGACTCAAATAACTCCCTGTCTGAGATGACACATTTTCGCCCTCAGCTCC | |
| | ATCACAGCGGGGACATGGTGTTCACTCCAGAGTCCGGACTTCAGCTGCGCCTCAACGAGAAACT | |
| | CGGTACTACAGCCGCGACAGAACTCAAAAAGCTGGATTTCAAGGTTTCCAGCACCAGCAATAAC | |
| | CTGATCTCTACAATTCCCAGCGATAACCTGGCGGCTGGAACCGACAACACTTCCAGCCTGGGAC | |
| | CTCCGTCCATGCCTGTGCACTACGACTCCCAGCTCGACACCACTCTGTTCGGCAAGAAAAGTAGC | |
| | CCCCTGACCGAATCCGGCGGTCCGCTGTCCCTCTCCGAAGAGAATAACGATAGCAAGCTCCTGG | |
| | AATCTGGGCTTATGAACTCTCAAGAGTCATCCTGGGGCAAGAACGTTTCATCAACTAGGGAGAT | |
| | CACCAGGACCACCCTGCAGTCTGACCAGGAGGAGATTGACTATGATGACACCATCTCTGTGGAG | |
| | ATGAAGAAGGAGGACTTTGACATCTACGACGAGGACGAGAACCAGAGCCCCAGGAGCTTCCAG | |
| | AAGAAGACCAGGCACTACTTCATTGCTGCTGTGGAGAGGCTGTGGGACTATGGCATGAGCAGCA | |
| | GCCCCCATGTGCTGAGGAACAGGGCCCAGTCTGGCTCTGTGCCCCAGTTCAAGAAGGTGGTGTT | |
| | CCAGGAGTTCACTGATGGCAGCTTCACCCAGCCCCTGTACAGAGGGGAGCTGAATGAGCACCTG | |
| | GGCCTGCTGGGCCCCTACATCAGGGCTGAGGTGGAGGACAACATCATGGTGACCTTCAGGAACC | |
| | AGGCCAGCAGGCCCTACAGCTTCTACAGCAGCCTGATCAGCTATGAGGAGGACCAGAGGCAGG | |
| | GGGCTGAGCCCAGGAAGAACTTTGTGAAGCCCAATGAAACCAAGACCTACTTCTGGAAGGTGCA | |
| | GCACCACATGGCCCCCACCAAGGATGAGTTTGACTGCAAGGCCTGGGCCTACTTCTCTGATGTG | |
| | GACCTGGAGAAGGATGTGCACTCTGGCCTGATTGGCCCCCTGCTGGTGTGCCACACCAACACCC | |
| | TGAACCCTGCCCATGGCAGGCAGGTGACTGTGCAGGAGTTTGCCCTGTTCTTCACCATCTTTGAT | |
| | GAAACCAAGAGCTGGTACTTCACTGAGAACATGGAGAGGAACGGCAGGGCCCCCGGCAACATC | |
| | CAGATGGAGGACCCCACCTTCAAGGAGAACTACAGGTTCCATGCCATCAATGGCTACATCATGG | |
| | ACACCCTGCCTGGCCTGGTGATGGCCCAGGACCAGAGGATCAGGTGGTACCTGCTGAGCATGGG | |
| | CAGCAATGAGAACATCCACAGCATCCACTTCTCTGGCCATGTGTTCACTGTGAGGAAGAAGGAG | |
| | GAGTACAAGATGGCCCTGTACAACCTGTACCCTGGGGTGTTTGAGACTGTGGAGATGCTGCCCA | |
| | GCAAGGCTGGCATCTGGAGGGTGGAGTGCCTGATTGGGGAGCACCTGCATGCTGGCATGAGCAC | |
| | CCTGTTCCTGGTGTACAGCAACAAGTGCCAGACCCCCCTGGGCATGGCCTCTGGCCACATCAGG | |
| | GACTTCCAGATCACTGCCTCTGGCCAGTATGGCCAGTGGGCCCCCAAGCTGGCCAGGCTGCACT | |
| | ACTCTGGCAGCATCAATGCCTGGAGCACCAAGGAGCCCTTCAGCTGGATCAAGGTGGACCTGCT | |
| | GGCCCCCATGATCATCCATGGCATCAAGACCCAGGGGGCCAGGCAGAAGTTCAGCAGCCTGTAC | |
| | ATCAGCCAGTTCATCATCATGTACAGCCTGGATGGCAAGAAGTGGCAGACCTACAGGGGCAACA | |
| | GCACTGGCACCCTGATGGTGTTCTTTGGCAATGTGGACAGCTCTGGCATCAAGCACAACATCTTC | |
| | AACCCCCCCATCATTGCCAGATACATCAGGCTGCACCCCACCCACTACAGCATCAGGAGCACCC | |
| | TGAGGATGGAGCTGATGGGCTGTGACCTGAACAGCTGCAGCATGCCCCTGGGCATGGAGAGCA | |
| | AGGCCATCTCTGATGCCCAGATCACTGCCAGCAGCTACTTCACCAACATGTTTGCCACCTGGAGC | |
| | CCCAGCAAGGCCAGGCTGCACCTGCAGGGCAGGAGCAATGCCTGGAGGCCCCAGGTCAACAAC | |

-continued

SEQUENCE LISTING

| Element | Sequence | # |
|---|---|---|
| | CCCAAGGAGTGGCTGCAGGTGGACTTCCAGAAGACCATGAAGGTGACTGGGGTGACCACCCAG<br>GGGGTGAAGAGCCTGCTGACCAGCATGTATGTGAAGGAGTTCCTGATCAGCAGCAGCCAGGATG<br>GCCACCAGTGGACCCTGTTCTTCCAGAATGGCAAGGTGAAGGTGTTCCAGGGCAACCAGGACAG<br>CTTCACCCCTGTGGTGAACAGCCTGGACCCCCCCCTGCTGACCAGATACCTGAGGATTCACCCCC<br>AGAGCTGGGTGCACCAGATTGCCCTGAGGATGGAGGTGCTGGGCTGTGAGGCCCAGGACCTGTA<br>CTGAAATCAACCTCTGGATTACAAAATTTGTGAAAGATTGACTGGTATTCTTAACTATGTTGCTC<br>CTTTTACGCTATGTGGATACGCTGCTTTAATGCCTTTGTATCATGCTATTGCTTCCCGTATGGCTT<br>TCATTTTCTCCTCCTTGTATAAATCCTGGTTGCTGTCTCTTTATGAGGAGTTGTGGCCCGTTGTCA<br>GGCAACGTGGCGTGGTGTGCACTGTGTTTGCTGACGCAACCCCCACTGGTTGGGGCATTGCCAC<br>CACCTGTCAGCTCCTTTCCGGGACTTTCGCTTTCCCCCTCCCTATTGCCACGGCGGAACTCATCGC<br>CGCCTGCCTTGCCCGCTGCTGGACAGGGGCTCGGCTGTTGGGCACTGACAATTCCGTGGGAGCT<br>GTGCGATCCCTGCTGGGGACTTTCCGCTGGGGACTTTCCGCTGGGGACTTTCCGCCTTCAGCTAA<br>GGAAGCTACCAATATTTAGAGGTACATTTTGTTCTAGAACAAAATGTACCGGTACATTTTGTTCT<br>GGTACATTTTGTTCT | |
| APOE-<br>AAT-hBGi-<br>FIX-bGH-<br>poly A-DTS | GAGCTGTGCGATCCCTGCTGGGGACTTTCCGCTGGGGACTTTCCGCTGGGGACTTTCCGCCTTCA<br>GCTAAGGAAGCTACCAATATTTAGAGGTACATTTTGTTCTAGAACAAAATGTACCGGTACATTTT<br>GTTCTGGTACATTTTGTTCTTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAATGAGGAAATTGCATC<br>GCATTGTCTGAGTAGGTGTCATTCTATTCTGGGGGGTGGGGTGGGGCAGGACAGCAAGGGGGAG<br>GATTGGGAAGACAATAGCAGGCATGCTGGGGATGCGGTGGGCTCTATGGATGCAGCGCGTGAA<br>CATGATCATGGCAGAATCACCAGGCCTCATCACCATCTGCCTTTTAGGATATCTACTCAGTGCTG<br>AATGTACAGTTTTTCTTGATCATGAAAACGCCAACAAAATTCTGAATCGGCCAAAGAGGTATAA<br>TTCAGGTAAATTGGAAGAGTTTGTTCAAGGGAACCTTGAGAGAGAATGTATGGAAGAAAGTGT<br>AGTTTTGAAGAAGCACGAGAAGTTTTTGAAAACACTGAAAGAACAACTGAATTTTGGAAGCAGT<br>ATGTTGATGGAGATCAGTGTGAGTCCAATCCATGTTTAAATGGCGGCAGTTGCAAGGATGACAT<br>TAATTCCTATGAATGTTGGTGTCCCTTTGGATTTGAAGGAAAGAACTGTGAATTAGATGTAACAT<br>GTAACATTAAGAATGGCAGATGCGAGCAGTTTTGTAAAAATAGTGCTGATAACAAGGTGGTTTG<br>CTCCTGTACTGAGGGATATCGACTTGCAGAAAACCAGAAGTCCTGTGAACCAGCAGTGCCATTT<br>CCATGTGGAAGAGTTTCTGTTTCACAAACTTCTAAGCTCACCCGTGCTGAGACTGTTTTTCCTGA<br>TGTGGACTATGTAAATTCTACTGAAGCTGAAACCATTTTGGATAACATCACTCAAAGCACCCAAT<br>CATTTAATGACTTCACTCGGGTTGTTGGTGGAGAAGATGCCAAACCAGGTCAATTCCCTTGGCAG<br>GTTGTTTTGAATGGTAAAGTTGATGCATTCTGTGGAGGCTCTATCGTTAATGAAAAATGGATTGT<br>AACTGCTGCCCACTGTGTTGAAACTGGTGTTAAAATTACAGTTGTCGCAGGTGAACATAATATTG<br>AGGAGACAGAACATACAGAGCAAAAGCGAAATGTGATTCGAATTATTCCTCACCACAACTACA<br>ATGCAGCTATTAATAAGTACAACCATGACATTGCCCTTCTGGAACTGGACGAACCCTTAGTGCTA<br>AACAGCTACGTTACACCTATTTGCATTGCTGACAAGGAATACACGAACATCTTCCTCAAATTTGG<br>ATCTGGCTATGTAAGTGGCTGGGGAAGAGTCTTCCACAAAGGGAGATCAGCTTTAGTTCTTCAG<br>TACCTTAGAGTTCCACTTGTTGACCGAGCCACATGTCTTCGATCTACAAAGTTCACCATCTATAA<br>CAACATGTTCTGTGCTGGCTTCCATGAAGGAGGTAGAGATTCATGTCAAGGAGATAGTGGGGGA<br>CCCCATGTTACTGAAGTGGAAGGGACCAGTTTCTTAACTGGAATTATTAGCTGGGGTGAAGAGT<br>GTGCAATGAAAGGCAAATATGGAATATATACCAAGGTATCCCGGTATGTCAACTGGATTAAGGA<br>AAAAACAAAGCTCACTTAATGAGTAAGTACTAGCAGCTACAATCCAGCTACCATTCTGCTTTTAT<br>TTTATGGTTGGGATAAGGCTGGATTATTCTGAGTCCAAGCTAGGCCCTTTTGCTAATCATGTTCA<br>TACCTCTTATCTTCCTCCCACAGCGCGTCTGCAGGCTCAGAGGCACACAGGAGTTTCTGGGCTCA<br>CCCTGCCCCCTTCCAACCCCTCAGTTCCCATCCTCCAGCAGCTGTTTGTGTGCTGCCTCTGAAGTC<br>CACACTGAACAAACTTCAGCCTACTCATGTCCCTAAAATGGGCAAACATTGCAAGCAGCAAACA<br>GCAAACACACAGCCCTCCCTGCCTGCTGACCTTGGAGCTGGGGCAGAGGTCAGAGACCTCTCTG<br>GGCCCATGCCACCTCCAACATCCACTCGACCCCTTGGAATTTCGGTGGAGAGGAGCAGAGGTTG<br>TCCTGGCGTGGTTTAGGTAGTGTGAGAGGGGTCGACTGGACACAGGACGCTGTGGTTTCTGAGC<br>CAGGGGGCGACTCAGATCCCAGCCAGTGGACTTAGCCCCTGTTTGCTCCTCCGATAACTGGGGT<br>GACCTTGGTTAATATTCACCAGCAGCCTCCCCCGTTGCCCC | 40 |
| APOE-<br>AAT-hBGi-<br>FIX<br>WPRE3-<br>bGH-poly A | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCGTAAGTACTAGCAGCTACAATCCAGCTACCATTCTGCTTTTATTTTAT<br>GGTTGGGATAAGGCTGGATTATTCTGAGTCCAAGCTAGGCCCTTTTGCTAATCATGTTCATACCT<br>CTTATCTTCCTCCCACAGATGCAGCGCGTGAACATGATCATGGCAGAATCACCAGGCCTCATCAC<br>CATCTGCCTTTTAGGATATCTACTCAGTGCTGAATGTACAGTTTTTCTTGATCATGAAAACGCCA<br>ACAAAATTCTGAATCGGCCAAAGAGGTATAATTCAGGTAAATTGGAAGAGTTTGTTCAAGGGAA<br>CCTTGAGAGAGAATGTATGGAAGAAAGTGTAGTTTTGAAGAAGCACGAGAAGTTTTTGAAAAC<br>ACTGAAAGAACAACTGAATTTTGGAAGCAGTATGTTGATGGAGATCAGTGTGAGTCCAATCCAT<br>GTTTAAATGGCGGCAGTTGCAAGGATGACATTAATTCCTATGAATGTTGGTGTCCCTTTGGATTT<br>GAAGGAAAGAACTGTGAATTAGATGTAACATGTAACATTAAGAATGGCAGATGCGAGCAGTTTT<br>GTAAAAATAGTGCTGATAACAAGGTGGTTTGCTCCTGTACTGAGGGATATCGACTTGCAGAAAA<br>CCAGAAGTCCTGTGAACCAGCAGTGCCATTTCCATGTGGAAGAGTTTCTGTTTCACAAACTTCTA<br>AGCTCACCCGTGCTGAGACTGTTTTTCCTGATGTGGACTATGTAAATTCTACTGAAGCTGAAACC<br>ATTTTGGATAACATCACTCAAAGCACCCAATCATTTAATGACTTCACTCGGGTTGTTGGTGGAGA<br>AGATGCCAAACCAGGTCAATTCCCTTGGCAGGTTGTTTTGAATGGTAAAGTTGATGCATTCTGTG<br>GAGGCTCTATCGTTAATGAAAAATGGATTGTAACTGCTGCCCACTGTGTTGAAACTGGTGTTAAA | 41 |

| SEQUENCE LISTING | | |
|---|---|---|
| Element | Sequence | # |
| | ATTACAGTTGTCGCAGGTGAACATAATATTGAGGAGACAGAACATACAGAGCAAAAGCGAAAT<br>GTGATTCGAATTATTCCTCACCACAACTACAATGCAGCTATTAATAAGTACAACCATGACATTGC<br>CCTTCTGGAACTGGACGAACCCTTAGTGCTAAACAGCTACGTTACACCTATTTGCATTGCTGACA<br>AGGAATACACGAACATCTTCCTCAAATTTGGATCTGGCTATGTAAGTGGCTGGGGAAGAGTCTT<br>CCACAAAGGGAGATCAGCTTTAGTTCTTCAGTACCTTAGAGTTCCACTTGTTGACCGAGCCACAT<br>GTCTTCGATCTACAAAGTTCACCATCTATAACAACATGTTCTGTGCTGGCTTCCATGAAGGAGGT<br>AGAGATTCATGTCAAGGAGATAGTGGGGGACCCCATGTTACTGAAGTGGAAGGGACCAGTTTCT<br>TAACTGGAATTATTAGCTGGGGTGAAGAGTGTGCAATGAAAGGCAAATATGGAATATATACCAA<br>GGTATCCCGGTATGTCAACTGGATTAAGGAAAAAACAAAGCTCACTTAATGAAATCAACCTCTG<br>GATTACAAAATTTGTGAAAGATTGACTGGTATTCTTAACTATGTTGCTCCTTTTACGCTATGTGG<br>ATACGCTGCTTTAATGCCTTTGTATCATGCTATTGCTTCCCGTATGGCTTTCATTTTCTCCTCCTTG<br>TATAAATCCTGGTTGCTGTCTCTTTATGAGGAGTTGTGGCCCGTTGTCAGGCAACGTGGCGTGGT<br>GTGCACTGTGTTTGCTGACGCAACCCCCACTGGTTGGGGCATTGCTCACCACCTGTCAGCTCCTTT<br>CCGGGACTTTCGCTTTCCCCCTCCCTATTGCCACGGCGGAACTCATCGCCGCCTGCCTTGCCCGC<br>TGCTGGACAGGGGCTCGGCTGTTGGGCACTGACAATTCCGTGGTGTGCCTTCTAGTTGCCAGCCA<br>TCTGTTGTTTGCCCCTCCCCCGTGCCTTCCTTGACCCTGGAAGGTGCCACTCCCACTGTCCTTTCC<br>TAATAAAATGAGGAAATTGCATCGCATTGTCTGAGTAGGTGTCATTCTATTCTGGGGGGTGGGG<br>TGGGGCAGGACAGCAAGGGGGAGGATTGGGAAGACAATAGCAGGCATGCTGGGGATGCGGTGG<br>GCTCTATGG | |
| ITR-APOE-<br>AAT-hBGi-<br>FIX-bGH-<br>poly A-ITR | GCTCACTCACTCACTCACTGAGGCCTGCAGAGCAAAGCTCTGCAGTCTGGGGACCCTTTGGTCCCC<br>AGGCCTCAGTGAGTGAGTGAGTGAGCAGAGAGGGAGTGGCCAACTCCATCACTAGGGGTTCCTC<br>GCGTCTGCAGGCTCAGAGGCACACAGGAGTTTCTGGGCTCACCCTGCCCCCTTCCAACCCCTCAG<br>TTCCCATCCTCCAGCAGCTGTTTGTGTGCTGCCTCTGAAGTCCACACTGAACAAACTTCAGCCTA<br>CTCATGTCCCTAAAATGGGCAAACATTGCAAGCAGCAAACAGCAAACACACAGCCCTCCCTGCC<br>TGCTGACCTTGGAGCTGGGGCAGAGGTCAGAGACCTCTCTGGGCCCATGCCACCTCCAACATCC<br>ACTCGACCCCTTGGAATTTCGGTGGAGAGGAGCAGAGGTTGTCCTGGCGTGGTTTAGGTAGTGT<br>GAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCGTAAGTACTAGCAGCTACAATCCAGCTACCATTCTGCTTTTATTTTAT<br>GGTTGGGATAAGGCTGGATTATTCTGAGTCCAAGCTAGGCCCTTTTGCTAATCATGTTCATACCT<br>CTTATCTTCCTCCCACAGATGCAGCGCGTGAACATGATCATGGCAGAATCACCAGGCCTCATCAC<br>CATCTGCCTTTTAGGATATCTACTCAGTGCTGAATGTACAGTTTTTCTTGATCATGAAAACGCCA<br>ACAAAATTCTGAATCGGCCAAAGAGGTATAATTCAGGTAAATTGGAAGAGTTTGTTCAAGGGAA<br>CCTTGAGAGAGAATGTATGGAAGAAAAGTGTAGTTTTGAAGAAGCACGAGAAGTTTTTGAAAAC<br>ACTGAAAGAACAACTGAATTTTGGAAGCAGTATGTTGATGGAGATCAGTGTGAGTCCAATCCAT<br>GTTTAAATGGCGGCAGTTGCAAGGATGACATTAATTCCTATGAATGTTGGTGTCCCTTTGGATTT<br>GAAGGAAAGAACTGTGAATTAGATGTAACATGTAACATTAAGAATGGCAGATGCGAGCAGTTTT<br>GTAAAAATAGTGCTGATAAACAAGGTGGTTTGCTCCTGTACTGAGGGATATCGACTTGCAGAAAA<br>CCAGAAGTCCTGTGAACCAGCAGTGCCATTTCCATGTGGAAGAGTTTCTGTTTCACAAACTTCTA<br>AGCTCACCCGTGCTGAGACTGTTTTTTCCTGATGTGGACTATGTAAATTCTACTGAAGCTGAAACC<br>ATTTTGGATAACATCACTCAAAGCACCCAATCATTTAATGACTTCACTCGGGTTGTTGGTGGAGA<br>AGATGCCAAACCAGGTCAATTCCCTTGGCAGGTTGTTTTGAATGGTAAAGTTGATGCATTCTGTG<br>GAGGCTCTATCGTTAATGAAAAATGGATTGTAACTGCTGCCCACTGTGTTGAAACTGGTGTTAAA<br>ATTACAGTTGTCGCAGGTGAACATAATATTGAGGAGACAGAACATACAGAGCAAAAGCGAAAT<br>GTGATTCGAATTATTCCTCACCACAACTACAATGCAGCTATTAATAAGTACAACCATGACATTGC<br>CCTTCTGGAACTGGACGAACCCTTAGTGCTAAACAGCTACGTTACACCTATTTGCATTGCTGACA<br>AGGAATACACGAACATCTTCCTCAAATTTGGATCTGGCTATGTAAGTGGCTGGGGAAGAGTCTT<br>CCACAAAGGGAGATCAGCTTTAGTTCTTCAGTACCTTAGAGTTCCACTTGTTGACCGAGCCACAT<br>GTCTTCGATCTACAAAGTTCACCATCTATAACAACATGTTCTGTGCTGGCTTCCATGAAGGAGGT<br>AGAGATTCATGTCAAGGAGATAGTGGGGGACCCCATGTTACTGAAGTGGAAGGGACCAGTTTCT<br>TAACTGGAATTATTAGCTGGGGTGAAGAGTGTGCAATGAAAGGCAAATATGGAATATATACCAA<br>GGTATCCCGGTATGTCAACTGGATTAAGGAAAAAACAAAGCTCACTTAATGATGTGCCTTCTAG<br>TTGCCAGCCATCTGTTGTTTGCCCCTCCCCCGTGCCTTCCTTGACCCTGGAAGGTGCCACTCCCAC<br>TGTCCTTTCCTAATAAAATGAGGAAATTGCATCGCATTGTCTGAGTAGGTGTCATTCTATTCTGG<br>GGGGTGGGGTGGGGCAGGACAGCAAGGGGGAGGATTGGGAAGACAATAGCAGGCATGCTGGG<br>GATGCGGTGGGCTCTATGGAGGAACCCCTAGTGATGGAGTTGGCCACTCCCTCTGCTCACTCA<br>CTCACTCACTGAGGCCTGGGGACCAAAGGTCCCCAGACTGCAGAGCTTTGCTCTGCAGGCCTCA<br>GTGAGTGAGTGAGTGAGCAGA | 42 |
| ApoE-AAT-<br>hBGi-<br>FVIII-v3-<br>WPRE3-<br>DTS | CGCGTCTGCAGGCTCAGAGGCACACAGGAGTTTCTGGGCTCACCCTGCCCCCTTCCAACCCCTCA<br>GTTCCCATCCTCCAGCAGCTGTTTGTGTGCTGCCTCTGAAGTCCACACTGAACAAACTTCAGCCT<br>ACTCATGTCCCTAAAATGGGCAAACATTGCAAGCAGCAAACAGCAAACACACAGCCCTCCCTGC<br>CTGCTGACCTTGGAGCTGGGGCAGAGGTCAGAGACCTCTCTGGGCCCATGCCACCTCCAACATC<br>CACTCGACCCCTTGGAATTTCGGTGGAGAGGAGCAGAGGTTGTCCTGGCGTGGTTTAGGTAGTG<br>TGAGAGGGGTCGACTGGACACAGGACGCTGTGGTTTCTGAGCCAGGGGGCGACTCAGATCCCAG<br>CCAGTGGACTTAGCCCCTGTTTGCTCCTCCGATAACTGGGGTGACCTTGGTTAATATTCACCAGC<br>AGCCTCCCCCGTTGCCCCTCTGGATCCACTGCTTAAATACGGACGAGGACAGGGCCCTGTCTCCT<br>CAGCTTCAGGCACCACCACTGACCTGGGACAGTGAATCGTAAGTACTAGCAGCTACAATCCAGC<br>TACCATTCTGCTTTTATTTTATGGTTGGGATAAGGCTGGATTATTCTGAGTCCAAGCTAGGCCCTT<br>TTGCTAATCATGTTCATACCTCTTATCTTCCTCCCACAGCTCCTGGGCAACGTGCTGGTCTGTGTG<br>CTGGCCCATCACTTTGGCAAAGAATTGCGATCGCCACCATGCAGATTGAGCTGAGCACCTGCTTC<br>TTCCTGTGCCTGCTGAGGTTCTGCTTCTCTGCCACCAGGAGATACTACCTGGGGGCTGTGGAGCT<br>GAGCTGGGACTACATGCAGTCTGACCTGGGGGAGCTGCCTGTGGATGCCAGGTTCCCCCCCAGA<br>GTGCCCAAGAGCTTCCCCCTTCAACACCTCTGTGGTGTACAAGAAGACCCTGTTTGTGGAGTTCAC | 43 |

| Element | Sequence | # |
|---------|----------|---|

```
TGACCACCTGTTCAACATTGCCAAGCCCCAGGCCCCCCTGGATGGGCCTGCTGGGCCCCACCATCC
AGGCTGAGGTGTATGACACTGTGGTGATCACCCTGAAGAACATGGCCAGCCACCCTGTGAGCCT
GCATGCTGTGGGGGTGAGCTACTGGAAGGCCTCTGAGGGGGCTGAGTATGATGACCAGACCAGC
CAGAGGGAGAAGGAGGATGACAAGGTGTTCCCTGGGGGCAGCCACACCTATGTGTGGCAGGTG
CTGAAGGAGAATGGCCCCATGGCCTCTGACCCCCTGTGCCTGACCTACAGCTACCTGAGCCATG
TGGACCTGGTGAAGGACCTGAACTCTGGCCTGATTGGGGCCCTGCTGGTGTGCAGGGAGGGCAG
CCTGGCCAAGGAGAAGACCCAGACCCTGCACAAGTTCATCCTGCTGTTTGCTGTGTTTGATGAG
GGCAAGAGCTGGCACTCTGAAACCAAGAACAGCCTGATGCAGGACAGGGATGCTGCCTCTGCC
AGGGCCTGGCCCAAGATGCACACTGTGAATGGCTATGTGAACAGGAGCCTGCCTGGCCTGATTG
GCTGCCACAGGAAGTCTGTGTACTGGCATGTGATTGGCATGGGCACCACCCCTGAGGTGCACAG
CATCTTCCTGGAGGGCCACACCTTCCTGGTCAGGAACCACAGGCAGGCCAGCCTGGAGATCAGC
CCCATCACCTTCCTGACTGCCCAGACCCTGCTGATGGACCTGGGCCAGTTCCTGCTGTTCTGCCA
CATCAGCAGCCACCAGCATGATGGCATGGAGGCCTATGTGAAGGTGGACAGCTGCCCTGAGGA
GCCCCAGCTGAGGATGAAGAACAATGAGGAGGCTGAGGACTATGATGATGACCTGACTGACTCT
GAGATGGATGTGGTGAGGTTTGATGATGACAACAGCCCCAGCTTCATCCAGATCAGGTCTGTGG
CCAAGAAGCACCCCAAGACCTGGGTGCACTACATTGCTGCTGAGGAGGAGGACTGGGACTATGC
CCCCCTGGTGCTGGCCCCTGATGACAGGAGCTACAAGAGCCAGTACCTGAACAATGGCCCCCAG
AGGATTGGCAGGAAGTACAAGAAGGTCAGGTTCATGGCCTACACTGATGAAACCTTCAAGACCA
GGGAGGCCATCCAGCATGAGTCTGGCATCCTGGGCCCCCTGCTGTATGGGGAGGTGGGGGACAC
CCTGCTGATCATCTTCAAGAACCAGGCCAGCAGGCCCTACAACATCTACCCCCATGGCATCACT
GATGTGAGGCCCCTGTACAGCAGGAGGCTGCCCAAGGGGGTGAAGCACCTGAAGGACTTCCCC
ATCCTGCCTGGGGAGATCTTCAAGTACAAGTGGACTGTGACTGTGGAGGATGGCCCCACCAAGT
CTGACCCCAGGTGCCTGACCAGATACTACAGCAGCTTTGTGAACATGGAGAGGGACCTGGCCTC
TGGCCTGATTGGCCCCCTGCTGATCTGCTACAAGGAGTCTGTGGACCAGAGGGGCAACCAGATC
ATGTCTGACAAGAGGAATGTGATCCTGTTCTCTGTGTTTGATGAGAACAGGAGCTGGTACCTGA
CTGAGAACATCCAGAGGTTCCTGCCCAACCCTGCTGGGGTGCAGCTGGAGGACCCTGAGTTCCA
GGCCAGCAACATCATGCACAGCATCAATGGCTATGTGTTTGACAGCCTGCAGCTGTCTGTGTGCC
TGCATGAGGTGGCCTACTGGTACATCCTGAGCATTGGGGCCCAGACTGACTTCCTGTCTGTGTTC
TTCTCTGGCTACACCTTCAAGCACAAGATGGTGTATGAGGACACCCTGACCCTGTTCCCCTTCTC
TGGGGAGACTGTGTTCATGAGCATGGAGAACCCTGGCCTGTGGATTCTGGGCTGCCACAACTCT
GACTTCAGGAACAGGGGCATGACTGCCCTGCTGAAAGTCTCCAGCTGTGACAAGAACACTGGGG
ACTACTATGAGGACAGCTATGAGGACATCTCTGCCTACCTGCTGAGCAAGAACAATGCCATTGA
GCCCAGGAGCTTCAGCCAGAATGCCACTAATGTGTCTAACAACAGCAACACCAGCAATGACAGC
AATGTGTCTCCCCCAGTGCTGAAGAGGCACCAGAGGGAGATCACCAGGACCACCCTGCAGTCTG
ACCAGGAGGAGATTGACTATGATGACACCATCTCTGTGGAGATGAAGAAGGAGGACTTTGACAT
CTACGACGAGGACGAGAACCAGAGCCCCAGGAGCTTCCAGAAGAAGACCAGGCACTACTTCAT
TGCTGCTGTGGAGAGGCTGTGGGACTATGGCATGAGCAGCAGCCCCCATGTGCTGAGGAACAGG
GCCCAGTCTGGCTCTGTGCCCCAGTTCAAGAAGGTGGTGTTCCAGGAGTTCACTGATGGCAGCTT
CACCCAGCCCCTGTACAGAGGGGAGCTGAATGAGCACCTGGGCCTGCTGGGCCCCTACATCAGG
GCTGAGGTGGAGGACAACATCATGGTGACCTTCAGGAACCAGGCCAGCAGGCCCTACAGCTTCT
ACAGCAGCCTGATCAGCTATGAGGAGGACCAGAGGCAGGGGGCTGAGCCCAGGAAGAACTTTG
TGAAGCCCAATGAAACCAAGACCTACTTCTGGAAGGTGCAGCACCACATGGCCCCCACCAAGGA
TGAGTTTGACTGCAAGGCCTGGGCCTACTTCTCTGATGTGGACCTGGAGAAGGATGTGCACTCTG
GCCTGATTGGCCCCCTGCTGGTGTGCCACACCAACACCCTGAACCCTGCCCATGGCAGGCAGGT
GACTGTGCAGGAGTTTGCCCTGTTCTTCACCATCTTTGATGAAACCAAGAGCTGGTACTTCACTG
AGAACATGGAGAGGAACTGCAGGGCCCCCTGCAACATCCAGATGGAGGACCCCCACCTTCAAGG
AGAACTACAGGTTCCATGCCATCAATGGCTACATCATGGACACCCTGCCTGGCCTGGTGATGGC
CCAGGACCAGAGGATCAGGTGGTACCTGCTGAGCATGGGCAGCAATGAGAACATCCACAGCAT
CCACTTCTCTGGCCATGTGTTCACTGTGAGGAAGAAGGAGGAGTACAAGATGGCCCTGTACAAC
CTGTACCCTGGGGTGTTTGAGACTGTGGAGATGCTGCCCAGCAAGGCTGGCATCTGGAGGGTGG
AGTGCCTGATTGGGGAGCACCTGCATGCTGGCATGAGCACCCTGTTCCTGGTGTACAGCAACAA
GTGCCAGACCCCCCTGGGCATGGCCTCTGGCCACATCAGGGACTTCCAGATCACTGCCTCTGGCC
AGTATGGCCAGTGGGCCCCCAAGCTGGCCAGGCTGCACTACTCTGGCAGCATCAATGCCTGGAG
CACCAAGGAGCCCTTCAGCTGGATCAAGGTGGACCTGCTGGCCCCCATGATCATCCATGGCATC
AAGACCCAGGGGGCCAGGCAGAAGTTCAGCAGCCTGTACATCAGCCAGTTCATCATCATGTACA
GCCTGGATGGCAAGAAGTGGCAGACCTACAGGGGCAACAGCACTGGCACCCTGATGGTGTTCTT
TGGCAATGTGGACAGCTCTGGCATCAAGCACAACATCTTCAACCCCCCCATCATTGCCAGATAC
ATCAGGCTGCACCCCACCCACTACAGCATCAGGAGCACCCTGAGGATGGAGCTGATGGGCTGTG
ACCTGAACAGCTGCAGCATGCCCCTGGGCATGGAGAGCAAGGCCATCTCTGATGCCCAGATCAC
TGCCAGCAGCTACTTCACCAACATGTTTGCCACCTGGAGCCCCAGCAAGGCCAGGCTGCACCTG
CAGGGCAGGAGCAATGCCTGGAGGCCCCAGGTCAACAACCCCAAGGAGTGGCTGCAGGTGGAC
TTCCAGAAGACCATGAAGGTGACTGGGGTGACCACCCAGGGGGTGAAGAGCCTGCTGACCAGC
ATGTATGTGAAGGAGTTCCTGATCAGCAGCAGCCAGGATGGCCACCAGTGGACCCTGTTCTTCC
AGAATGGCAAGGTGAAGGTGTTCCAGGGCAACCAGGACAGCTTCACCCCTGTGGTGAACAGCCT
GGACCCCCCCCTGCTGACCAGATACCTGAGGATTCACCCCCAGAGCTGGGTGCACCAGATTGCC
CTGAGGATGGAGGTGCTGGGCTGTGAGGCCCAGGACCTGTACTGAAATCAACCTCTGGATTACA
AAATTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTATAAAT
CCTGGTTGCTGTCTCTTTATGAGGAGTTGTGGCCCGTTGTCAGGCAACGTGGCGTGGTGTGCACT
GTGTTTGCTGACGCAACCCCCCACTGGTTGGGGCATTGCCACCACCTGTCAGCTCCTTTCCGGGAC
TTTCGCTTTCCCCCTCCCTATTGCCACGCGGGAACTCATCGCCGCCTGCCTTGCCCGCTGCTGGAC
AGGGGCTCGGCTGTTGGGCACTGACAATTCCGTGGGAGCTGTGCGATCCCTGCTGGGGACTTTC
CGCTGGGGACTTTCCGCTGGGGACTTTCCGCCTTCAGCTAAGGAAGCTACCAATATTTAGAGGTA
CATTTTGTTCTAGAACAAAATGTACCGGTACATTTTGTTCTGGTACATTTTGTTCT
```

SEQUENCE LISTING

| Element | Sequence | # |
|---|---|---|
| ITR-ApoE-<br>AAT-hBGi-<br>FVIII-SQ-<br>N6-F309S-<br>DM-<br>WPRE3-<br>DTS-ITR | CCTGCAGGCAGCTGCGCGCTCGCTCGCTCACTGAGGCCGCCCGGGCGTCGGGCGACCTTTGGTC<br>GCCCGGCCTCAGTGAGCGAGCGCGCAGAGAGGGAGTGGCCAACTCCATCACTAGGGGTTCCTGC<br>GGCCGCACGCGTCTAGTTATTAATAGTAATCGAATTCGCGTCTGCAGGCTCAGAGGCACACAGG<br>AGTTTCTGGGCTCACCCTGCCCCCTTCCAACCCCTCAGTTCCCATCCTCCAGCAGCTGTTTGTGTG<br>CTGCCTCTGAAGTCCACACTGAACAAACTTCAGCCTACTCATGTCCCTAAAATGGGCAAACATTG<br>CAAGCAGCAAACAGCAAACACACAGCCCTCCCTGCCTGCTGACCTTGGAGCTGGGGCAGAGGTC<br>AGAGACCTCTCTGGGCCCATGCCACCTCCAACATCCACTCGACCCCTTGGAATTTCGGTGGAGA<br>GGGAGCAGAGGTTGTCCTGGCGTGGTTTAGGTAGTGTGAGAGGGGTCGACTGGACACAGGACGCT<br>GTGGTTTCTGAGCCAGGGGGCGACTCAGATCCCAGCCAGTGGACTTAGCCCCTGTTTGCTCCTCC<br>GATAACTGGGGTGACCTTGGTTAATATTCACCAGCAGCCTCCCCCGTTGCCCCTCTGGATCCACT<br>GCTTAAATACGGACGAGGACAGGGCCCTGTCTCCTCAGCTTCAGGCACCACCACTGACCTGGGA<br>CAGTGAATCGTAAGTACTAGCAGCTACAATCCAGCTACCATTCTGCTTTTATTTTATGGTTGGGA<br>TAAGGCTGGATTATTCTGAGTCCAAGCTAGGCCCTTTTGCTAATCATGTTCATACCTCTTATCTTC<br>CTCCCACAGCTCCTGGGCAACGTGCTGGTCTGTGTGCTGGCCCATCACTTTGGCAAAGAATTGCG<br>ATCGCCACCATGCAGATTGAGCTGAGCACCTGCTTCTTCCTGTGCCTGCTGAGGTTCTGCTTCTCT<br>GCCACCAGGAGATACTACCTGGGGGCTGTGGAGCTGAGCTGGGACTACATGCAGTCTGACCTGG<br>GGGAGCTGCCTGTGGATGCCAGGTTCCCCCCCAGAGTGCCCAAGAGCTTCCCCTTCAACACCTCT<br>GTGGTGTACAAGAAGACCCTGTTTGTGGAGTTCACTGACCACCTGTTCAACATTGCCAAGCCCA<br>GGCCCCCCTGGATGGGCCTGCTGGGCCCCACCATCCAGGCTGAGGTGTATGACACTGTGGTGAT<br>CACCCTGAAGAACATGGCCAGCCACCCTGTGAGCCTGCATGCTGTGGGGGTGAGCTACTGGAAG<br>GCCTCTGAGGGGGCTGAGTATGATGACCAGACCAGCCAGAGGGAGAAGGAGGATGACAAGGTG<br>TTCCCTGGGGGCAGCCACACCTATGTGTGGCAGGTGCTGAAGGAGAATGGCCCCATGGCCTCTG<br>ACCCCCTGTGCCTGACCTACAGCTACCTGAGCCATGTGGACCTGGTGAAGGACCTGAACTCTGG<br>CCTGATTGGGGCCCTGCTGGTGTGCAGGGAGGGCAGCCTGGCCAAGGAGAAGACCCAGACCCT<br>GCACAAGTTCATCCTGCTGTTTGCTGTGTTTGATGAGGGCAAGAGCTGGCACTCTGAAACCAAG<br>AACAGCCTGATGCAGGACAGGGATGCTGCCTCTGCCAGGGCCTGGCCCAAGATGCACACTGTGA<br>ATGGCTATGTGAACAGGAGCCTGCCTGGCCTGATTGGCTGCCACAGGAAGTCTGTGTACTGGCA<br>TGTGATTGGCATGGGCACCACCCCTGAGGTGCACAGCATCTTCCTGGAGGGCCACACCTTCCTG<br>GTCAGGAACCACAGGCAGGCCAGCCTGGAGATCAGCCCCATCACCTTCCTGACTGCCCAGACCC<br>TGCTGATGGACCTGGGCCAGTTCCTGCTGAGCTGCCACATCAGCAGCCACCAGCATGATGGCAT<br>GGAGGCCTATGTGAAGGTGGACAGCTGCCCTGAGGAGCCCCAGCTGAGGATGAAGAACAATGA<br>GGAGGCTGAGGACTATGATGATGACCTGACTGACTCTGAGATGGATGTGGTGAGGTTTGATGAT<br>GACAACAGCCCCAGCTTCATCCAGATCAGGTCTGTGGCCAAGAAGCACCCCAAGACCTGGGTGC<br>ACTACATTGCTGCTGAGGAGGAGGACTGGGACTATGCCCCCCTGGTGCTGGCCCCTGATGACAG<br>GAGCTACAAGAGCCAGTACCTGAACAATGGCCCCCAGAGGATTGGCAGGAAGTACAAGAAGGT<br>CAGGTTCATGGCCTACACTGATGAAACCTTCAAGACCAGGGAGGCCATCCAGCATGAGTCTGGC<br>ATCCTGGGCCCCCTGCTGTATGGGGAGGTGGGGGACACCCTGCTGATCATCTTCAAGAACCAGG<br>CCAGCAGGCCCTACAACATCTACCCCCATGGCATCACTGATGTGAGGCCCCTGTACAGCAGGAG<br>GCTGCCCAAGGGGGTGAAGCACCTGAAGGACTTCCCCATCCTGCCTGGGGAGATCTTCAAGTAC<br>AAGTGGACTGTGACTGTGGAGGATGGCCCCACCAAGTCTGACCCCAGGTGCCTGACCAGATACT<br>ACAGCAGCTTTGTGAACATGGAGAGGGACCTGGCCTCTGGCCTGATTGGCCCCCTGCTGATCTG<br>CTACAAGGAGTCTGTGGACCAGAGGGGCAACCAGATCATGTCTGACAAGAGGAATGTGATCCTG<br>TTCTCTGTGTTTGATGAGAACAGGAGCTGGTACCTGACTGAGAACATCCAGAGGTTCCTGCCCA<br>ACCCTGCTGGGGTGCAGCTGGAGGACCCTGAGTTCCAGGCCAGCAACATCATGCACAGCATCAA<br>TGGCTATGTGTTTGACAGCCTGCAGCTGTCTGTGTGCCTGCATGAGGTGGCCTACTGGTACATCC<br>TGAGCATTGGGGCCCAGACTGACTTCCTGTCTGTGTTCTTCTCTGGCTACACCTTCAAGCACAAG<br>ATGGTGTATGAGGACACCCTGACCCTGTTCCCCTTCTCTGGGGAGACTGTGTTCATGAGCATGGA<br>GAACCCTGGCCTGTGGATTCTGGGCTGCCACAACTCTGACTTCAGGAACAGGGGCATGACTGCC<br>CTGCTGAAAGTCTCCAGCTGTGACAAGAACACTGGGGACTACTATGAGGACAGCTATGAGGACA<br>TCTCTGCCTACCTGCTGAGCAAGAACAATGCCATTGAGCCCAGGAGCTTCAGCCAGAATCCCCC<br>AGTGCTCACCCGGTCCTTTAGCCAGAATTCTCGCCATCCCTCCACCCGGCAAAAGCAGTTCAACG<br>CCACTACCATCCCAGAGAACGACATCGAAAAAACCGACCCCTGGTTCGCCCACAGAACTCCCAT<br>GCCAAAGATTCAGAATGTTTCCAGTTCTGACCTCCTTATGTTGCTGCGCCAGTCTCCGACCCCTC<br>ATGGACTGTCCCTGAGTGACTTGCAGGAGGCCAAGTACGAGACGTTCTCTGATGACCCCAGCCC<br>AGGCGCGATTGACTCAAATAACTCCCTGTCTGAGATGACACATTTTCGCCCCTCAGCTCCATCACA<br>GCGGGGACATGGTGTTCACTCCAGAGTCCGGACTTCAGCTGCGCCTCAACGAGAAACTCGGTAC<br>TACAGCCGCGACAGAACTCAAAAAGCTGGATTTCAAGGTTTCCAGCACCAGCAATAACCTGATC<br>TCTACAATTCCCAGCGATAACCTGGCGGCTGGAACCGACAACACTTCCAGCCTGGGACCTCCGT<br>CCATGCCGTGCACTACGACTCCCAGCTCGACACCACTCTGTTCGGCAAGAAAAGTAGCCCCCT<br>GACCGAATCCGGCGGTCCGCTGTCCCTCTCCGAAGAGAATAACGATAGCAAGCTCCTGGAATCT<br>GGGCTTATGAACTCTCAAGAGTCATCCTGGGGCAAGAACGTTTCATCAACTAGGGAGATCACCA<br>GGACCACCCTGCAGTCTGACCAGGAGGAGATTGACTATGATGACACCATCTCTGTGGAGATGAA<br>GAAGGAGGACTTTGACATCTACGACGAGGACGAGAACCAGAGCCCCAGGAGCTTCCAGAAGAA<br>GACCAGGCACTACTTCATTGCTGCTGTGGAGAGGCTGTGGGACTATGGCATGAGCAGCAGCCCC<br>CATGTGCTGAGGAACAGGGCCCAGTCTGGCTCTGTGCCCCAGTTCAAGAAGGTGGTGTTCCAGG<br>AGTTCACTGATGGCAGCTTCACCCAGCCCCTGTACAGAGGGGAGCTGAATGAGCACCTGGGCCT<br>GCTGGGCCCCTACATCAGGGCTGAGGTGGAGGACAACATCATGGTGACCTTCAGGAACCAGGCC<br>AGCAGGCCCTACAGCTTCTACAGCAGCCTGATCAGCTATGAGGAGGACCAGAGGCAGGGGGCT<br>GAGCCCAGGAAGAACTTTGTGAAGCCCAATGAAACCAAGACCTACTTCTGGAAGGTGCAGCACC<br>ACATGGCCCCCACCAAGGATGAGTTTGACTGCAAGGCCTGGGCCTACTTCTCTGATGTGGACCT<br>GGAGAAGGATGTGCACTCTGGCCTGATTGGCCCCCTGCTGGTGTGCCACACCAACACCCTGAAC<br>CCTGCCCATGGCAGGCAGGTGACTGTGCAGGAGTTTGCCCTGTTCTTCACCATCTTTGATGAAAC<br>CAAGAGCTGGTACTTCACTGAGAACATGGAGAGGAACGGCAGGGCCCCCGGCAACATCCAGAT<br>GGAGGACCCCACCTTCAAGGAGAACTACAGGTTCCATGCCATCAATGGCTACATCATGGACACC<br>CTGCCTGGCCTGGTGATGGCCCAGGACCAGAGGATCAGGTGGTACCTGCTGAGCATGGGCAGCA | 44 |

-continued

---

SEQUENCE LISTING

---

| Element | Sequence | # |
|---------|----------|---|
| | ATGAGAACATCCACAGCATCCACTTCTCTGGCCATGTGTTCACTGTGAGGAAGAAGGAGGAGTA<br>CAAGATGGCCCTGTACAACCTGTACCCTGGGGTGTTTGAGACTGTGGAGATGCTGCCCAGCAAG<br>GCTGGCATCTGGAGGGTGGAGTGCCTGATTGGGGAGCACCTGCATGCTGGCATGAGCACCCTGT<br>TCCTGGTGTACAGCAACAAGTGCCAGACCCCCCTGGGCATGGCCTCTGGCCACATCAGGGACTT<br>CCAGATCACTGCCTCTGGCCAGTATGGCCAGTGGGCCCCCAAGCTGGCCAGGCTGCACTACTCT<br>GGCAGCATCAATGCCTGGAGCACCAAGGAGCCCTTCAGCTGGATCAAGGTGGACCTGCTGGCCC<br>CCATGATCATCCATGGCATCAAGACCCAGGGGGCCAGGCAGAAGTTCAGCAGCCTGTACATCAG<br>CCAGTTCATCATCATGTACAGCCTGGATGGCAAGAAGTGGCAGACCTACAGGGGCAACAGCACT<br>GGCACCCTGATGGTGTTCTTTGGCAATGTGGACAGCTCTGGCATCAAGCACAACATCTTCAACCC<br>CCCCATCATTGCCAGATACATCAGGCTGCACCCCACCCACTACAGCATCAGGAGCACCCTGAGG<br>ATGGAGCTGATGGGCTGTGACCTGAACAGCTGCAGCATGCCCCTGGGCATGGAGAGCAAGGCC<br>ATCTCTGATGCCCAGATCACTGCCAGCAGCTACTTCACCAACATGTTTGCCACCTGGAGCCCCAG<br>CAAGGCCAGGCTGCACCTGCAGGGCAGGAGCAATGCCTGGAGGCCCCAGGTCAACAACCCCAA<br>GGAGTGGCTGCAGGTGGACTTCCAGAAGACCATGAAGGTGACTGGGGTGACCACCCAGGGGGT<br>GAAGAGCCTGCTGACCAGCATGTATGTGAAGGAGTTCCTGATCAGCAGCAGCCAGGATGGCCAC<br>CAGTGGACCCTGTTCTTCCAGAATGGCAAGGTGAAGGTGTTCCAGGGCAACCAGGACAGCTTCA<br>CCCCTGTGGTGAACAGCCTGGACCCCCCCCTGCTGACCAGATACCTGAGGATTCACCCCCAGAG<br>CTGGGTGCACCAGATTGCCCTGAGGATGGAGGTGCTGGGCTGTGAGGCCCAGGACCTGTACTGA<br>CTCGA | |
| WPRE3 + bG hPolyA | AATCAACCTCTGGATTACAAAATTTGTGAAAGATTGACTGGTATTCTTAACTATGTTGCTCCTTTT<br>ACGCTATGTGGATACGCTGCTTTAATGCCTTTGTATCATGCTATTGCTTCCCGTATGGCTTTCATT<br>TTCTCCTCCTTGTATAAATCCTGGTTGCTGTCTCTTTATGAGGAGTTGTGGCCCGTTGTCAGGCAA<br>CGTGGCGTGGTGTGCACTGTGTTTGCTGACGCAACCCCCACTGGTTGGGGCATTGCCACCACCTG<br>TCAGCTCCTTTCCGGGACTTTCGCTTTCCCCCTCCCTATTGCCACGGCGGAACTCATCGCCGCCTG<br>CCTTGCCCGCTGCTGGACAGGGGCTCGGCTGTTGGGCACTGACAATTCCGTGGTGTGCCTTCTAG<br>TTGCCAGCCATCTGTTGTTTGCCCCTCCCCCGTGCCTTCCTTGACCCTGGAAGGTGCCACTCCCAC<br>TGTCCTTTCCTAATAAAATGAGGAAATTGCATCGCATTGTCTGAGTAGGTGTCATTCTATTCTGG<br>GGGGTGGGGTGGGGCAGGACAGCAAGGGGGAGGATTGGGAAGACAATAGCAGGCATGCTGGG<br>GATGCGGTGGGCTCTATGG | 45 |
| FVIII v3 AA | FVIIIVTRANSLATIQNMQIELSTCFFLCLLRFCFSATRRYYLGAVELSWDYMQSDLGELPVDARFPPR<br>VPKSFPFNTSVVYKKTLFVEFTDHLFNIAKPRPPWMGLLGPTIQAEVYDTVVITLKNMASHPVSLHA<br>VGVSYWKASEGAEYDDQTSQREKEDDKVFPGGSHTYVWQVLKENGPMASDPLCLTYSYLSHVDLV<br>KDLNSGLIGALLVCREGSLAKEKTQTLHKFILLFAVFDEGKSWHSETKNSLMQDRDAASARAWPKM<br>HTVNGYVNRSLPGLIGCHRKSVYWHVIGMGTTPEVHSIFLEGHTFLVRNHRQASLEISPITFLTAQTLL<br>MDLGQFLLFCHISSHQHDGMEAYVKVDSCPEEPQLRMKNNEEAEDYDDDLTDSEMDVVRFDDDNS<br>PSFIQIRSVAKKHPKTWVHYIAAEEEDWDYAPLVLAPDDRSYKSQYLNNGPQRIGRKYKKVRFMAY<br>TDETFKTREAIQHESGILGPLLYGEVGDTLLIIFKNQASRPYNIYPHGITDVRPLYSRRLPKGVKHLKD<br>FPILPGEIFKYKWTVTVEDGPTKSDPRCLTRYYSSFVNMERDLASGLIGPLLICYKESVDQRGNQIMS<br>DKRNVILFSVFDENRSWYLTENIQRFLPNPAGVQLEDPEFQASNIMHSINGYVFDSLQLSVCLHEVAY<br>WYILSIGAQTDFLSVFFSGYTFKHKMVYEDTLTLFPFSGETVFMSMENPGLWILGCHNSDFRNRGMT<br>ALLKVSSCDKNTGDYYEDSYEDISAYLLSKNNAIEPRSFSQNATNVSNNSNTSNDSNVSPPVLKRHQ<br>REITRTTLQSDQEEIDYDDTISVEMKKEDFDIYDEDENQSPRSFQKKTRHYFIAAVERLWDYGMSSSP<br>HVLRNRAQSGSVPQFKKVVFQEFTDGSFTQPLYRGELNEHLGLLGPYIRAEVEDNIMVTFRNQASRP<br>YSFYSSLISYEEDQRQGAEPRKNFVKPNETKTYFWKVQHHMAPTKDEFDCKAWAYFSDVDLEKDV<br>HSGLIGPLLVCHTNTLNPAHGRQVTVQEFALFFTIFDETKSWYFTENMERNCRAPCNIQMEDPTFKEN<br>YRFHAINGYIMDTLPGLVMAQDQRIRWYLLSMGSNENIHSIHFSGHVFTVRKKEEYKMALYNLYPG<br>VFETVEMLPSKAGIWRVECLIGEHLHAGMSTLFLVYSNKCQTPLGMASGHIRDFQITASGQYGQWAP<br>KLARLHYSGSINAWSTKEPFSWIKVDLLAPMIIHGIKTQGARQKFSSLYISQFIIMYSLDGKKWQTYR<br>GNSTGTLMVFFGNVDSSGIKHNIFNPPIIARYIRLHPTHYSIRSTLRMELMGCDLNSCSMPLGMESKAI<br>SDAQITASSYFTNMFATWSPSKARLHLQGRSNAWRPQVNNPKEWLQVDFQKTMKVTGVTTQGVKS<br>LLTSMYVKEFLISSSQDGHQWTLFFQNGKVKVFQGNQDSFTPVVNSLDPPLLTRYLRIHPQSWVHQI<br>ALRMEVLGCEAQDL | 46 |

---

SEQUENCE LISTING

---

Sequence total quantity: 46
SEQ ID NO: 1          moltype = DNA   length = 469
FEATURE               Location/Qualifiers
source                1..469
                      mol_type = other DNA
                      note = ApoE-AAT promoter
                      organism = synthetic construct
SEQUENCE: 1
cgcgtctgca ggctcagagg cacacaggag tttctgggct caccctgccc ccttccaacc   60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360

-continued

```
gagccagggg gcgactcaga tcccagccag tggacttagc ccctgtttgc tcctccgata   420
actggggtga ccttggttaa tattcaccag cagcctcccc cgttgcccc              469

SEQ ID NO: 2          moltype = DNA  length = 281
FEATURE               Location/Qualifiers
source                1..281
                      mol_type = other DNA
                      note = hBGi intron
                      organism = synthetic construct
SEQUENCE: 2
tctggatcca ctgcttaaat acggacgagg acagggccct gtctcctcag cttcaggcac    60
caccactgac ctgggacagt gaatcgtaag tactagcagc tacaatccag ctaccattct   120
gctttattt tatggttggg ataaggctgg attattctga gtccaagcta ggcccttttg   180
ctaatcatgt tcatacctct tatcttcctc ccacagctcc tgggcaacgt gctggtctgt   240
gtgctggccc atcactttgg caaagaattg cgatcgccac c                       281

SEQ ID NO: 3          moltype = DNA  length = 4425
FEATURE               Location/Qualifiers
source                1..4425
                      mol_type = other DNA
                      note = FVIII-v3 ORF
                      organism = synthetic construct
SEQUENCE: 3
atgcagattg agctgagcac ctgcttcttc ctgtgcctgc tgaggttctg cttctctgcc    60
accaggagat actacctggg ggctgtggag ctgagctggg actacatgca gtctgacctg   120
ggggagctgc ctgtggatgc caggttcccc cccagagtga ccaagagctt ccccttcaac   180
acctctgtgg tgtacaagaa gaccctgttt gtggagttca ctgaccacct gttcaacatt   240
gccaagccca ggccccctg gatgggcctg ctgggcccca ccatccaggc tgaggtgtat   300
gacactgtg tgatcaccct gaagaacatg gccagccacc ctgtgagcct gcatgctgtg   360
ggggtgagct actggaaggc ctctgagggg gctgagtatg atgaccagac cagccagagg   420
gagaaggagg atgacaaggt gttccctggg ggcagccaca cctatgtgtg gcaggtgctg   480
aaggagaatg gccccatggc ctctgacccc ctgtgcctga cctacagcta cctgagccat   540
gtggacctgt gaaggacct gaactctggc ctgattgggg ccctgctggt gtgcaggag   600
ggcagctg ccaggagaa gacccagacc ctgcacaagt tcatcctgct gtttgctgtg   660
tttgatgagg gcaagagctg gcactctgaa accaagaaca gcctgatgca ggacagggat   720
gctgcctctg ccagggcctg gcccaagatg cacactgtga atggctatgt gaacaggagc   780
ctgcctggcc tgattggctg ccacaggaag tctgtgtact ggcatgtgat tggcatgggc   840
accacccctg aggtgcacag catcttcctg gagggccaca ccttcctggt caggaaccac   900
aggcaggcca gcctggagat cagccccatc accttcctga ctgcccagac cctgctgatg   960
gacctgggcc agttcctgct gttctgccac atcagcagcc accagcatga tggcatggag  1020
gcctatgtga aggtggacag ctgccctgag gagccccagc tgaggatgaa gaacaatgag  1080
gaggctgagg actatgatga tgacctgact gactctgaga tggatgtggt gaggtttgat  1140
gatgacaaca gcccagctt catccagatc aggtctgtgg ccaagaagca ccccaagacc  1200
tgggtgcact acattgctgc tgaggaggag gactgggact atgccccct ggtgctggcc  1260
cctgatgaca ggagctacaa gagccagtac ctgaacaatg gccccagag gattggcagg  1320
aagtacaaga aggtcaggtt catggcctac actgatgaaa ccttcaagac cagggaggcc  1380
atccagcatg agtctggcat cctgggcccc ctgctgtatg gggaggtggg ggacaccctg  1440
ctgatcatct tcaagaacca ggccagcagg ccctacaaca tctacccca tggcatcact  1500
gatgtgaggc ccctgtacag caggaggctg cccaagggg tgaagcacct gaaggacttc  1560
cccatcctgc ctgggga gat cttcaagtac aagtggactg tgactgtgga ggatggcccc  1620
accaagtctg accccaggtg cctgaccaga tactacagca gctttgtgaa catggagagg  1680
gacctggcct ctggcctgat tggccccctg ctgatctgct acaaggagtc tgtggaccag  1740
aggggcaacc agatcatgtc tgacaagagg aatgtgatcc tgttctctgt gtttgatgag  1800
aacaggagct ggtacctgac tgagaacatc cagaggttcc tgcccaaccc tgctggggtg  1860
cagctggagg accctgagtt ccaggccagc aacatcatgc acagcatcaa tggctatgtg  1920
tttgacagcc tgcagctgtc tgtgtgcctg catgaggtgg cctactggta tatcctgagc  1980
attggggccc agactgactt cctgtctgtg ttcttctctg ctacacctt caagcacaag  2040
atggtgtatg aggacaccct gaccctgttc cccttctctg gggagactgt gttcatgagc  2100
atggagaacc ctggcctgtg gattctgggc tgccacaact ctgacttcag gaacagggc  2160
atgactgccc tgctgaaagt ctccagctgt gacaagaaca ctggggacta ctatgaggac  2220
agctatgagg acatctctgc ctacctgctg agcaagaaca tgccattga gcccaggagc  2280
ttcagccaga atgccactaa tgtgtctaac aacagcaaca ccagcaatga cagcaatgtg  2340
tctcccccag tgctgaagag gcaccagagg gagatcacca ggaccaccct gcagtctgac  2400
caggaggaca ttgactatga tgacaccatc tctgtggaga tgaagaagga ggactttgat  2460
atctacgacg aggacgagaa ccagagcccc aggagcttcc agaagaagac caggcactac  2520
ttcattgctg ctgtggagag gctgtgggac tatggcatga gcagcagccc ccatgtgctg  2580
aggaacaggg cccagtctgg ctctgtgccc cagttcaaga aggtggtgtt ccaggagttc  2640
actgatggca gcttcaccca gcccctgtac agaggggagc tgaatgagca cctgggcctg  2700
ctgggccct catccagggc tgaggtggag gacaacatca tggtgacctt caggaaccag  2760
gccagcaggc cctacagctt ctacagcagc ctgatcagct atgaggagga ccagaggcag  2820
ggggctgagc caggaagaa cttttgtgaag cccaatgaaa ccaagaccta cttctggaag  2880
gtgcagcacc acatggcccc caccaaggat gagtttgact gcaggcctg gcctacttc  2940
tctgatgtgg acctggagaa ggatgtgcac tctggcctga ttggcccct gctggtgtgc  3000
cacaccaaca cctgaaccc tgcccatgc aggcaggtga ctgtgcagga gtttgccctg  3060
ttcttcacca tctttgatga aaccaagagc tggtacttca ctgagaacat ggagaggaac  3120
tgcagggccc cctgcaacat ccagatggag gacccccacct tcaaggagaa ctacaggttc  3180
catgccatca tggctacat catggacacc ctgcctggcc tggtgatggc ccaggaccag  3240
aggatcaggt ggtacctgct gagcatgggc agcaatgaga acatccacag catccacttc  3300
tctggccatg tgttcactgt gaggaagaag gaggagtaca gatggccct gtacaacctg  3360
```

```
taccctgggg tgtttgagac tgtggagatg ctgcccagca aggctggcat ctggagggtg    3420
gagtgcctga ttggggagca cctgcatgct ggcatgagca ccctgttcct ggtgtacagc    3480
aacaagtgcc agaccccct gggcatggcc tctggccaca tcagggactt ccagatcact    3540
gcctctggcc agtatggcca gtgggcccc aagctggcca ggctgcacta ctctggcagc    3600
atcaatgcct ggagcaccaa ggagcccttc agctggatca aggtggacct gctggcccc    3660
atgatcatcc atggcatcaa gacccagggg gccaggcaga agttcagcag cctgtacatc    3720
agccagttca tcatcatgta cagcctggat ggcaagaagt ggcagaccta cagggggcaac    3780
agcactggca ccctgatggt gttctttggc aatgtggaca gctctggcat caagcacaac    3840
atcttcaacc cccccatcat tgccagatac atcaggctgc accccaccca ctacagcatc    3900
aggagcaccc tgaggatgga gctgatgggc tgtgacctga acagctgcag catgccctg    3960
ggcatggaga gcaaggccat ctctgatgcc cagatcactg ccagcagcta cttcaccaac    4020
atgtttgcca cctggagccc cagcaaggcc aggctgcacc tgcagggcag gagcaatgcc    4080
tggaggccc aggtcaacaa ccccaaggag tggctgcagg tggacttcca gaagaccatg    4140
aaggtgacct gggtgaccac ccaggggggtg aagagcctga tgaccagcat gtatgtgaag    4200
gagttcctga tcagcagcag ccaggatggc caccagtgga ccctgttctt ccagaatggc    4260
aaggtgaagg tgtccagggg caaccaggac agcttcaccc ctgtggtgaa cagcctggac    4320
cccccctgc tgaccagata cctgaggatt caccccaga gctgggtgca ccagattgcc    4380
ctgaggatgg aggtgctggg ctgtgaggcc caggacctgt actga               4425
```

SEQ ID NO: 4                    moltype = DNA   length = 382
FEATURE                        Location/Qualifiers
source                         1..382
                               mol_type = other DNA
                               note = WPRE3
                               organism = synthetic construct
SEQUENCE: 4
```
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt gg                                      382
```

SEQ ID NO: 5                    moltype = DNA   length = 224
FEATURE                        Location/Qualifiers
source                         1..224
                               mol_type = other DNA
                               note = bGH polyA
                               organism = synthetic construct
SEQUENCE: 5
```
tgtgccttct agttgccagc catctgttgt ttgcccctcc cccgtgcctt ccttgaccct    60
ggaaggtgcc actcccactg tcctttccta ataaaatgag gaaattgcat cgcattgtct    120
gagtaggtgt cattctattc tggggggtgg ggtggggcag gacagcaagg gggaggattg    180
ggaagacaat agcaggcatg ctggggatgc ggtgggctct atgg               224
```

SEQ ID NO: 6                    moltype = DNA   length = 150
FEATURE                        Location/Qualifiers
source                         1..150
                               mol_type = other DNA
                               note = DTS
                               organism = synthetic construct
SEQUENCE: 6
```
gagctgtgcg atccctgctg gggactttcc gctggggact ttccgctggg gactttccgc    60
cttcagctaa ggaagctacc aatatttaga ggtacatttg ttctagaac aaaatgtacc    120
ggtacatttt gttctggtac attttgttct                              150
```

SEQ ID NO: 7                    moltype = DNA   length = 449
FEATURE                        Location/Qualifiers
source                         1..449
                               mol_type = other DNA
                               note = NP Backbone
                               organism = synthetic construct
SEQUENCE: 7
```
tggcttgttg tccacaacca ttaaacctta aagctttaa aagccttata tattctttt    60
tttcttataa aacttaaaac cttagaggct atttaagttg ctgatttata ttaattttat    120
tgttcaaaca tgagagctta gtacgtgaaa catgagagct tagtacatta gccatgagag    180
cttagtacat tagccatgag ggtttagttc attaaacatg agagcttagt acattaaaca    240
tgagagctta gtacattaaa catgagagct tagtacatac tatcaacagg ttgaactgct    300
gatctgtaca gtagaattgg taaagagagt tgtgtaaaat attgagttcg cacatcttgt    360
tgtctgatta ttgattttg gcgaaaccat ttgatcatat gacaagatgt gtatctacct    420
taacttaatg attttgataa aaatcatta                               449
```

SEQ ID NO: 8                    moltype = AA   length = 1474
FEATURE                        Location/Qualifiers
source                         1..1474
                               mol_type = protein
                               note = FVIII-v3 AA sequence
                               organism = synthetic construct

```
SEQUENCE: 8
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNATNVSN NSNTSNDSNV   780
SPPVLKRHQR EITRTTLQSD QEEIDYDDTI SVEMKKEDFD IYDEDENQSP RSFQKKTRHY   840
FIAAVERLWD YGMSSSPHVL RNRAQSGSVP QFKKVVFQEF TDGSFTQPLY RGELNEHLGL   900
LGPYIRAEVE DNIMVTFRNQ ASRPYSFYSS LISYEEDQRQ GAEPRKNFVK PNETKTYFWK   960
VQHHMAPTKD EFDCKAWAYF SDVDLEKDVH SGLIGPLLVC HTNTLNPAHG RQVTVQEFAL  1020
FFTIFDETKS WYFTENMERN CRAPCNIQME DPTFKENYRF HAINGYIMDT LPGLVMAQDQ  1080
RIRWYLLSMG SNENIHSIHF SGHVFTVRKK EEYKMALYNL YPGVFETVEM LPSKAGIWRV  1140
ECLIGEHLHA GMSTLFLVYS NKCQTPLGMA SGHIRDFQIT ASGQYGQWAP KLARLHYSGS  1200
INAWSTKEPF SWIKVDLLAP MIIHGIKTQG ARQKFSSLYI SQFIIMYSLD GKKWQTYRGN  1260
STGTLMVFFG NVDSSGIKHN IFNPPIIARY IRLHPTHYSI RSTLRMELMG CDLNSCSMPL  1320
GMESKAISDA QITASSYFTN MFATWSPSKA RLHLQGRSNA WRPQVNNPKE WLQVDFQKTM  1380
KVTGVTTQGV KSLLTSMYVK EFLISSSQDG HQWTLFFQNG KVKVFQGNQD SFTPVVNSLD  1440
PPLLTRYLRI HPQSWVHQIA LRMEVLGCEA QDLY                              1474

SEQ ID NO: 9             moltype = DNA  length = 750
FEATURE                  Location/Qualifiers
source                   1..750
                         mol_type = other DNA
                         note = ApoE-AAT-hbGi
                         organism = synthetic construct
SEQUENCE: 9
cgcgtctgca ggctcagagg cacacaggag tttctgggct caccctgccc ccttccaacc    60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtgggaggga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga cagggccctg tctcctcagc ttcaggaccac accactgacc   540
tgggacagtg aatcgtaagt actagcagct acaatccagc taccattctg cttttatttt   600
atggttggga taaggctgga ttattctgag tccaagctag gcccttttgc taatcatgtt   660
catacctctt atcttcctcc cacagctcct gggcaacgtg ctggtctgtg tgctggccca   720
tcactttggc aaagaattgc gatcgccacc                                   750

SEQ ID NO: 10            moltype = DNA  length = 1389
FEATURE                  Location/Qualifiers
source                   1..1389
                         mol_type = other DNA
                         note = FIX NA sequence
                         organism = synthetic construct
SEQUENCE: 10
atgcagcgcg tgaacatgat catggcagaa tcaccaggcc tcatcaccat ctgcctttta    60
ggatatctac tcagtgctga atgtacagtt tttcttgatc atgaaaacgc caacaaaatt   120
ctgaatcggc aaagaggta taattcaggt aaattggaag agtttgttca agggaacctt   180
gagagagaat gtatggaaga aaagtgtagt tttgaagcag cacgagaagt ttttgaaaac   240
actgaaagaa caactgaatt ttggaagcag tatgttgatg gagatcagtg tgagtccaat   300
ccatgtttaa atggcggcag ttgcaaggat gacattaatt cctatgaatg ttggtgtccc   360
tttgattttg aaggaaagaa ctgtgaatta gatgtaacat gtaacattaa gaatggcaga   420
tgcgagcagt tttgtaaaaa tagtgctgat aacaaggtgg tttgctcctg tactgaggga   480
tatcgacttg cagaaaacca gaagtcctgt gaaccagaag tgccatttcc atgtggaaga   540
gtttctgttt cacaaacttc taagctcacc cgtgctgaga ctgttttttcc tgatgtggac   600
tatgtaaatt ctactgaagc tgaaaccatt ttggataaca tcactcaaag cacccaatca   660
tttaatgact tcactcgggt tgttggtgga gaagatgcca aaccaggtca attcccttgg   720
caggttgttt tgaatggtaa agttgatgca ttctgtggag gctctatcgt taatgaaaaa   780
tggattgtaa ctgctgccca ctgtgttgaa actggtgtta aaattacagt tgtcgcaggt   840
gaacataata ttgaggagac agaacataca gagcaaaagc gaaatgtgat tcgaattatt   900
cctcaccaca actacaatgc agctattaat aagtacaacc atgacattgc ccttctggaa   960
ctggacgaac ccttagtgct aaacagctac gttacaccta tttgcattgc tgacaaggaa  1020
tacacgaaca tcttcctcaa atttggatct ggctatgtaa gtggctgggg aagagtcttc  1080
cacaaaggga gatcagcttt agttcttcag taccttaagg ttccacttgt tgaccagagg  1140
gcatgtcttc gatctacaaa gttcaccatc tataacaaca tgttctgtgc tggcttccat  1200
gaaggaggta gagattcatg tcaaggagat agtgggggac cccatgttac tgaagtggaa  1260
gggaccagtg tcttaactgg aattattagc tggggtgaag agtgtgcaat gaaaggcaaa  1320
tatggaatat ataccaaggt atcccggtat gtcaactgga ttaaggaaaa aacaaagctc  1380
acttaatga                                                          1389
```

-continued

```
SEQ ID NO: 11              moltype = DNA  length = 126
FEATURE                    Location/Qualifiers
source                     1..126
                           mol_type = other DNA
                           note = 5 ITR
                           organism = synthetic construct
SEQUENCE: 11
cctgcaggca gctgcgcgct cgctcgctca ctgaggccgc ccgggcgtcg ggcgaccttt    60
ggtcgcccgg cctcagtgag cgagcgcgca gagagggagt ggccaactcc atcactaggg   120
gttcct                                                              126

SEQ ID NO: 12              moltype = DNA  length = 2139
FEATURE                    Location/Qualifiers
source                     1..2139
                           mol_type = other DNA
                           note = APOE-AAT-hBGi-FIX
                           organism = synthetic construct
SEQUENCE: 12
cgcgtctgca ggctcagagg cacacaggag tttctgggct caccctgccc ccttccaacc    60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga cagggccctg tctcctcagc ttcaggcacc accactgacc   540
tgggacagtg aatcgtaagt actagcagct acaatccagc taccattctg cttttatttt   600
atggttggga taaggctgga ttattctgag tccaagctag gcccttttgc taatcatgtt   660
catacctctt atcttcctcc cacagctcct gggcaacgtg ctggtctgtg tgctggccca   720
tcactttggc aaagaattgc gatcgccacc atgcagcgcg tgaacatgat catggcagaa   780
tcaccaggcc tcatcaccat ctgccttta ggatatctac tcagtgctga atgtacagtt   840
tttcttgatc atgaaaacgc caacaaaatt ctgaatcggc aaagaggta taattcaggt   900
aaattggaag agtttgttca agggaacctt gagagagaat gtatggaaga aaagtgtagt   960
tttgaagaag cacgagaagt ttttgaaaac actgaaagaa caactgaatt ttggaagcag  1020
tatgttgatg gagatcagtg tgagtccaat ccatgtttaa atggcggcag ttgcaaggat  1080
gacattaatt cctatgaatg ttggtgtccc tttggatttg aaggaaagaa ctgtgaatta  1140
gatgtaacat gtaacattaa gaatggcaga tgcgagcagt tttgtaaaaa tagtgctgat  1200
aacaaggtgg tttgctcctg tactgaggga tatcgacttg cagaaaacca gaagtcctgt  1260
gaaccagcag tgccatttcc atgtggaaga gtttctgttt cacaaacttc taagctcacc  1320
cgtgctgaga ctgtttttcc tgatgtggac tatgtaaatt ctactgaagc tgaaaccatt  1380
ttggataaca tcactcaaag cacccaatca tttaatgact tcactcgggt tgttggtgga  1440
gaagatgcca aaccaggtca attcccttgg caggttgttt tgaatggtaa agttgatgca  1500
ttctgtggag gctctatcgt taatgaaaaa tggattgtaa ctgctgccca ctgtgttgaa  1560
actggtgtta aaattacagt tgtcgcaggt gaacataata ttgaggagac agaacataca  1620
gagcaaaagc gaaatgtgat tcgaattatt cctcaccaca actacaatgc agctattaat  1680
aagtacaacc atgacattgc ccttctggaa ctggacgaac ccttagtgct aaacagctac  1740
gttacaccta tttgcattgc tgacaaggaa tacacgaaca tcttcctcaa atttggatct  1800
ggctatgtaa gtggctgggg aagagtcttc cacaaaggga gatcagcttt agttcttcag  1860
tacctttagag ttccacttgt tgaccgagcc acatgtcttc gatctacaaa gttcaccatc  1920
tataacaaca tgttctgtgc tggcttccat aaggaggta gagattcatg tcaaggagat  1980
agtggggggac cccatgttac tgaagtggaa gggaccagtt tcttaactgg aattattagc  2040
tggggtgaag agtgtgcaat gaaaggcaaa tatggaatat ataccaaggt atcccggtat  2100
gtcaactgga ttaaggaaaa aacaaagctc acttaatga                        2139

SEQ ID NO: 13              moltype = DNA  length = 2371
FEATURE                    Location/Qualifiers
source                     1..2371
                           mol_type = other DNA
                           note = APOE-AAT-hBGi-FIX-bGH-polyA
                           organism = synthetic construct
SEQUENCE: 13
cgcgtctgca ggctcagagg cacacaggag tttctgggct caccctgccc ccttccaacc    60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga cagggccctg tctcctcagc ttcaggcacc accactgacc   540
tgggacagtg aatcgtaagt actagcagct acaatccagc taccattctg cttttatttt   600
atggttggga taaggctgga ttattctgag tccaagctag gcccttttgc taatcatgtt   660
catacctctt atcttcctcc cacagctcct gggcaacgtg ctggtctgtg tgctggccca   720
tcactttggc aaagaattgc gatcgccacc atgcagcgcg tgaacatgat catggcagaa   780
tcaccaggcc tcatcaccat ctgccttta ggatatctac tcagtgctga atgtacagtt   840
tttcttgatc atgaaaacgc caacaaaatt ctgaatcggc aaagaggta taattcaggt   900
aaattggaag agtttgttca agggaacctt gagagagaat gtatggaaga aaagtgtagt   960
```

```
tttgaagaag cacgagaagt ttttgaaaac actgaaagaa caactgaatt ttggaagcag  1020
tatgttgatg gagatcagtg tgagtccaat ccatgtttaa atggcggcag ttgcaaggat  1080
gacattaatt cctatgaatg ttggtgtccc tttggatttg aaggaaagaa ctgtgaatta  1140
gatgtaacat gtaacattaa gaatggcaga tgcgagcagt tttgtaaaaa tagtgctgat  1200
aacaaggtgg tttgctcctg tactgaggga tatcgacttg cagaaaacca gaagtcctgt  1260
gaaccagcag tgccatttcc atgtggaaga gtttctgttt cacaaacttc taagctcacc  1320
cgtgctgaga ctgtttttcc tgatgtggac tatgtaaatt ctactgaagc tgaaaccatt  1380
ttggataaca tcactcaaag cacccaatca tttaatgact tcactcgggt tgttggtgga  1440
gaagatgcca aaccaggtca attcccttgg caggttgttt tgaatggtaa agttgatgca  1500
ttctgtggag gctctatcgt taatgaaaaa tggattgtaa ctgctgccca ctgtgttgaa  1560
actggtgtta aaattacagt tgtcgcaggt gaacataata ttgaggagac agaacataca  1620
gagcaaaagc gaaatgtgat tcgaattatt cctcaccaca actacaatgc agctattaat  1680
aagtacaacc atgacattgc ccttctggaa ctggacgaac ccttagtgct aaacagctac  1740
gttacaccta tttgcattgc tgacaaggaa tacacgaaca tcttcctcaa atttggatct  1800
ggctatgtaa gtggctgggg aagagtcttc cacaaaggga gatcagcttt agttcttcag  1860
taccttagag ttccacttgt tgaccgagcc acatgtcttc gatctacaaa gttcaccatc  1920
tataacaaca tgttctgtgc tggcttccat gaaggaggta gagattcatg tcaaggagat  1980
agtgggggac cccatgttac tgaagtggaa gggaccagtt tcttaactgg aattattagc  2040
tggggtgaag agtgtgcaat gaaaggcaaa tatggaatat ataccaaggt atcccggtat  2100
gtcaactgga ttaaggaaaa aacaaagctc acttaatgac ctcgaggtgt gccttctagt  2160
tgccagccat ctgttgtttg cccctccccc gtgccttcct tgaccctgga aggtgccact  2220
cccactgtcc tttcctaata aaatgaggaa attgcatcgc attgtctgag taggtgtcat  2280
tctattctgg ggggtggggt ggggcaggac agcaaggggg aggattggga agacaatagc  2340
aggcatgctg gggatgcggt gggctctatg g                                    2371
```

```
SEQ ID NO: 14          moltype = DNA   length = 2918
FEATURE                Location/Qualifiers
source                 1..2918
                       mol_type = other DNA
                       note = APOE-AAT-hBGi-FIX WPRE3-bGH-polyA-DTS
                       organism = synthetic construct
SEQUENCE: 14
cgcgtctgca ggctcagagg cacacaggag tttctgggct caccctgccc ccttccaacc  60
cctcagttcc catcctccag cagctgtttg tgtgctgcct ctgaagtcca cactgaacaa  120
acttcagcct actcatgtcc ctaaaatggg caaacattgc aagcagcaaa cagcaaacac  180
acagccctcc ctgcctgctg accttggagc tggggcagag gtcagagacc tctctgggcc  240
catgccacct ccaacatcca ctcgacccct tggaatttcg gtggagagga gcagaggttg  300
tcctggcgtg gtttaggtag tgtgagaggg gtcgactgga cacaggacgc tgtggtttct  360
gagccagggg gcgactcaga tcccagccag tggacttagc ccctgtttgc tcctccgata  420
actggggtga ccttggttaa tattcaccag cagcctcccc cgttgcccct ctggatccac  480
tgcttaaata cggacgagga cagggccctg tctcctcagc ttcaggcacc accactgacc  540
tgggacagtg aatcgtaagt actagcagct acaatccagc taccattctg cttttatttt  600
atggttggga taaggctgga ttattctgag tccaagctag gcccttttgc taatcatgtt  660
catacctctt atcttcctcc cacagctcct gggcaacgtg ctggtctgtg tgctggccca  720
tcactttggc aaagaattgc gatcgccacc atgcagcgcg tgaacatgat catggcagaa  780
tcaccaggcc tcatcaccat ctgccttta ggatatctac tcagtgctga atgtacagtt  840
tttcttgatc atgaaaacgc caacaaaatt ctgaatcggc caaagaggta taattcaggt  900
aaattggaag agtttgttca agggaacctt gagagagaat gtatggaaga aaagtgtagt  960
tttgaagaag cacgagaagt ttttgaaaac actgaaagaa caactgaatt ttggaagcag  1020
tatgttgatg gagatcagtg tgagtccaat ccatgtttaa atggcggcag ttgcaaggat  1080
gacattaatt cctatgaatg ttggtgtccc tttggatttg aaggaaagaa ctgtgaatta  1140
gatgtaacat gtaacattaa gaatggcaga tgcgagcagt tttgtaaaaa tagtgctgat  1200
aacaaggtgg tttgctcctg tactgaggga tatcgacttg cagaaaacca gaagtcctgt  1260
gaaccagcag tgccatttcc atgtggaaga gtttctgttt cacaaacttc taagctcacc  1320
cgtgctgaga ctgtttttcc tgatgtggac tatgtaaatt ctactgaagc tgaaaccatt  1380
ttggataaca tcactcaaag cacccaatca tttaatgact tcactcgggt tgttggtgga  1440
gaagatgcca aaccaggtca attcccttgg caggttgttt tgaatggtaa agttgatgca  1500
ttctgtggag gctctatcgt taatgaaaaa tggattgtaa ctgctgccca ctgtgttgaa  1560
actggtgtta aaattacagt tgtcgcaggt gaacataata ttgaggagac agaacataca  1620
gagcaaaagc gaaatgtgat tcgaattatt cctcaccaca actacaatgc agctattaat  1680
aagtacaacc atgacattgc ccttctggaa ctggacgaac ccttagtgct aaacagctac  1740
gttacaccta tttgcattgc tgacaaggaa tacacgaaca tcttcctcaa atttggatct  1800
ggctatgtaa gtggctgggg aagagtcttc cacaaaggga gatcagcttt agttcttcag  1860
taccttagag ttccacttgt tgaccgagcc acatgtcttc gatctacaaa gttcaccatc  1920
tataacaaca tgttctgtgc tggcttccat gaaggaggta gagattcatg tcaaggagat  1980
agtgggggac cccatgttac tgaagtggaa gggaccagtt tcttaactgg aattattagc  2040
tggggtgaag agtgtgcaat gaaaggcaaa tatggaatat ataccaaggt atcccggtat  2100
gtcaactgga ttaaggaaaa aacaaagctc acttaatgac cctcgagaat caacctctgg  2160
attacaaaat ttgtgaaaga ttgactggta ttcttaacta tgttgctcct tttacgctat  2220
gtggatacgc tgctttaatg cctttgtatc atgctattgc ttcccgtatg gctttcattt  2280
tctcctcctt gtataaatcc tggttgctgt ctctttatga ggagttgtgg cccgttgtca  2340
ggcaacgtgg cgtggtgtgc actgtgtttg ctgacgcaac ccccactggt tggggcattg  2400
ccaccacctg tcagctcctt ccgggacttc tcgctttccc cctcccatt gccacggcgg  2460
aactcatcgc cgcctgcctt gcccgctgct ggacaggggc tcggctgttg ggcactgaca  2520
attccgtggt gtgtgccttc tagttgccag ccatctgttg tttgcccctc cccgtgcct  2580
tccttgaccc tggaaggtgc cactcccact gtccttcct aataaaatga ggaaattgca  2640
tcgcattgtc tgagtaggtg tcattctatt ctggggggtg gggtggggca ggacagcaag  2700
ggggaggatt gggaagacaa tagcaggcat gctggggatg cggtgggctc tatgggaaga  2760
tgtctactga gctgtgcgat ccctgctggg gactttccgc tggggacttt ccgctgggga  2820
```

```
ctttccgcct tcagctaagg aagctaccaa tatttagagg tacattttgt tctagaacaa  2880
aatgtaccgg tacattttgt tctggtacat tttgttct                          2918

SEQ ID NO: 15          moltype = DNA   length = 3236
FEATURE                Location/Qualifiers
source                 1..3236
                       mol_type = other DNA
                       note = ITR-APOE-AAT-hBGi-FIX-WPRE3-bGH-polyA-DTS-ITR
                       organism = synthetic construct
SEQUENCE: 15
cctgcaggca gctgcgcgct cgctcgctca ctgaggccgc ccgggcgtcg ggcgaccttt  60
ggtcgcccgg cctcagtgag cgagcgcgca gagagggagt ggccaactcc atcactaggg  120
gttcctgcgg ccgcacgcgt ctagttatta atagtaatcg aattcgcgtc tgcaggctca  180
gaggcacaca ggagtttctg ggctcaccct gcccctcc aacccctcag ttcccatcct    240
ccagcagctg tttgtgtgct gcctctgaag tccacactga acaaacttca gcctactcat  300
gtccctaaaa tgggcaaaca ttgcaagcag caaacagcaa acacacagcc ctccctgcct  360
gctgaccttg gagctggggc agaggtcaga gacctctctg ggcccatgcc acctccaaca  420
tccactcgac cccttggaat ttcggtggag aggagcagag gttgtcctgg cgtggtttag  480
gtagtgtgag aggggtcgac tggacacagg acgctgtggt ttctgagcca gggggcgact  540
cagatcccag ccagtggact tagcccctgt ttgctcctcc gataactggg gtgaccttgg  600
ttaatattca ccagcagcct cccccgttgc ccctctggat ccactgctta aatacggacg  660
aggacagggc cctgtctcct cagcttcagg caccaccact gacctgggac agtgaatcgt  720
aagtactagc agctacaatc cagctaccat tctgctttta ttttatggtt gggataaggc  780
tggattattc tgagtccaag ctaggccctt ttgctaatca tgttcatacc tcttatcttc  840
ctcccacagc tcctgggcaa cgtgctggtc tgtgtgctgg cccatcactt ggcaaagaa   900
ttgcgatcgc caccatgcag cgcgtgaaca tgatcatggc agaatcacca ggcctcatca  960
ccatctgcct tttaggatat ctactcagtg ctgaatgtac agtttttctt gatcatgaaa  1020
acgccaacaa aattctgaat cggccaaaga ggtataattc aggtaaattg gaagagtttg  1080
ttcaagggaa ccttgagaga gaatgtatgg aagaaaagtg tagttttgaa gaagcacgag  1140
aagtttttga aaacactgaa agaacaactg aattttgaca gcagtatgtt gatggagatc  1200
agtgtgagtc caatccatgt ttaaatggcg gcagttgcaa ggatgacatt aattcctatg  1260
aatgttggtg tcccttggaa tttgaaggaa agaactgtga attagatgta acatgtaaca  1320
ttaagaatgg cagatgcgag cagttttgta aaaatagtgc tgataacaag gtggtttgct  1380
cctgtactga gggatatcga cttgcagaaa accagaagtc ctgtgaacca gcagtgccat  1440
ttccatgtgg aagagtttct gtttcacaaa cttctaagct caccgtgct gagactgttt   1500
ttcctgatgt ggactatgta aattctactg aagctgaaac cattttggat aacatcactc  1560
aaagcaccca atcatttaat gacttcactc gggttgttgg tggagaagat gccaaaccag  1620
gtcaattccc ttggcaggtt gttttgaatg gtaaagttga tgcattctgt ggaggctcta  1680
tcgttaatga aaaatggatt gtaactgctg cccactgtgt tgaaactggt gttaaaatta  1740
cagttgtcgc aggtgaacat aatattgagg acagaacaca tacagagcaa aagcgaaatg  1800
tgattcgaat tattcctcac cacaactaca atgcagctat taataagtac aaccatgaca  1860
ttgcccttct ggaactggac gaacccttag tgctaaacag ctacgttaca cctatttgca  1920
ttgctgacaa ggaatacacg aacatcttcc tcaaatttga atctggctat gtaagtgatg  1980
ggggaagagt cttccacaaa gggagatcag ctttagttct tcagtacctt agagttccac  2040
ttgttgaccg agccacatgt cttcgatcta caaagttcac catctataac aacatgttct  2100
gtgctggctt ccatgaagga ggtagagatt catgtcaagg agatagtggg ggaccccatg  2160
ttactgaagt ggaagggacc agtttcttaa ctggaattat tagctgggtg gaagagtgtg  2220
caatgaaagg caaatatgga atatatacca aggtatcccg gtatgtcaac tggattaagg  2280
aaaaaacaaa gctcacttaa tgaccctcga gaatcaacct ctggattaca aaatttgtga  2340
aagattgact ggtattctta actatgttgc tccttttacg ctatgtggat acgctgcttt  2400
aatgcctttg tatcatgcta ttgcttcccg tatggctttc attttctcct ccttgtataa  2460
atcctggttg ctgtctcttt atgaggagtt gtggcccgtt gtcaggcaac gtggcgtggt  2520
gtgcactgtg tttgctgacg caaccccac tggttggggc attgccacca cctgtcagct   2580
cctttccggg actttcgctt tccccctccc tattgccacg cggaactca tcgccgcctg    2640
ccttgcccgc tgctggacag gggctcggct gttgggcact gacaattccg tggggtgtgc  2700
cttctagttg ccagccatct gttgtttgcc cctcccccgt gccttccttg accctggaag  2760
gtgccactcc cactgtcctt tcctaataaa atgaggaaat tgcatcgcat tgtctgagta  2820
ggtgtcattc tattctgggg ggtggggtgg gcaggacag caaggggag dattgggaag     2880
acaatagcag gcatgctggg gatgcggtgg gctctatggg cacgtgcgga gctgtgcgat  2940
ccctgctggg gacttccgc tgggggacttt ccgctgggga cctttccgcc tcagctaagg  3000
aagctaccaa tatttagagg tacattttgt tctagaacaa aatgtaccgg tacattttgt  3060
tctggtacat tttgttctat cgatcgacgc gccgcaggaa ccctagtga tggagttggc    3120
cactccctct ctgcgcgctc gctcgctcac tgaggccggg cgaccaaagg tcgcccgacg  3180
cccgggcttt gcccgggcgg cctcagtgag cgagcgagcg cgcagctgcc tgcagg        3236

SEQ ID NO: 16          moltype = DNA   length = 5955
FEATURE                Location/Qualifiers
source                 1..5955
                       mol_type = other DNA
                       note = APOE-AAT-hBGi-FVIII-v3- bGH-polyA
                       organism = synthetic construct
SEQUENCE: 16
cgcgtctgca ggctcagagg cacacaggag tttctgggct caccctgccc ccttccaacc  60
cctcagttcc catcctccag cagctgtttg tgtgcctgcct ctgaagtcca cactgaacaa  120
acttcagcct actcatgtcc ctaaaatggg caaacattgc aagcagcaaa cagcaaacac  180
acagccctcc ctgcctgctg accttggagc tggggcagag gtcagagacc tctctgggcc  240
catgccacct ccaacatcca ctcgaccct tggaatttcg gtggagagga gcagaggttg    300
tcctggcgtg gtttaggtag tgtgagaggg gtcgactgga cacaggacgc tgtggtttct  360
gagccagggg gcgactcaga tcccagccag tggacttagc cctgtttgc tcctccgata   420
```

-continued

```
actggggtga ccttggttaa tattcaccag cagcctcccc cgttgccccct ctggatccac   480
tgcttaaata cggacgagga cagggccctg tctcctcagc ttcaggcacc accactgacc   540
tgggacagtg aatcgtaagt actagcagct acaatccagc taccattctg ctttttatttt  600
atggttggga taaggctgga ttattctgag tccaagctag gcccttttgc taatcatgtt   660
catacctctt atcttcctcc cacagctcct gggcaacgtg ctggtctgtg tgctggccca   720
tcactttggc aaagaattgc gatcgccacc atgcagattg agctgagcac ctgcttcttc   780
ctgtgcctgc tgaggttctg cttctctgcc accaggagat actacctggg ggctgtggag   840
ctgagctggg actacatgca gtctgacctg ggggagctgc ctgtggatgc caggttcccc   900
cccagagtgc ccaagagctt cccccttcaac acctctgtgg tgtacaagaa gaccctgttt   960
gtggagttca ctgaccacct gttcaacatt gccaagccca ggcccccctg gatgggcctg  1020
ctgggcccca ccatccaggc tgaggtgtat gacactgtgg tgatcaccct gaagaacatg  1080
gccagccacc ctgtgagcct gcatgctgtg ggggtgagct actggaaggc ctctgagggg  1140
gctgagtatg atgaccagac cagccagagg gagaaggagg atgacaaggt gttccctggg  1200
ggcagccaca cctatgtgtg gcaggtgctg aaggagaatg gccccatggc ctctgacccc  1260
ctgtgcctga cctacagcta cctgagccat gtggacctgg tgaaggacct gaactctggc  1320
ctgattgggg ccctgctggt gtgcagggag ggcagcctgg ccaaggagaa gacccagacc  1380
ctgcacaagt tcatcctgct gtttgctgtg tttgatgagg gcaagagctg gcactctgaa  1440
accaagaaca gcctgatgca ggacaaggat gctgcctctg ccagggcctg gcccaagatg  1500
cacactgtga atggctatgt gaacaggagc ctgcctggcc tgattggctg ccacaggaag  1560
tctgtgtact ggcatgtgat tggcatgggc accaccccctg aggtgcacag catcttcctg  1620
gagggccaca ccttcctggt caggaaccac aggcaggcca gcctggagat cagccccatc  1680
accttcctga ctgcccagac cctgctgatg gacctgggcc agttcctgct gttctgccac  1740
atcagcagcc accagcatga tggcatggag gcctatgtga aggtggacag ctgcctgag  1800
gagccccagc tgaggatgaa gaacaatgag gaggctgagg actatgatga tgacctgact  1860
gactctgaga tggatgtggt gaggtttgat gatgacaaca gccccagctt catccagatc  1920
aggtctgtgg ccaagaagca ccccaagacc tgggtgcact acattgctgc tgaggaggag  1980
gactgggact atgcccccct ggtgctggcc cctgatgaca ggagctacaa gagccagtac  2040
ctgaacaatg gcccccagag gattggcagg aagtacaaga aggtcaggtt catggcctac  2100
actgatgaaa ccttcaagac cagggaggcc atccagcatg agtctggcat cctgggcccc  2160
ctgctgtatg gggaggtggg ggacaccctg ctgatcatct tcaagaacca ggccagcagg  2220
ccctacaaca tctaccccca tggcatcact gatgtgaggc ccctgtacag caggaggctg  2280
cccaaggggg tgaagcacct gaaggacttc cccatcctgc ctggggagat cttcaagtac  2340
aagtggactg tgactgtgga ggatggcccc accaagtctg accccaggtg cctgaccaga  2400
tactacagca gctttgtgaa catggagagg gacctggcct ctggcctgat tggccccctg  2460
ctgatctgct acaaggagtc tgtggaccag aggggcaacc agatcatgtc tgacaagagg  2520
aatgtgatcc tgttctctgt gtttgatgag aacaggagct ggtacctgac tgagaacatc  2580
cagaggttcc tgcccaaccc tgctggggtg cagctggagg accctgagtt ccaggccagc  2640
aacatcatgc acagcatcaa tggctatgtg tttgacagcc tgcagctgtc tgtgtgcctg  2700
catgaggtgg cctactggta catcctgagc attggggccc agactgactt cctgtctgtg  2760
ttcttctctg gctacacctt caagcacaag atggtgtatg aggacaccct gacccctgttc  2820
cccttctctg gggagactgt gttcatgagc atggagaacc ctggcctgtg gattctgggc  2880
tgccacaact ctgacttcag gaacagggtc atgactgccc tgctgaaagt ctccagctgt  2940
gacaagaaca ctggggacta ctatgaggac agctatgagg acatctctgc ctacctgctg  3000
agcaagaaca atgccattga gcccaggagc ttcagccaga atgccactaa tgtgtctaac  3060
aacagcaaca ccagcaatga cagcaatgtg tctcccccag tgctgaagag gcaccagagg  3120
gagatcacca ggaccaccct gcagtctgac caggaggaga ttgactatga tgacaccatc  3180
tctgtggaga tgaagaagga ggactttgac atctacgacg aggacgaaaa ccagagcccc  3240
aggagcttcc agaagaagac caggcactac ttcattgctg ctgtggagag gctgtgggac  3300
tatggcatga gcagcagccc ccatgtgctg aggaacaggg cccagtctgg ctctgtgccc  3360
cagttcaaga aggtggtgtt ccaggagttc actgatggca gcttcaccca gccccctgtac  3420
agaggggagc tgaatgagca cctgggcctg ctgggcccct acatcagggc tgaggtggag  3480
gacaacatca tggtgacctt caggaaccag gccagcaggc cctacagctt ctacagcagc  3540
ctgatcagct atgaggagga ccagaggcag ggggctgagc caggaagaa ctttgtgaag  3600
cccaatgaaa ccaagaccta cttctggaag gtgcagcacc acatggcccc caccaaggat  3660
gagtttgact gcaaggcctg ggcctacttc tctgatgtgg acctggagga ggatgtgcac  3720
tctggcctga ttggcccccct gctggtgtgc cacaccaaca ccctgaaccc tgcccatgac  3780
aggcaggtga ctgtgcagga gtttgccctg ttcttcacca tctttgatga aaccaagagc  3840
tggtacttca ctgagaacat ggagaggaac tgcagggccc cctgcaacat ccagatggag  3900
gaccccaacct tcaaggagaa ctacaggttc catgccatca atggctacat catggacacc  3960
ctgcctggcc tggtgatggc ccaggaccag aggatcaggt ggtacctgct gagcatgggc  4020
agcaatgaga acatccacag catccacttc tctggccatg tgttcactgt gaggaagaag  4080
gaggagtaca gatggccct gtacaacctg taccctgggg tgtttgagac tgtggagatg  4140
ctgcccagca aggctggcat ctggaggggtg gagtgcctga ttggggagca cctgcatgct  4200
ggcatgagca ccctgttcct ggtgtacagc aacaagtgcc agacccccctg tgtctgtgtg  4260
tctggccaca tcaggggactt ccagatcact gcctctggcc agtatggcca gtgggcccc  4320
aagctggcca ggctgcacta ctctggcagc atcaatgcct ggagcaccaa ggagcccttc  4380
agctggatca aggtggacct gctggccccc atgatcatcc atggcatcaa gacccagggg  4440
gccaggcaga agttcagcag cctgtacatc agccagttca tcatcatgta cagcctggat  4500
ggcaagaagt ggcagaccta caggggcaac agcactggca ccctgatggt gttctttggg  4560
aatgtggaca gctctggcat caagcacaac atcttcaacc ccccatcat tgccagatac  4620
atcaggctgc accccacca ctacagcatc aggagcaccc tgaggatgga gctgatgggc  4680
tgtgacctga acagctgcag catgcccctg ggcatggaga gcaaggccat ctctgatgcc  4740
cagatcactg ccagcagcta cttcaccaac atgtttgcca cctggagccc cagcaaggcc  4800
aggctgcacc tgcagggagca gagcaatgcc tggaggcccca ggtcaacaa ccccaaggag  4860
tggctgcagg tggacttcca gaagaccatg aaggtgactg gggtgaccac caggggggtg  4920
aagagcctgc tgaccagcat gtatgtgaag gagttcctga tcagcagcag ccaggatggc  4980
caccagtgga cccctgttctt ccagaatggc aaggtgaagg tgttccaggg caaccaggac  5040
agcttcaccc ctgtggtgaa cagcctggac cccccccctgc tgaccagata cctgaggatt  5100
cacccccaga gctgggtgca ccagattgcc ctgaggatgg aggtgctggg ctgtgaggcc  5160
```

-continued

```
caggacctgt actgataact cgagaatcaa cctctggatt acaaaatttg tgaaagattg  5220
actggtattc ttaactatgt tgctcctttt acgctatgtg gatacgctgc tttaatgcct  5280
ttgtatcatg ctattgcttc ccgtatggct ttcattttct cctccttgta taaatcctgg  5340
ttgctgtctc tttatgagga gttgtggccc gttgtcaggc aacgtggcgt ggtgtgcact  5400
gtgtttgctg acgcaacccc cactggttgg ggcattgcca ccacctgtca gctcctttcc  5460
gggactttcg ctttccccct ccctattgcc acggcggaac tcatcgccgc ctgccttgcc  5520
cgctgctgga caggggctcg gctgttgggc actgacaatt ccgtggggtg tgccttctag  5580
ttgccagcca tctgttgttt gcccctcccc cgtgccttcc ttgaccctgg aaggtgccac  5640
tcccactgtc ctttcctaat aaaatgagga aattgcatcg cattgtctga gtaggtgtca  5700
ttctattctg gggggtgggg tggggcagga cagcaagggg gaggattggg aagacaatag  5760
caggcatgct ggggatgcgg tgggctctat gggaagatgt ctactgagct gtgcgatccc  5820
tgctggggac tttccgctgg ggactttccg ctggggactt tccgccttca gctaaggaag  5880
ctaccaatat ttagaggtac attttgttct agaacaaaat gtaccggtac attttgttct  5940
ggtacatttt gttct                                                    5955
```

SEQ ID NO: 17               moltype = DNA   length = 5955
FEATURE                     Location/Qualifiers
source                      1..5955
                            mol_type = other DNA
                            note = APOE-AAT-hBGi-FVIII-v3-WPRE3- bGH-polyA-DTS
                            organism = synthetic construct
SEQUENCE: 17

```
cgcgtctgca ggctcagagg cacacaggag tttctgggct caccctgccc ccttccaacc  60
cctcagttcc catcctccag cagctgtttg tgtgctgcct ctgaagtcca cactgaacaa  120
acttcagcct actcatgtcc ctaaaatggg caaacattgc aagcagcaaa cagcaaacac  180
acagccctcc ctgcctgctg accttggagc tggggcagga gtcagagacc tctctgggcc  240
catgccacct ccaacatcca ctcgacccct tggaatttcg gtggagagga gcagaggttg  300
tcctggcgtg gtttaggtag tgtgagaggg gtcgactgga cacaggacgc tgtggtttct  360
gagccagggg gcgactcaga tcccagccag tggacttagc ccctgtttgc tcctccgata  420
actggggtga ccttggttaa tattcaccag cagcctcccc cgttgcccct ctggatccac  480
tgcttaaata cggacgagga cagggccctg tctcctcagc ttcaggcacc accactgacc  540
tgggacagtg aatcgtaagt actagcagct caaatccagc taccattctg cttttatttt  600
atggttggga taaggctgga ttattctgag tccaagctag gcccttttgc taatcatgtt  660
catacctctt atcttcctcc cacagctcct gggcaacgtg ctggtctgtg tgctggccac  720
tcactttggc aaagaattgc gatcgccacc atgcagattc agctgagcac ctgcttcttc  780
ctgtgcctgc tgaggttctg cttctctgcc accaggagat actacctggg ggctgtggag  840
ctgagctggg actacatgca gtctgacctg ggggagctgc ctgtggatgc caggttcccc  900
cccagagtgc ccaagagctt cccccttcaac acctctgtgt gtacaagaa gaccctgttt  960
gtggagttca ctgaccacct gttcaacatt gccaagccca ggccccctg gatgggcctc  1020
ctgggcccca ccatccaggc tgaggtgtat gacactgtgg tgatcaccct gaagaacatg  1080
gccagccacc ctgtgagcct gcatgctgtg ggggtgagct actggaaggc ctctgagggg  1140
gctgagtatg atgaccagac cagccagagg gagaaggagg atgacaaggt gttccctggg  1200
ggcagccaca cctatgtgtg gcaggtgctg aaggagaatg gccccatggc ctctgacccc  1260
ctgtgcctga cctacagcta cctgagccat gtggacctgg tgaaggacct gaactctggc  1320
ctgattgggg ccctgctggt gtgcagggag ggcagcctgg ccaaggagaa gacccagacc  1380
ctgcacaagt tcatcctgct gtttgctgtg tttgatgagg gcaagagctg gcactctgaa  1440
accaagaaca gcctgatgca ggacagggat gctgcctctg cccaggatg  1500
cacactgtga atggctatgt gaacaggagc ctgcctggcc tgattggctg ccacaggaag  1560
tctgtgtact ggcatgtgat tggcatgggc accacccctg aggtgcacag catcttcctg  1620
gagggccaca ccttcctggt caggaaccac aggcaggcca gcctggagat cagccccatc  1680
accttcctga ctgcccagac cctgctgatg gacctggggc agttcctgct gttctgccac  1740
atcagcagcc accagcatga tggcatggag gcctatgtga aggtggacag ctgccctgag  1800
gagccccagc tgaggatgaa gaacaatgag gaggtgagg actatgatga tgacctgact  1860
gactctgaga tggatgtggt gaggtttgat gatgacaaca gccccagctt catccagatc  1920
aggtctgtgg ccaagaagca ccccaagacc tgggtgcact acattgctgc tgaggaggag  1980
gactgggact atgcccccct ggtgctggcc cctgatgaca ggagctacaa gagccagtac  2040
ctgaacaatg gccccagag gattggcagg aagtacaaga aggtcaggt catggcctac  2100
actgatgaaa ccttcaagac cagggaggcc atccagcatg agtctggcat cctgggcccc  2160
ctgctgtatg gggaggtggg ggacacectg ctgatcatct tcaagaacca ggccagcagg  2220
ccctacaaca tctacccca tggcatcact gatgtgaggc ccctgtacag caggaggctg  2280
cccaaggggg tgaagcacct gaaggacttc cccatcctgc ctggggagat cttcaagtac  2340
aagtggactg tgactgtgga ggatggcccc accaagtctg accccaggtg cctgaccaga  2400
tactacagca gctttgtgaa catggagagg gacctggcct ctggcctgat ggcccccctg  2460
ctgatctgct acaaggagtc tgtggaccag aggggcaacc agatcatgtc tgacaagagg  2520
aatgtgatcc tgttctctgt gtttgatgag aacaggagct ggtacctgac tgagaacatc  2580
cagaggttcc tgcccaaccc tgctggggtg cagctggagg accctgagtt ccaggccagc  2640
aacatcatgc acagcatcaa tggctatgtg tttgacagcc tgcagctgtc tgtgtgcctg  2700
catgaggtgg cctactggta catcctgagc attggggccc agactgactt cctgtctgtg  2760
ttcttctctg gctacacctt caagcacaag atggtgtatg aggacacect gaccctgttc  2820
ccettctctg gggagactgt gttcatgagc atggagaacc ctggcctgtg gattctgggc  2880
tgccacaact ctgacttcag gaacagggc atgactgccc tgctgaaagt ctccagctgt  2940
gacaagaaca ctgggggacta ctatgaggac agctatgagg acatctctgc ctacctgctg  3000
agcaagaaca tgccattga gcccaggagc ttcagccaga atgccactaa tgtgtctaac  3060
aacagcaaca cagcaaatga cagcaatgtg tctcccccag tgctgaaga gcaccagagg  3120
gagatcacca ggaccaccct gcagtctgac caggaggga ttgactatga tgacaccatc  3180
tctgtggaga tgaagaagga ggactttgac atctacgacg aggacgagaa ccagagcccc  3240
aggagcttcc agaagaagac caggcactac ttcattgctg ctgtggagag gctgtgggac  3300
tatgGCatga gcagcagccc ccatgtgctg aggaacaggg cccagtctgg ctctgtgccc  3360
cagttcaaga aggtggtgtt ccaggagttc actgatggca gcttcaccca gcccctgtac  3420
```

```
agaggggagc tgaatgagca cctgggcctg ctgggcccct acatcagggc tgaggtggag   3480
gacaacatca tggtgacctt caggaaccag gccagcaggc cctacagctt ctacagcagc   3540
ctgatcagct atgaggagga ccagaggcag ggggctgagc ccaggaagaa ctttgtgaag   3600
cccaatgaaa ccaagaccta cttctggaag gtgcagcacc acatggcccc caccaaggat   3660
gagtttgact gcaaggcctg ggcctacttc tctgatgtgg acctggagaa ggatgtgcac   3720
tctggcctga ttggcccccct gctggtgtgc cacaccaaca ccctgaaccc tgcccatggc   3780
aggcaggtga ctgtgcagga gtttgccctg ttcttcacca tctttgatga aaccaagagc   3840
tggtacttca ctgagaacat ggagaggaac tgcagggccc cctgcaacat ccagatggag   3900
gaccccacct tcaaggagaa ctacaggttc catgccatca atggctacat catggacacc   3960
ctgcctggcc tggtgatggc ccaggaccag aggatcaggt ggtacctgct gagcatgggc   4020
agcaatgaga acatccacag catccacttc tctggccatg tgttcactgt gaggaagaag   4080
gaggagtaca agatggccct gtacaacctg taccctgggg tgtttgagac tgtggagatg   4140
ctgcccagca aggctggcat ctggagggtg gagtgcctga ttggggagca cctgcatgct   4200
ggcatgagca ccctgttcct ggtgtacagc aacaagtgcc agacccccct gggcatggcc   4260
tctggccaca tcagggactt ccagatcact gcctctggcc agtatggcca gtgggccccc   4320
aagctggcca ggctgcacta ctctggcagc atcaatgcct ggagcaccaa ggagcccttc   4380
agctggatca aggtggacct gctggccccc atgatcatcc atggcatcaa gacccagggg   4440
gccaggcaga agttcagcag cctgtacatc agccagttca tcatcatgta cagcctggat   4500
ggcaagaagt ggcagaccta caggggcaac agcactggca ccctgatggt gttctttggc   4560
aatgtggaca gctctggcat caagcacaac atcttcaacc cccccatcat tgccagatac   4620
atcaggctgc accccaccca ctacagcatc aggagcaccc tgaggatgga gctgatgggc   4680
tgtgacctga acagctgcag catgcccctg ggcatggagg gcaaggccat ctctgatgcc   4740
cagatcactg ccagcagcta cttcaccaac atgtttgcca cctggagccc cagcaaggcc   4800
aggctgcacc tgcagggcag gagcaatgcc tggaggcccc aggtcaacaa ccccaaggag   4860
tggctgcagg tggacttcca gaagaccatg aaggtgactg gggtgaccac ccagggggtg   4920
aagagcctgc tgaccagcat gtatgtgaag gagttcctga tcagcagcac ccaggatggc   4980
caccagtgga cccctgttct tccagaatggc aaggtgaagg tgttccaggg caaccaggac   5040
agcttcaccc ctgtggtgaa cagcctggac ccccccctgc tgaccagata cctgaggatt   5100
caccccccaga gctgggtgca ccagattgcc ctgaggatgg aggtgctggg ctgtgaggcc   5160
caggacctgt actgataact cgagaatcaa cctctggatt acaaaatttg tgaaagattg   5220
actggtattc ttaactatgt tgctcctttt acgctatgtg gatacgctgc tttaatgcct   5280
ttgtatcatg ctattgcttc ccgtatggct ttcattttct cctccttgta taaatcctgg   5340
ttgctgtctc tttatgagga gttgtggccc gttgtcaggc aacgtggcgt ggtgtgcact   5400
gtgtttgctg acgcaacccc cactggttgg ggcattgcca ccacctgtca gctccttttcc   5460
gggactttcg ctttccccct ccctattgcc acggcggaac tcatcgccgc ctgccttgcc   5520
cgctgctgga caggggctcg gctgttgggc actgacaatt ccgtggggtg tgccttctag   5580
ttgccagcca tctgttgttt gcccctcccc cgtgccttcc ttgaccctgg aaggtgccac   5640
tcccactgtc ctttcctaat aaaatgagga aattgcatcg cattgtctga gtaggtgtca   5700
ttctattctg gggggtgggg tggggcagga gcagcaagtg ggggaggatt ggg aagacaatag  5760
caggcatgct ggggatgcgg tgggctctat gggaagatgt ctactgagct gtgcgatccc   5820
tgctggggac tttccgctgg gactttccg ctggggactt ccgccttca gctaaggaag   5880
ctaccaatat ttagaggtac attttgttct agaacaaaat gtaccggtac attttgttct   5940
ggtacatttt gttct                                                    5955
```

```
SEQ ID NO: 18              moltype = DNA  length = 2918
FEATURE                    Location/Qualifiers
source                     1..2918
                           mol_type = other DNA
                           note = APOE-AAT-hBGi-FIX-WPRE3- bGH-polyA DTS
                           organism = synthetic construct
SEQUENCE: 18
cgcgtctgca ggctcagagg cacacaggag tttctgggct caccctgccc ccttccaacc   60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagga gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga caggccctg tctcctcagc ttcaggcacc accactgacc   540
tgggacagtg aatcgtaagt actagcagct acaatccagc taccattctg cttttatttt   600
atggttggga taaggctgga ttattctgag tccaagctag gcccttttgc taatcatgtt   660
catacctctt atcttcctcc cacagctcct gggcaacgtg ctggtctgtg tgctggccca   720
tcactttggc aaagaattgc gatcgccacc atgcagcgcg tgaacatgat catcaggtg   780
tcaccaggcc tcatcaccat ctgccttttat ggatatctac tcagtgctga atgtacagtt   840
tttcttgatc atgaaaacgc caacaaaatt ctgaatcggc caaagaggta taattcaggt   900
aaattggaag agtttgttca agggaacctt gagagagaat gtatggaaga aaagtgtagt   960
tttgaagaag cacgagaagt ttttgaaaac actgaaagaa caactgaatt ttggaagcag   1020
tatgttgatg gagatcagtg tgagtccaat ccatgtttaa atggcggcag ttgcaaggat   1080
gacattaatt cctatgaatg ttggtgtccc tttggatttg aaggaaagaa ctgtgaatta   1140
gatgtaacat gtaacattaa gaatggcaga tgcgagcagt tttgtaaaaa tagtgctgat   1200
aacaaggtgg tttgctcctg tactgaggga tatcgacttg cagaaaacca gaagtcctgt   1260
gaaccagcag tgccattttcc atgtggaaga gtttctgttt cacaaacttc taagctcacc   1320
cgtgctgaga ctgtttttcc tgatgtggac tatgtaaatt ctactgaagc tgaaaccatt   1380
ttggataaca tcactcaaag cacccaatca tttaatgact tcactcgggt tgttggtgga   1440
gaagatgcca aaccaggtca attcccttgg caggttgttt tgaatggtaa agttgatgca   1500
ttctgtggag ctctatcgt taatgaaaaa tggattgtaa ctgctgccca ctgtgttgaa   1560
actggtgtta aaattacagt tgtcgcaggt gaacataata ttgaggagac agaacataca   1620
gagcaaaagc gaaatgtgat tcgaattatt cctcaccaca actacaatgc agctattaat   1680
```

-continued

```
aagtacaacc atgacattgc ccttctggaa ctggacgaac ccttagtgct aaacagctac   1740
gttacaccta tttgcattgc tgacaaggaa tacacgaaca tcttcctcaa atttggatct   1800
ggctatgtaa gtggctgggg aagagtcttc cacaaaggga gatcagcttt agttcttcag   1860
taccttagag ttccacttgt tgaccgagcc acatgtcttc gatctacaaa gttcaccatc   1920
tataacaaca tgttctgtgc tggcttccat gaaggaggta gagattcatg tcaaggagat   1980
agtgggggac cccatgttac tgaagtggaa gggaccagtt tcttaactgg aattattagc   2040
tggggtgaag agtgtgcaat gaaaggcaaa tatggaatat ataccaaggt atcccggtat   2100
gtcaactgga ttaaggaaaa aacaaagctc acttaatgac cctcgagaat caacctctgg   2160
attacaaaat ttgtgaaaga ttgactggta ttcttaacta tgttgctcct tttacgctat   2220
gtggatacgc tgctttaatg cctttgtatc atgctattgc ttcccgtatg gctttcattt   2280
tctcctcctt gtataaatcc tggttgctgt ctctttatga ggagttgtgg cccgttgtca   2340
ggcaacgtgg cgtggtgtgc actgtgtttg ctgacgcaac ccccactggt tggggcattg   2400
ccaccacctg tcagctcctt tccgggactt tcgctttccc cctccctatt gccacggcgg   2460
aactcatcgc cgcctgcctt gcccgctgct ggacaggggc tcggctgttg ggcactgaca   2520
attccgtggg gtgtgccttc tagttgccag ccatctgttg tttgccctc ccccgtgcct   2580
tccttgaccc tggaaggtgc cactcccact gtcctttcct aataaaatga ggaaattgca   2640
tcgcattgtc tgagtaggtg tcattctatt ctggggggtg gggtggggca ggacagcaag   2700
ggggaggatt gggaagacaa tagcaggcat gctgggggatg gctgggggctc tatgggaaga   2760
tgtctactga gctgtgcgat ccctgctggg gactttccgc tggggacttt ccgctgggga   2820
ctttccgcct tcagctaagg aagctaccaa tatttagagg tacattttgt tctagaacaa   2880
aatgtaccgg tacattttgt tctggtacat tttgttct                           2918
```

SEQ ID NO: 19          moltype = DNA  length = 5175
FEATURE                Location/Qualifiers
source                 1..5175
                       mol_type = other DNA
                       note = APOE-AAT-hbGi-FVIIIv3-
                       organism = synthetic construct
SEQUENCE: 19

```
cgcgtctgca ggctcagagg cacacaggag tttctgggct caccctgccc ccttccaacc   60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga cagggccctg tctcctcagc ttcaggcacc accactgacc   540
tgggacagtg aatcgtaagt actagcagct acaatccagc taccattctg ctttttatttt   600
atggttggga taaggctgga ttattctgag tccaagctag gccctttttgc taatcatgtt   660
catacctctt atcttcctcc cacagctcct gggcaacgtg ctggtctgtg tgctggccca   720
tcactttggc aaagaattgc gatcgccacc atgcagattg agctgagcac ctgcttcttc   780
ctgtgcctgc tgaggttctg cttctctgcc accaggagat actacctggg ggctgtggag   840
ctgagctggg actacatgca gtctgacctg ggggagctgc ctgtggatgc caggttcccc   900
cccagagtgc ccaagagctt ccccttcaac acctctgtgg tgtacaagaa gaccctgttt   960
gtggagttca ctgaccacct gttcaacatt gccaagccca ggcccccctg gatgggcctg   1020
ctgggcccca ccatccaggc tgaggtgtat gacactgtgg tgatcaccct gaagaacatg   1080
gccagccacc ctgtgagcct gcatgctgtg ggggtgagct actggaaggc ctctgagggg   1140
gctgagtatg atgaccagac cagccagagg gagaaggagg atgacaaggt gttccctggg   1200
ggcagccaca cctatgtgtg gcaggtgctg aaggagaatg gccccatggc ctctgacccc   1260
ctgtgcctga cctacagcta cctgagccat gtggacctgg tgaaggacct gaactctgac   1320
ctgattgggg ccctgctggt gtgcaggag ggcagcctgg ccaaggagaa gacccagacc   1380
ctgcacaagt catcctgct gtttgctgtg tttgatgagg gcaagagctg gcactctgaa   1440
accaagaaca gcctgatgca ggacagggat gctgcctctg ccaggggcctg gcccaagatg   1500
cacactgtga atggctatgt gaacaggagc ctgcctggcc tgattggctg ccacaggaag   1560
tctgtgtact ggcatgtgat tggcatgggc accacccctg aggtgcacag catcttcctg   1620
gagggccaca ccttcctggt caggaaccac aggcaggcca gctggagat cagccccatc   1680
accttcctga ctgcccagac cctgctgatg gacctgggc agttcctgct gttctgccac   1740
atcagcagcc accagcatga tggcatggag gcctatgtga aggtggacag ctgccctgag   1800
gagcccagc tgaggatgaa gaacaatgag gaggctgagg actatgatga tgacctgact   1860
gactctgaga tggatgtggt gaggtttgat gatgacaaca gccccagctt catccagatc   1920
aggtctgtgg ccaagaagca ccccaagacc tgggtgcact acattgctgc tgaggaggag   1980
gactgggact atgcccccct ggtgctgcc cctgatgaca ggagctacaa gagccagtac   2040
ctgaacaatg gcccccagag gattggcagg aagtacaagg aagttcaggtt catggcctac   2100
actgatgaaa ccttcaagac cagggaggcc atccagcatg agtctggcat cctgggcccc   2160
ctgctgtatg gggaggtggg ggacaccctg ctgatcatct tcaagaacca ggccagcagg   2220
ccctacaaca tctaccccca tggcatcact gatgtgaggc ccctgtacag caggaggctg   2280
cccaaggggg tgaagcacct gaaggacttc cccatcctgc ctgggggagat cttcaagtac   2340
aagtggactg tgactgtgga ggatggcccc accaagtctg aacccaggtg cctgaccaga   2400
tactacagca gctttgtgaa catggagagg gacctggcct ctggcctgat ggcccccctg   2460
ctgatctgct acaaggagtc tgtggaccag aggggcaacc agatcatgtc tgacaagagg   2520
aatgtgatcc tgttctctgt gtttgatgag aacaggagct ggtacctgac tgagaacatc   2580
cagaggttcc tgcccaaccc tgctggggtg cagctggagg acccctgagtt ccaggccagc   2640
aacatcatgc acagcatcaa tggctatgtg tttgacagcc tgcagctgtc tgtgtgcctg   2700
catgaggtgg cctactggta tatcctgagc attggggccc agactgactt cctgtctgtg   2760
ttcttctctg gctacacctt caagcacaag atggtgtatg aggaccaccct gaccctgttc   2820
cccttctctg gggagactgt gttcatgagc atggagaacc ctggcctgtg gattctgggc   2880
tgccacaact ctgacttcag gaacagggc atgactgccc tgctgaaagt ctccagctgt   2940
gacaagaaca ctgggggacta ctatgaggac agctatgagg acatctctgc ctacctgctg   3000
```

-continued

```
agcaagaaca atgccattga gcccaggagc ttcagccaga atgccactaa tgtgtctaac    3060
aacagcaaca ccagcaatga cagcaatgtg tctcccccag tgctgaagag gcaccagagg    3120
gagatcacca ggaccaccct gcagtctgac caggaggaga ttgactatga tgacaccatc    3180
tctgtggaga tgaagaagga ggactttgac atctacgacg aggacgagaa ccagagcccc    3240
aggagcttcc agaagaagac caggcactac ttcattgctg ctgtggagag gctgtgggac    3300
tatggcatga gcagcagccc ccatgtgctg aggaacaggg cccagtctgg ctctgtgccc    3360
cagttcaaga aggtggtgtt ccaggagttc actgatggca gcttcaccca gccctgtac    3420
agaggggagc tgaatgagca cctgggcctg ctgggcccct acatcagggc tgaggtggag    3480
gacaacatca tggtgacctt caggaaccag gccagcaggc cctacagctt ctacagcagc    3540
ctgatcagct atgaggagga ccagaggcag ggggctgagc ccaggaagaa ctttgtgaag    3600
cccaatgaaa ccaagaccta cttctggaag gtgcagcacc acatggcccc caccaaggat    3660
gagtttgact gcaaggcctg ggcctacttc tctgatgtgg acctggagaa ggatgtgcac    3720
tctggcctga ttggcccccct gctggtgtgc cacaccaaca ccctgaaccc tgcccatggc    3780
aggcaggtga ctgtgcagga gtttgccctg ttcttcacca tctttgatga aaccaagagc    3840
tggtacttca ctgagaacat ggagaggaac tgcagggccc cctgcaacat ccagatggag    3900
gacccccacct tcaaggagaa ctacaggttc atgccatca atggctacat catggacacc    3960
ctgcctggcc tggtgatggc ccaggaccag aggatcaggt ggtacctgct gagcatgggc    4020
agcaatgaga acatccacag catccacttc tctggccatg tgttcactgt gaggaagaag    4080
gaggagtaca agatggccct gtacaacctg taccctgggg tgtttgagac tgtggagatg    4140
ctgcccagca aggctggcat ctggagggtg gagtgcctga ttggggagca cctgcatgct    4200
ggcatgagca ccctgttcct ggtgtacagc aacaagtgcc agaccccct gggcatggc    4260
tctggccaca tcagggactt ccagatcact gcctctggcc agtatggcca gtgggccccc    4320
aagctggcca ggctgcacta ctctggcagc atcaatgcct ggagcaccaa ggagcccttc    4380
agctggatca aggtggacct gctggcccc atgatcatcc atggcatcaa gacccaggg    4440
gccaggcaga agttcagcag cctgtacatc agccagttca tcatcatgta cagcctggat    4500
ggcaagaagt ggcagaccta caggggcaac agcactggca cccctgatgg tgttctttgg    4560
aatgtggaca gctctggcat caagcacaac atcttcaacc ccccatcat tgccagatac    4620
atcaggctgc accccaccca ctacagcatc aggagcaccc tgaggatgga gctgatgggc    4680
tgtgacctga acagctgcag catgcccctg ggcatggaga gcaaggccat ctctgatgcc    4740
cagatcactg ccagcagcta cttcaccaac atgtttgcca cctggagccc cagcaaggcc    4800
aggctgcacc tgcagggcag gagcaatgcc tggaggcccc aggtcaacaa ccccaaggag    4860
tggctgcagg tggacttcca gaagaccatg aaggtgactg gggtgaccac ccaggggtg    4920
aagagcctgc tgaccagcat gtatgtgaag gagttcctga tcagcagcag ccaggatggc    4980
caccagtgga ccctgttctt ccagaatggc aaggtgaagg tgttccaggg caaccaggac    5040
agcttcaccc ctgtggtgaa cagcctggac ccccccctgc tgaccagata cctgaggatt    5100
cacccccaga gctgggtgca ccagattgcc ctgaggatgg aggtgctggg ctgtgaggcc    5160
caggacctgt actga                                                     5175

SEQ ID NO: 20         moltype = DNA  length = 5955
FEATURE               Location/Qualifiers
source                1..5955
                      mol_type = other DNA
                      note = APOE-AAT-hBGi-FVIIIv3-WPRE3- bGH-polyA DTS
                      organism = synthetic construct
SEQUENCE: 20
cgcgtctgca ggctcagagg cacacaggag tttctgggct caccctgccc ccttccaacc    60
cctcagcct catcctccag cagctgtttg tgtgctgcct ctgaagtcca cactgaacaa    120
acttcagcct actcatgtcc ctaaaatggg caaacattgc aagcagcaaa cagcaaacac    180
acagccctcc ctgcctgctg accttggagc tggggcagag gtcagagacc tctctgggcc    240
catgccacct ccaacatcca ctcgacccct tggaatttcg gtggagagga gcagaggttg    300
tcctggcgtg gtttaggtag tgtgagaggg gtcgactgga cacaggacgc tgtggtttct    360
gagccagggg gcgactcaga tcccagccag tggacttagc ccctgtttgc tcctccgata    420
actggggtga ccttggttaa tattcaccag cagcctcccc cgttgccct ctggatccac    480
tgcttaaata cggacgagga cagggccctg tctcctcagc ttcaggcacc accactgacc    540
tgggacagtg aatcgtaagt actagcagct acaatccagc taccattctg cttttatttt    600
atggttggga taaggctgga ttattctgag tccaagctag gcccttttgc taatcatgtt    660
catacctctt atcttcctcc cacagctcct gggcaacgtg ctggtctgtg tgctggccca    720
tcactttggc aaagaattgc gatcgccacc atgcagattg agctgagcac ctgcttcttc    780
ctgtgcctgc tgaggttctg cttctctgcc accaggagat actacctggg ggctgtggag    840
ctgagctgga actacatgca gtctgacctg ggggagctgc ctgtggatgc caggttccca    900
cccagagtgc ccaagagctt cccttcaac acctctgtgg tgtacaagaa gaccctgttt    960
gtggagttca ctgaccacct gttcaacatt gccaagccca gcccccctg gatgggcct     1020
ctgggccca ccatccaggc tgaggtgtat gacactgtg tgatcaccct gaagaacatg     1080
gccagccacc ctgtgagcct gcatgctgtg ggggtgagct actggaaggc ctctgagggg     1140
gctgagtatg atgaccagac cagccagagg gagaaggagg atgacaaggt gttccctggg     1200
ggcagccaca cctatgtgtg gcaggtgctg aaggagaatg gccccatggc ctctgacccc    1260
ctgtgcctga cctacagcta cctgagccat gtggacctgg tgaaggacct gaactctggc    1320
ctgattgggg ccctgctggt gtgcagggag ggcagcctgg ccaaggagac gacccagacc    1380
ctgcacaagt tcatcctgct gtttgctgtg tttgatgagg gcaagagctg gcactctgac    1440
accaagaaca gcctgatgca ggacagggat gctgctgctg ccaggggcctg gcccaagatg    1500
cacactgtga atggctatgt gaacaggagc ctgcctggcc tgattggctg ccacaggaag    1560
tctgtgtact ggcatgtgat tggcatgggc accaccctg aggtgcacag catcttcctg    1620
gagggccaca ccttcctggt caggaaccac aggcaggcca gcctggagat cagccccatc    1680
accttcctga ctgcccagac cctgctgatg gacctgggcca gttcctgct gttctgccac    1740
atcagcagcc accagcatga tggcatggag gcctatgtga aggtggacag ctgccctgag    1800
gagcccagc tgaggatgaa gaacaatgag gaggctgagg actatgatga tgacctgact    1860
gactctgaga tggatgtggt gaggtttgat gatgacaaca gccccagctt catccagatc    1920
aggtctgtgg ccaagaagca ccccaagacc tgggtgcact acattgctgc tgaggaggag    1980
gactgggact atgcccccct ggtgctggcc cctgatgaca ggagctacaa gagccagtac    2040
```

-continued

```
ctgaacaatg gcccccagag gattggcagg aagtacaaga aggtcaggtt catggcctac  2100
actgatgaaa ccttcaagac cagggaggcc atccagcatg agtctggcat cctgggcccc  2160
ctgctgtatg gggagtgggg ggacaccctg ctgatcatct tcaagaacca ggccagcagg  2220
ccctacaaca tctacccca tggcatcact gatgtgaggc ccctgtacag caggaggctg  2280
cccaaggggg tgaagcacct gaaggacttc cccatcctgc ctggggagat cttcaagtac  2340
aagtggactg tgactgtgga ggatggcccc accaagtctg accccaggtg cctgaccaga  2400
tactacagca gctttgtgaa catggagagg gacctggcct ctggcctgat tggccccctg  2460
ctgatctgct acaaggagtc tgtggaccag aggggcaacc agatcatgtc tgacaagagg  2520
aatgtgatcc tgttctctgt gtttgatgag aacaggagct ggtacctgac tgagaacatc  2580
cagaggttcc tgcccaaccc tgctggggtg cagctgaggg accctgagtt ccaggccagc  2640
aacatcatgc acagcatcaa tggctatgtg tttgacagcc tgcagctgtc tgtgtgcctg  2700
catgaggtgg cctactggta catcctgagc attgggccc agactgactt cctgtctgtg  2760
ttcttctctg gctcacctt caagcacaag atggtgtatg aggacaccct gaccctgttc  2820
cccttctctg gggagactgt gttcatgagc atggagaacc ctggcctgtg gattctgggc  2880
tgccacaact ctgacttcag gaacaggggc atgactgccc tgctgaaagt ctccagctgt  2940
gacaagaaca ctgggggacta ctatgaggac agctatgagg acatctctgc ctacctgctg  3000
agcaagaaca atgccattga gcccaggagc ttcagccaga tgccactaa tgtgtctaac  3060
aacagcaaca ccagcaatga cagcaatgtg tctcccccag tgctgaagag gcaccagagg  3120
gagatcacca ggaccaccct gcagtctgac caggaggaga ttgactatga tgacaccatc  3180
tctgtggaga tgaagaagga ggactttgac atctacgacg aggacgagaa ccagagcccc  3240
aggagcttcc agaagaagac caggcactac ttcattgctg ctgtggagag gctgtgggac  3300
tatggcatga gcagcagccc ccatgtgctg aggaacaggg cccagtctgg ctctgtgccc  3360
cagttcaaga aggtggtgtt ccaggagttc actgatggca gcttcaccca gcccctgtac  3420
agaggggagc tgaatgagca cctgggcctg ctgggccct acatcagggc tgaggtggag  3480
gacaacatca tggtgacctt caggaaccag gccagcaggc cctacagctt ctacagcagc  3540
ctgatcagct atgaggagga cagaggcag ggggctgagc cagggaagaa ctttgtgaag  3600
cccaatgaaa ccaagaccta cttctggaag gtgcagcacc acatggcccc caccaaggat  3660
gagtttgact gcaaggcctg ggcctacttc tctgatgtgg acctggagaa ggatgtgcac  3720
tctggcctga ttggcccct gctggtgtgc cacaccaaca ccctgaaccc tgcccatggc  3780
aggcaggtga ctgtgcagga gtttgccctg ttcttcacca tctttgatga aaccaagagc  3840
tggtacttca ctgagaacat ggagaggaac tgcagggccc cctgcaacat ccagatggag  3900
gaccccacct tcaaggagaa ctacaggttc atgccatca atggctacat catggacacc  3960
ctgcctggcc tggtgatggc ccaggaccag aggatcaggt ggtacctgct gagcatgggc  4020
agcaatgaga acatccacag catccacttc tctggccatg tgttcactgt gaggaagaac  4080
gaggagtaca agatgccct gtacaacctg taccctgggg tgtttgagac tgtggagatg  4140
ctgcccagca aggctggcat ctggagggtg agtgcctga ttggggagca cctgcatgct  4200
ggcatgagca ccctgttcct ggtgtacagc aacaagtgcc agaccccct gggcatggcc  4260
tctggccaca tcagggactt ccagatcact gcctctggcc agtatggcca gtgggccccc  4320
aagctggcca ggctgcacta ctctggcagc atcaatgcct ggagcaccaa ggagcccttc  4380
agctggatca aggtggacct gctggccccc atgatcatcc atggcatcaa gacccagggg  4440
gccaggcaga agttcagcag cctgtacatc agccagttca tcatcatgta cagcctggat  4500
ggcaagaagt ggcagaccta caggggcaac agcactggca ccctgatggt gttctttggc  4560
aatgtggaca gctctggcat caagcacaac atcttcaacc ccccatcat tgccagatac  4620
atcaggctgc acccccaccca ctacagcatc aggagcaccc tgaggatgga gctgatgggc  4680
tgtgacctga acagctgcag catgcccctg ggcatggaga gcaaggccat ctctgatgcc  4740
cagatcactg ccagcagcta cttcaccaac atgtttgcca cctggagccc cagcaaggcc  4800
aggctgcacc tgcagggcag gagcaatgcc tggaggccc aggtcaacaa ccccaaggag  4860
tggctgcagg tggacttcca gaagaccatg aaggtgactg gggtgaccac caggggggtg  4920
aagagcctgc tgaccagcat gtatgtgaag gagttcctga tcagcagcag ccaggatggc  4980
caccagtgga cctgttctt ccagaatggc aaggtgaagt tgttccaggg caaccaggac  5040
agcttcaccc ctgtggtgaa cagcctggac ccccccctgc tgaccagata cctgaggatt  5100
cacccccaga gctgggtgca ccagattgcc ctgaggatgg aggtgctggg ctgtgaggcc  5160
caggacctgt actgataact cgagaatcaa cctctggatt acaaaatttg tgaaagattg  5220
actggtattc ttaactatgt tgctcctttt acgctatgtg gatacgctgc tttaatgcct  5280
ttgtatcatg ctattgcttc ccgtatggct ttcattttct cctccttgta taaatcctgg  5340
ttgctgtctc tttatgagga gttgtggccc gttgtcagge aacgtggcgt ggtgtgcact  5400
gtgtttgctg acgcaacccc cactggttgg ggcattgcca ccacctgtca gctcctttcc  5460
gggactttcg ctttccccct ccctattgcc acggcggaac tcatcgccgc ctgccttgcc  5520
cgctgctgga caggggctcg gctgttgggc actgacaatt ccgtggggtg tgccttctag  5580
ttgccagcca tctgttgttt gcccctcccc cgtgccttcc ttgaccctgg aaggtgccac  5640
tcccactgtc ctttcctaat aaaatgagga aattgcatcg cattgtctga gtaggtgtca  5700
ttctattctg gggggtgggg tggggcagga cagcaagggg gaggattggg aagacaatag  5760
caggcatgct ggggatgcgg tgggctctat gggaagatg ctactgagct gtgcgatccc  5820
tgctggggac tttccgctgg gactttccg ctggggactt ccgccttca gctaaggaag  5880
ctaccaatat ttagaggtac atttttgttct agaacaaaat gtaccggtac atttttgttct  5940
ggtacatttt gttct                                                5955
```

```
SEQ ID NO: 21         moltype = AA  length = 461
FEATURE               Location/Qualifiers
source                1..461
                      mol_type = protein
                      note = FIX AA Sequence
                      organism = synthetic construct
SEQUENCE: 21
MQRVNMIMAE SPGLITICLL GYLLSAECTV FLDHENANKI LNRPKRYNSG KLEEFVQGNL  60
ERECMEEKCS FEEAREVFEN TERTTEFWKQ YVDGDQCESN PCLNGGSCKD DINSYECWCP  120
FGFEGKNCEL DVTCNIKNGR CEQFCKNSAD NKVVCSCTEG YRLAENQKSC EPAVPFPCGR  180
VSVSQTSKLT RAETVFPDVD YVNSTEAETI LDNITQSTQS FNDFTRVVGG EDAKPGQFPW  240
QVVLNGKVDA FCGGSIVNEK WIVTAAHCVE TGVKITVVAG EHNIEETEHT EQKRNVIRII  300
```

-continued

```
PHHNYNAAIN KYNHDIALLE LDEPLVLNSY VTPICIADKE YTNIFLKFGS GYVSGWGRVF  360
HKGRSALVLQ YLRVPLVDRA TCLRSTKFTI YNNMFCAGFH EGGRDSCQGD SGGPHVTEVE  420
GTSFLTGIIS WGEECAMKGK YGIYTKVSRY VNWIKEKTKL T                      461

SEQ ID NO: 22          moltype = DNA   length = 141
FEATURE                Location/Qualifiers
source                 1..141
                       mol_type = other DNA
                       note = 3 ITR
                       organism = synthetic construct
SEQUENCE: 22
aggaaccoct agtgatggag ttggccactc cctctctgcg cgctcgctcg ctcactgagg  60
ccgggcgacc aaaggtcgcc cgacgcccgg gctttgcccg ggcggcctca gtgagcgagc  120
gagcgcgcag ctgcctgcag g                                            141

SEQ ID NO: 23          moltype = DNA   length = 449
FEATURE                Location/Qualifiers
source                 1..449
                       mol_type = other DNA
                       note = NP Backbone
                       organism = synthetic construct
SEQUENCE: 23
tggcttgttg tccacaacca ttaaacctta aaagctttaa aagccttata tattcttttt  60
tttcttataa aacttaaaac cttagaggct atttaagttg ctgatttata ttaattttat  120
tgttcaaaca tgagagctta gtacgtgaaa catgagagct tagtacatta gccatgagag  180
cttagtacat tagccatgag ggtttagttc attaaacatg agagcttagt acattaaaca  240
tgagagctta gtacattaaa catgagagct tagtacatac tatcaacagg ttgaactgct  300
gatctgtaca gtagaattgg taaagagagt tgtgtaaaat attggttcg cacatcttgt  360
tgtctgatta ttgattttg gcgaaaccat ttgatcatat gacaagatgt gtatctacct  420
taacttaatg attttgataa aaatcatta                                    449

SEQ ID NO: 24          moltype = AA   length = 1682
FEATURE                Location/Qualifiers
source                 1..1682
                       mol_type = protein
                       note = FVIII-SQ-N6-F309S-DM
                       organism = synthetic construct
SEQUENCE: 24
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
AASARAWPKM HTVNGYVNRS LPGLIGCHRK SVYWHVIGMG TTPEVHSIFL EGHTFLVRNH  300
RQASLEISPI TFLTAQTLLM DLGQFLLSCH ISSHQHDGME AYVKVDSCPE EPQLRMKNNE  360
EAEDYDDDLT DSEMDVVRFD DDNSPSFIQI RSVAKKHPKT WVHYIAAEEE DWDYAPLVLA  420
PDDRSYKSQY LNNGPQRIGR KYKKVRFMAY TDETFKTREA IQHESGILGP LLYGEVGDTL  480
LIIFKNQASR PYNIYPHGIT DVRPLYSRRL PKGVKHLKDF PILPGEIFKY KWTVTVEDGP  540
TKSDPRCLTR YYSSFVNMER DLASGLIGPL LICYKESVDQ RGNQIMSDKR NVILFSVFDE  600
NRSWYLTENI QRFLPNPAGV QLEDPEFQAS NIMHSINGYV FDSLQLSVCL HEVAYWYILS  660
IGAQTDFLSV FFSGYTFKHK MVYEDTLTLF PFSGETVFMS MENPGLWILG CHNSDFRNRG  720
MTALLKVSSC DKNTGDYYED SYEDISAYLL SKNNAIEPRS FSQNPPVLTR SFSQNSRHPS  780
TRQKQFNATT IPENDIEKTD PWFAHRTPMP KIQNVSSSDL LMLLRQSPTP HGLSLSDLQE  840
AKYETFSDDP SPGAIDSNNS LSEMTHFRPQ LHHSGDMVFT PESGLQLRLN EKLGTTAATE  900
LKKLDFKVSS TSNNLISTIP SDNLAAGTDN TSSLGPPSMP VHYDSQLDTT LFGKKSSPLT  960
ESGGPLSLSE ENNDSKLLES GLMNSQESSW GKNVSSTREI TRTTLQSDQE EIDYDDTISV  1020
EMKKEDFDIY DEDENQSPRS FQKKTRHYFI AAVERLWDYG MSSSPHVLRN RAQSGSVPQF  1080
KKVVFQEFTD GSFTQPLYRG ELNEHLGLLG PYIRAEVEDN IMVTFRNQAS RPYSFYSSLI  1140
SYEEDQRQGA EPRKNFVKPN ETKTYFWKVQ HHMAPTKDEF DCKAWAYFSD VDLEKDVHSG  1200
LIGPLLVCHT NTLNPAHGRQ VTVQEFALFF TIFDETKSWY FTENMERNGR APGNIQMEDP  1260
TFKENYRFHA INGYIMDTLP GLVMAQDQRI RWYLLSMGSN ENIHSIHFSG HVFTVRKKEE  1320
YKMALYNLYP GVFETVEMLP SKAGIWRVEC LIGEHLHAGM STLFLVYSNK CQTPLGMASG  1380
HIRDFQITAS GQYGQWAPKL ARLHYSGSIN AWSTKEPFSW IKVDLLAPMI IHGIKTQGAR  1440
QKFSSLYISQ FIIMYSLDGK KWQTYRGNST GTLMVFFGNV DSSGIKHNIF NPPIIARYIR  1500
LHPTHYSIRS TLRMELMGCD LNSCSMPLGM ESKAISDAQI TASSYFTNMF ATWSPSKARL  1560
HLQGRSNAWR PQVNNPKEWL QVDFQKTMKV TGVTTQGVKS LLTSMYVKEF LISSSQDGHQ  1620
WTLFFQNGKV KVFQGNQDSF TPVVNSLDPP LLTRYLRIHP QSWVHQIALR MEVLGCEAQD  1680
LY                                                                 1682

SEQ ID NO: 25          moltype = AA   length = 391
FEATURE                Location/Qualifiers
source                 1..391
                       mol_type = protein
                       note = FVIII-SQ-N6-F309S-DM: A1 domain
                       organism = synthetic construct
SEQUENCE: 25
MQIELSTCFF LCLLRFCFSA TRRYYLGAVE LSWDYMQSDL GELPVDARFP PRVPKSFPFN  60
TSVVYKKTLF VEFTDHLFNI AKPRPPWMGL LGPTIQAEVY DTVVITLKNM ASHPVSLHAV  120
GVSYWKASEG AEYDDQTSQR EKEDDKVFPG GSHTYVWQVL KENGPMASDP LCLTYSYLSH  180
VDLVKDLNSG LIGALLVCRE GSLAKEKTQT LHKFILLFAV FDEGKSWHSE TKNSLMQDRD  240
```

-continued

```
AASARAWPKM HTVNGYVNRS LPGLIGCHRK SVYWHVIGMG TTPEVHSIFL EGHTFLVRNH   300
RQASLEISPI TFLTAQTLLM DLGQFLLSCH ISSHQHDGME AYVKVDSCPE EPQLRMKNNE   360
EAEDYDDDLT DSEMDVVRFD DDNSPSFIQI R                                  391

SEQ ID NO: 26              moltype = AA  length = 368
FEATURE                    Location/Qualifiers
source                     1..368
                           mol_type = protein
                           note = FVIII-SQ-N6-F309S-DM: A2 domain
                           organism = synthetic construct
SEQUENCE: 26
SVAKKHPKTW VHYIAAEEED WDYAPLVLAP DDRSYKSQYL NNGPQRIGRK YKKVRFMAYT   60
DETFKTREAI QHESGILGPL LYGEVGDTLL IIFKNQASRP YNIYPHGITD VRPLYSRRLP   120
KGVKHLKDFP ILPGEIFKYK WTVTVEDGPT KSDPRCLTRY YSSFVNMERD LASGLIGPLL   180
ICYKESVDQR GNQIMSDKRN VILFSVFDEN RSWYLTENIQ RFLPNPAGVQ LEDPEFQASN   240
IMHSINGYVF DSLQLSVCLH EVAYWYILSI GAQTDFLSVF FSGYTFKHKM VYEDTLTLFP   300
FSGETVFMSM ENPGLWILGC HNSDFRNRGM TALLKVSSCD KNTGDYYEDS YEDISAYLLS   360
KNNAIEPR                                                           368

SEQ ID NO: 27              moltype = AA  length = 11
FEATURE                    Location/Qualifiers
source                     1..11
                           mol_type = protein
                           note = FVIII-SQ-N6-F309S-DM: SQ domain
                           organism = synthetic construct
SEQUENCE: 27
SFSQNPPVLT R                                                        11

SEQ ID NO: 28              moltype = AA  length = 227
FEATURE                    Location/Qualifiers
source                     1..227
                           mol_type = protein
                           organism = synthetic construct
SEQUENCE: 28
SFSQNSRHPS TRQKQFNATT IPENDIEKTD PWFAHRTPMP KIQNVSSSDL LMLLRQSPTP   60
HGLSLSDLQE AKYETFSDDP SPGAIDSNNS LSEMTHFRPQ LHHSGDMVFT PESGLQLRLN   120
EKLGTTAATE LKKLDFKVSS TSNNLISTIP SDNLAAGTDN TSSLGPPSMP VHYDSQLDTT   180
LFGKKSSPLT ESGGPLSLSE ENNDSKLLES GLMNSQESSW GKNVSST               227

SEQ ID NO: 29              moltype = AA  length = 373
FEATURE                    Location/Qualifiers
source                     1..373
                           mol_type = protein
                           note = FVIII-SQ-N6-F309S-DM: A3 domain
                           organism = synthetic construct
SEQUENCE: 29
REITRTTLQS DQEEIDYDDT ISVEMKKEDF DIYDEDENQS PRSFQKKTRH YFIAAVERLW   60
DYGMSSSPHV LRNRAQSGSV PQFKKVVFQE FTDGSFTQPL YRGELNEHLG LLGPYIRAEV   120
EDNIMVTFRN QASRPYSFYS SLISYEEDQR QGAEPRKNFV KPNETKTYFW KVQHHMAPTK   180
DEFDCKAWAY FSDVDLEKDV HSGLIGPLLV CHTNTLNPAH GRQVTVQEFA LFFTIFDETK   240
SWYFTENMER NGRAPGNIQM EDPTFKENYR FHAINGYIMD TLPGLVMAQD QRIRWYLLSM   300
GSNENIHSIH FSGHVFTVRK KEEYKMALYN LYPGVFETVE MLPSKAGIWR VECLIGEHLH   360
AGMSTLFLVY SNK                                                     373

SEQ ID NO: 30              moltype = AA  length = 153
FEATURE                    Location/Qualifiers
source                     1..153
                           mol_type = protein
                           organism = synthetic construct
SEQUENCE: 30
CQTPLGMASG HIRDFQITAS GQYGQWAPKL ARLHYSGSIN AWSTKEPFSW IKVDLLAPMI   60
IHGIKTQGAR QKFSSLYISQ FIIMYSLDGK KWQTYRGNST GTLMVFFGNV DSSGIKHNIF   120
NPPIIARYIR LHPTHYSIRS TLRMELMGCD LNS                               153

SEQ ID NO: 31              moltype = AA  length = 159
FEATURE                    Location/Qualifiers
source                     1..159
                           mol_type = protein
                           note = FVIII-SQ-N6-F309S-DM: C1 domain
                           organism = synthetic construct
SEQUENCE: 31
CSMPLGMESK AISDAQITAS SYFTNMFATW SPSKARLHLQ GRSNAWRPQV NNPKEWLQVD   60
FQKTMKVTGV TTQGVKSLLT SMYVKEFLIS SSQDGHQWTL FFQNGKVKVF QGNQDSFTPV   120
VNSLDPPLLT RYLRIHPQSW VHQIALRMEV LGCEAQDLY                         159

SEQ ID NO: 32              moltype = DNA  length = 5052
FEATURE                    Location/Qualifiers
source                     1..5052
                           mol_type = other DNA
```

-continued

```
                    note = FVIII-SQ-N6-F309S-DM: NA Coding Sequence 1
                    organism = synthetic construct
SEQUENCE: 32
atgcagatcg agctgtctac ctgcttcttc ctgtgcctgc tgcggttctg cttcagcgcc   60
accagaagat attacctggg cgccgtggaa ctgagctgga actacatgca gtctgacctg   120
ggagagctgc ccgtggacgc tagatttcct ccaagagtgc ccaagagctt cccccttcaac  180
acctccgtgg tgtacaagaa aaccctgttc gtggaattca ccgaccacct gttcaatatc   240
gccaagcctc ggcctccttg gatgggactg ctgggaccta caattcaggc cgaggtgtac   300
gacaccgtgg tcatcaccct gaagaacatg gccagccatc ctgtgtctct gcacgccgta   360
ggagtgtctt actggaaggc ttctgagggc gccagtacg acgatcagac aagccagaga   420
gagaaagagg acgacaaggt tttccctggc ggcagccaca cctatgtctg gcaggtcctg   480
aaagaaaacg gccctatggc ctccgatcct ctgtgcctga catacagcta cctgagccac   540
gtggacctgg tcaaggacct gaattctggc ctgatcggag ccctgctcgt gtgtagagaa   600
ggcagcctgg ccaaagagaa aacccagaca ctgcacaagt tcatcctgct gttcgccgtg   660
ttcgacgagg gcaagagctg gcacagcgag acaaagaaca gcctgatgca ggacagggat   720
gccgcctctg ctagagcttg gcctaagatg cacaccgtga acggctacgt gaacagaagc   780
ctgcctggac tgatcggctg ccacagaaag tccgtgtact ggcacgtgat cggcatgggc   840
acaacacctg aggtgcacag catcttctg gaaggacaca cctcctgt gcggaaccat   900
agacaggcca gcctgaaat cagccctatc accttcctga ccgctcagac cctgctgatg   960
gatctggggc agtttctgct gagctgccac atcagctccc accagcacga tggcatggaa   1020
gcctacgtga aggtggacag ctgccccgaa gaaccccagc tgcggatgaa gaacaacgag   1080
gaagccgaga actacgacga cgacctgacc gactctgaga tggacgtcgt cagattcgac   1140
gacgataaca gccccagctt catccagatc agaagcgtgg ccaagaagca ccccaagacc   1200
tgggtgcact atatcgccgc cgaggaagag gactgggatt acgctcctct ggtgctggcc   1260
cctgacgaca gaagctacaa gagccagtac ctgaacaacg ccctcagcg gatcggccgg   1320
aagtataaga aagtgcggtt catggcctac accgacgaga cattcaagac cagagaggcc   1380
atccagcacg agagcggaat tctgggccct ctgctgtatg gcgaagtggg cgatacactg   1440
ctgatcatct tcaagaacca ggccagcaga ccctacaaca tctaccctca cggcatcacc   1500
gatgtgcggc ccctgtattc tagaaggctg cccaagggcg tgaagcacct gaaggacttc   1560
cctatcctgc ctggcgagat cttcaagtac aagtggaccg tgaccgtgga agatggccac   1620
accaagagcg accctagatg tctgacacgg tactacagca gcttcgtgaa catggaacgc   1680
gacctggcca gcggcctgat tggacctctg ctgatctgct acaaagaaag cgtggaccag   1740
cggggcaacc agatcatgag cgacaagcgg aacgtgatcc tgtttagcgt gttcgatgag   1800
aaccggtcct ggtatctgac cgagaacatc cagcggtttc tgcccaatcc tgctggcgtg   1860
cagctggaag atcctgagtt ccaggcctcc aacatcatgc actccatcaa tggctatgtg   1920
ttcgacagcc tgcagctgag cgtgtgcctg cacgaagtgg cctactggta catcctgagc   1980
attggcgccc agaccgactt cctgtccgtg ttctttagcg gctacacctt caagcacaag   2040
atggtgtacg aggataccct gacactgttc ccattcagcg gcgagacagt gttcatgagc   2100
atggaaaacc ccggcctgtg gatcctgggc tgtcacaaca gcgacttccg gaacagaggc   2160
atgacagccc tgctgaaggt gtccagctgc gacaagaaca ccggcgacta ctacgaggac   2220
agctatgagg acatcagcgc ctacctgctg agcaagaaca atgccatcga gcccagaagc   2280
ttctcccaaa atcctccggt cctcacacgt tccttcagcc agaatagcag acacccctcc   2340
accagacaga agcagttcaa cgccacaaca atccccgaga acgacatcga gaaaaccgat   2400
ccttggtttg cccacagaac ccctatgcct aagatccaga acgtgtcctc cagcgatctg   2460
ctgatgctcc tgagacagag ccctacacct cacggactga gcctgtccga tctgcaagag   2520
gccaaatacg aaaccttcag cgacgaccct tctcctggcg ccatcgacag caacaatagc   2580
ctgagcgaga tgacccactt cagaccacag ctgcaccaca ggcggacact ggtgtttaca   2640
cctgagagcg gcctccagct gagactgaat gagaagctgg gaaccaccgc cgccaccgag   2700
ctgaagaaac tggacttcaa ggtgtcctct accagcaaca acctgatcag cacaatcccc   2760
tccgacaacc tggctgccgg caccgacaac acatcttctc tgggcccacc tagcatgccc   2820
gtgcactacg atagccagct ggataccaca ctgttcggca agaagtctag ccctctgaca   2880
gagtctggcg gccctctgtc tctgagcgag gaaaacaacg acagcaagct gctggaatcc   2940
ggcctgatga cagccaagaa gtcctcctgg ggcaagaatg tgtccagcac cagagaaatc   3000
acccggacca cactgcagag cgaccaagaa gagatcgatt acgacgatac catcagcgtc   3060
gagatgaaga aagaagattt cgacatctac gacgaggacg agaatcagag ccctcggagc   3120
ttccagaaga aaaccaggca ctactttatt gccgccgtcg agcggctgtg ggactacgga   3180
atgtctagct ctcctcacgt gctgcggaat agagcccagt ctggtagcgt gccccagttc   3240
aaaaaggtcg tgttccaaga gttcaccgac ggcagcttca cccagccact gtatagaggc   3300
gagctgaacg agcatctggg cctgctgggc ccttatatca gagccgaagt ggaagataac   3360
atcatggtca ccttccggaa tcaggcctct cggccctaca gcttctacag ctccctgatc   3420
tcctacgaag aggaccagag acaggggcgca gagccccgga agaatttcgt gaagcccaac   3480
gagactaaga cctactttttg gaaggtgcag caccatatgg cccctacaaa ggacgagttc   3540
gactgcaaag cctgggccta cttctccgat gtggaccttg agaaggatgt gcacagcgga   3600
ctcatcggcc cactgcttgt gtgccacacc aacacactga accccgctca cggcagacaa   3660
gtgacagtgc aagaattcgc cctgttttc accatcttcg acgaaacgaa gtcctggtac   3720
ttcaccgaaa acatggaaag aaacggacgc gcgcctggca acattcagat ggaagatccc   3780
accttcaaag agaactaccg gttccacgcc atcaacggct acatcatgga cacactgccc   3840
ggcctggtta tggctcagga tcagagaatc cggtggtatc tgctgtccat gggctccaac   3900
gagaatatcc actccatcca cttcagcggc cacgtgttca cacgtccgca gaaagaagag   3960
tacaagatgg ccctgtacaa tctgtacccc ggcgttttcg aaaccgttga gatgctgcct   4020
agcaaggccg gaatttggag agtggaatgt ctgattggag agcacctcca cgccgggatg   4080
agcaccctgt ttctggtgta ctccaacaag tgtcagaccc ctctcggcat ggcctctggc   4140
cacattagag acttccagat caccgccagc ggacagtatg gacagtgggc ccctaaactg   4200
gccagactgc actactccgg cagcatcaat gcctggtcca ccaaagagcc tttcagctgg   4260
atcaaagtgg acctgctggc tcccatgatc atccaccgaa tcaagaccca gggcgcccaga   4320
caaaagttca gcagcctgta catcagccag ttcatcatca tgtacagcct ggacggaaag   4380
aagtggcaga cctaccgggg caatagcacc ggcacactga tggtgttctt cggcaacgtg   4440
gactccagcg gcattaagca caacatcttc aaccctccaa tcattgcccg gtacatccgg   4500
ctgcacccca cacactacag catcaggtct acccctgaaa tggaactgat gggctgcgac   4560
```

-continued

```
ctgaacagct gcagcatgcc cctcggaatg gaaagcaagg ccatcagcga cgcccagatc   4620
acagcctcta gctacttcac caacatgttc gccacttgga gcccctctaa ggccggctt    4680
catctgcaag gcagaagcaa cgcttggagg ccccaagtga acaaccccaa agaatggctg   4740
caggtcgact ttcagaaaac catgaaagtg acaggcgtga ccacacaggg cgtcaagtcc   4800
ctgctgacct ctatgtacgt gaaagagttt ctgatcagct ccagccagga cggccaccag   4860
tggaccctgt tcttccagaa cggcaaagtg aaagtgttcc agggaaatca ggacagcttc   4920
acacccgtgg tcaactccct ggatcctcca ctgctgacaa gatacctgcg gattcaccct   4980
cagtcttggg tgcaccagat tgccctgcgg atggaagtgc tgggctgtga agctcaggac   5040
ctctactgat ag                                                       5052
```

SEQ ID NO: 33          moltype = DNA   length = 5049
FEATURE                Location/Qualifiers
source                 1..5049
                       mol_type = other DNA
                       note = FVIII-SQ-N6-F309S-DM: NA Coding Sequence 2
                       organism = synthetic construct
SEQUENCE: 33

```
atgcagattg agctgagcac ctgcttcttc ctgtgcctgc tgaggttctg cttctctgcc   60
accaggagat actacctggg ggctgtggag ctgagctggg actacatgca gtctgacctg   120
ggggagctgc ctgtggatgc caggttcccc cccagagtgc ccaagagctt ccccttcaac   180
acctctgtgt gtacaagaa gaccctgttt gtggagttca ctgaccacct gttcaacatt   240
gccaagccca ggccccctg gatgggcctg ctgggcccca ccatccaggc tgaggtgtat   300
gacactgtgg tgatcaccct gaagaacatg gccagccacc ctgtgagcct gcatgctgtg   360
ggggtgagct actggaaggc ctctgagggg gctgagtatg atgaccagac cagccagagg   420
gagaaggagg atgacaaggt gttccctggg ggcagccaca cctatgtgtg gcaggtgctg   480
aaggagaatg gccccatggc ctctgacccc gtgtgctgga cctacagcta cctgagccat   540
gtggacctgg tgaaggacct gaactctggc ctgattgggg ccctgctggt gtgcaggag    600
ggcagcctgg ccaaggagaa gacccagacc ctgcacaagt tcatcctgct gtttgctgtg   660
tttgatgagg gcaagagctg gcactctgaa accaagaaca gcctgatgca ggacaggat    720
gctgcctctg ccagggcctg gcccaagatg cacactgtga atggctatgt gaacaggagc   780
ctgcctggcc tgattggctg ccacaggaag tctgtgtact ggcatgtgat tggcatgggc   840
accacccctg aggtgcacag catcttcctg gagggccaca ccttcctggt caggaaccac   900
aggcaggcca gctggagat cagccccatc accttcctga ctgcccagac cctgctgatg   960
gacctgggc agttcctgct gagctgccac atcagcagc accagcatga tggcatggag   1020
gcctatgtga aggtggacag ctgccctgag gagccccagc tgaggatgaa gaacaatgag   1080
gaggctgagg actatgatga tgacctgact gactctgaga tggatgtggt gaggtttgat   1140
gatgacaaca gccccagctt catccagatc aggtctgtgg ccaagaagca ccccaagacc   1200
tgggtgcact acattgctgc tgaggaggag actgggact atgccccct ggtgctggcc   1260
cctgatgaca ggagctacaa gagccagtac ctgaacaatg gcccccagag gattggcagg   1320
aagtacaaga aggtcaggtt catggcctac actgatgaaa ccttcaagac cagggaggcc   1380
atccagcatg agtctggcat cctggggccc ctgctgtatg gggaggtggg ggacaccctg   1440
ctgatcatct tcaagaacca ggccagcagg ccctacaaca tctacccca tggcatcact   1500
gatgtgaggc ccctgtacag caggaggctg cccaaggggg tgaagcacct gaaggacttc   1560
cccatcctgc ctgggggagat cttcaagtac aagtggactg tgactgtgga ggatggcccc   1620
accaagtctg accccaggtg cctgaccaga tactacagca gctttgtgaa catggagagg   1680
gacctggcct ctggcctgat ggcccccctg ctgatctgct acaaggagtc tgtggaccag   1740
aggggcaacc agatcatgtc tgacaagagg aatgtgatct tgttctctgt gtttgatgag   1800
aacaggagc ggtacctgac tgagaacatc cagaggttcc tgcccaaccc tgctgggggtg   1860
cagctggagg accctgagtt ccaggccagc aacatcatgc acagcatcaa tggctatgtg   1920
tttgacagct gcagctgtc tgtgtgcctg catgaggtgg cctactggta tcctgagc    1980
attggggccc agactgactt cctgtctgtg ttcttctctg gctacacctt caagcacaag   2040
atggtgtatg aggacacct gaccctgttc cccttctctg gggagactgt gttcatgagc   2100
atggagaacc ctggcctgtg gattctgggc tgccacaact ctgacttcag gaacaggggc   2160
atgactgccc tgctgaaagt ctccagctgt gacaagaaca ctggggacta ctatgaggac   2220
agctatgagg acatctctgc ctacctgctg agcaagaaca tgccattga gcccaggagc   2280
ttcagccaga atcccccagt gctcaccgg tcctttagcc agaattctcg ccatcctcc   2340
acccggcaaa agcagttcaa cgccactacc atcccagaga acgacatcga aaaaccgac   2400
ccctggttcg cccacagaac tcccatgcca aagattcaga atgtttccag ttctgacctc   2460
cttatgttgc tgcgccagtc tccgaccct catggactgt ccctgagtga cttgcaggag   2520
gccaagtacg agacgttctc tgatgacccc agcccaggcg cgattgactc aaataactcc   2580
ctgtctgaga tgacacattt tcgccctcag ctccatcaca gcggggacat ggtgttcact   2640
ccagagtccg gacttcagct gcgcctcaac gagaaactcg gtactacagc cgcgacagaa   2700
ctcaaaaagc tggatttcaa ggtttccagc accagcaata acctgatctc tacaattccc   2760
agcgataacc tggcggctgg aaccgacaac acttccagc tgggacctcc gtccatgcct   2820
gtgcactacg actcccagct cgacaccact ctgttcggca agaaaagtag ccccctgacc   2880
gaatccggcg gtccgctgtc cctctccgaa gagaataacg atagcaagct cctggaatct   2940
gggcttatga ctctcaagaa gtcatcctgg ggcaagaacg tttcatcaac tagggagatc   3000
accaggacca ccctgcagtc tgaccaggag gagattgact atgatgacac catctctgtg   3060
gagatgaaga aggaggactt tgacatctac gacgaggacg agaaccagag ccccagagc   3120
ttccagaaga gaccaggca ctacttcatt gctgctgtgg agaggctgtg ggactatggc   3180
atgagcagca gcccccatgt gctgaggaac agggcccagt ctggctctgt gccccagttc   3240
aagaaggtgt gttccagga gttcactgat ggcagcttca cccagcccct gtacagaggg   3300
gagctgaatg agcacctggg cctgctgggc ccctacatca gggctgaggt ggaggacaac   3360
atcatggtga ccttcaggaa ccaggccag aggcctaca gcttctacag cagcctgatc   3420
agctatgagg aggaccagag gcagggggct gagcccagga gaacttgt gaagcccaat   3480
gaaaccaaga cctacttctg aaggtgcag caccacatgg cccccaccaa ggatgagttt   3540
gactgcaagg cctgggccta cttctctgat gtggacctgg agaaggatgt gcactctggc   3600
ctgattggcc cctgctggt gtgccacacc aacacctga ccctgccca tggcaggcag   3660
gtgactgtgc aggagtttgc cctgttcttc accatctttg atgaaccaa gagctggtac   3720
```

```
ttcactgaga acatggagag gaacggcagg gccccggca acatccagat ggaggacccc   3780
accttcaagg agaactacag gttccatgcc atcaatggct acatcatgga caccctgcct   3840
ggcctggtga tggcccagga ccagaggatc aggtggtacc tgctgagcat gggcagcaat   3900
gagaacatcc acagcatcca cttctctggc catgtgttca ctgtgaggaa gaaggaggag   3960
tacaagatgg ccctgtacaa cctgtaccct ggggtgtttg agactgtgga gatgctgcct   4020
agcaaggctg gcatctggag ggtgagtgc ctgattgggg agcacctgca tgctggcatg   4080
agcaccctgt tcctggtgta cagcaacaag tgccagaccc ccctgggcat ggcctctggc   4140
cacatcaggg acttccagat cactgcctct ggccagtatg gccagtgggc ccccaagctg   4200
gccaggctgc actactctgg cagcatcaat gcctggagca ccaaggagcc cttcagctgg   4260
atcaaggtgg acctgctggc ccccatgatc atccatggca tcaagaccca ggggggccagg   4320
cagaagttca gcagcctgta catcagccag ttcatcatca tgtacagcct ggatggcaag   4380
aagtggcaga cctacagggg caacagcact ggcaccctga tggtgttctt tggcaatgtg   4440
gacagctctg gcatcaagca caacatcttc aacccccca tcattgccag atacatcagg   4500
ctgcacccca cccactacag catcaggagc accctgagga tggagctgat gggctgtgac   4560
ctgaacagct gcagcatgcc cctgggcatg gagagcaagg ccatctctga tgcccagatc   4620
actgccagca gctacttcac caacatgttt gccacctgga gccccagcaa ggccaggctg   4680
cacctgcagg gcaggagcaa tgcctggagg ccccaggtca caaccccaa ggagtggctg   4740
caggtggact tccagaagac catgaaggtg actgggggtga ccaaccaggg ggtgaagagc   4800
ctgctgacca gcatgtatgt gaaggagttc ctgatcagca gcagccagga tggccaccag   4860
tggaccctgt tcttccagaa tggcaaggtg aaggtgttcc agggcaacca ggacagcttc   4920
accccctgtg tgaacagcct ggacccccc ctgctgacca gatacctgag gattcacccc   4980
cagagctggg tgcaccagat tgccctgagg atggaggtgc tgggctgtga ggcccaggac   5040
ctgtactga                                                           5049

SEQ ID NO: 34                moltype = AA   length = 238
FEATURE                      Location/Qualifiers
source                       1..238
                             mol_type = protein
                             note = N6-SQ domain
                             organism = synthetic construct
SEQUENCE: 34
SFSQNPPVLT RSFSQNSRHP STRQKQFNAT TIPENDIEKT DPWFAHRTPM PKIQNVSSSD    60
LLMLLRQSPT PHGLSLSDLQ EAKYETFSDD PSPGAIDSNN SLSEMTHFRP QLHHSGDMVF   120
TPESGLQLRL NEKLGTTAAT ELKKLDFKVS STSNNLISTI PSDNLAAGTD NTSSLGPPSM   180
PVHYDSQLDT TLFGKKSSPL TESGGPLSLS EENNDSKLLE SGLMNSQESS WGKNVSST     238

SEQ ID NO: 35                moltype = AA   length = 1682
FEATURE                      Location/Qualifiers
source                       1..1682
                             mol_type = protein
                             note = FVIII   (SQ+N6)
                             organism = synthetic construct
SEQUENCE: 35
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI RSVAKKHPKT WVHYIAAEEE DWDYAPLVLA   420
PDDRSYKSQY LNNGPQRIGR KYKKVRFMAY TDETFKTREA IQHESGILGP LLYGEVGDTL   480
LIIFKNQASR PYNIYPHGIT DVRPLYSRRL PKGVKHLKDF PILPGEIFKY KWTVTVEDGP   540
TKSDPRCLTR YYSSFVNMER DLASGLIGPL LICYKESVDQ RGNQIMSDKR NVILFSVFDE   600
NRSWYLTENI QRFLPNPAGV QLEDPEFQAS NIMHSINGYV FDSLQLSVCL HEVAYWYILS   660
IGAQTDFLSV FFSGYTFKHK MVYEDTLTLF PFSGETVFMS MENPGLWILG CHNSDFRNRG   720
MTALLKVSSC DKNTGDYYED SYEDISAYLL SKNNAIEPRS FSQNPPVLTR SFSQNSRHPS   780
TRQKQFNATT IPENDIEKTD PWFAHRTPMP KIQNVSSSDL LMLLRQSPTP HGLSLSDLQE   840
AKYETFSDDP SPGAIDSNNS LSEMTHFRPQ LHHSGDMVFT PESGLQLRLN EKLGTTAATE   900
LKKLDFKVSS TSNNLISTIP SDNLAAGTDN TSSLGPPSMP VHYDSQLDTT LFGKKSSPLT   960
ESGGPLSLSE ENNDSKLLES GLMNSQESSW GKNVSSTREI TRTTLQSDQE EIDYDDTISV  1020
EMKKEDFDIY DEDENQSPRS FQKKTRHYFI AAVERLWDYG MSSSPHVLRN RAQSGSVPQF  1080
KKVVFQEFTD GSFTQPLYRG ELNEHLGLLG PYIRAEVEDN IMVTFRNQAS RPYSFYSSLI  1140
SYEEDQRQGA EPRKNFVKPN ETKTYFWKVQ HHMAPTKDEF DCKAWAYFSD VDLEKDVHSG  1200
LIGPLLVCHT NTLNPAHGRQ VTVQEFALFF TIFDETKSWY FTENMERNCR APCNIQMEDP  1260
TFKENYRFHA INGYIMDTLP GLVMAQDQRI RWYLLSMGSN ENIHSIHFSG HVFTVRKKEE  1320
YKMALYNLYP GVFETVEMLP SKAGIWRVEC LIGEHLHAGM STLFLVYSNK CQTPLGMASG  1380
HIRDFQITAS GQYGQWAPKL ARLHYSGSIN AWSTKEPFSW IKVDLLAPMI IHGIKTQGAR  1440
QKFSSLYISQ FIIMYSLDGK KWQTYRGNST GTLMVFFGNV DSSGIKHNIF NPPIIARYIR  1500
LHPTHYSIRS TLRMELMGCD LNSCSMPLGM ESKAISDAQI TASSYFTNMF ATWSPSKARL  1560
HLQGRSNAWR PQVNNPKEWL QVDFQKTMKV TGVTTQGVKS LLTSMYVKEF LISSSQDGHQ  1620
WTLFFQNGKV KVFQGNQDSF TPVVNSLDPP LLTRYLRIHP QSWVHQIALR MEVLGCEAQD  1680
LY                                                                1682

SEQ ID NO: 36                moltype = AA   length = 391
FEATURE                      Location/Qualifiers
source                       1..391
                             mol_type = protein
                             note = FVIII A1
                             organism = synthetic construct
```

```
SEQUENCE: 36
MQIELSTCFF LCLLRFCFSA TRRYYLGAVE LSWDYMQSDL GELPVDARFP PRVPKSFPFN    60
TSVVYKKTLF VEFTDHLFNI AKPRPPWMGL LGPTIQAEVY DTVVITLKNM ASHPVSLHAV   120
GVSYWKASEG AEYDDQTSQR EKEDDKVFPG GSHTYVWQVL KENGPMASDP LCLTYSYLSH   180
VDLVKDLNSG LIGALLVCRE GSLAKEKTQT LHKFILLFAV FDEGKSWHSE TKNSLMQDRD   240
AASARAWPKM HTVNGYVNRS LPGLIGCHRK SVYWHVIGMG TTPEVHSIFL EGHTFLVRNH   300
RQASLEISPI TFLTAQTLLM DLGQFLLFCH ISSHQHDGME AYVKVDSCPE EPQLRMKNNE   360
EAEDYDDDLT DSEMDVVRFD DDNSPSFIQI R                                  391

SEQ ID NO: 37                moltype = AA  length = 373
FEATURE                      Location/Qualifiers
source                       1..373
                             mol_type = protein
                             note = FVIII A3
                             organism = synthetic construct
SEQUENCE: 37
REITRTTLQS DQEEIDYDDT ISVEMKKEDF DIYDEDENQS PRSFQKKTRH YFIAAVERLW    60
DYGMSSSPHV LRNRAQSGSV PQFKKVVFQE FTDGSFTQPL YRGELNEHLG LLGPYIRAEV   120
EDNIMVTFRN QASRPYSFYS SLISYEEDQR QGAEPRKNFV KPNETKTYFW KVQHHMAPTK   180
DEFDCKAWAY FSDVDLEKDV HSGLIGPLLV CHTNTLNPAH GRQVTVQEFA LFFTIFDETK   240
SWYFTENMER NCRAPCNIQM EDPTFKENYR FHAINGYIMD TLPGLVMAQD QRIRWYLLSM   300
GSNENIHSIH FSGHVFTVRK KEEYKMALYN LYPGVFETVE MLPSKAGIWR VECLIGEHLH   360
AGMSTLFLVY SNK                                                      373

SEQ ID NO: 38                moltype = DNA  length = 7342
FEATURE                      Location/Qualifiers
source                       1..7342
                             mol_type = other DNA
                             note =
                             NP-ITR-ApoE-AAT-hBGi-FVIII-SQ-N6-F309S-DM-WPRE3-DTS-ITR
                             organism = synthetic construct
SEQUENCE: 38
gaatcaacct ctggattaca aaatttgtga aagattgact ggtattctta actatgttgc    60
tcctttacg ctatgtggat acgctgcttt aatgcctttg tatcatgcta ttgcttcccg   120
tatggctttc attttctcct ccttgtataa atcctggttg ctgtctcttt atgaggagtt   180
gtggcccgtt gtcaggcaac gtggcgtggt gtgcactgtg tttgctgacg caaccccca   240
tggttggggc attgccacca cctgtcagct ccttttccggg actttcgctt tcccctccc   300
tattgccacg gcggaactca tcgccgcctg ccttgcccgc tgctggacag gggctcggct   360
gttgggcact gacaattccg tggggtgtgc cttctagttg ccagccatct gttgtttgcc   420
cctcccccgt gccttccttg accctggaag gtgccactcc cactgtcctt tcctaataaa   480
atgaggaaat tgcatcgcat tgtctgagta ggtgtcattc tattctgggg ggtgggtgg   540
ggcaggacag caagggggag gattgggaag acaatagcag gcatgctggg gatgcggtgg   600
gctctatggg cacgtgcgga gctgtgcgat ccctgctggg gacttccgc tggggactttt   660
ccgctgggga ctttccgcct tcagctaagg aagctaccaa tatttagagg tacattttgt   720
tctagaacaa aatgtaccgg tacatttttgt tctggtacat tttgttctat cgatcgagcg   780
gccgcaggaa ccctagtga tggagttggc cactccctct ctgcgcgctc gctcgctcac   840
tgaggccggg cgaccaaagg tcgcccgacg cccgggcttt gcccgggcgg cctcagtgag   900
cgagcgagcg cgcagctgcc tgcagggggc tgttgtccac aaccattaaa ccttaaaagc   960
tttaaaagcc ttatatattc ttttttttct tataaaactt aaaaccttag aggctattta  1020
agttgctgat ttatattaat tttattgttc aaacatgaga gcttagtacg tgaaacatga  1080
gagcttagta cattagccat gagagcttag tacattattaa agttcattaa  1140
acatgagagc ttagtacatt aaacatgaga gcttagtaca ttaaacatga gagcttagta  1200
catactatca acaggttgaa ctgctgatct gtacagtaga attggtaaag agagttgtgt  1260
aaaatattga gttcgcacat cttgttgtct gattattgat ttttggcgaa accatttgat  1320
catatgacaa gatgtgtatc taccttaact taatgatttt gataaaaatc attacctgca  1380
ggcagctgcg cgctcgctcg ctcactgagg ccgcccgggc gtcgggcgac ctttggtcgc  1440
ccggcctcag tgagcgagcg cgcagagagg gagtggccaa ctccatcact aggggttcct  1500
gcggccgcac gcgtctagtt attaatagta atcgaattcg cgtctgcagg ctcagaggca  1560
cacaggagtt tctgggctca ccctgccccc ttccaacccc tcagttccca tcctccagca  1620
gctgtttgtg tgctgcctct gaagtccaca ctgaacaaac ttcagcctac tcatgtccct  1680
aaaatgggca acattgcaa gcagcaaaca gcaaacacac agccctcct gcctgctgac  1740
cttggagctg gggcagaggt cagagacctc tctgggccca tgccacctcc aacatccact  1800
cgaccccttg gaatttcggt ggagaggagc agaggttgtc ctggcgtggt ttaggtagtg  1860
tgagaggggt cgactggaca caggacgctg tggtttctga gcaggggggc gactcagatc  1920
ccagccagtg gacttagccc ctgtttgctc ctccgataac tggggtgacc ttggttaata  1980
ttcaccagca gcctccccg ttgcccctct ggatccactg cttaaatacg gacgaggaca  2040
gggccctgtc tcctcagctt caggcaccac cactgacctg ggacagtgaa tcgtaagtac  2100
tagcagctac aatccagcta ccattctgct tttattttat ggttgggata aggctggatt  2160
attctgagtc caagctaggc cctttttgcta atcatgttat tacctcttat cttcctcaca  2220
cagctcctgg gcaacgtgct ggtctgtgtg ctggcccatc actttggcaa agaattgcga  2280
tcgccaccat gcagattgag ctgagcacct gcttcttcct gtgcctgctg aggttctgct  2340
tctctgccac caggagatac tacctggggg ctgtggagct gagctgggac tacatgcagt  2400
ctgacctggg ggagctgcct gtggatgcca ggttcccccc cagagtgccc aagagcttcc  2460
ccttcaacac ctctgttggt g tacaagaaga ccctgttttg gaggttcagg gaccacctgt  2520
tcaacattgc caagcccagg ccccctggg tgggcctgct gggccccac atccaggctg  2580
aggtgtatga cactgtggtg atcaccctga gaaacatggc cagccaccct gtgagcctgc  2640
atgctgtggg ggtgagctac tggaaggcct ctgaggggc tgagtatgat gaccagacca  2700
gccagaggga gaaggaggat gacaaggtgt ccctgggggg cagccacacc tatgtgtggc  2760
aggtgctgaa ggagaatggc cccatggcct ctgacccccc tgtgcctgacc tacagctacc  2820
```

-continued

```
tgagccatgt ggacctggtg aaggacctga actctggcct gattgggggc ctgctggtgt   2880
gcagggaggg cagcctggcc aaggagaaga cccagaccct gcacaagttc atcctgctgt   2940
ttgctgtgtt tgatgagggc aagagctggc actctgaaac caagaacagc ctgatgcagg   3000
acagggatgc tgcctctgcc agggcctggc ccaagatgca cactgtgaat ggctatgtga   3060
acaggagcct gcctggcctg attggctgcc acaggaagtc tgtgtactgg catgtgattg   3120
gcatgggcac caccctgag gtgcacagca tcttcctgga gggccacacc ttcctggtca   3180
ggaaccacag gcaggccagc ctggagatca gccccatcac cttcctgact gcccagaccc   3240
tgctgatgga cctgggccag ttcctgctga gctgccacat cagcagccac cagcatgatg   3300
gcatggaggc ctatgtgaag gtggacagct gccctgagga gccccagctg aggatgaaga   3360
acaatgagga ggctgaggac tatgatgatg acctgactga ctctgagatg gatgtggtga   3420
ggtttgatga tgacaacagc cccagcttca tccagatcag gtctgtggcc aagaagcacc   3480
ccaagacctg ggtgcactac attgctgctg aggaggagga ctgggactat gccccctgg   3540
tgctggcccc tgatgacagg agctacaaga gccagtacct gaacaatggc ccccagagga   3600
ttggcaggaa gtacaagaag gtcaggttca tggcctacac tgatgaaacc ttcaagacca   3660
gggaggccat ccagcatgag tctggcatcc tgggcccccct gctgtatggg gaggtggggg   3720
acaccctgct gatcatcttc aagaaccagg ccagcaggcc ctacaacatc tacccccatg   3780
gcatcactga tgtgaggccc ctgtacagca ggaggctgcc caaggggtg aagcacctga   3840
aggacttccc catcctgcct ggggagatct tcaagtacaa ggtggactgtg actgtggagc   3900
atggcccccac caagtctgac cccaggtgcc tgaccagata ctacagcagc tttgtgaaca   3960
tggagaggga cctggcctct ggcctgattg gccccctgct gatctgctac aaggagtctg   4020
tggaccagag gggcaaccag atcatgtctg acaagaggaa tgtgatcctg ttctctgtgt   4080
ttgatgagaa caggagctgg tacctgactg agaacatcca gaggttcctg cccaaccctg   4140
ctggggtgca gctggaggac cctgagttcc aggccagcaa catcatgcac agcatcaatg   4200
gctatgtgtt tgacagcctg cagctgtctg tgtgcctgca tgaggtggcc tactggtaca   4260
tcctgagcat tggggcccag actgacttcc tgtctgtgtt cttctctggc tacaccttca   4320
agcacaagat ggtgtatgag gacaccctga ccctgttccc cttctctggg gagactgtgt   4380
tcatgagcat ggagaaccct ggcctgtgga ttctgggctg ccacaactct gacttcagga   4440
acagggggcat gactgccctg ctgaaagtct ccagctgtga caagaacact ggggactact   4500
atgaggacag ctatgaggac atctctgcct acctgctgag caagaacaat gccattgagc   4560
ccaggagctt cagccagaat cccccagtgc tcacccggtc ctttagccag aattctcgcc   4620
atccctccac ccggcaaaag cagttcaacg ccactaccat cccagagaac gacatcgaaa   4680
aaaccgaccc ctggttcgcc cacagaactc ccatgccaaa gattcagaat gtttccagtt   4740
ctgacctcct tatgttgctg cgccagtctc cgaccctca tggactgtcc ctgagtgact   4800
tgcaggaggc caagtacgag acgttctctg atgacccca cccaggcgcg attgactcaa   4860
ataactccct gtctgagatg acacatttttc gccctcagct ccatcacagc ggggacatgg   4920
tgttcactcc agagtccgga cttcagctgc gcctcaacga gaaactcggt actacagccg   4980
cgacagaact caaaaagctg gatttcaagg tttccagcac cagcaataac ctgatctcta   5040
caattcccag cgataacctg gcggctggaa ccgacaacac ttccagcctg ggacctccgt   5100
ccatgcctgt gcactacgac tcccagctcg acaccactct gttcggcaag aaaagtagcc   5160
ccctgaccga atccggcggt ccgctgtccc tctccgaaga gaataacgat agcaagctcc   5220
tggaatctgg gcttatgaac tctcaagagt catcctgggg caagaacgtt tcatcaacta   5280
gggagatcac caggaccacc ctgcagtctg accaggagga gattgactat gatgacacca   5340
tctctgtgga gatgaagaag gaggactttg acatctacga aaccagagcc caggagcttc   5400
ccaggagctt ccagaagaag accaggcact acttcattgc tgctgtggag aggctgtggg   5460
actatggcat gagcagcagc ccccatgtgc tgaggaacag ggcccagtct ggctctgtgc   5520
cccagttcaa gaaggtggtg ttccaggagt tcactgatgg cagcttcacc cagcccctgt   5580
acagagggga gctgaatgag cacctgggcc tgctgggccc ctacatcagg gctgaggtgg   5640
aggacaacat catggtgacc ttcaggaacc aggccagcag gccctacagc ttctacagca   5700
gcctgatcag ctatgaggag gaccagaggc aggggggctga gcccaggaag aacttttgtga   5760
agcccaatga aaccaagacc tacttctgga aggtgcagca ccacatggcc cccaccaagg   5820
atgagtttga ctgcaaggcc tgggcctact tctctgatgt ggacctggag aaggatgtgc   5880
actctggcct gattggcccc ctgctggtgt gccacaccaa caccctgaac cctgccatg   5940
gcaggcaggt gactggtgcag gagtttgccc tgttcttcac catctttgat gaaaccaaga   6000
gctggtactt cactgagaac atggagagga cggcagggc ccccggcaac atccagatgg   6060
aggaccccac cttcaaggag aactacaggt tccatgccat caatggctac atcatggaca   6120
ccctgcctgg cctggtgatg gcccaggacc agaggatcag gtggtacctg ctgagcatgg   6180
gcagcaatga gaacatccac agcatccact ctctggcca tgtgttcact gtgaggaaga   6240
aggaggagta caagatggcc ctgtacaacc tgtaccctgg ggtgtttgag actgtggaga   6300
tgctgcccag caaggctggc atctggaggg tggagtgcct gattggggag cacctgcatg   6360
ctggcatgag caccctgttc ctggtgtaca gcaacaagtg ccagaccccc ctgggcatgg   6420
cctctggcca catcagggac ttccagatca ctgcctctgg ccagtatggc cagtgggccc   6480
ccaagctggc caggctgcac tactctggca gcatcaatgc ctggagcacc aaggagcct   6540
tcagctggat caaggtggac ctgctggccc ccatgatcat ccatggcatc aagacccagg   6600
gggccaggga agttcagc agcctgtaca tcagccagtt catcatcgtg tacagcctgg   6660
atggcaagaa gtggcagacc tacaggggca acagcactgg caccctgatg gtgttctttg   6720
gcaatgtgga cagctctggc atcaagcaca acatcttcaa cccccccatc attgccagat   6780
acatcaggct gcaccccacc cactacagca tcaggagcac cctgaggatg gagctgatgg   6840
gctgtgacct gaacagctgc agcatgcccc tgggcatgga gagcaaggcc atctctgatg   6900
cccagatcac tgccagcagc tacttcacca acatgtttgc cacctggagc cccagcaagg   6960
ccaggctgca cctgcagggc aggagcaatg cctggaggcc ccaggtcaac aaccccaagg   7020
agtggctgca ggtggacttc cagaaagacca tgaaggtgac tggggtgacc acccagggggg   7080
tgaagagcct gctgaccagc atgtatgtga aggagttcct gatcagcagc agccaggatg   7140
gccaccagtg gaccctgttc ttccagaatg gcaaggtgaa ggtgttccag ggcaaccagg   7200
acagcttcac ccctgtggtg aacagcctga gcccccccct gctgaccaga tacctgagga   7260
ttcacccccca gagctggggtg caccagattg ccctgaggat ggaggtgctg ggctgtgagg   7320
cccaggacct gtactgactc ga   7342
```

SEQ ID NO: 39    moltype = DNA    length = 6181
FEATURE          Location/Qualifiers -continued

```
source              1..6181
                    mol_type = other DNA
                    note = ApoE-AAT-hBGi-FVIII-N6-F309S-DM-WPRE3-DTS
                    organism = synthetic construct
SEQUENCE: 39
cgcgtctgca ggctcagagg cacacaggag tttctgggct caccctgccc ccttccaacc  60
cctcagttcc catcctccag cagctgtttg tgtgctgcct ctgaagtcca cactgaacaa  120
acttcagcct actcatgtcc ctaaaatggg caaacattgc aagcagcaaa cagcaaacac  180
acagccctcc ctgcctgctg accttggagc tggggcagag gtcagagacc tctctgggcc  240
catgccacct ccaacatcca ctcgaccct tggaatttcg gtggagagga gcagaggttg  300
tcctggcgtg gtttaggtag tgtgagaggg gtcgactgga cacaggacgc tgtggtttct  360
gagccagggg gcgactcaga tcccagccag tggacttagc ccctgtttgc tcctccgata  420
actggggtga ccttggttaa tattcaccag cagcctcccc cgttgccccg taagtactag  480
cagctacaat ccagctacca ttctgctttt attttatggt tgggataagg ctggattatt  540
ctgagtccaa gctaggccct tttgctaatc atgttcatac ctcttatctt cctcccacag  600
atgcagattg agctgagcac ctgcttcttc ctgtgcctgc tgaggttctg cttctctgcc  660
accaggagat actacctggg ggctgtggag ctgagctggg actacatgca gtctgacctg  720
ggggagctgc ctgtggatgc caggttcccc ccagagtgc ccaagagctt ccccttcaac  780
acctctgtgg tgtacaagaa gaccctgttt gtggagttca ctgaccacct gttcaacatt  840
gccaagccca ggccccctg gatgggcctg ctgggcccca ccatccaggc tgaggtgtat  900
gacactgtg tgatcaccct gaagaacatg gccagccacc ctgtgagcct gcatgctgtg  960
ggggtgagct actggaaggc ctctgagggg gctgagtatg atgaccagac cagccagagg  1020
gagaaggagg atgacaaggt gttccctggg ggcagccaca cctatgtgtg gcaggtgctg  1080
aaggagaatg gccccatggc ctctgacccc ctgtgcctga cctacagcta cctgagccat  1140
gtggacctgg tgaaggacct gaactctggc ctgattgggg ccctgctggt gtgcagggag  1200
ggcagccggg ccaaggagaa gacccagacc tgcacaagt tcatcctgct gtttgctgtg  1260
tttgatgagg gcaagagctg gcactctgaa accaagaaca gcctgatgca ggacagggat  1320
gctgcctctg ccagggcctg gcccaagatg cacactgtga atggctatgt gaacaggagc  1380
ctgcctggcc tgattggctg ccacaggaag tctgtgtact ggcatgtgat tggcatgggc  1440
accaccccctg aggtgcacag catcttcctg gagggccaca cctccttct caggaaccac  1500
aggcaggcca gcctggagat cagccccatc accttcctga ctgcccagac cctgctgatg  1560
gacctgggcc agttcctgct gagctgccac atcagcagcc accagcatga tggcatggag  1620
gcctatgtga aggtggacag ctgccctgag gagcccagc tgaggatgaa gaacaatgag  1680
gaggctgagg actatgatga tgacctgact gactctgaga tggatgtggt gaggtttgat  1740
gatgacaaca gccccagctt catccagatc aggtctgtg ccaagaagca ccccaagacc  1800
tgggtgcact acattgctgc tgaggaggag gactgggact atgcccccct ggtgctggcc  1860
cctgatgaca ggagctacaa gagccagtac ctgaacaatg gccccagag gattggcagg  1920
aagtacaaga aggtcaggtt catggcctac actgatgaaa ccttcaagac cagggaggcc  1980
atccagcatg agtctggcat cctgggcccc ctgctgtatg gggaggtggg ggacaccctg  2040
ctgatcatct tcaagaacca ggccagcagg ccctacaaca tctacccca tggcatcact  2100
gatgtgaggc ccctgtacag caggaggctg cccaagggg tgaagcacct gaaggacttc  2160
cccatcctgc ctggggagat cttcaagtac aagtggactg tgactgtgga ggatggcccc  2220
accaagtctg accccaggtg cctgaccaga tactacagca gcttgtgaa catggagagg  2280
gacctggcct ctggcctgat tggcccctg ctgatctgct acaaggagtc tgtggaccag  2340
aggggcaacc agatcatgtc tgacaagagg aatgtgatcc tgttctctgt gtttgatgag  2400
aacaggagct ggtacctgac tgagaacatc cagaggttcc tgcccaaccc tgctggggtg  2460
cagctggagg accctgagtt ccaggccagc aacatcatga tcagatcaa tggctatgtg  2520
tttgacagcc tgcagctgtc tgtgtgcctg catgaggtgg cctactggta catcctgagc  2580
attggggccc agactgactt cctgtctgtg ttcttctctg gctacacctt caagcacaag  2640
atggtgtatg aggacaccct gaccctgttc cccttctctg gggagactgt gttcatgagc  2700
atggagaacc ctggcctgtg gattctgggc tgccacaact ctgacttcag gaacagggc  2760
atgactgccc tgctgaaagt ctccagctgt gacaagaaca ctggggacta ctatgaggac  2820
agctatgagg acatctctgc ctacctgctg agcaagaaca tgccattga gcccaggagc  2880
ttcagccaga atccccagt gctcaccgg tcctttagcc agaattctcg ccatccctcc  2940
acccggcaaa agcagttcaa cgccactacc atcccagaga acgacatcga aaaaaccgaa  3000
ccctggttcg cccacagaac tcccatgcca aagattcaga atgtttccag ttctgacctc  3060
cttatgttgc tgcgccagtc tccgacccct catggactgt ccctgagtga cttgcaggag  3120
gccaagtacg agacgttctc tgatgacccc agcccaggcg cgattgactc aaataactcc  3180
ctgtctgaga tgacacattt tcgccctcag ctccatcaca gcgggacat ggtgttcact  3240
ccagagtccg gacttcagct gcgcctcaac gagaaactcg gtactacagc cgcgacagaa  3300
ctcaaaaagc tggatttcaa ggtttccagc accagcaata acctgatctc tacaattccc  3360
agcgataacc tggcggctgg aaccgacaac acttccagcc tgggacctcc gtccatgcct  3420
gtgcactacg actcccagct cgacaccact ctgttcggca gaaaagtag ccccctgacc  3480
gaatccggcg gtccgctgtc cctctccgaa gagaataacg atagcaagct cctggaatct  3540
gggcttatga actctcaaga gtcatcctgg ggcaagaacg tttcatcaac tagggagatc  3600
accaggacca ccctgagtc tgaccaggag gagattgact atgatgacac catctctgtg  3660
gagatgaaga ggaggactt tgacatctac gacgaggacg agaaccagag ccccaggagc  3720
ttccagaaga gaccaggca ctacttcatt gctgctgtgg agaggctgtg ggactatggc  3780
atgagcagca gccccatgt gctgaggaac agggcccagt ctggctctgt gccccagttc  3840
aagaaggtgg tgttccagga gttcactgat ggcagcttca cccagcccct gtacagaggg  3900
gagctgaatg agcacctggg cctgctgggc ccctacatca gggctgaggt ggaggacaac  3960
atcatggtga ccttcaggaa ccaggccagc aggccctaca gcttctacag cagcctgatc  4020
agctatgagg aggaccagag gcaggggct gagcccagga gaactttgt gaagcccaat  4080
gaaaccaaga cctacttctg gaaggtgcag caccacatgg ccccaccaa ggatgagttt  4140
gactgcaagg cctgggccta cttctctgat gtggacctgg agaaggatgt ggactctggc  4200
ctgattggcc ccctgctggt gtgccacacc aacaccctga accctgccca tggcaggcag  4260
gtgactgtgc aggagtttgc cctgttcttc accatctttg atgaaccaa gagctggtac  4320
ttcactgaga acatggagag gaacggcagg gccccggca acatccagat ggaggacccc  4380
accttcaagg agaactacag gttccatgcc atcaatggct acatcatgga cacctgcct  4440
```

-continued

```
ggcctggtga tggcccagga ccagaggatc aggtggtacc tgctgagcat gggcagcaat   4500
gagaacatcc acagcatcca ctttctctggc catgtgttca ctgtgaggaa gaaggaggag   4560
tacaagatgg ccctgtacaa cctgtaccct ggggtgtttg agactgtgga gatgctgccc   4620
agcaaggctg gcatctggag ggtggagtgc ctgattgggg agcacctgca tgctggcatg   4680
agcaccctgt tcctggtgta cagcaacaag tgccagacca ccctgggcat ggcctctgtgg   4740
cacatcaggg acttccagat cactgcctct ggccagtatg gccagtgggc ccccaagctg   4800
gccaggctgc actactctgg cagcatcaat gcctggagca ccaaggagcc cttcagctgg   4860
atcaaggtg acctgctggc ccccatgatc atccatggca tcaagaccca gggggccagg   4920
cagaagttca gcagcctgta catcagccag ttcatcatca tgtacagcct ggatggcaag   4980
aagtggcaga cctacagggg caacagcact ggcaccctga tggtgttctt tggcaatgtg   5040
gacagctctg gcatcaagca caacatcttc aacccccca tcattgccag atacatcagg   5100
ctgcacccca cccactacag catcaggagc accctgagga tggagctgat gggctgtgac   5160
ctgaacagct gcagcatgcc cctgggcatg gagagcaagg ccatctctga tgcccagatc   5220
actgccagca gctacttcac caacatgttt gccacctgga gcccagcaa ggccaggctg   5280
cacctgcagg gcaggagcaa tgcctggagg ccccaggtca acaacccaa ggagtggctg   5340
caggtggact tccagaagac catgaaggtg actggggtga ccacccaggg ggtgaagagc   5400
ctgctgacca gcatgtatgt gaaggagttc ctgatcagca gcagccagga tggccaccag   5460
tggaccctgt tcttccagaa tggcaaggtg aaggtgttcc agggcaacca ggacagcttc   5520
acccctgtgg tgaacagcct ggacccccc ctgctgacca gatacctgag gattcacccc   5580
cagagctggg tgcaccagat tgccctgagg atggaggtgc tgggctgtga ggcccaggac   5640
ctgtactgaa atcaacctct ggattacaaa atttgtgaaa gattgactgg tattcttaac   5700
tatgttgctc ctttttacgct atgtggatac gctgctttaa tgcctttgta tcatgctatt   5760
gcttcccgta tggctttcat tttctcctcc ttgtataaat cctggttgct gtctctttat   5820
gaggagttgt ggcccgttgt caggcaacgt ggcgtggtgt gcactgtgtt tgctgacgca   5880
acccccactg gttggggcat tgccaccacc tgtcagctcc tttccgggac tttcgctttc   5940
ccctccta ttgccacggc ggaactcatc gccgcctgcc ttgcccgctg ctggacaggg   6000
gctcggctgt tgggcactga caattccgtg gagctgtgc gatccctgct ggggactttc   6060
cgctggggac tttccgctgg ggactttccg ccttcagcta aggaagctac caatatttag   6120
aggtacattt tgttctagaa caaaatgtac cggtacattt tgttctggta cattttgttc   6180
t                                                                    6181

SEQ ID NO: 40          moltype = DNA  length = 2363
FEATURE                Location/Qualifiers
source                 1..2363
                       mol_type = other DNA
                       note = APOE-AAT-hBGi-FIX -bGH-polyA-DTS
                       organism = synthetic construct
SEQUENCE: 40
gagctgtgcg atccctgctg gggactttcc gctggggact ttcgctggg gactttccgc   60
cttcagctaa ggaagctacc aatatttaga ggtacatttt gttctagaac aaaatgtacc   120
ggtacatttt gttctggtac attttgttct tgtgccttct agttgccagc catctgttgt   180
ttgcccctcc cccgtgcctt ccttgaccct ggaaggtgcc actcccactg tcctttccta   240
ataaaatgag gaaattgcat cgcattgtct gagtaggtgt cattctattc tggggggtg   300
ggtggggcag gacagcaagg gggaggattg ggaagacaat agcaggcatg ctggggatgc   360
ggtgggctct atggatcag cgcgtgaaca tgatcatggc agaatcacca ggcctcatca   420
ccatctgcct tttaggatat ctactcagtg ctgaatgtac agttttct gatcatgaaa   480
acgccaacaa aattctgaat cggccaaaga ggtataattc aggtaaattg gaagagtttg   540
ttcaagggaa ccttgagaga gaatgtatg aagaaaagtg tagttttgaa gaagcacagg   600
aagttttga aaacactgaa agaacaactg aattttggaa gcagtatgtt gatggagatc   660
agtgtgagtc caatccatgt ttaaatggcg gcagttgcaa ggatgacatt aattcctatg   720
aatgttggtg tcccttggga tttgaaggaa agaactgtga attagatgta acatgtaaca   780
ttaagaatgg cagatgcgag cagttttgta aaaatagtgc tgataacaag gtggtttgct   840
cctgtactga gggatatcga cttgcagaaa accagaagtc ctgtgaacca gcagtgccat   900
ttccatgtgg aagagtttct gtttcacaaa cttctaagct cacccgtgct gagactgttt   960
ttcctgatgt ggactatgta aattctactg aagctgaaac cattttggat aacatcactc   1020
aaagcacccA atcatttaat gacttcactc gggttgttgg tggagaagat gccaaaccag   1080
gtcaattccc ttggcaggtt gtttttgaatg gtaaagttga tgcattctgt ggaggctcta   1140
tcgttaatga aaaatggatt gtaactgctg cccactgtgt tgaaactggt gttaaaatta   1200
cagttgtcgc aggtgaacat aatattgagg agacagaaca tacagagcaa aagcgaaatg   1260
tgattcgaat tattcctcac cacaactaca atggcagctat taataagtac aaccatgaca   1320
ttgcccttct ggaactggac gaaccttag tgctaaacag ctacgttaca cctatttgca   1380
ttgctgacaa ggaatacacg aacatcttcc tcaaatttgg atctggctat gtaagtggct   1440
ggggaagagt cttccacaaa gggagatcag ctttagttct tcagtacctt agagttccac   1500
ttgttgaccg agccacatgt cttcgatcta caaagttcac catctataac acatgtttct   1560
gtgctggctt ccatgaagga ggtagagatt catgtcaagg agatagtggg ggaccccatg   1620
ttactggaag ggaagggacc agtttcttaa ctggaattat tagctggggt gaagagtgtg   1680
caatgaaagg caaatatgga atatatacca aggtatcccg gtatgtcaac tggattaagg   1740
aaaaaacaaa gctcacttaa tgagtaagta ctagcagcta caatccagct accattctgc   1800
ttttatttta tggttgggat aaggctggat tattctgagt ccaagctagg cccttttgct   1860
aatcatgttc atacctctta tcttcctccc acagcgcgtc tgcaggctca gaggcacaca   1920
ggagtttctg ggctcaccct gccccttcc aacccctcag ttcccatcct ccagcagctg   1980
tttgtgtgct gcctctgaag tccacactga acaaacttca gcctactcat gtccctaaaa   2040
tgggcaaaca ttgcaagcag caaacagcaa acacacagcc ctccctgcct gctgaccttg   2100
gagctgggg agaggtcaga gacctctctg ggccatgcc acctccaaca tccactcgac   2160
cccttgggaat ttcggtggag aggagcagag gttgtcctgg cgtggtttag gtagtgtgag   2220
aggggtcgac tggacacagg acgctgtggt ttctgagcca gggggcgact cagatcccag   2280
ccagtggact tagcccctgt ttgctcctcc gataactggg gtgaccttgg ttaatattca   2340
ccagcagcct cccccgttgc ccc                                           2363
```

-continued

```
SEQ ID NO: 41          moltype = DNA  length = 2595
FEATURE                Location/Qualifiers
source                 1..2595
                       mol_type = other DNA
                       note = APOE-AAT-hBGi-FIX WPRE3-bGH-polyA
                       organism = synthetic construct
SEQUENCE: 41
cgcgtctgca ggctcagagg cacacaggag tttctgggct caccctgccc ccttccaacc   60
cctcagttcc catcctccag cagctgtttg tgtgctgcct ctgaagtcca cactgaacaa  120
acttcagcct actcatgtcc ctaaaatggg caaacattgc aagcagcaaa cagcaaacac  180
acagccctcc ctgcctgctg accttggagc tggggcagag gtcagagacc tctctgggcc  240
catgccacct ccaacatcca ctcgacccct tggaatttcg gtggagagga gcagaggttg  300
tcctggcgtg gtttaggtag tgtgagaggg gtcgactgga cacaggacgc tgtggtttct  360
gagccagggg gcgactcaga tcccagccag tggacttagc ccctgtttgc tcctccgata  420
actggggtga ccttggttaa tattcaccag cagcctcccc cgttgccccg taagtactag  480
cagctacaat ccagctacca ttctgctttt attttatggt tgggataagg ctggattatt  540
ctgagtccaa gctaggccct tttgctaatc atgttcatac ctcttatctt cctcccacag  600
atgcagcgcg tgaacatgat catggcagaa tcaccaggcc tcatcaccat ctgccttta  660
ggatatctac tcagtgctga atgtacagtt tttcttgatc atgaaaacgc caacaaaatt  720
ctgaatcggc caaagaggta taattcaggt aaattggaag agtttgttca agggaacctt  780
gagagagaat gtatggaaga aaagtgtagt tttgaagaag cacgagaagt ttttgaaaac  840
actgaaagaa caactgaatt ttggaagcag tatgttgatg gagatcagtg tgagtccaat  900
ccatgtttaa atggcggcag ttgcaaggat gacattaatt cctatgaatg ttggtgtccc  960
tttggatttg aaggaaagaa ctgtgaatta gatgtaacat gtaacattaa gaatggcaga 1020
tgcgagcagt tttgtaaaaa tagtgctgat aacaaggtgg tttgctcctg tactgaggga 1080
tatcgacttg cagaaaacca gaagtcctgt gaaccagcac tgccatttcc atgtggaaga 1140
gtttctgttt cacaaacttc taagctcacc cgtgctgaga ctgttttcc tgatgtggac 1200
tatgtaaatt ctactgaagc tgaaaccatt ttggataaca tcactcaaag cacccaatca 1260
tttaatgact tcactcgggt tgttggtgga aagatgccaa aaccaggtca attcccttgg 1320
caggttgttt tgaatggtaa agttgatgca ttctgtggag gctctatcgt taatgaaaaa 1380
tggattgtaa ctgctgccca ctgtgttgaa actggtgtta aaattacagt tgtcgcaggt 1440
gaacataata ttgaggagac agaacataca gagcaaaagc gaaatgtgat tcgaattatt 1500
cctcaccaca actacaatgc agctattaat aagtacaacc atgacattgc ccttctggaa 1560
ctggacgaac ccttagtgct aaacagctac gttacaccta tttgcattgc tgacaaggaa 1620
tacacgaaca tcttcctcaa atttggatct ggctatgtaa gtggctgggg aagagtcttc 1680
cacaaaggga gatcagcttt agttcttcag taccttagag ttccacttgt tgaccgagcc 1740
acatgtcttc gatctacaaa gttcaccatc tataacaaca tgttctgtgc tggcttccat 1800
gaaggaggta gagattcatg tcaaggagat agtgggggac cccatgttac tgaagtggaa 1860
gggaccagtt tcttaactgg aattattagc tggggtgaag agtgtgcaat gaaaggcaaa 1920
tatggaatat ataccaaggt atcccggtat gtcaactgga ttaaggaaaa aacaaagctc 1980
acttaatgaa atcaacctct ggattacaaa atttgtgaaa gattgactgg tattcttaac 2040
tatgttgctc cttttacgct atgtggatac gctgctttaa tgcctttgta tcatgctatt 2100
gcttcccgta tggctttcat tttctcctcc ttgtataaat cctggttgct gtctctttta 2160
gaggagttgt ggcccgttgt caggcaacgt ggcgtggtgt gcactgtgtt tgctgacgca 2220
accccccactg gttggggcat tgccaccacc tgtcagctcc tttccgggac tttcgctttc 2280
ccctcccta ttgccacggc ggaactcatc gccgcctgcc ttgcccgctg ctggacaggg 2340
gctcggctgt tgggcactga caattccgtg gtgttgcctc tagttgccag ccatctgttg 2400
tttgcccctc ccccgtgcct tccttgaccc tggaaggtgc cactcccact gtcctttcct 2460
aataaaatga ggaaattgca tcgcattgtc tgagtaggtg tcattctatt ctgggggtg 2520
gggtggggca ggacagcaag ggggaggatt gggaagacaa tagcaggcat gctggggatg 2580
cggtgggctc tatgg                                                   2595

SEQ ID NO: 42          moltype = DNA  length = 2472
FEATURE                Location/Qualifiers
source                 1..2472
                       mol_type = other DNA
                       note = ITR-APOE-AAT-hBGi-FIX- bGH-polyA-ITR
                       organism = synthetic construct
SEQUENCE: 42
gctcactcac tcactcactg aggcctgcag agcaaagctc tgcagtctgg ggacctttgg   60
tccccaggcc tcagtgagtg agtgagtgag cagagaggga gtggccaact ccatcactag  120
gggttcctcg cgtctgcagg ctcagaggca cacaggagtt tctgggctca ccctgccccc  180
ttccaacccc tcagttccca tcctccagca gctgtttgtg tgctgcctct gaagtccaca  240
ctgaacaaac ttcagcctac tcatgtccct aaaatggca aacattgcag cagcaaacac  300
gcaaacacac agccctccct gcctgctgac cttggagctg ggggcagagg cagagacctc  360
tctgggccca tgccacctcc aacatccact cgacccttg gaatttcggt ggagaggagc  420
agaggttgtc ctggcgtggt ttaggtagtg tgagaggggt cgactggaca caggacgctg  480
tggtttctga gccaggggc gactcagatc ccagccagtg gacttagccc ctgtttgctc  540
ctccgataac tggggtgacc ttggttaata ttcaccagca gcctccccg ttgccccgta  600
agtactagca gctacaatcc agctaccatt ctgctttat tttatggttg ggataaggct  660
ggattattct gagtccaagc taggcccttt gctaatcat gttcatacct ttatcttcc  720
tcccacagat gcagcgcgtg aacatgatca tggcagaatc accaggcctc atcaccatct  780
gccttttagg atatctactc agtgctgaat gtacagtttt tcttgatcat gaaaacgcca  840
acaaaattct gaatcggcca aagaggtata attcaggtaa aattggaag agtttgttcaag  900
ggaaccttga gagagaatgt atggaagaaa agtgtagttt tgaagaagca cgagaagttt  960
ttgaaaacac tgaaagaaca actgaatttt ggaagcagta tgttgatgga gatcagtgtg  1020
agtccaatcc atgtttaaat ggcggcagtt gcaaggatga cattaattcc tatgaatgtt  1080
ggtgtccctt tggatttgaa ggaaagaact gtgaattaga tgtaacatgt aacattaaga  1140
atggcagatg cgagcagttt gtaaaaata gtgctgataa caaggtggtt tgctcctgta  1200
```

```
ctgagggata tcgacttgca gaaaaccaga agtcctgtga accagcagtg ccatttccat    1260
gtggaagagt ttctgtttca caaacttcta agctcacccg tgctgagact gttttttcctg  1320
atgtggacta tgtaaattct actgaagctg aaaccatttt ggataacatc actcaaagca   1380
cccaatcatt taatgacttc actcgggttg ttggtggaga agatgccaaa ccaggtcaat    1440
tcccttggca ggttgttttg aatggtaaag ttgatgcatt ctgtggaggc tctatcgtta   1500
atgaaaaatg gattgtaact gctgcccact gtgttgaaac tggtgttaaa attacagttg   1560
tcgcaggtga acataatatt gaggagacag aacatacaga gcaaaagcga aatgtgattc   1620
gaattattcc tcaccacaac tacaatgcag ctattaataa gtacaaccat gacattgccc   1680
ttctggaact ggacgaaccc ttagtgctaa acagctacgt tacacctatt tgcattgctg   1740
acaaggaata cacgaacatc ttcctcaaat ttggatctgg ctatgtaagt ggctgggaa    1800
gagtcttcca caaagggaga tcagctttag ttcttcagta ccttagagtt ccacttgttg   1860
accgagccac atgtcttcga tctacaaagt tcaccatcta taacaacatg ttctgtgctg   1920
gcttccatga aggaggtaga gattcatgtc aaggagatag tgggggaccc catgttactg   1980
aagtggaagg gaccagtttc ttaactggaa ttattagctg gggtgaagag tgtgcaatga   2040
aaggcaaata tggaatatat accaaggtat cccggtatgt caactggatt aaggaaaaaa   2100
caaagctcac ttaatgatgt gccttctagt tgccagccat ctgttgtttg cccctcccc    2160
gtgccttcct tgaccctgga aggtgccact cccactgtcc tttcctaata aaatgaggaa   2220
attgcatcgc attgtctgag taggtgtcat tctattctgg ggggtggggt ggggcaggac   2280
agcaaggggg aggattggga agacaatagc aggcatgctg gggatgcggt gggctctatg   2340
gaggaacccc tagtgatgga gttggccact ccctctctgc tcactcactc actcactgag   2400
gcctggggac caaaggtccc cagactgcag agctttgctc tgcaggcctc agtgagtgag   2460
tgagtgagca ga                                                        2472
```

```
SEQ ID NO: 43             moltype = DNA  length = 5707
FEATURE                   Location/Qualifiers
source                    1..5707
                          mol_type = other DNA
                          note = ApoE-AAT-hBGi-FVIII-v3-WPRE3-DTS
                          organism = synthetic construct
SEQUENCE: 43
cgcgtctgca ggctcagagg cacacaggag tttctgggct caccctgccc ccttccaacc    60
cctcagttcc catcctccag cagctgtttg tgtgctgcct ctgaagtcca cactgaacaa   120
acttcagcct actcatgtcc ctaaaatggg caaacattgc aagcagcaaa cagcaaacac   180
acagccctcc ctgcctgctg accttggagc tggggcagag gtcagagacc tctctgggcc   240
catgccacct ccaacatcca ctcgacccct tggaatttcg gtggagagga gcagaggttg   300
tcctggcgtg gtttaggtag tgtgagaggg gtcgactgga cacaggacgc tgtggtttct   360
gagccagggg gcgactcaga tcccagccag tggacttagc ccctgtttgc tcctccgata   420
actggggtga ccttggttaa tattcaccag cagcctcccc cgttgcccct ctggatccac   480
tgcttaaata cggacgagga cagggccctg tctcctcagc ttcaggcacc accactgacc   540
tgggacagta aatcgtaagt actagcagct acaatccagc taccattctg cttttatttt   600
atggttggga taaggctgga ttattctgag tccaagctag gccctttgc taatcatgtt    660
catacctctt atcttcctcc cacagctcct gggcaacgtg ctggtctgtg tgctggccca   720
tcactttggc aaagaattgc gatcgccacc atgcagattg agctgagcac ctgcttcttc   780
ctgtgcctgc tgaggttctg cttctctgcc accaggagat actacctggg ggctgtggag   840
ctgagctggg actacatgca gtctgacctg ggggagctgc ctgtggatgc caggttcccc   900
cccagagtgc ccaagagctt cccttcaac acctctgtgg tgtacaagaa gaccctgttt    960
gtggagttca ctgaccacct gttcaacatt gccaagccca gaccccctg gatgggcctg   1020
ctgggcccca ccatccaggc tgaggtgtat gacactgtgg tgatcaccct gaagaacatg   1080
gccagccacc ctgtgagcct gcatgctgtg ggggtgagct actggaaggc ctctgagggg   1140
gctgagtatg atgaccagac cagccagagg gagaaggagg atgacaaggt gttccctggg   1200
ggcagccaca cctatgtgtg gcaggtgctg aaggagaatg gccccatggc ctctgacccc   1260
ctgtgcctga cctacagcta cctgagccat gtggacctgg tgaaggacct gaactctggc   1320
ctgattgggg ccctgctggt gtgcagggag ggcagcctgg ccaaggagaa gacccagacc   1380
ctgcacaagt tcatcctgct gtttgctgtg tttgatgagg gcaagagctg gcactctgaa   1440
accaagaaca gcctgatgca ggacagggat gctgcctctg ccagggcctg gcccaagatg   1500
cacactgtga atggctatgt gaacaggagc ctgcctggcc tgattggctg ccacaggaag   1560
tctgtgtact ggcatgtgat tggcatgggc accacccctg aggtgcacag catcttcctg   1620
gagggccaca ccttcctggt caggaaccac aggcaggcca gcctggagat cagccccatc   1680
accttcctga ctgcccagac cctgctgatg gacctgggcc agttcctgct gttctgccac   1740
atcagcagcc accagcatga tggcatggag gccatgtga aggtggacag ctgccctgag   1800
gagcccagc tgaggatgaa gaacaatgag gaggctgagg actatgatga tgacctgact   1860
gactctgaga tggatgtggt gaggtttgat gatgacaaca gccccagctt catccagatc   1920
aggtctgtgg ccaagaagca cccaagacc tgggtgcact acattgctgc tgaggaggag   1980
gactgggact atgcccccct ggtgctggcc cctgatgaca gagcccagtac catgcctac   2040
ctgaacaatg cccccagag gattggcagg aagtacaaga aggtcaggtt catgtgctac   2100
actgatgaaa ccttcaagac cagggaggcc atccagcatg agtctggcat cctgggccc    2160
ctgctgtatg gggaggtggg ggacaccctg ctgatcatct tcaagaacca ggccagcagg   2220
ccctacaaca tctacccca tggcatcact gatgtgaggc ccctgtacag caggaggctg   2280
cccaaggggg tgaagcacct gaaggacttc cccatcctgc ctggggagat cttcaagtac   2340
aagtggactg tgactgtgga ggatggcccc accaagtctg accccaggtg cctgaccaga   2400
tactacagca gctttgtgaa catggagagg gacctggcct ctggcctgat tggccccctg   2460
ctgatctgct acaaggagtc tgtggaccag aggggcaacc agatcatgtc tgacaagagg   2520
aatgtgatcc tgttctctgt gtttgatgag aacaggagct ggtacctgac tgagaacatc   2580
cagaggttcc tgcccaaccc tgctggggtg cagctggagg accctgagtt ccaggccag   2640
aacatcatgc acagcatcaa tggctatgtg tttgacagcc tgcagctgtc tgtgtgcctg   2700
catgaggtgg cctactggta catcctgagc attgggggcc agactgactt cctgtctgtg   2760
ttcttctctg ctacacctt caagcacaag atggtgtatg aggacaccct gaccctgttc   2820
cccttctctg gggagactgt gttcatgagc atggagaacc ctggcctgtg gattctgggc   2880
tgccacaact ctgacttcag gaacaggggc atgactgccc tgctgaaagt ctccagctgt   2940
```

```
gacaagaaca ctggggacta ctatgaggac agctatgagg acatctctgc ctacctgctg    3000
agcaagaaca atgccattga gcccaggagc ttcagccaga atgccactaa tgtgtctaac    3060
aacagcaaca ccagcaatga cagcaatgtg tctcccccag tgctgaagag gcaccagagg    3120
gagatcacca ggaccaccct gcagtctgac caggaggaga ttgactatga tgacaccatc    3180
tctgtggaga tgaagaagga ggactttgac atctacgacg aggacgagaa ccagagcccc    3240
aggagcttcc agaagaagac caggcactac ttcattgctg ctgtggagag gctgtgggac    3300
tatggcatga gcagcagccc ccatgtgctg aggaacaggg cccagtctgg ctctgtgccc    3360
cagttcaaga aggtggtgtt ccaggagttc actgatggca gcttcaccca gcccctgtac    3420
agaggggagc tgaatgagca cctgggcctg ctgggcccct acatcagggc tgaggtggag    3480
gacaacatca tggtgacctt caggaaccag gccagcaggc cctacagctt ctacagcagc    3540
ctgatcagct atgaggagga ccagaggcag ggggctgagc ccaggaagaa ctttgtgaag    3600
cccaatgaaa ccaagaccta cttctggaag gtgcagcacc acatggcccc caccaaggat    3660
gagtttgact gcaaggcctg ggcctacttc tctgatgtgg acctggagaa ggatgtgcac    3720
tctggcctga ttggcccct gctggtgtgc cacaccaaca ccctgaaccc tgcccatggc    3780
aggcaggtga ctgtgcagga gtttgccctg ttcttcacca tctttgatga aaccaagagc    3840
tggtacttca ctgagaacat ggagaggaac tgcagggccc cctgcaacat ccagatggag    3900
gacccccacct tcaaggagaa ctacaggttc catgccatca atggctacat catggacacc    3960
ctgcctggcc tggtgatggc ccaggaccag aggatcaggt ggtacctgct gagcatgggc    4020
agcaatgaga acatccacag catccacttc tctggccatg tgttcactgt gaggaagaag    4080
gaggagtaca agatggccct gtacaacctg taccctgggg tgtttgagac tgtggagatg    4140
ctgcccagca aggctggcat ctggaggggtg gagtgcctga ttggggagca cctgcatgct    4200
ggcatgagca ccctgttcct ggtgtacagc aacaagtgcc agacccccct gggcatggcc    4260
tctggccaca tcagggactt ccagatcact gcctctggcc agtatggcca gtgggccccc    4320
aagctggcca ggctgcacta ctctggcagc atcaatgcct ggagcaccaa ggagcccttc    4380
agctggatca aggtggacct gctggccccc atgatcatcc atggcatcaa gacccagggg    4440
gccaggcaga agttcagcag cctgtacatc agccagttca tcatcatgta cagcctggat    4500
ggcaagaagt ggcagaccta caggggcaac agcactggca cccctgatggt gttctttggc    4560
aatgtggaca gctctggcat caagcacaac atcttcaacc cccccatcat tgccagatac    4620
atcaggctgc accccacccca ctacagcatc aggagcaccc tgaggatgga gctgatgggc    4680
tgtgacctga acagctgcag catgcccctg ggcatggaga gcaaggccat ctctgatgcc    4740
cagatcactg ccagcagcta cttcaccaac atgtttgcca cctggagccc cagcaaggcc    4800
aggctgcacc tgcagggcag gagcaatgcc tggaggcccc aggtcaacaa ccccaaggag    4860
tggctgcagg tggacttcca gaagaccatg aaggtgactg gggtgaccac ccagggggtg    4920
aagagcctgc tgaccagcat gtatgtgaag gagttcctga tcagcagcag ccaggatggc    4980
caccagtgga ccctgttctt ccagaatggc aaggtgaagg tgttccaggg caaccaggac    5040
agcttcaccc ctgtggtgaa cagcctggac ccccccctgc tgaccagata cctgaggatt    5100
cacccccaga gctgggtgca ccagattgcc ctgaggatgg aggtgctggg ctgtgaggcc    5160
caggacctgt actgaaatca acctctggat tacaaaattt gtgaaagatt gactggtatt    5220
cttaactatg ttgctccttt tacgctatgt ggatacgctg cttaatgcct tttgtatcat    5280
gctattgctt cccgtatggc tttcattttc tcctccttgt ataaatcctg gttgctgtct    5340
ctttatgagg agttgtggcc cgttgtcagg caacgtggcg tggtgtgcac tgtgtttgct    5400
gacgcaaccc ccactggttg gggcattgcc accacctgtc agctcctttc cgggactttc    5460
gctttccccc tccctattgc cacggcggaa ctcatcgccg cctgccttgc ccgctgctgg    5520
acaggggctc ggctgttggg cactgacaat tccgtgggag ctgtgcgatc cctgctgggg    5580
actttccgct ggggactttc cgctggggac tttccgcctt cagctaagga agctaccaat    5640
atttagaggt acattttgtt ctagaacaaa atgtaccggt acattttgtt ctggtacatt    5700
ttgttct                                                                5707
```

```
SEQ ID NO: 44          moltype = DNA   length = 5968
FEATURE                Location/Qualifiers
source                 1..5968
                       mol_type = other DNA
                       note = ITR-ApoE-AAT-hBGi-FVIII-SQ-N6-F309S-DM-WPRE3-DTS-ITR
                       organism = synthetic construct
SEQUENCE: 44
cctgcaggca gctgcgcgct cgctcgctca ctgaggccgc ccgggcgtcg ggcgaccttt    60
ggtcgcccgg cctcagtgag cgagcgcgca gagagggagt ggccaactcc atcactaggg    120
gttcctgcgg ccgcacgcgt ctagttatta atagtaatcg aattcgcgtc tgcaggctca    180
gaggcacaca ggagtttctg ggctcaccct gcccccttcc aacccctcag ttcccatcct    240
ccagcagctg tttgtgtgct gcctctgaag tccacactga acaaacttca gcctactcat    300
gtccctaaaa tgggcaaaca ttgcaagcag caaacagcaa acacacagcc ctccctgcct    360
gctgaccttg gagctggggc agaggtcaga gacctctctg ggcccatgcc acctccaaca    420
tccactcgac cccttggaat ttcggtggag aggagcagag gttgtcctgg cgtggtttag    480
gtagtgtgag aggggtcgac ttctgacacagg acgctgtggt ttctgagcga ggggcgagtc    540
cagatcccag ccagtggact tagccccctgt ttgctcctcc gataactggg gtgaccttgg    600
ttaatattca ccagcagcct ccccgttgc ccctctggat ccactgctta aatacggacg    660
aggacagggc cctgtctcct cagcttcagg caccaccact gacctgggac agtgaatcgt    720
aagtactagc agctacaatc cagctaccat tctgctttta ttttatggtt gggataaggc    780
tggattattc tgagtccaag ctaggccctt ttgctaatca tgttcatacc tcttatcttc    840
ctcccacagc tcctgggcaa cgtgctggtc tgtgtgctgg cccatcactt ggcaaagaa    900
ttgcgatcgc caccatgcag attgagctga gcacctgctt cttcctgtgc ctgctgaggt    960
tctgcttctc tgccaccagg agatactacc tggggggctgt ggagctgagc tgggactaca    1020
tgcagtctga cctggggggag ctgcctgtgg atgccaggtt cccccccaga gtgcccaaga    1080
gcttcccctt caacacctct gtggtgtaca aagaagaccct gtttgtggag ttcactgacc    1140
acctgttcaa cattgccaag cccaggcccc cctggatggg cctgctgggc cccaccatcc    1200
aggctgaggt gtatgacact gtggtgatca ccctgaagaa catggccagc caccctgtga    1260
gcctgcatgt gtggggggtg agctactgga aggcctctga gggggctgag tatgatgacc    1320
agaccagcca gagggagaag gaggatgaca aggtgttccc tgggggcagc cacacctatg    1380
tgtgcaggt gctgaaggag aatggcccca tggcctctga ccccctgtgc ctgacctaca    1440
```

```
gctacctgag ccatgtggac ctggtgaagg acctgaactc tggcctgatt gggggccctgc     1500
tggtgtgcag ggagggcagc ctggccaagg agaagaccca gaccctgcac aagttcatcc     1560
tgctgtttgc tgtgtttgat gagggcaaga gctggcactc tgaaaccaag aacagcctga     1620
tgcaggacag ggatgctgcc tctgccaggg cctggcccaa gatgcacact gtgaatggct     1680
atgtgaacag gagcctgcct ggcctgattg gctgccacag gaagtctgtg tactggcatg     1740
tgattggcat gggcaccacc cctgaggtgc acagcatctt cctggagggc cacaccttcc     1800
tggtcaggaa ccacaggcag gccagcctgg agatcagccc catcaccttc ctgactgccc     1860
agaccctgct gatggacctg ggccagttcc tgctgagctg ccacatcagc agccaccagc     1920
atgatggcat ggaggcctat gtgaaggtgg acagctgccc tgaggagccc cagctgagga     1980
tgaagaacaa tgaggaggct gaggactatg atgatgacct gactgactct gagatggatg     2040
tggtgaggtt tgatgatgac aacagcccca gcttcatcca gatcaggtct gtggccaaga     2100
agcaccccaa gacctgggtg cactacattg ctgctgagga ggaggactgg gactatgccc     2160
ccctggtgct ggccctgat gacaggagct acaagagcca gtacctgaac aatggccccc     2220
agaggattgg caggaagtac aagaaggtca ggttcatggc ctacactgat gaaaccttca     2280
agaccaggga ggccatccag catgagtctg gcatcctggg ccccctgctg tatggggagg     2340
tgggggacac cctgctgatc atcttcaaga accaggccag caggccctac aacatctacc     2400
cccatggcat cactgatgtg aggcccctgt acagcaggag gctgcccaag ggggtgaagc     2460
acctgaagga cttccccatc ctgcctgggg agatcttcaa gtacaagtgg actgtgactg     2520
tggaggatgg ccccaccaag tctgacccca ggtgcctgac cagatactac agcagctttg     2580
tgaacatgga gagggacctg gcctctggcc tgattggccc cctgctgatc tgctacaagg     2640
agtctgtgga ccagaggggc aaccagatca tgtctgacaa gaggaatgtg atcctgttct     2700
ctgtgtttga tgagaacagg agctggtacc tgactgagaa catccagagg ttcctgccca     2760
accctgctgg ggtgcagctg gaggaccctg agttccaggc cagcaacatc atgcacagca     2820
tcaatggcta tgtgtttgac agcctgcagc tgtctgtgtg cctgcatgag gtggcctact     2880
ggtacatcct gagcattggg gcccagactg acttcctgtc tgtgttcttc tctggctaca     2940
ccttcaagca caagatggtg tatgaggaca ccctgacct gttcccctc tctggggaga     3000
ctgtgttcat gagcatggag aaccctggcc tgtggattct gggctgccac aactctgact     3060
tcaggaacag gggcatgact gccctgctga agtctccag ctgtgacaag aacactgggg     3120
actactatga ggacagctat gaggacatct ctgcctacct gctgagcaag aacaatgcca     3180
ttgagcccag gagcttcagc cagaatcccc cagtgctcac ccggtccttt agccagaatt     3240
ctcgccatcc ctccacccgg caaaagcagt tcaacgccac taccatccca gagaacgaca     3300
tcgaaaaaac cgaccctgg ttcgcccaca gaactccat gccaaagatt cagaatgttt     3360
ccagttctga cctcttatg ttgctgcgcc agtctccgac ccctcatgga ctgtccctga     3420
gtgacttgca ggaggccaag tacgagacgt tctctgatga ccccagccca ggcgcgattg     3480
actcaaataa ctccctgtct gagatgacac attttcgccc tcagctccat cacagcgggg     3540
acatggtgtt cactccagag tccggacttc agctgcgcct caacgagaaa ctcggtacta     3600
cagccgcgac agaactcaaa aagctggatt tcaaggtttc cagcaccagc aataacctga     3660
tctctacaat tcccagcgat aacctggcgg ctggaaccga caacacttcc agcctgggac     3720
ctccgtccat gcctgtgcac tacgactccc agctcgacac cactctgttc ggcaagaaaa     3780
gtagcccct gaccgaatcc ggcggtccgc tgtccctctc cgaagagaat aacgatagca     3840
agctcctgga atctgggctt atgaactctc aagagtcatc ctggggcaag aacgtttcat     3900
caactaggga gatcaccagg accaccctgc agtctgacca ggaggagatt gactatgatg     3960
acaccatctc tgtggagatg aagaaggagg actttgacat ctacgacgag gacgagaacc     4020
agagcccccag gagcttccag aagaagacca ggcactactt cattgctgct gtggagaggc     4080
tgtgggacta tggcatgagc agcagcccccc atgtgctgag gaacagggcc cagtctggct     4140
ctgtgcccca gttcaagaag gtggtgttcc aggagttcac tgatggcagc ttcacccagc     4200
ccctgtacag aggggagctg aatgagcacc tgggcctgct gggcccctac atcaggggctg     4260
aggtggagga caacatcatg gtgaccttca ggaaccagg cagcaggccc tacagcttct     4320
acagcagcct gatcagctat gaggaggacc agaggcaggg ggctgagccc aggaagaact     4380
ttgtgaagcc caatgaaacc aagacctact tctggaaggt gcagcaccac atggccccca     4440
ccaaggatga gtttgactgc aaggcctggg cctacttctc tgatgtggac ctggagaagg     4500
atgtgcactc tggcctgatt ggcccctgc tggtgtgcca caccaacacc ctgaaccctg     4560
cccatggcag gcaggtgact gtgcaggagt ttgccctgtt cttcaccatc tttgatgaaa     4620
ccaagagctg gtacttcact gagaacatgg agaggaacgg cagggccccc ggcaacatcc     4680
agatggagga ccccacctc aaggagaact acaggttcca tgccatcaat ggctacatca     4740
tggacaccct gcctggcctg gtgatggccc aggaccagag gatcaggtgg tacctgctga     4800
gcatgggcag caatgagaac atccacagca tccacttctc tggccatgtg ttcactgtga     4860
ggaagaagga ggagtacaag atggcctgt acaaactgta ccctgggtg tttgagactg     4920
tggagatgct gcccagcaag gctggcatct ggagggtgga gtgctgatt ggggagcacc     4980
tgcatgctgg catgagcacc ctgttcctgg tgtacagcaa caagtgccag accccccttg     5040
gcatggcctc tggccacatc agggacttcc agatcactgc ctctggccag tatggccagt     5100
gggcccccaa gctggccagg ctgcactact ctggcagcat caatgcctgg agcaccaagg     5160
agcccttcag ctggatcaag gtggacctgc tggccccat gatcatccat ggcatcaaga     5220
cccaggggc caggcagaag ttcagcagcc tgtacatcag ccagttcatc atcatgtaca     5280
gcctggatgg caagaagtgg cagacctaca ggggcaacag cactggcacc ctgatggtgt     5340
tctttggcaa tgtggacagc tctggcatca agcacaacat cttcaacccc ccatcattg     5400
ccagatacat caggctgcac cccacccact acagcatcag gagcacccctg aggatggagc     5460
tgatgggctg tgacctgaac agctgcagca tgccctggg catggagagc aaggccatct     5520
ctgatgccca gatcactgcc agcagctact tcaccaacat gtttgccacc tggagcccca     5580
gcaaggccag gctgcacctg caggcagga gcaatgcctg gaggccccag gtcaacaacc     5640
ccaaggagtg gctgcaggtg gacttccaga agaccatgaa ggtgactggg gtgaccaccc     5700
agggggtgaa gagcctgctg accagcatgt atgtgaagga gttcctgatc agcagcagcc     5760
aggatggcca ccagtggacc ctgttcttcc agaatggcaa ggtgaaggtg ttccagggca     5820
accaggacag cttcacccct gtggtgaaca gcctgaccc cccctgctg accagatacc     5880
tgaggattca ccccccagagc tgggtgcacc agattgccct gaggatggag gtgctgggct     5940
gtgaggccca ggacctgtac tgactcga                                       5968
```

SEQ ID NO: 45        moltype = DNA    length = 606
FEATURE              Location/Qualifiers -continued

```
source                  1..606
                        mol_type = other DNA
                        note = WPRE3+bGhPolyA
                        organism = synthetic construct
SEQUENCE: 45
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt cccctccct   300
attgccacgg cggaactcat cgccgcctgc cttgcccgct gctggacagg ggctcggctg  360
ttgggcactg acaattccgt ggtgtgcctt ctagttgcca gccatctgtt gtttgcccct  420
cccccgtgcc ttccttgacc ctggaaggtg ccactcccac tgtcctttcc taataaaatg  480
aggaaattgc atcgcattgt ctgagtaggt gtcattctat tctgggggt ggggtggggc   540
aggacagcaa ggggaggat tgggaagaca atagcaggca tgctggggat gcggtgggct  600
ctatgg                                                             606

SEQ ID NO: 46          moltype = AA  length = 1490
FEATURE                Location/Qualifiers
source                 1..1490
                       mol_type = protein
                       organism = synthetic construct
SEQUENCE: 46
FVIIIVTRAN SLATIONMQI ELSTCFFLCL LRFCFSATRR YYLGAVELSW DYMQSDLGEL   60
PVDARFPPRV PKSFPFNTSV VYKKTLFVEF TDHLFNIAKP RPPWMGLLGP TIQAEVYDTV  120
VITLKNMASH PVSLHAVGVS YWKASEGAEY DDQTSQREKE DDKVFPGGSH TYVWQVLKEN  180
GPMASDPLCL TYSYLSHVDL VKDLNSGLIG ALLVCREGSL AKEKTQTLHK FILLFAVFDE  240
GKSWHSETKN SLMQDRDAAS ARAWPKMHTV NGYVNRSLPG LIGCHRKSVY WHVIGMGTTP  300
EVHSIFLEGH TFLVRNHRQA SLEISPITFL TAQTLLMDLG QFLLFCHISS HQHDGMEAYV  360
KVDSCPEEPQ LRMKNNEEAE DYDDDLTDSE MDVVRFDDDN SPSFIQIRSV AKKHPKTWVH  420
YIAAEEEDWD YAPLVLAPDD RSYKSQYLNN GPQRIGRKYK KVRFMAYTDE TFKTREAIQH  480
ESGILGPLLY GEVGDTLLII FKNQASRPYN IYPHGITDVR PLYSRRLPKG VKHLKDFPIL  540
PGEIFKYKWT VTVEDGPTKS DPRCLTRYYS SFVNMERDLA SGLIGPLLIC YKESVDQRGN  600
QIMSDKRNVI LFSVFDENRS WYLTENIQRF LPNPAGVQLE DPEFQASNIM HSINGYVFDS  660
LQLSVCLHEV AYWYILSIGA QTDFLSVFFS GYTFKHKMVY EDTLTLFPFS GETVFMSMEN  720
PGLWILGCHN SDFRNRGMTA LLKVSSCDKN TGDYYEDSYE DISAYLLSKN NAIEPRSFSQ  780
NATNVSNNSN TSNDSNVSPP VLKRHQREIT RTTLQSDQEE IDYDDTISVE MKKEDFDIYD  840
EDENQSPRSF QKKTRHYFIA AVERLWDYGM SSSPHVLRNR AQSGSVPQFK KVVFQEFTDG  900
SFTQPLYRGE LNEHLGLLGP YIRAEVEDNI MVTFRNQASR PYSFYSSLIS YEEDQRQGAE  960
PRKNFVKPNE TKTYFWKVQH HMAPTKDEFD CKAWAYFSDV DLEKDVHSGL IGPLLVCHTN 1020
TLNPAHGRQV TVQEFALFFT IFDETKSWYF TENMERNCRA PCNIQMEDPT FKENYRFHAI 1080
NGYIMDTLPG LVMAQDQRIR WYLLSMGSNE NIHSIHFSGH VFTVRKKEEY KMALYNLYPG 1140
VFETVEMLPS KAGIWRVECL IGEHLHAGMS TLFLVYSNKC QTPLGMASGH IRDFQITASG 1200
QYGQWAPKLA RLHYSGSINA WSTKEPFSWI KVDLLAPMII HGIKTQGARQ KFSSLYISQF 1260
IIMYSLDGKK WQTYRGNSTG TLMVFFGNVD SSGIKHNIFN PPIIARYIRL HPTHYSIRST 1320
LRMELMGCDL NSCSMPLGME SKAISDAQIT ASSYFTNMFA TWSPSKARLH LQGRSNAWRP 1380
QVNNPKEWLQ VDFQKTMKVT GVTTQGVKSL LTSMYVKEFL ISSSQDGHQW TLFFQNGKVK 1440
VFQGNQDSFT PVVNSLDPPL LTRYLRIHPQ SWVHQIALRM EVLGCEAQDL           1490
```

What is claimed is:

1. A nucleic acid composition comprising a nucleic acid sequence of SEQ ID NO: 6.

2. The nucleic acid composition of claim 1, further comprising a therapeutic nucleic acid sequence, wherein the nucleic acid sequence of SEQ ID NO: 6 increases expression of the therapeutic nucleic acid sequence in a cell by at least 1.25-fold as compared to an otherwise identical control composition lacking the nucleic acid sequence of SEQ ID NO: 6.

3. The nucleic acid composition of claim 1, wherein the nucleic acid sequence of SEQ ID NO: 6 is a nuclear targeting sequence.

4. The nucleic acid composition of claim 1, wherein the nucleic acid composition is an isolated nucleic acid molecule.

5. The nucleic acid composition of claim 1, wherein the nucleic acid composition further comprises one or more Inverted Terminal Repeat (ITR) sequences.

6. The nucleic acid composition of claim 1, wherein the nucleic acid composition is a non-viral vector.

7. A kit comprising a sonoactive agent and a nucleic acid composition, wherein the nucleic acid composition comprises a nucleic acid sequence of SEQ ID NO: 6.

8. The kit of claim 7, wherein the nucleic acid composition further comprises a therapeutic nucleic acid sequence, wherein the nucleic acid sequence of SEQ ID NO: 6 increases expression of the therapeutic nucleic acid sequence in a cell by at least 1.25-fold as compared to an otherwise identical control composition lacking the nucleic acid sequence of SEQ ID NO: 6.

9. The kit of claim 7, wherein the nucleic acid sequence of SEQ ID NO: 6 is a nuclear targeting sequence.

10. The kit of claim 7, wherein the nucleic acid composition is an isolated nucleic acid molecule.

11. The kit of claim 7, wherein the nucleic acid composition further comprises one or more Inverted Terminal Repeat (ITR) sequences.

12. The kit of claim 7, wherein the nucleic acid composition is a non-viral vector.

13. The kit of claim 7, wherein the sonoactive agent comprises a shell filled with a perfluorinated gas.

14. The kit of claim 7, wherein the sonoactive agent comprises protein-stabilized microstructures.

15. The kit of claim 7, wherein the sonoactive agent comprises lipid-stabilized microstructures.

16. The kit of claim 15, wherein the lipid-stabilized microstructures comprise a lipid stabilized shell surrounding a perfluorinated gas core.

17. The kit of claim 16, wherein the lipid stabilized shell comprises a monomolecular membrane of hydrogenated egg yolk phosphatidyl serine, wherein the perfluorinated gas core comprises perfluorobutane gas.

18. The kit of claim 7, further comprising instructions for administering ultrasound acoustic energy to a subject to facilitate delivery of the nucleic acid composition to the subject.

\* \* \* \* \*